(12) United States Patent
Fryszman et al.

(10) Patent No.: US 8,242,117 B2
(45) Date of Patent: Aug. 14, 2012

(54) 5-MEMBERED HETEROCYCLE-BASED P38 KINASE INHIBITORS

(75) Inventors: Olga M. Fryszman, San Diego, CA (US); Hengyuan Lang, San Diego, CA (US); Jiong Lan, Emeryville, CA (US); Edcon Chang, San Diego, CA (US); Yunfeng Fang, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/950,649

(22) Filed: Nov. 19, 2010

(65) Prior Publication Data

US 2011/0071152 A1 Mar. 24, 2011

Related U.S. Application Data

(62) Division of application No. 10/877,534, filed on Jun. 25, 2004, now Pat. No. 7,863,314.

(60) Provisional application No. 60/560,481, filed on Apr. 7, 2004, provisional application No. 60/499,054, filed on Aug. 29, 2003, provisional application No. 60/483,428, filed on Jun. 26, 2003.

(51) Int. Cl.
| | |
|---|---|
| *A61K 31/5355* | (2006.01) |
| *A61K 31/415* | (2006.01) |
| *A61K 31/4164* | (2006.01) |
| *A61K 31/4245* | (2006.01) |
| *A61K 31/4439* | (2006.01) |
| *A61K 31/506* | (2006.01) |
| *A61K 31/497* | (2006.01) |
| *A61P 13/00* | (2006.01) |
| *A61P 9/00* | (2006.01) |
| *A61P 11/06* | (2006.01) |
| *A61P 25/28* | (2006.01) |
| *A61P 31/12* | (2006.01) |
| *A61P 1/00* | (2006.01) |

(52) U.S. Cl. ........... 514/236.5; 514/254.05; 514/256; 514/341; 514/364; 514/386; 514/407

(58) Field of Classification Search .................. None
See application file for complete search history.

(56) References Cited

U.S. PATENT DOCUMENTS

| | | | |
|---|---|---|---|
| RE28,819 E | 5/1976 | Thompson | |
| 6,441,018 B2 | 8/2002 | Faraci et al. | |
| 6,444,696 B1 | 9/2002 | Goldstein et al. | |
| 6,448,265 B1 | 9/2002 | Faraci et al. | |
| 2002/0016333 A1 | 2/2002 | Faraci et al. | |
| 2002/0049227 A1 | 4/2002 | Faraci et al. | |
| 2002/0103245 A1 | 8/2002 | Goldstein et al. | |
| 2002/0156114 A1 | 10/2002 | Goldstein et al. | |
| 2003/0018051 A1 | 1/2003 | Goldstein et al. | |

FOREIGN PATENT DOCUMENTS

| | | |
|---|---|---|
| DE | 1152421 B1 | 8/1963 |
| DE | 19518054 A1 | 9/1992 |
| EP | 0691128 B1 | 1/1996 |
| EP | 0713876 A1 | 5/1996 |
| EP | 0639574 B1 | 6/1998 |
| JP | 47031979 A | 11/1972 |
| JP | 49101373 A | 9/1974 |
| JP | 51112341 A | 10/1976 |
| WO | 9413643 A1 | 6/1994 |
| WO | 9828269 A1 | 7/1998 |
| WO | 9921845 A3 | 5/1999 |
| WO | 9957101 A1 | 11/1999 |
| WO | 0012074 A3 | 3/2000 |
| WO | 0012497 A3 | 3/2000 |
| WO | 0025780 A1 | 5/2000 |
| WO | 0056738 A1 | 9/2000 |
| WO | 0062778 A1 | 10/2000 |
| WO | 0121591 A1 | 3/2001 |
| WO | 0127089 A1 | 4/2001 |
| WO | 0134605 A1 | 5/2001 |
| WO | 0156567 A1 | 8/2001 |
| WO | 0224200 A1 | 3/2002 |
| WO | 0240486 A3 | 5/2002 |
| WO | 02057261 A3 | 7/2002 |
| WO | 02092087 A1 | 11/2002 |
| WO | 03004467 A3 | 1/2003 |
| WO | 03032970 A1 | 4/2003 |
| WO | 03032971 A1 | 4/2003 |
| WO | 03032972 A1 | 4/2003 |
| WO | 03032980 A1 | 4/2003 |
| WO | 03032986 A1 | 4/2003 |
| WO | 03032987 A1 | 4/2003 |
| WO | 03033457 A1 | 4/2003 |
| WO | 03033482 A1 | 4/2003 |
| WO | 03033483 A1 | 4/2003 |
| WO | 2004010995 A1 | 2/2004 |

(Continued)

OTHER PUBLICATIONS

Gao et al., Cardiovascular Research, 2002, 53, 414-422.* RA, 2011, http://www.entrepreneur.com/tradejournals/article/74806026.html.*
Fischer et al., Cancer Treatment Reviews 2007, 33, 391-406.*
Arbiser, The Journal of Clinical Investigation, 117, 10, 2762-2765.*
Arteaga et al., Clinical Cancer Research, vol. 9, 2003, 1579-1589.*
Madhusudan et al., Clinical Biochemistry, 2004, 37, 618-635.*
Alzheimer's Disease Treatment Phases, http://www.alzheimerstreatment.org/treatment/disease-treatment.htm.*
Alzheimer's Drugs, Consumer Reports Best Buy Drugs (p. 1-5).*
RheumatoidArthritis, 2012, http://www.prnewswire.com/news-releases/pharmacopeia-partnership-advances-rheumatoid-arthritis-candidate-with-second-novel-p38-kinase-inhibitor-in-canadian-clinical-trial-53554687.html.*

(Continued)

*Primary Examiner* — Sun Jae Loewe
(74) *Attorney, Agent, or Firm* — John B. Alexander

(57) ABSTRACT

Provided are 5-membered heterocycle-based p38 kinase inhibitors. Further provided are pyrazole and imidazole-based p38 kinase, including p38α and p38β kinase, inhibitors. Pharmaceutical compositions containing the compounds are also provided. Methods of use of the compounds and compositions are also provided, including methods of treatment, prevention, or amelioration of one or more symptoms of p38 kinase mediated diseases and disorders, including, but not limited to, inflammatory diseases and disorders.

14 Claims, No Drawings

FOREIGN PATENT DOCUMENTS

| | | |
|---|---|---|
| WO | 2005/063766 A2 | 7/2005 |
| WO | 2005063736 A2 | 7/2005 |

OTHER PUBLICATIONS

Zhang et al., caplus an 2003:694882.*
McCulloch, et al. "Signalling platforms that modulate the inflammatory response: new targets for drug development" www.nature.com/reviews/drugdisc; vol. 5; pp. 864-876 (2006).
MayoClinic, "Alzheimer's Disease", www.mayclinic.com; pp. 1-3.
Barnes, Peter J., "Mediators of Chronic Obstructive Pulmonary Disease", Pharmacological Reviews, vol. 56, No. 4, pp. 515-548.
Boehm et al., "New Inhibitors of p38 Kinase," Expert Opinion on Therapeutic Patents, 10(1):25-37 (2000).
Daidone et al., "Studies on the synthesis of heterocyclic compounds. Part VIII. A facile synthesis of new pyrazolo[3,4-b]benzazepine-4,9-diones", Journal of Heterocyclic Chemistry (1982) 19(3):689-690.
Rudorf et al., "Reactions of substituted 1-thiochromones and 4-(1H)-quinolinones with nucleophiles", Journal fuer Praktische Chemie (Leipzig) (1981), 323(1):55-62.
Priede, J. et al., "Reaction of 2-cyano-3-ethoxyindenone with hydrazine and some of its derivatives," Latvijas PSR Zinatnu Akademijas Vestis, Kimijas Serija (1978) 5:579-582.
Rudorf, W.D. et al., "Acylketene-S,S- and acylketene-S,N-acetals as building blocks for heterocycles: pyrazoles and isoxazoles," Journal fuer Praktische Chemie (Leipzig) (1978) 320(4):585-599.
DeWald et ai. "Pyrazolodiazepines. 2,4-Aryl-1,3-dialkyl-6,8-dihydropyrazolo[3,4-e][1,4j]diazepin-7(1H)-ones as antianxiety and anticonvulsant agents," Journal of Medicinal Chemistry (1977) 20(12): 1562-1569.
Nishiwaki et al., "Studies on Heterocyclic chemistry. Part XIX. Synthesis of 4-aroyl-1-aryl-pyrazoles from alpha-aroyl-beta-anilinoacrylonitriles and photochemistry of 4-carbonyl substituted pyrazoles"; Journal of the Chemical Society, Perkin Transactions; Organic and Bio-Organic Chemistry (1972-1999) (1974) 15:1871-1875.
Butler et al., "(1,3-Dialkyl-5-amino-1H-pyrazol-4-yl)arylmethanones. A series of novel central nervous system depressants," Journal of Medicinal Chemistry 27(11):1396-1400 (1984).
Hennig et al., "Synthesis of pyrazolo[3,4-b]quinolines from 4-aroyl-5-chloropyrazoles," Journal fuer Praktische Chemie (Leipzig) 332(5):693-698 (1990).
Bruns et al., "Structure-activity relationships for enhancement of adenosine A1 receptor binding by 2-amino-3-benzoylthiophenes," Molecular Pharmacology 38(6):950-958 (1990).
Charris et al., "Synthesis of some thiochrome derivatives and activity against *Plasmodium falciparum* in-vitro," Pharmacy and Pharmacology Communications 5(2): 107-110 (1999).
Chiba et al., "Substituted 4-Acylpyrazoles and 4-Acylpyrazolones: Synthesis and Multi-drug Resistance-Modulating Activity," Journal of Medicinal Chemistry 41 (21 ):400 1-40 11 (1998).
Henry et al., "p38 Mitogen-activated Protein Kinase as a Target for Drug Discovery," Drugs Fut., 24: 1345-1354 (1999).
Salituro et ai., "Inhibitors of p38 MAP Kinase: Therapeutic Intervention in Cytokine-Mediated Diseases," Curro Med. Chern., 6:807-823 (1999).
Rankin et al., "The Terapeutic Effects of an Engineered Human Anti-tumour Necrosis Factor Alpha Antibody (CDP571) in Rheumatoid Arthritis," Br. J. Rheumatol., 34:334-342 (1995).
Moreland et al., "Etanercept Therapy in Rheumatoid Arthritis," Ann. Intern. Med., 130:478-486 (1999).
Han J, Richter B, Li Z, Kravchenko V, Ulevitch RJ. Molecular cloning of human p38 MAP kinase. Biochim Biophys Acta. 1995 ; 1265(2-3):224-7.
Jiang Y, Chen C, Li Z, Guo W, Gegner JA, Lin S, Han J. Characterization of the structure and function of a new mitogen-activated protein kinase (p38beta). J Bio Chem. Jul. 26, 1996;271 (30): 17920-6.
Li, Z.; Jiang, Y.; Ulevitch, R. J.; Han, J. : The primary structure of p38-gamma: a new member of p38 group of MAP kinases. Biochem Biophys. Res. Commun. 228: 334-340, 1996.
Wang, et al., Molecular Cloning and Characterization of a Novel p38 Mitogen-activated Protein Kinase,. J Biol Chern. Sep. 19, 1997;272(38):23668-74.
Nogrady (1985) Medicinal Chemistry A Biochemical Approach, Oxford University Press, New York, pp. 388-392.
Ceccarelli, S. et al, "Imidazo(I,2-a)quinoxalin-4-amines: A Novel Class of Nonxanthine A1-adenosine Receptor Antagonists," European Journal of Medicinal Chemistry vol. 33, (1998), at pp. 943-955.
Murali Dhar, et al., "A Survey of Cyclic Replacements for the Central Diamide Moiety of Inhibitors of Inosine Monophosphate Dehydrogenase," Bioorg. Med. Chem. Letters 12: 3125-3128 (2002).
Zhao et al., "A new facile synthesis of 2-aminothiazole-5-carboxylates," Tetrahedron Lett., 42: 2101-2102 (2001).
Gabriele et al., "Stereoselective Synthesis of (E)-3-(Methoxycarbonyl)methylene-I ,3-dihydroindol-2-ones by Palladium-Catalyzed Oxidative Carbonylation of 2-Ethynylanilines," Eur. J. Org. Chern, 4607 (2001).
Lancelot et al., "Pyrrolo[I,2-d]triazines-I,2,4. II. Etude des pyrrolo[I,2-d]triazinones-1 et -4," J. Heterocyclic Chem 17, 631 (1980).
Frenzen et al., "Thermisch induzierte formale [3+2]-Cycloadditionen von 3,3-Dimethoxycyclopropen and Triazine, eine neue Synthese von Pyrrolo[I,2-d][I,2,4]triazinen," Chemische Berichte 126(10),2317 (1993).
Sakai et al., "Synthesis of Mesomeric Betaines Containing a Pyrrolo- or Imidazotriaziniumolate System and Their Cycloaddition with Acetylenic Dipolarophiles Leading to Triazocinone Derivatives," Tetrahedron 55(48), 13703 (1999).
Komatsu et al., "Ring Englargement of Diaziridinone with 2-Substituted Pyrrole Leading to Bicyclic Triazine and Its Transformation to Novel Mesomeric Betaine," Journal of Organic Chern. 58(24), 6620 (1993).
Robba et al., "Etude D'une Nouvelle Synthese du Cycle Pyrrolo [1,2-d]-as-trazinique," Tetrahedron Letters 35, 3239 (1973).
Gebel et al., "Photo isomerization of 2-(Hept-6-enyl)cyclopent-12-enones to Tricyclo[7.3.0.01,7]dodecan-12-ones," Journal of Chemical Research, Synopses 1,2 (1997).
Monge Vega et al., "1-Hidrazino-pirrolo [1,2-d] [1,2,4] triazinas y Derivados. Preparacion y Estudio Preliminar de Sus Propiedades Antihipertensoras," Boletin de la Sociedad Quimica del Peru 53(3), 150 (1987).
Cress et al., "Pyrrolo[1,2-d]-as-triazine. A new Heteroaromatic System," Journal of the Chemical Society, Chemical Communications 2, 35 (1973).
Jaureguiberry et al., "Synthese de pyrrolo-[1,2-d] triazines," Comptes Rendus des Seances de l' Academie des Sciences, Series C: Sciences Chimiques 274(20), 1703 (1972).
Ansel Introduction to Pharmaceutical Dosage Forms, Fourth Edition 1985, 126.
Catarzi et al., "Tricyclic Heteroaromatic Systems. Synthesis of A1 and A2a Adenosine Binding Activities of 1-Aryl-1,4-dihydro-3-methyl[1]benzopyrano[2,3-c]pyrazol-4-ones, 1-Aryl-4,9-dihydro-3-methyl-1H-pyrazolo[3,4-b ]quinolin-4-ones, and 1-Aryl-(1H)imidazo[4,5-b]quinoxalines," Journal of Medicinal Chemistry 38(8):1330-1336 (1995).
Tupper et al., "Steric and electronic control in the addition of hydrazine and phenylhydrazine to alpha-[(dimethylamino)methylene]-beta-oxoarylpropanenitriles," Synthesis (3): 337-341(1997).
Han et al. "Cyclic HIV Protease Inhibitors: Design and Synthesis of Orally Bioavailable, Pyrazole P2/P2' Cyclic Ureas with Improved Potency," J. Med. Chem., 41, 2019-2028 (1998).
Chemical Abstracts Abstr. No. 1964: 16758, Document No. 60:16758 (1964).
Chemical Abstracts Abstr. No. 1973: 19769, Document No. 78:29769 (1973).
Chemical Abstracts Abstr. No. 1975:140121, Document No. 82: 140121 (1975).
Chemical Abstracts Abstr. No. 1977:56766, Document No. 86:56766 (1977).
Chemical Abstracts Abstr. No. 1996:643997, Document No. 125:275869 (1996).
Chemical Abstracts Abstr. No. 1973:546496, Document No. 79:146496 (1973).

Chemical Abstracts Abstr. No. 1972:461962, Document No. 77:61962 (1972).

Al-Afaleq et al., "Heterocyclic synthesis via enaminonitriles: an efficient, one step synthesis of some novel azolo[1,5-a]pyrimidine, pyrimido[1,2-a]benzimidazole, pyrido[1,2-a]benzimidazole, pyrimidine and pyrazole derivatives," Synthetic Communications 30(II): 1985-1999 (2000).

Al-Zaydi et al., "Enaminonitriles in heterocyclic synthesis: New routes for the synthesis of some. novel azolo[1,5-a ]pyrimidine, pyrimido[1,2-a]benzimidazole, pyrido[1,2-a]benzimidazole, pyrazole[3,4-b]pyridine, pyrazole and pyrimidine derivatives," Journal of Chemical Research, Synopses (1):13-15,173-192 (2000).

Koraiem et ai., "The synthesis of pyrazolo- and isoxazolo-[3,4-c]-pyrazole hemiazadicarbocyanine dyes," Journal of Chemical Technology and Biotechnology, Chemical Technology 34A(2):43-50 (1984).

Alzheimer's Association; "Fact Sheet—Alzheimer's Disease"; pp. 1-2 (2006).

Furuichi et al.; "Administration of FR167653, a new anti-inflammatory compound, prevents renal ischaemia/reperfusion injury in mice"; Nephrol Dial Transplant; 17:399-407 (2002).

Kay; "Allergy and Allergic Diseases"; The New England Journal of Medicine—Review Articles (Advances in Immunology); 344(1):30-37 (2001).

Park et al.; "Prevention of Kidney Ischemia/Reperfusion-induced Functional Injury and JNK, p38, and MAPK Kinase Activation by Remote Ischemic Pretreatment"; The Journal of Biological Chemistry; 276(15):11870-11876 (2001).

Renda et al.; "Increased activation of p38 MAPK in COPD"; Eur Respir J; 31(1):62-69 (2008).

Singh et al.; "Differential Expression of Inflammatory Cytokines and Chemokines Genes by Homocysteine in the Human Retinal Pigmented Epithelial Cells"; The FASEB Journal; 20:A719 (2006).

* cited by examiner

5-MEMBERED HETEROCYCLE-BASED P38 KINASE INHIBITORS

This application is a Divisional Application of U.S. application Ser. No. 10/877,534 filed Jun. 25, 2004 which claims benefit under 35 U.S.C. §119(e) of U.S. Provisional Application Nos. 60/560,481, filed Apr. 7, 2004, 60/499,054, filed Aug. 28, 2003, and 60/483,428 filed Jun. 26, 2003, the contents of which are incorporated herein by reference in their entirety.

RELATED APPLICATIONS

Priority is claimed herein under 35 U.S.C. §119(e) to U.S. Provisional Patent Application Nos. 60/483,428, 60/499,054 and 60/560,481, filed Jun. 26, 2003, Aug. 29, 2003 and Apr. 7, 2004, respectively; and entitled "PYRAZOLE-BASED p38 INHIBITORS," "5-MEMBERED HETEROCYCLE-BASED p38 KINASE INHIBITORS," and "5-MEMBERED HETEROCYCLE-BASED p38 KINASE INHIBITORS," respectively. The disclosures of the above-referenced applications are incorporated by reference herein in their entirety.

FIELD

Provided herein are 5-membered heterocycle-, including pyrazole- and imidazole-, based compounds which have cytokine inhibitory activity. Also provided are uses of the compounds for treating conditions associated with p38α and β kinases and for treating p38 kinase-associated conditions.

BACKGROUND

A large number of cytokines participate in the inflammatory response, including IL-1, IL6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others (Henry et al., *Drugs Fut.* 24:1345-1354 (1999); Salituro et al., *Curr. Med. Chem.*, 6:807-823 (1999)). Evidence in human patients indicates that protein antagonists of cytokines are effective in treating chronic inflammatory diseases, such as, for example, a monoclonal antibody to TNF-α (Remicade) (Rankin et al., *Br. J. Rheumatol.*, 34:334-342 (1995)), and a soluble TNF-α receptor-Fc fusion protein (Etanercept) (Moreland et al., 25 Ann. Intern. Med., 130:478-486 (1999)).

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinases. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38α, p38β, p38γ, and p38δ. The α and β isoforms are expressed in inflammatory cells and are key modulators of TNF-α production. Inhibiting the p38α and β enzymes in cells results in reduced levels of TNF-α expression. Also, administering inhibitors of p38α and β in animal models of inflammatory disease has proven that such inhibitors are effective in treating those diseases. Accordingly, the p38 enzymes serve an important role in inflammatory processes mediated by IL-1 and TNF-α. See, e.g., U.S. Pat. Nos. 6,277,989, 6,130,235, 6,147,080, 5,945,418, 6,251,914, 5,977,103, 5,658,903, 5,932,576, and 6,087,496; and in International Patent Application Publication Nos. WO 00/56738, WO 01/27089, WO 01/34605, WO 00/12497, WO 00/56738, WO 00/12497 and WO 00/12074. See also, U.S. Pat. Nos. 6,376,527; 6,316,466 and 6,444,696; and International Patent Application Publication Nos. WO 99/57101, WO 02/40486, WO 03/032970, WO 03/033482, WO 03/032971, WO 03/032986, WO 03/032980, WO 03/032987, WO 03/033483, WO 03/033457 and WO 03/032972.

Thus, there is a need for inhibitors of p38 kinases, including p38a and p38b kinase, for treatment, prevention, or amelioration of one or more symptoms of diseases and disorders associated with p38 kinase activity.

SUMMARY

Provided herein are compounds, compositions and methods of treating, preventing, or ameliorating one or more symptoms of conditions associated with p38 kinase activity. In one embodiment, the compounds for use in the compositions and methods are pyrazole- or imidazole-based compounds. In another embodiment, the pyrazole- or imidazole-based compounds are useful as kinase inhibitors, including p38α and p38β kinases.

In one embodiment, the compounds provided herein have the formula:

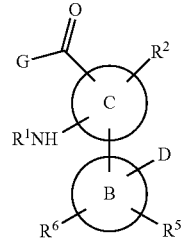

or a pharmaceutically acceptable derivative thereof, where:
$R^1$ is hydrogen, acyl or —P(O)(OH)$_2$;
$R^2$ is hydrogen, halo, optionally substituted alkyl, alkylthio, alkylsulfinyl, alkylsulfonyl, optionally substituted alkoxy, optionally substituted heterocyclyloxy or alkylamino;
G is an aryl, aralkyl, cycloalkyl, heteroaryl, heteroaralkyl or a heterocyclyl ring optionally fused to a phenyl ring, and is substituted with $R^3$ and $R^4$, provided that the heterocyclyl ring is attached to the carbonyl group via a carbon ring atom, or G is OR$^{83}$ or NR$^{80}$R$^{81}$;
B is an aryl or heteroaryl ring;
C is a 5-membered heteroaryl ring containing one or two heteroatoms in the ring;
D is heteroaryl, optionally substituted heteroaryl or –C(O)NR$^{80}$R$^{81}$;
each R$^{80}$ and R$^{81}$ is independently hydrogen, alkyl, cycloalkyl, alkoxy, hydroxy, heteroaryl or optionally substituted heteroaryl;
R$^{83}$ is hydrogen, alkyl, cycloalkyl, heteroaryl or optionally substituted heteroaryl;
R$^3$ is selected from the group consisting of:
(a) amino, alkylamino or dialkylamino;
(b) acylamino;
(c) optionally substituted heterocyclyl;

(d) optionally substituted aryl or heteroaryl;
(e) heteroalkyl;
(f) heteroalkenyl;
(g) heteroalkynyl;
(h) heteroalkoxy;
(i) heteroalkylamino;
(j) optionally substituted heterocyclylalkyl;
(k) optionally substituted heterocyclylalkenyl;
(l) optionally substituted heterocyclylalkynyl;
(m) optionally substituted heterocyclylalkoxy or heterocyclyloxy;
(n) optionally substituted heterocyclylalkylamino;
(o) optionally substituted heterocyclylalkylcarbonyl;
(p) heteroalkylcarbonyl;
(q) —NHSO$_2$R$^6$ where R$^6$ is alkyl, heteroalkyl or optionally substituted heterocyclylalkyl;
(r) —NHSO$_2$NR$^7$R$^8$ where R$^7$ and R$^8$ are, independently of each other, hydrogen, alkyl or heteroalkyl;
(s) —Y-(alkylene)-R$^9$ where: Y is a single bond, —O—, —NH— or —S(O)$_n$— (where n is an integer from 0 to 2); and R$^9$ is halo, cyano, optionally substituted aryl, optionally substituted heteroaryl, optionally substituted heterocyclyl, —COOH, —COR$^{10}$, —COOR$^{11}$, —CONR$^{12}$R$^{13}$, —SO$_2$R$^{14}$, —SO$_2$NR$^{15}$R$^{16}$, —NHSO$_2$R$^{17}$ or —NHSO$_2$NR$^{18}$R$^{19}$, where R$^{10}$ is alkyl or optionally substituted heterocycle, R$^{11}$ is alkyl, and R$^{12}$, R$^{13}$, R$^{14}$, R$^{15}$, R$^{16}$, R$^{17}$, R$^{18}$ and R$^{19}$ are, independently of each other, hydrogen, alkyl or heteroalkyl;
(t) —C(=NR$^{20}$)(NR$^{21}$R$^{22}$) where R$^{20}$, R$^{21}$ and R$^{22}$ independently represent hydrogen, alkyl or hydroxy, or R$^{20}$ and R$^{21}$ together are —(CH$_2$)$_n$— where n is 2 or 3 and R$^{22}$ is hydrogen or alkyl;
(u) —NHC(X)NR$^{23}$R$^{24}$ where X is —O— or —S—, and R$^{23}$ and R$^{24}$ are, independently of each other, hydrogen, alkyl or heteroalkyl;
(v) —CONR$^{25}$R$^{26}$ where R$^{25}$ and R$^{26}$ independently represent hydrogen, alkyl, heteroalkyl or optionally substituted heterocyclylalkyl, or R$^{25}$ and R$^{26}$ together with the nitrogen to which they are attached form an optionally substituted heterocyclyl ring;
(w) —S(O)$_n$R$^{27}$ where n is an integer from 0 to 2, and R$^{27}$ is alkyl, heteroalkyl, optionally substituted heterocyclylalkyl or —NR$^{28}$R$^{29}$ where R$^{28}$ and R$^{29}$ are, independently of each other, hydrogen, alkyl or heteroalkyl;
(x) cycloalkylalkyl, cycloalkylalkynyl and cycloalkylalkynyl, all optionally substituted with alkyl, halo, hydroxy or amino;
(y) arylaminoalkylene or heteroarylaminoalkylene;
(z) Z-alkylene-NR$^{30}$R$^{31}$ or Z-alkylene-OR$^{32}$ where Z is —NH—, —N(lower alkyl)- or —O—, and R$^{30}$, R$^{31}$ and R$^{32}$ are independently of each other, hydrogen, alkyl or heteroalkyl;
(aa) —OC(O)-alkylene-CO$_2$H or —OC(O)—NR'R" (where R' and R" are independently hydrogen or alkyl);
(bb) heteroarylalkenylene or heteroarylalkynylene;
(cc) hydrogen;
(dd) halo;
(ee) pseudohalo;
(ff) hydroxy;
(gg) optionally substituted alkoxy;
(hh) C(L)R$^{40}$, where L is O, S or NR$^{55}$; R$^{40}$ is hydrogen, optionally substituted alkyl, optionally substituted alkenyl, optionally substituted alkynyl, optionally substituted aryl, optionally substituted heteroaryl, optionally substituted heteroarylium, optionally substituted cycloalkyl, optionally substituted heterocyclyl, C(L)R$^{56}$, halo pseudohalo, OR$^{55}$, SR$^{55}$, NR$^{57}$R$^{58}$ or SiR$^{52}$R$^{53}$R$^{54}$; where R$^{52}$, R$^{53}$ and R$^{54}$ are selected as in (i) or (ii) as follows (i) R$^{52}$, R$^{53}$ and R$^{54}$ are each independently hydrogen, alkyl, alkenyl, alkynyl, aryl, heteroaryl, heteroarylium, cycloalkyl, heterocyclyl, OR$^{55}$ or NR$^{62}$R$^{63}$; or (ii) any two of R$^{52}$, R$^{53}$ and R$^{54}$ together form alkylene, alkenylene, alkynylene, heteroalkylene; and the other is selected as in (i); R$^{55}$ is hydrogen, alkyl, alkenyl, alkynyl, aryl, heteroaryl, heteroarylium, cycloalkyl or heterocyclyl; R$^{56}$ is hydrogen, alkyl, alkenyl, alkynyl, aryl, heteroaryl, heteroarylium, cycloalkyl, heterocyclyl, OR$^{55}$ or NR$^{64}$R$^{65}$; where R$^{64}$ and R$^{65}$ are each independently hydrogen, alkyl, alkenyl, alkynyl, aryl, heteroaryl, heteroarylium, cycloalkyl, heterocyclyl, OR$^{66}$ or NR$^{62}$R$^{63}$, or R$^{64}$ and R$^{65}$ together form alkylene, alkenylene, alkynylene, heteroalkylene, where R$^{66}$ is hydrogen, alkyl, alkenyl, alkynyl, aryl, heteroaryl, heteroarylium, cycloalkyl or heterocyclyl; R$^{57}$ and R$^{58}$ are selected as in (i) or (ii) as follows (i) R$^{57}$ and R$^{58}$ are each independently hydrogen, optionally substituted alkyl, alkenyl, alkynyl, aryl, heteroaryl, heteroarylium, cycloalkyl, heterocyclyl, OR$^{55}$, NR$^{67}$R$^{68}$ or C(L)R$^{69}$, where R$^{67}$ and R$^{68}$ are each independently hydrogen, alkyl, alkenyl, alkynyl, aryl, heteroaryl, heteroarylium, cycloalkyl or heterocyclyl, or together form alkylene, alkenylene, alkynylene, heteroalkylene; and R$^{69}$ is hydrogen, alkyl, alkenyl, alkynyl, aryl, heteroaryl, heteroarylium, cycloalkyl, heterocyclyl, OR$^{70}$ or NR$^{62}$R$^{63}$, where R$^{70}$ is alkyl, alkenyl, alkynyl, aryl, heteroaryl, heteroarylium, cycloalkyl, heterocyclyl; or (ii) R$^{57}$ and R$^{58}$ together form alkylene, alkenylene, alkynylene, heteroalkylenem or alkylenoxyalkylene; R$^{62}$ and R$^{63}$ are each independently hydrogen, alkyl, alkenyl, alkynyl, aryl, heteroaryl, heteroarylium, cycloalkyl, heterocyclyl, or R$^{62}$ and R$^{63}$ together form alkylene, alkenylene, alkynylene, heteroalkylene; and
(ii) optionally substituted alkyl;
R$^4$ is selected from the group consisting of:
(a) hydrogen;
(b) halo;
(c) alkyl;
(d) alkoxy; and
(e) hydroxy;
R$^5$ is selected from the group consisting of
(a) hydrogen;
(b) halo;
(c) alkyl;
(d) haloalkyl;
(e) thioalkyl;
(f) hydroxy;
(g) amino;
(h) alkylamino;
(i) dialkylamino;
(j) heteroalkyl;
(k) optionally substituted heterocycle;
(l) optionally substituted heterocyclylalkyl;
(m) optionally substituted heterocyclylalkoxy;
(n) alkylsulfonyl;
(o) aminosulfonyl, mono-alkylaminosulfonyl or di-alkylaminosulfonyl;
(p) heteroalkoxy; and
(q) carboxy;
R$^6$ is selected from the group consisting of:
(a) hydrogen;
(b) halo;
(c) alkyl; and
(d) alkoxy.

Also provided herein are pharmaceutical compositions containing a compound provided herein in combination with a pharmaceutically acceptable carrier.

Methods of treating, preventing or ameliorating one or more symptoms of cytokine mediated disease in a mammal, by administering to a mammalian patient, in need of such treatment, a compound of formula I are provided. Diseases and disorders treated, prevented, or whose symptoms are ameliorated, include, but are not limited to, chronic inflammatory diseases, inflammatory bowel disease, rheumatoid arthritis, psoriasis, multiple sclerosis, endotoxin shock, osteoporosis, Alzheimer's disease, and congestive heart failure.

Methods of preventing or inhibiting inflammatory responses using the compounds and compositions provided herein are also provided.

Further provided are methods of inhibiting p38 kinases, including p38α and p38β kinases, using the compounds and compositions provided herein.

Articles of manufacture are provided containing packaging material, a compound or composition provided herein which is useful for treating, preventing, or ameliorating one or more symptoms of p38 kinase-mediated diseases or disorders, and a label that indicates that the compound or composition is useful for treating, preventing, or ameliorating one or more symptoms of p38 kinase-mediated diseases or disorders.

DETAILED DESCRIPTION

A. Definitions

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, p38α refers to the enzyme disclosed in Han et al. (1995) *Biochim. Biophys. Acta* 1265(2-3):224-7. As used herein, p38β refers to the enzyme disclosed in Jiang et al. (1996) *J. Biol. Chem.* 271(30):17920-6. As used herein, p38γ refers to the enzyme disclosed in Li et al. (1996) *Biochem. Biophys. Res. Commun.* 228: 334-340. As used herein, p38δ refers to the enzyme disclosed in Wang et al. (1997) *J. Biol. Chem.* 272(38):23668-74.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, oxalates, benzoates, salicylates, maleates, lactates, malates, tartrates, citrates, ascorbates, succinates, butyrates, valerates and fumarates. In addition, zwitterions ("inner salts") may be formed. In certain embodiments, salt forms of the compounds improve the compounds' dissolution rate and oral bioavailability. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

The term "cycloalkyl" refers to a saturated or partially unsaturated nonaromatic cyclic hydrocarbon ring system, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cycloctyl, cyclodecyl, cyclododecyl, and adamantyl. A "substituted cycloalkyl" is substituted with one or more alkyl or substituted alkyl groups as described above, or one or more groups described above as alkyl substituents. The expression "lower cycloalkyl" refers to an unsubstituted saturated or unsaturated nonaromatic cyclic hydrocarbon ring system containing 3 to 5 carbon atoms.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkenylene" means a linear divalent hydrocarbon radical of two to six carbon atoms or a branched divalent hydrocarbon radical of three to six carbon atoms, containing at least one double bond, e.g., ethenylene, propenylene, and the like.

"Alkynyl" means a linear monovalent hydrocarbon radical of two to six carbon atoms or a branched divalent hydrocarbon radical of three to six carbon atoms, containing at least one triple bond, e.g., ethynyl, propynyl, and the like.

"Alkynylene" means a linear divalent hydrocarbon radical of two to six carbon atoms or a branched monovalent hydrocarbon radical of three to six carbon atoms, containing at least one triple bond, e.g., ethynylene, propynylene, and the like.

"Alkoxy" means a radical —OR where R is alkyl as defined above, e.g., methoxy, ethoxy, propoxy, 2-propoxy, the like.

"Acyl" means a radical —C(O)R where R is alkyl or haloalkyl e.g., acetyl, trifluoroacetyl, and the like.

"Acylamino" means a radical —NRC(O)R' where R is hydrogen or alkyl, and R' is alkyl, heteroalkyl or optionally substituted heterocyclylalkyl, e.g., acetylamino, 2-amino-2-methylpropionamide, and the like.

"Halo" means fluoro, chloro, bromo, or iodo, generally fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Aryl" means a monovalent monocyclic or bicyclic aromatic hydrocarbon radical of 6 to 10 ring atoms e.g., phenyl, 1-naphthyl, 2-naphthyl, and the like. The aryl ring may optionally be fused to a 5-, 6- or 7-membered monocyclic saturated ring optionally containing 1 or 2 heteroatoms independently selected from oxygen, nitrogen or sulfur, the remaining ring atoms being C where one or two C atoms are optionally replaced by a carbonyl group. Representative aryl radicals with fused rings include, but are not limited to, 2,3-dihydrobenzo[1,4]dioxan, chroman, isochroman, 2,3-dihydrobenzofuran, 1,3-dihydroisobenzofuran, benzo[1,3]dioxole, 1,2,3,4-tetrahydroisoquinoline, 1,2,3, 4tetrahydroquinoline, 2,3-dihydro-1H-indole, 2,3-dihydro-1H-isoindole, benzimidazol-2-one, 3H-benzoxazol-2-one, and the like.

"Heteroaryl" means a monovalent monocyclic or bicyclic aromatic radical of 5 to 10 ring atoms containing one, two, or three ring heteroatoms selected from N, O, or S, the remaining ring atoms being C. The term also includes those radicals where a heteroatom within the ring has been oxidized or quaternized, such as, for example, to form an N-oxide or a quaternary salt. Representative examples include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and their corresponding N-oxides, (e.g. pyridyl N-oxide, quinolinyl N-oxide), their quaternary salts and the like.

"Heterocycle" or "heterocyclyl" means a cyclic nonaromatic radical of 3 to 8 ring atoms in which one or two ring atoms are heteroatoms selected from N, O, or $S(O)_n$, (where n is an integer from 0 to 2), the remaining ring atoms being C where one or two C atoms are optionally replaced by a carbonyl group. The term also includes those radicals where a ring nitrogen atom has been oxidized or quaternized, such as, for example, to form an N-oxide or a quaternary salt. Representative examples include, but are not limited to, tetrahydropyranyl, tetrahydrofuranyl, tetrahydrothiophenyl, piperidino, morpholino, piperazino, pyrrolidino, oxiranyl, dioxane, 1,3-dioxolanyl, 2,2-dimethyl-1,3-dioxalanyl, sulfolanyl, 2-oxazolidonyl, 2-imidazolidonyl, S,S-dioxo-thiomorpholino, and the like.

"Heterocycloamino" means a saturated monovalent cyclic group of 4 to 8 ring atoms, wherein at least one ring atom is N and optionally contains one additional ring atom selected from N or O, the remaining ring atoms being C. The term includes groups such as pyrrolidino, piperidino, morpholino, piperazino and the like.

"Optionally substituted alkyl, alkenyl, alkynyl, alkoxy or cycloalkyl" means an alkyl, alkenyl, alkynyl, alkoxy or cycloalkyl group, as defined herein, which is optionally substituted independently with one or two substituents selected from alkyl, phenyl, benzyl, haloalkyl, heteroalkyl, halo, cyano, heterocyclyl, acyl, —OR (where R is hydrogen or alkyl), —NRR' (where R and R' are independently selected from hydrogen, acyl, or alkyl which is optionally substituted with hydroxy, alkoxy, cyano, halo or heterocyclyl), —NHCOR (where R is alkyl which is optionally substituted with hydroxy, alkoxy, cyano, halo or heterocyclyl), —$NRS(O)_n$R' (where R is hydrogen or alkyl, n is an integer from 0 to 2; and R' is hydrogen, alkyl or heteroalkyl, and is optionally substituted with hydroxy, alkoxy, cyano, halo or heterocyclyl), —$NRS(O)_n$NR'R" (where R is hydrogen or alkyl, n is an integer from 0 to 2; and R' and R" are independently hydrogen, alkyl or heteroalkyl and are optionally substituted with hydroxy, alkoxy, cyano, halo or heterocyclyl), —$S(O)_n$R (where n is an integer from 0 to 2; and R is hydrogen, alkyl or heteroalkyl and is optionally substituted with hydroxy, alkoxy, cyano, halo or heterocyclyl), —$S(O)_n$NRR' (where n is an integer from 0 to 2; and R and R' are independently hydrogen, alkyl or heteroalkyl and are optionally substituted with hydroxy, alkoxy, cyano, halo or heterocyclyl), —COOR, -(alkylene)COOR (where R is hydrogen or alkyl), —CONR'R" or -(alkylene)CONR'R" (where R' and R" are independently hydrogen or alkyl, or together form a heterocyclyl ring with the nitrogen atom to which they are attached).

"Optionally substituted aryl, heteroaryl or heterocyclyl" means an aryl, heteroaryl or heterocyclyl ring as defined above, which is optionally substituted independently with one or two substituients selected from alkyl, phenyl, benzyl, haloalkyl, heteroalkyl, halo, cyano, acyl, —OR (where R is hydrogen or alkyl), —NRR' (where R and R' are independently selected from hydrogen, alkyl or acyl), —NHCOR (where R is alkyl), —$NRS(O)_n$R' (where R is hydrogen or alkyl, n is an integer from 0 to 2 and R' is hydrogen, alkyl or heteroalkyl), —$NRS(O)_n$NR'R" (where R is hydrogen or alkyl, n is an integer from 0 to 2 and R' and R" are independently hydrogen, alkyl or heteroalkyl), —$S(O)_n$R (where n is an integer from 0 to 2 and R is hydrogen, alkyl or heteroalkyl), —$S(O)_n$NRR' (where n is an integer from 0 to 2 and R and R' are independently hydrogen, alkyl or heteroalkyl), —COOR, -(alkylene)COOR (where R is hydrogen or alkyl), —CONR'R" or -(alkylene)CONR'R" (where R' and R" are independently hydrogen or alkyl).

"Heteroalkyl" means an alkyl radical as defined above, carrying one, two or three substituents selected from —$NR^aR^b$, —$OR^c$ wherein $R^a$, $R^b$ and $R^c$ are independently of each other hydrogen, alkyl or acyl, or $R^a$ and $R^b$ together form heterocycloamino group. Representative examples include, but are not limited to, hydroxymethyl, acetoxymethyl, 3-hydroxypropyl, 1,2-dihydroxyethyl, 2-methoxyethyl, 2-aminoethyl, 2-dimethylaminoethyl, 2-acetylaminoethyl, 3-[pyrrolidin-1-yl]ethyl and the like.

"Heteroalkenyl" means an alkenyl radical as defined above, carrying one or two substituents selected from —$NR^aR^b$, —$OR^c$ or —$S(O)_nR^d$ wherein $R^a$, $R^b$ and $R^c$ are independently of each other hydrogen or alkyl, and $R^d$ is alkyl or —NRR' (where R and R' are independently of each other hydrogen or alkyl. Representative examples include, but are not limited to, 3-hydroxy-1-propenyl, 3-aminoprop-1-enyl, 2-aminosulfonylethenyl, 2-methylsulfonylethenyl, and the like.

"Heteroalkynyl" means an alkynyl radical as defined above, carrying one or two substituents selected —$NR^aR^b$, —$OR^c$, —$S(O)_nR^d$ or —$S(O)_n$NRR' (where R and R' are independently of each other hydrogen or alkyl) wherein $R^a$, $R^b$ and $R^c$ are independently of each other hydrogen or alkyl, and $R^d$ is alkyl and n is an integer from zero to two. Representative examples include, but are not limited to, 3-hydroxy-1-propynyl, 3dimethylaminoprop-1-ynyl and the like.

"Heteroalkoxy" means a radical —OR where R is heteroalkyl group as defined above, e.g., 2-hydroxyethoxy, 3-hydroxypropoxy, 2,3-dihydroxypropoxy, 2-aminoethoxy, and the like.

"Heteroalkylamino" means a radical —$NR^aR^b$ where $R^a$ is hydrogen or alkyl, and $R^b$ is a heteroalkyl group as defined above, e.g., 2-hydroxyethylamino, 3-dimethylaminopropylamino, and the like.

"Optionally substituted heterocyclylalkyl" means a radical —$R^aR^b$ where $R^a$ is an alkylene group, and $R^b$ is an optionally substituted heterocyclyl group as defined above e.g., 2-(morpholin-4-yl)ethyl, 3(piperidin-1-yl)-2-methylpropyl, and the like.

"Optionally substituted heterocyclylalkenyl" means a radical —$R^aR^b$ where $R^a$ is an alkenylene group and $R^b$ is an optionally substituted heterocyclyl group as defined above e.g., 3-(morpholin-4-yl)prop-1-enyll, 3-(piperidin-1-yl)prop-1-enyl, 3-(4-methylpiperazin-1-yl)prop-1-enyl, and the like.

"Optionally substituted heterocyclylalkynyl" means a radical —$R^aR^b$ where $R^a$ is an alkynyl group and $R^b$ is an optionally substituted heterocyclyl group as defined above e.g., 3-(morpholin-4-yl)prop-1-ynyl, 3-(piperidin-1-yl)prop-1-ynyl, and the like.

"Optionally substituted heterocyclylalkoxy" means a radical —OR where R is an optionally substituted heterocyclylalkyl group as defined above, e.g., 2-(morpholin-4-yl)-ethoxy, 3-(piperazin-1-yl)propoxy, 2-[2-oxopyrrolidin-1-yl]ethoxy, and the like.

"Optionally substituted heterocyclylalkylamino" means a radical —$NR^aR^b$ where $R^a$ is hydrogen or alkyl and $R^b$ is an optionally substituted heterocyclylalkyl group as defined above, e.g., 2-(pyrrolidin-2-yl)ethylamino, 3-(piperidin-1-yl) propylamino, and the like.

"Optionally substituted heteroaralkyloxy means a radical —O—$R^a$ where $R^a$ is a heteroaralkyl radical e.g. 2-(pyridin-3-yl)ethoxy, 2-[3(2H)-pyridazon-1-yl]ethoxy and the like.

"Optional" or "optionally" means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the heterocyclo group is not substituted with the alkyl group.

"Amino protecting group" refers to those organic groups intended to protect nitrogen atoms against undesirable reactions during synthetic procedures e.g., benzyl, benzyloxycarbonyl (CBZ), tert-butoxycarbonyl (Boc), trifluoroacetyl, and the like.

Throughout the specification, groups and substituents thereof may be chosen by one skilled in the field to provide stable moieties and compounds. It is also understood that the chemical groups, as described herein, can be substituted or unsubstituted, branched or unbranched, as appropriate and desired.

All stereoisomers of the compounds provided herein are contemplated, either in admixture or in pure or substantially pure form. The definition of compounds provided herein embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The compounds provided herein may also have prodrug forms. Any compound that will be converted in vivo to provide the bioactive agent is a prodrug. Various forms of prodrugs are well known in the art. For examples of such prodrug derivatives, see, e.g.:

a) *Design of Prodrugs*, edited by H. Bundgaard, (Elsevier, 1985) and *Methods in Enzymology*, Vol. 42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992), each of which is incorporated herein by reference.

As used herein, treatment means any manner in which one or more of the symptoms of a disease or disorder are ameliorated or otherwise beneficially altered. Treatment also encompasses any pharmaceutical use of the compounds and compositions herein, such as use for treating p38 kinase mediated diseases or disorders, or diseases or disorders in which p38 kinase activity, including p38α and p38β kinase activity, is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response, such as modulation of p38a kinase activity, in an assay that measures such response.

B. Compounds

The compounds provided herein for use in the compositions and methods are active in assays that measure p38 kinase activity, including, but not limited to, p38α and p38β kinase activity. In one embodiment, the compounds provided herein have formulae I:

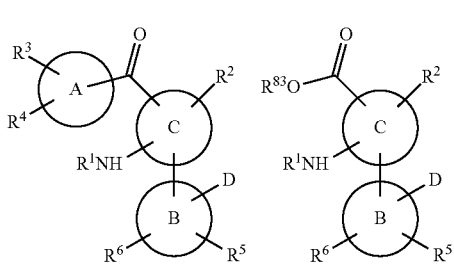

-continued

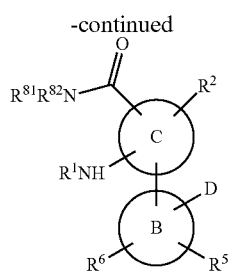

or a pharmaceutically acceptable derivative thereof, where:

$R^1$ is hydrogen, acyl or —P(O)(OH)$_2$;

$R^2$ is hydrogen, halo, alkyl or alkylthio;

A is an aryl, heteroaryl or a heterocyclyl ring optionally fused to a phenyl ring, provided that the heterocyclyl ring is attached to the carbonyl group via a carbon ring atom;

B is an aryl or heteroaryl ring;

C is a 5-membered heteroaryl ring containing one or two heteroatoms in the ring;

D is heteroaryl, optionally substituted heteroaryl or —C(O)NR$^{80}$R$^{81}$, where R$^{80}$ and R$^{81}$ are independently hydrogen, alkyl, cycloalkyl, alkoxy, hydroxy, heteroaryl or optionally substituted heteroaryl;

$R^3$ is selected from the group consisting of:
(a) amino, alkylamino or dialkylamino;
(b) acylamino;
(c) optionally substituted heterocyclyl;
(d) optionally substituted aryl or heteroaryl;
(e) heteroalkyl;
(f) heteroalkenyl;
(g) heteroalkynyl;
(h) heteroalkoxy;
(i) heteroalkylamino;
(j) optionally substituted heterocyclylalkyl;
(k) optionally substituted heterocyclylalkenyl;
(l) optionally substituted heterocyclylalkynyl;
(m) optionally substituted heterocyclylalkoxy or heterocyclyloxy;
(n) optionally substituted heterocyclylalkylamino;
(o) optionally substituted heterocyclylalkylcarbonyl;
(p) heteroalkylcarbonyl;
(q) —NHSO$_2$R$^6$ where R$^6$ is alkyl, heteroalkyl or optionally substituted heterocyclylalkyl;
(r) —NHSO$_2$NR$^7$R$^8$ where R$^7$ and R$^8$ are, independently of each other, hydrogen, alkyl or heteroalkyl;
(s) —Y-(alkylene)-R$^9$ where: Y is a single bond, —O—, —NH— or —S(O)$_n$— (where n is an integer from 0 to 2); and R$^9$ is halo, cyano, optionally substituted aryl, optionally substituted heteroaryl, optionally substituted heterocyclyl, —COOH, —COR$^{10}$, —COOR$^{11}$, —CONR$^{12}$R$^{13}$, —SO$_2$R$^{14}$, —SO$_2$NR$^{15}$R$^{16}$, —NHSO$_2$R$^{17}$ or —NHSO$_2$NR$^{18}$R$^{19}$ (where R$^{10}$ is alkyl or optionally substituted heterocycle, R$^{11}$ is alkyl, and R$^{12}$, R$^{13}$, R$^{14}$, R$^{15}$, R$^{16}$, R$^{17}$, R$^{18}$ and R$^{19}$ are, independently of each other, hydrogen, alkyl or heteroalkyl;
(u) —C(=NR$^{20}$)(NR$^{21}$R$^{22}$) where R$^{20}$, R$^{21}$ and R$^{22}$ independently represent hydrogen, alkyl or hydroxy, or R$^{20}$ and R$^{21}$ together are —(CH$_2$)$_n$— where n is 2 or 3 and R$^{22}$ is hydrogen or alkyl;
(u) —NHC(X)NR$^{23}$R$^{24}$ where X is —O— or —S—, and R$^{23}$ and R$^{24}$ are, independently of each other, hydrogen, alkyl or heteroalkyl;
(v) —CONR$^{25}$R$^{26}$ where R$^{25}$ and R$^{26}$ independently represent hydrogen, alkyl, heteroalkyl or optionally substituted heterocyclylalkyl, or R$^{25}$ and R$^{26}$ together with the nitrogen to which they are attached form an optionally substituted heterocyclyl ring;
(w) —S(O)$_n$R$^{27}$ where n is an integer from 0 to 2, and R$^{27}$ is alkyl, heteroalkyl, optionally substituted heterocyclylalkyl or —NR$^{28}$R$^{29}$ where R$^{28}$ and R$^{29}$ are, independently of each other, hydrogen, alkyl or heteroalkyl;
(x) cycloalkylalkyl, cycloalkylalkynyl and cycloalkylalkynyl, all optionally substituted with alkyl, halo, hydroxy or amino;
(y) arylaminoalkylene or heteroarylaminoalkylene;
(z) Z-alkylene-NR$^{30}$R$^{31}$ or Z-alkylene-OR$^{32}$ where Z is —NH—, —N(lower alkyl)- or —O—, and R$^{30}$, R$^{31}$ and R$^{32}$ are independently of each other, hydrogen, alkyl or heteroalkyl;
(aa) —OC(O)-alkylene-CO$_2$H or —OC(O)—NR'R" (where R' and R" are independently hydrogen or alkyl);
(bb) heteroarylalkenylene or heteroarylalkynylene;
(cc) hydrogen;
(dd) halo;
(ee) pseudohalo;
(ff) hydroxy;
(gg) optionally substituted alkoxy;
(hh) C(L)R$^{40}$, where L is O, S or NR$^{55}$; R$^{40}$ is hydrogen, optionally substituted alkyl, optionally substituted alkenyl, optionally substituted alkynyl, optionally substituted aryl, optionally substituted heteroaryl, optionally substituted heteroarylium, optionally substituted cycloalkyl, optionally substituted heterocyclyl, C(L)R$^{56}$, halo pseudohalo, OR$^{55}$, SR$^{55}$, NR$^{57}$R$^{58}$ or SiR$^{52}$R$^{53}$R$^{54}$; where R$^{52}$, R$^{53}$ and R$^{54}$ are selected as in (i) or (ii) as follows (i) R$^{52}$, R$^{53}$ and R$^{54}$ are each independently hydrogen, alkyl, alkenyl, alkynyl, aryl, heteroaryl, heteroarylium, cycloalkyl, heterocyclyl, OR$^{55}$ or NR$^{62}$R$^{63}$; or (ii) any two of R$^{52}$, R$^{53}$ and R$^{54}$ together form alkylene, alkenylene, alkynylene, heteroalkylene; and the other is selected as in (i); R$^{55}$ is hydrogen, alkyl, alkenyl, alkynyl, aryl, heteroaryl, heteroarylium, cycloalkyl or heterocyclyl; R$^{56}$ is hydrogen, alkyl, alkenyl, alkynyl, aryl, heteroaryl, heteroarylium, cycloalkyl, heterocyclyl, OR$^{55}$ or NR$^{64}$R$^{65}$; where R$^{64}$ and R$^{65}$ are each independently hydrogen, alkyl, alkenyl, alkynyl, aryl, heteroaryl, heteroarylium, cycloalkyl, heterocyclyl, OR$^{66}$ or NR$^{62}$R$^{63}$, or R$^{64}$ and R$^{65}$ together form alkylene, alkenylene, alkynylene, heteroalkylene, where R$^{66}$ is hydrogen, alkyl, alkenyl, alkynyl, aryl, heteroaryl, heteroarylium, cycloalkyl or heterocyclyl; R$^{57}$ and R$^{58}$ are selected as in (i) or (ii) as follows (i) R$^{57}$ and R$^{58}$ are each independently hydrogen, alkyl, alkenyl, alkynyl, aryl, heteroaryl, heteroarylium, cycloalkyl, heterocyclyl, OR$^{55}$, NR$^{67}$R$^{68}$ or C(L)R$^{69}$, where R$^{67}$ and R$^{68}$ are each independently hydrogen, alkyl, alkenyl, alkynyl, aryl, heteroaryl, heteroarylium, cycloalkyl or heterocyclyl, or together form alkylene, alkenylene, alkynylene, heteroalkylene; and R$^{69}$ is hydrogen, alkyl, alkenyl, alkynyl, aryl, heteroaryl, heteroarylium, cycloalkyl, heterocyclyl, OR$^{70}$ or NR$^{62}$R$^{63}$, where R$^{70}$ is alkyl, alkenyl, alkynyl, aryl, heteroaryl, heteroarylium, cycloalkyl, heterocyclyl; or (ii) R$^{57}$ and R$^{58}$ together form alkylene, alkenylene, alkynylene, heteroalkylene; R$^{62}$ and R$^{63}$ are each independently hydrogen, alkyl, alkenyl, alkynyl, aryl, heteroaryl, heteroarylium, cycloalkyl, heterocyclyl, or R$^{62}$ and R$^{63}$ together form alkylene, alkenylene, alkynylene, heteroalkylene; and
(ii) optionally substituted alkyl;

$R^4$ is selected from the group consisting of:
(a) hydrogen;
(b) halo;
(c) alkyl;
(d) alkoxy; and
(e) hydroxy;

$R^5$ is selected from the group consisting of
(a) hydrogen;
(b) halo;
(c) alkyl;
(d) haloalkyl;
(e) thioalkyl;
(f) hydroxy;
(g) amino;
(h) alkylamino;
(i) dialkylamino;
(j) heteroalkyl;
(k) optionally substituted heterocycle;
(l) optionally substituted heterocyclylalkyl;
(m) optionally substituted heterocyclylalkoxy;
(n) alkylsulfonyl;
(o) aminosulfonyl, mono-alkylaminosulfonyl or di-alkylaminosulfonyl;
(p) heteroalkoxy; and
(q) carboxy;
$R^6$ is selected from the group consisting of:
(a) hydrogen;
(b) halo;
(c) alkyl; and
(d) alkoxy.

In one embodiment, C is a 5-membered heteroaryl ring containing one or two heteroatoms in the ring. In another embodiment, C is selected from pyrazole, imidazole, pyrrole, thiazole, isothiazole, oxazole, isoxazole, furan and thiophene rings. In another embodiment, C is a pyrazole or imidazole ring. In another embodiment, C is an imidazole ring. In another embodiment, C is a pyrazole ring.

1. Pyrazole-Based Compounds

In one embodiment, C is a pyrazole ring and the compounds provided herein have formulae

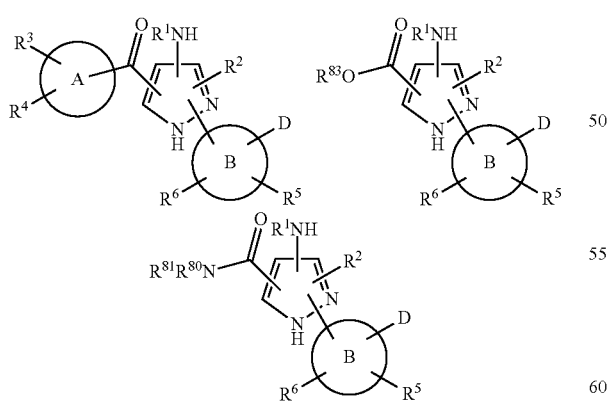

II or a pharmaceutically acceptable derivative thereof, where the variables are as defined elsewhere herein. In this embodiment, the hydrogen of the ring NH group may be replaced by one of the substituents shown in the structure (i.e., —C(O)-A($R^3$)($R^4$), —$R^2$, or —B(D)($R^6$)($R^5$)).

In another embodiment, the compounds provided herein have formulae III:

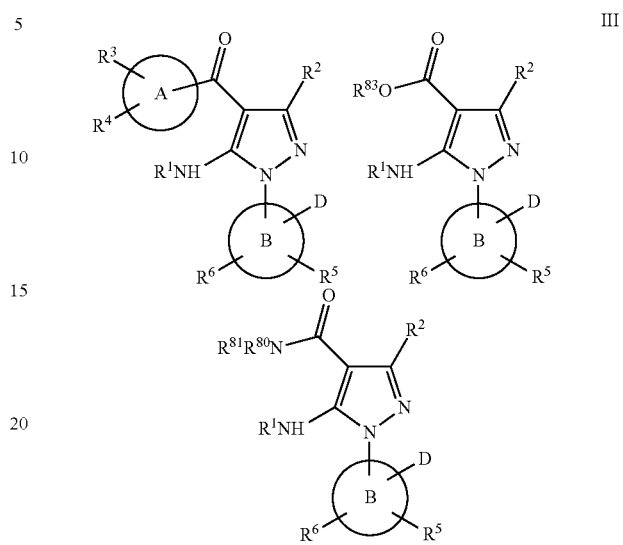

III or a pharmaceutically acceptable derivative thereof, where the variables are as defined elsewhere herein.

In another embodiment, the compounds provided herein have formulae IV:

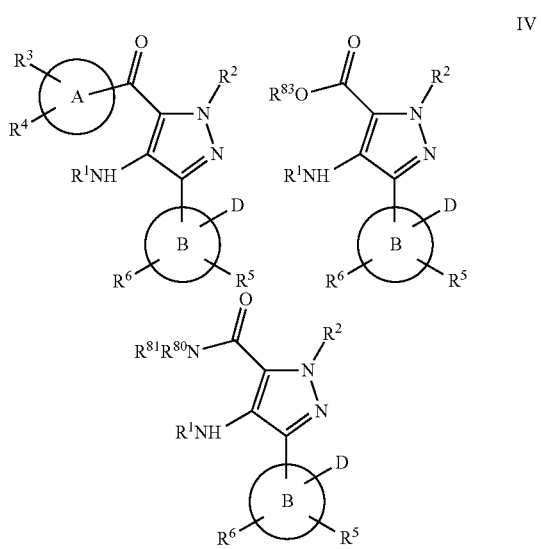

IV or a pharmaceutically acceptable derivative thereof, where the variables are as defined elsewhere herein.

In another embodiment, the compounds provided herein have formulae V:

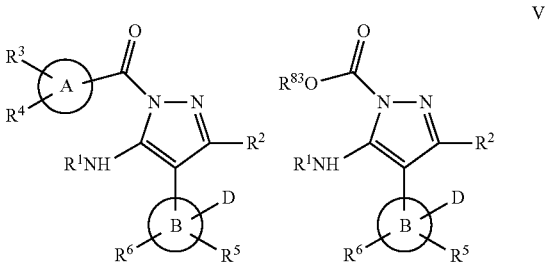

V

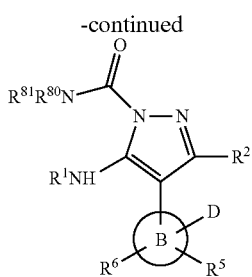

or a pharmaceutically acceptable derivative thereof, where the variables are as defined elsewhere herein.

In another embodiment, the compounds provided herein have formulae Va:

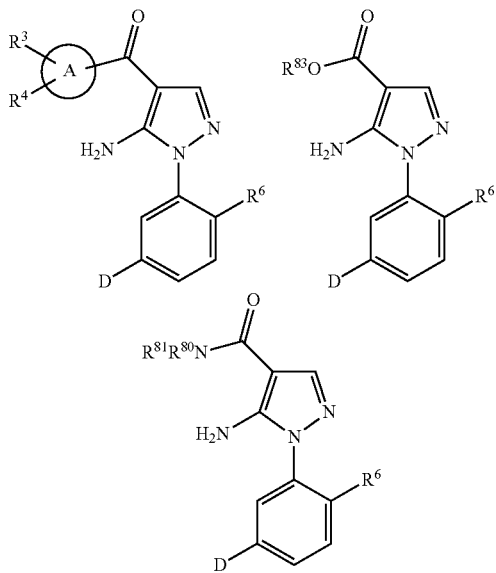

or a pharmaceutically acceptable derivative thereof, wherein A, D, $R^3$, $R^4$, and $R^6$ are as defined elsewhere herein.

2. Imidazole-Based Compounds

In another embodiment, the compounds are imidazole-based compounds of formulae VI:

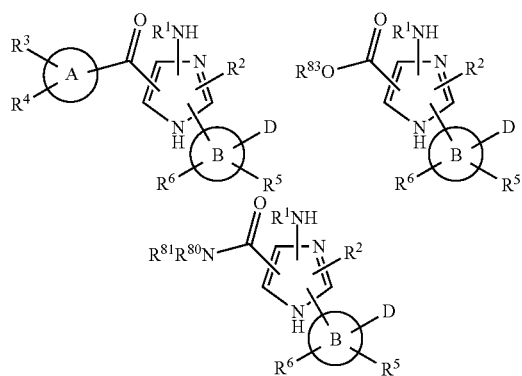

or a pharmaceutically acceptable derivative thereof, where the variables are as defined elsewhere herein. In this embodiment, the hydrogen of the ring NH group may be replaced by one of the substituents shown in the structure (i.e., —C(O)-A($R^3$)($R^4$), —$R^2$, or —B(D)($R^6$)($R^5$).

In another embodiment, the compounds provided herein have formulae VII:

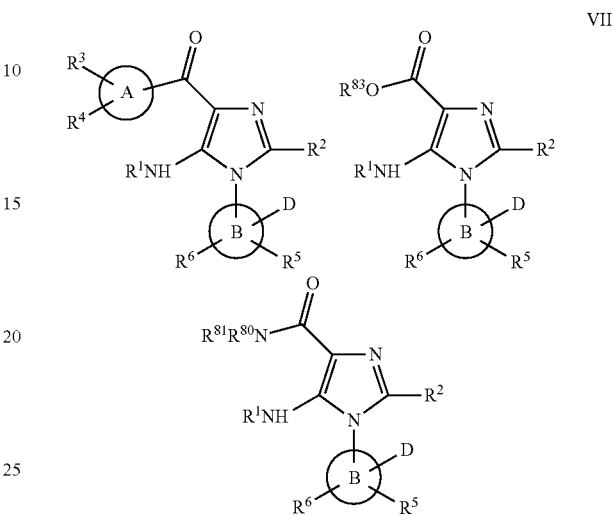

or a pharmaceutically acceptable derivative thereof, where the variables are as defined elsewhere herein.

In another embodiment, the compounds provided herein have formulae VIM

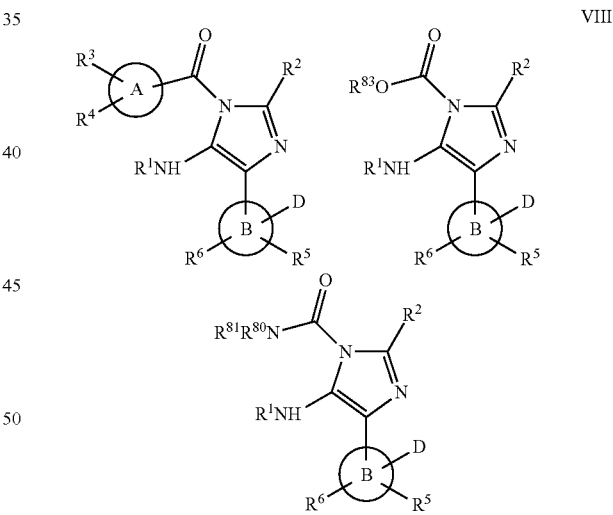

or a pharmaceutically acceptable derivative thereof, where the variables are as defined elsewhere herein.

3. Other embodiments

In other embodiments, the compounds for use in the compositions and methods provided herein have the above formulae, or pharmaceutically acceptable derivatives thereof, where $R^1$ is hydrogen. In another embodiment, $R^2$ is hydrogen or lower alkyl. In another embodiment, $R^2$ is hydrogen. In another embodiment, G is $OR^{83}$ or $NR^{80}R^{81}$. In another embodiment, $R^{83}$ is alkyl or cycloalkyl. In another embodiment, $R^{83}$ is alkyl. In another embodiment, $R^{83}$ is ethyl. In another embodiment, $R^{80}$ and $R^{81}$ are each independently hydrogen, alkyl or cycloalkyl. In another embodiment, $R^{80}$ and $R^{81}$ are each independently hydrogen or cycloalkyl. In another embodiment, $R^{80}$ and $R^{81}$ are each independently hydrogen or cyclohexyl. In another embodiment, G is $NH_2$ or NH(cyclohexyl).

In another embodiment, G is aryl, heteroaryl, cycloalkyl, heterocyclyl or heterocyclyl optionally fused to phenyl, and is substituted with $R^3$ and $R^4$, provided that the heterocyclyl ring is attached to the carbonyl group via a carbon ring atom. In another embodiment, G is phenyl, cyclohexyl, cyclopentyl or benzyl, and is substituted with $R^3$ and $R^4$. In another embodiment, G is phenyl and is substituted with $R^3$ and $R^4$.

In another embodiment, A is an aryl ring. In another embodiment, A is a phenyl ring.

In another embodiment, B is an aryl ring. In another embodiment, B is a phenyl ring.

In another embodiment, D is —C(O)NR$^{80}$R$^{81}$. In another embodiment, $R^{80}$ and $R^{81}$ are each independently hydrogen, cycloalkyl or alkoxy. In another embodiment, $R^{80}$ is hydrogen. In another embodiment, $R^{81}$ is cycloalkyl or alkoxy. In another embodiment, $R^{81}$ is $C_{3-6}$cycloalkyl or $C_{1-6}$alkoxy. In another embodiment, $R^{81}$ is cyclopropyl or methoxy.

In another embodiment, D is optionally substituted heteroaryl. In another embodiment, D is optionally substituted triazolyl. In another embodiment, D is 1,2,4-triazol-3-yl.

In another embodiment, $R^3$ is hydrogen, optionally substituted heterocyclyl, optionally substituted alkyl, C(L)R$^{40}$, halo, pseudohalo or OR$^{41}$; where L is O, S or NR$^{55}$; $R^{40}$ is hydrogen, optionally substituted alkyl, optionally substituted alkenyl, optionally substituted alkynyl, optionally substituted aryl, optionally substituted heteroaryl, optionally substituted heteroarylium, optionally substituted cycloalkyl, optionally substituted heterocyclyl, C(L)R$^{56}$, halo pseudohalo, OR$^{55}$, SR$^{55}$, NR$^{57}$R$^{58}$ or SiR$^{52}$R$^{53}$R$^{54}$; $R^{41}$ is hydrogen, optionally substituted alkyl, optionally substituted alkenyl, optionally substituted alkynyl, optionally substituted aryl, optionally substituted heteroaryl, optionally substituted heteroarylium, optionally substituted cycloalkyl, optionally substituted heterocyclyl, C(L)R$^{59}$, NR$^{60}$R$^{61}$ or SiR$^{52}$R$^{53}$R$^{54}$; where $R^{52}$, $R^{53}$ and $R^{54}$ are selected as in (i) or (ii) as follows (i) $R^{52}$, $R^{53}$ and $R^{54}$ are each independently hydrogen, alkyl, alkenyl, alkynyl, aryl, heteroaryl, heteroarylium, cycloalkyl, heterocyclyl, OR$^{55}$ or NR$^{62}$R$^{63}$; or (ii) any two of $R^{52}$, $R^{53}$ and $R^{54}$ together form alkylene, alkenylene, alkynylene, heteroalkylene; and the other is selected as in (i); $R^{55}$ is hydrogen, alkyl, alkenyl, alkynyl, aryl, heteroaryl, heteroarylium, cycloalkyl or heterocyclyl; $R^{56}$ is hydrogen, alkyl, alkenyl, alkynyl, aryl, heteroaryl, heteroarylium, cycloalkyl, heterocyclyl, OR$^{55}$ or NR$^{64}$R$^{65}$; where $R^{64}$ and $R^{65}$ are each independently hydrogen, alkyl, alkenyl, alkynyl, aryl, heteroaryl, heteroarylium, cycloalkyl, heterocyclyl, OR$^{66}$NR$^{62}$R$^{63}$, or $R^{64}$ and $R^{65}$ together form alkylene, alkenylene, alkynylene, heteroalkylene, where $R^{66}$ is hydrogen, alkyl, alkenyl, alkynyl, aryl, heteroaryl, heteroarylium, cycloalkyl or heterocyclyl; $R^{57}$ and $R^{58}$ are selected as in (i) or (ii) as follows (i) $R^{57}$ and $R^{58}$ are each independently hydrogen, alkyl, alkenyl, alkynyl, aryl, heteroaryl, heteroarylium, cycloalkyl, heterocyclyl, OR$^{55}$, NR$^{67}$R$^{68}$ or C(L)R$^{69}$, where $R^{67}$ and $R^{68}$ are each independently hydrogen, alkyl, alkenyl, alkynyl, aryl, heteroaryl, heteroarylium, cycloalkyl or heterocyclyl, or together form alkylene, alkenylene, alkynylene, heteroalkylene; and $R^{69}$ is hydrogen, alkyl, alkenyl, alkynyl, aryl, heteroarylium, cycloalkyl, heterocyclyl, OR$^{70}$ or NR$^{62}$R$^{63}$, where $R^{70}$ is alkyl, alkenyl, alkynyl, aryl, heteroaryl, heteroarylium, cycloalkyl, heterocyclyl; or (ii) $R^{57}$ and $R^{58}$ together form alkylene, alkenylene, alkynylene, heteroalkylene; $R^{59}$ is hydrogen, alkyl, alkenyl, alkynyl, aryl, heteroaryl, heteroarylium, cycloalkyl, heterocyclyl, OR$^{70}$ or NR$^{62}$R$^{63}$; $R^{60}$ and $R^{61}$ are each independently hydrogen, alkyl, alkenyl, alkynyl, aryl, heteroaryl, heteroarylium, cycloalkyl, heterocyclyl or C(L)R$^{71}$, where $R^{71}$ is alkyl, alkenyl, alkynyl, aryl, heteroaryl, heteroarylium, cycloalkyl, heterocyclyl, OR$^{55}$ or NR$^{62}$R$^{63}$; or $R^{60}$ and $R^{61}$ together form alkylene, alkenylene, alkynylene, heteroalkylene; $R^{62}$ and $R^{63}$ are each independently hydrogen, alkyl, alkenyl, alkynyl, aryl, heteroaryl, heteroarylium, cycloalkyl, heterocyclyl, or $R^{62}$ and $R^{63}$ together form alkylene, alkenylene, alkynylene, heteroalkylene.

In another embodiment, $R^3$ is hydrogen, optionally substituted heterocyclyl, optionally substituted alkyl, C(L)R$^{40}$, halo or OR$^{41}$. In another embodiment, $R^3$ is hydrogen, optionally substituted heterocyclyl, optionally substituted alkyl, C(L)R$^{40}$, iodo, chloro or OR$^{41}$. In another embodiment, $R^3$ is hydrogen, optionally substituted dioxolanyl, optionally substituted methyl, C(L)R$^{40}$, iodo, chloro or OR$^{41}$. In another embodiment, $R^3$ is hydrogen, 2-dioxolanyl, optionally substituted methyl, C(O)R$^{40}$, iodo, chloro or OR$^{41}$. In another embodiment, $R^3$ is hydrogen, 2-dioxolanyl, optionally substituted methyl, CHO, iodo, chloro or OR$^{41}$. In another embodiment, $R^3$ is hydrogen.

In another embodiment, $R^3$ is optionally substituted methyl. In another embodiment, $R^3$ is methyl which is optionally substituted with heterocyclyl, hydroxy, aralkylamino or heterocyclylalkylamino. In another embodiment, $R^3$ is N-morpholinylmethyl, hydroxymethyl, N-(2-(3-chlorophenyl)-1-ethyl)aminomethyl, N-(2-morpholinyl-1-ethyl)aminomethyl or 4-piperizinylmethyl.

In another embodiment, A is O. In another embodiment, $R^{40}$ is hydrogen, optionally substituted alkyl or cycloalkyl. In another embodiment, $R^{40}$ is hydrogen or alkyl. In another embodiment, $R^{40}$ is hydrogen.

In another embodiment, $R^{41}$ is hydrogen or optionally substituted alkyl. In another embodiment, $R^{41}$ is hydrogen, or alkyl optionally substituted with heterocyclyl, aryl, dialkylamino, halo or hydroxy. In another embodiment, $R^{41}$ is hydrogen, or $C_{1-3}$alkyl optionally substituted with heterocyclyl, phenyl, dialkylamino, halo or hydroxy. In another embodiment, $R^{41}$ is hydrogen, 2-(N-morpholinyl)eth-1-yl, benzyl, 2-(N,N-di-(2-hydroxy-1-ethyl)amino)-1-ethyl, 2-bromo-1-ethyl, 2,2-dioxolan-4-ylmethyl, 2-(4-methylpiperazin-1-yl)-1-ethyl or 2,3-dihydroxy-1-propyl. In another embodiment, $R^{41}$ is (S)-2,3-dihydroxy-1-propyl.

In another embodiment, $R^4$ is hydrogen. In another embodiment, $R^5$ is alkyl. In another embodiment $R^5$ is methyl. In another embodiment, $R^6$ is hydrogen.

In another embodiment, the compounds for use in the compositions and methods provide herein have the above formulae, including formulae or a pharmaceutically acceptable derivative thereof, where:

$R^1$ is hydrogen, acyl or —P(O)(OH)$_2$;

$R^2$ is hydrogen, halo, alkyl or alkylthio;

A is an aryl, heteroaryl or a heterocyclyl ring optionally fused to a phenyl ring provided that the heterocyclyl ring is attached to the carbonyl group via a carbon ring atom;

B is an aryl or heteroaryl ring;

D is heteroaryl, optionally substituted heteroaryl or —C(O)NR$^{80}$R$^{81}$ (where $R^{80}$ and $R^{81}$ are independently hydrogen, alkyl, cycloalkyl, alkoxy, hydroxy, heteroaryl or optionally substituted heteroaryl);

$R^3$ is selected from the group consisting of:
  (a) amino, alkylamino or dialkylamino;
  (b) acylamino;
  (c) optionally substituted heterocyclyl;
  (d) optionally substituted aryl or heteroaryl;

(e) heteroalkyl;
(f) heteroalkenyl;
(g) heteroalkynyl;
(h) heteroalkoxy;
(i) heteroalkylamino;
(j) optionally substituted heterocyclylalkyl;
(k) optionally substituted heterocyclylalkenyl;
(l) optionally substituted heterocyclylalkynyl;
(m) optionally substituted heterocyclylalkoxy or heterocyclyloxy;
(n) optionally substituted heterocyclylalkylamino;
(o) optionally substituted heterocyclylalkylcarbonyl;
(p) heteroalkylcarbonyl;
(q) —NHSO$_2$R$^6$ where R$^6$ is alkyl, heteroalkyl or optionally substituted heterocyclylalkyl;
(r) —NHSO$_2$NR$^7$R$^8$ where R$^7$ and R$^8$ are, independently of each other, hydrogen, alkyl or heteroalkyl;
(s) —Y-(alkylene)-R$^9$ where: Y is a single bond, —O—, —NH— or —S(O)$_n$ (where n is an integer from 0 to 2); and R$^9$ is cyano, optionally substituted heteroaryl, —COOH, —COOR$^{10}$, —CONR$^{12}$R$^{13}$, —SO$_2$R$^{14}$, —SO$_2$NR$^{15}$R$^{16}$, —NHSO$_2$R$^{17}$ or —NHSO$_2$NR$^{18}$R$^{19}$, where R$^{10}$ is alkyl or optionally substituted heterocycle, R$^{11}$ is alkyl, and R$^{12}$, R$^{13}$, R$^{14}$, R$^{15}$, R$^{16}$, R$^{17}$, R$^{18}$ and R$^{19}$ are, independently of each other, alkyl or heteroalkyl;
(t) —C(=NR$^{20}$)(NR$^{21}$R$^{22}$) where R$^{20}$, R$^{21}$ and R$^{22}$ independently represent hydrogen, alkyl or hydroxy, or R$^{20}$ and R$^{21}$ together are —(CH$_2$)$_n$— where n is 2 or 3 and R$^{22}$ is hydrogen or alkyl;
(u) —NHC(X)NR$^{23}$R$^{24}$ where X is —O— or —S—, and R$^{23}$ and R$^{24}$ are, independently of each other, hydrogen, alkyl or heteroalkyl;
(v) —CONR$^{25}$R$^{26}$ where R$^{25}$ and R$^{26}$ independently represent hydrogen, alkyl, heteroalkyl or optionally substituted heterocyclylalkyl, or R$^{25}$ and R$^{26}$ together with the nitrogen to which they are attached form an optionally substituted heterocyclyl ring;
(w) —S(O)$_n$R$^{27}$ where n is an integer from 0 to 2, and R$^{27}$ is alkyl, heteroalkyl, optionally substituted heterocyclylalkyl or —NR$^{28}$R$^{29}$ where R$^{28}$ and R$^{29}$ are, independently of each other, hydrogen, alkyl or heteroalkyl;
(x) cycloalkylalkyl, cycloalkylalkynyl and cycloalkylalkynyl, all optionally substituted with alkyl, halo, hydroxy or amino;
(y) arylaminoalkylene or heteroarylaminoalkylene;
(z) Z-alkylene-NR$^{30}$R$^{31}$ or Z-alkylene-OR$^{32}$ where Z is —NH—, —N(lower alkyl)- or —O—, and R$^{30}$, R$^{31}$ and R$^{32}$ are independently of each other, hydrogen, alkyl or heteroalkyl;
(aa) —OC(O)-alkylene-CO$_2$H or —OC(O)—NR'R" (where R' and R" are independently hydrogen or alkyl); and
(bb) heteroarylalkenylene or heteroarylalkynylene;
R$^4$ is selected from the group consisting of:
(a) hydrogen;
(b) halo;
(c) alkyl;
(d) alkoxy; and
(e) hydroxy;
R$^5$ is selected from the group consisting of
(a) hydrogen;
(b) halo;
(c) alkyl;
(d) haloalkyl;
(e) thioalkyl;
(f) hydroxy;
(g) amino;
(h) alkylamino;
(i) dialkylamino;
(j) heteroalkyl;
(k) optionally substituted heterocycle;
(l) optionally substituted heterocyclylalkyl;
(m) optionally substituted heterocyclylalkoxy;
(n) alkylsulfonyl;
(o) aminosulfonyl, mono-alkylaminosulfonyl or di-alkylaminosulfonyl;
(p) heteroalkoxy; and
(q) carboxy;
R$^6$ is selected from the group consisting of:
(a) hydrogen;
(b) halo;
(c) alkyl; and
(d) alkoxy;
prodrugs, individual isomers, mixtures of isomers and pharmaceutically acceptable salts thereof.
In another embodiment, the compounds are those wherein:
R$^1$ is hydrogen or acyl;
R$^2$ is hydrogen or alkyl;
A is an aryl or heteroaryl ring.
In another embodiment, the compounds are those wherein:
R$^1$ is hydrogen, acyl or —P(O)(OH)$_2$;
R$^2$ is hydrogen, halo, alkyl or alkylthio;
A is an aryl, heteroaryl or a heterocyclyl ring optionally fused to a phenyl ring provided that the heterocyclyl ring is attached to the carbonyl group via a carbon ring atom;
B is an aryl or heteroaryl ring;
R$^3$ is selected from the group consisting of:
(a) amino;
(b) acylamino;
(c) optionally substituted heterocycle;
(d) heteroaryl optionally substituted with a substituent selected from halo, alkyl or alkoxy;
(e) heteroalkyl;
(f) heteroalkenyl;
(g) heteroalkynyl;
(h) heteroalkoxy
(i) heteroalkylamino;
(j) optionally substituted heterocyclylalkyl;
(k) optionally substituted heterocyclylalkenyl;
(l) optionally substituted heterocyclylalkynyl;
(m) optionally substituted heterocyclylalkoxy;
(n) optionally substituted heterocyclylalkylamino;
(o) optionally substituted heterocyclylalkylcarbonyl;
(p) heteroalkylcarbonyl;
(q) —NHSO$_2$R$^6$ where R$^6$ is alkyl, heteroalkyl or optionally substituted heterocyclylalkyl;
(r) —NHSO$_2$NR$^7$R$^8$ where R$^7$ and R$^8$ are, independently of each other, hydrogen, alkyl or heteroalkyl;
(s) —Y-(alkylene)-R$^9$ where: Y is a single bond, —O—, —NH— or —S(O)$_n$— (where n is an integer from 0 to 2); and R$^9$ is cyano, heteroaryl, —COOH, —COR$^{10}$, —COOR$^{11}$—CONR$^{12}$R$^{13}$, —SO$_2$R$^{14}$, —SO$_2$R$^{15}$R$^{16}$, —NHSO$_2$R$^{17}$ or —NHSO$_2$NR$^{18}$R$^{19}$ where R$^{10}$ is alkyl or optionally substituted heterocycle, R$^{11}$ is alkyl, and R$^{12}$, R$^{13}$, R$^{14}$, R$^{15}$, R$^{16}$, R$^{17}$, R$^{18}$ and R$^{19}$ are independently of each other, hydrogen, alkyl or heteroalkyl;
(t) —C(=NR$^{20}$)(NR$^{21}$R$^{22}$) where R$^{20}$, R$^{21}$ and R$^{22}$ independently represent hydrogen, alkyl or hydroxy, or R$^{20}$ and R$^{21}$ together are —(CH$_2$)$_n$— where n is 2 or 3 and R$^{22}$ is hydrogen or alkyl;

(u) —NHC(X)NR$^{23}$R$^{24}$ where X is —O— or —S—, and R$^{23}$ and R$^{24}$ are, independently of each other, hydrogen, alkyl or heteroalkyl;

(v) —CONR$^{25}$R$^{26'}$ where R$^{25}$ and R25 independently represent hydrogen, alkyl, heteroalkyl or optionally substituted heterocyclylalkyl, or R$^{25}$ and R$^{26}$ together with the nitrogen to which they are attached form an optionally substituted heterocyclyl ring;

(w) —S(O)$_n$R$^{27}$ where n is an integer from 0 to 2, and R$^{27}$ is alkyl, heteroalkyl, optionally substituted heterocyclylalkyl or —NR$^{28}$R$^{29}$ where R$^{28}$ and R$^{29}$ are, independently of each other, hydrogen, alkyl or heteroalkyl;

R$^4$ is selected from the group consisting of:
(a) hydrogen;
(b) halo;
(c) alkyl; and
(d) alkoxy;

R$^5$ is selected from the group consisting of:
(a) hydrogen;
(b) halo;
(c) alkyl;
(d) haloalkyl;
(e) thioalkyl;
(f) hydroxy;
(g) amino;
(h) alkylamino;
(i) dialkylamino;
(j) heteroalkyl;
(k) optionally substituted heterocycle;
(l) optionally substituted heterocyclylalkyl; and
(m) optionally substituted heterocyclylalkoxy;

R$^6$ is selected from a group consisting of:
(a) hydrogen;
(b) halo;
(c) alkyl; and
(d) alkoxy.

In another embodiment the compounds are those where R$^3$ is:
(a) optionally substituted heterocyclyl;
(b) aryl or heteroaryl both optionally substituted with a substituent selected from halo, alkyl, amino, alkoxy, carboxy, lower alkoxy carbonyl, SO$_2$R' (where R' is alkyl) or —O$_2$NHR'R" (where R' and R" are independently hydrogen or alkyl);
(c) heteroalkyl;
(d) heteroalkenyl;
(e) heteroalkylamino;
(f) heteraloxy
(g) optionally substituted heterocyclylalkyl or heterocyclyloxy;
(h) optionally substituted heterocyclylalkenyl;
(i) optionally substituted heterocyclylalkynyl;
(j) optionally substituted heterocyclylalkoxy;
(k) optionally substituted heterocyclylalkylamino;
(l) optionally substituted heterocyclylalkylcarbonyl;
(s) —Y-(alkylene)-R$^9$ where Y is a single bond, —O— or —NH— and R$^9$ is optionally substituted heteroaryl, —CONR$^{12}$R$^{13}$, SO$_2$R$^{14}$, —SO$_2$NR$^{15}$R$^{16}$—NHSO$_2$R$^{17}$ or —NHSO$_2$NR$^{18}$R$^{19}$ where R$^{12}$R$^{13}$, R$^{14}$, R$^{15}$, R$^{16}$R$^{17}$, R$^{18}$ and R$^{19}$ are independently of each other heteroalkyl; hydrogen, alkyl or heteroalkyl;
(t) cycloalkylalkyl, cycloalkylalkynyl and cycloalkylalkynyl, all optionally substituted with alkyl, halo, hydroxy or amino;
(u) arylaminoalkylene or heteroarylaminoalkylene; or
(v) Z-alkylene-NR$^{30}$R$^{31}$ where Z is —NH—, —N(alkyl)- or -O-, and R$^{30}$ and R$^{31}$ are independently of each other, hydrogen, alkyl or heteroalkyl.

In still another embodiment, the compounds are those where R$^1$ and R$^2$ are hydrogen and B is phenyl. In an additional embodiment, the compounds are those wherein R$^4$ is hydrogen and R$^5$ is halo or alkyl. In another embodiment, the compounds are those wherein R$^5$ is chloro, fluoro or methyl and R$^6$ is hydrogen, chloro, fluoro, methyl or methoxy. In another embodiment, the compounds are those wherein R$^3$ is optionally substituted heteroaryl.

In yet another embodiment, the compounds are those wherein R$^3$ is pyridin-2-yl, pyridin-3-yl, pyridin-4-yl, N-oxidopyridin-2-yl, N-oxidopyridin-3-yl, Noxidopyridin-4-yl or pyridon-2-yl, all optionally substituted. In a further embodiment, the compounds are those wherein R$^3$ is at the 3-position. In still another embodiment, the compounds are those wherein R$^5$ is 4-F or 2-Me, and R$^6$ is hydrogen. In another embodiment, the compounds are those wherein R$^3$ is optionally substituted phenyl.

In a further embodiment, the compounds are those wherein R$^3$ is 3-sulfamoylphenyl, 3-methylsulfonylphenyl, 3-carboxyphenyl or 3-ethoxycarbonylphenyl. In yet another embodiment, the compounds are those wherein R$^5$ is 4-F and R$^6$ is hydrogen.

In another embodiment, the compounds are those wherein R$^3$ is:
(a) heteroalkyl;
(b) heteroalkoxy;
(c) heteroalkylamino;
(d) optionally substituted heterocyclylalkyl;
(e) optionally substituted heterocyclylalkoxy;
(f) optionally substituted heterocyclylalkylamino;
(g) Y-(alkylene)-R$^9$ where Y is a single bond, —O— or —NH— and R$^9$ is optionally substituted heteroaryl, —CONR$^{12}$R$^{13}$, —SO$_2$R$^{14}$, —SO$_2$NR$^{15}$R$^{16}$—NHSO$_2$R$^{17}$ or —NHSO$_2$NR$^{18}$R$^{19}$ where R$^{12}$, R$^{13}$, R$^{14}$, R$^{15}$, R$^{16}$, R$^{17}$, R$^{18}$ and R$^{19}$ are independently of each other hydrogen, alkyl or heteroalkyl; or
(h) Z-alkylene-NR$^{30}$R$^{31}$ where Z is —NH—, —N(alkyl)- or —O—, and R$^{30}$ and R$^{31}$ are independently of each other, hydrogen, alkyl or heteroalkyl.

In a further embodiment, the compounds are those wherein R$^3$ is heteroalkyl. In another embodiment, the compounds are those wherein R$^3$ is at the 3-position and is selected from the group consisting of 2-dimethylaminoethyl, 3-dimethylaminopropyl, 4-dimethylaminobutyl, 2-dimethylaminoethylamino, 3-dimethylaminopropylamino, hydroxymethyl, 1,2-dihydroxyethyl, 3-hydroxy-3-methyl-1-butyl or 3-hydroxybutyl. In yet another embodiment, the compounds are those wherein R$^5$ is 2-F and R$^6$ is 4-F.

In still another embodiment, the compounds are those wherein R$^5$ is 2-Me and R$^6$ is hydrogen. In an additional embodiment, the compounds are those wherein R$^9$ is heteroalkoxy or heteroalkylamino. In yet another embodiment, the compounds are those wherein R$^3$ is at the 3-position and is selected from the group consisting of 3-dimethylaminopropoxy, 2dimethylaminoethoxy, 2-hydroxyethoxy, 2,3-dihydroxypropoxy, 2-dimethylaminoethylamino and 3-dimethylaminopropylamino.

In yet another embodiment, the compounds are those wherein R$^3$ is optionally substituted heterocyclylalkyl, optionally substituted heterocyclylalkoxy or optionally substituted heterocyclylalkylamino. In still another embodiment, the compounds are those wherein R$^3$ is at the 3-position and is selected from the group consisting of 3-(morpholin-4-yl)propoxy, 2-(morpholin-4-yl)ethoxy, 2-(2-oxo-pyrrolidin-1-yl)

ethoxy, 3(morpholin-4-yl)propyl, 2-(morpholin-4-yl)ethyl, 4-(morpholin-4-yl)butyl, 3-(morpholin-4-yl)propylamino, 2-(morpholin-4-yl)ethylamino, 4-hydroxypiperidinylmethyl, 2-(S,S-dioxothiamorpholin-4-yl)ethyl, 3-(S,S-dioxothiamorpholin-4-yl)propyl and N-methylpiperazinylmethyl.

In an additional embodiment, the compounds are those wherein $R^3$ is —Y-(alkylene)-$R^9$ where Y is a single bond, —O— or —NH— and $R^9$ is optionally substituted heteroaryl, —CONR$^{12}$R$^{13}$, —SO$_2$R$^{14}$, —SO$_2$NR$^{15}$R$^{16}$NHSO$_2$R$^{17}$ or —NHSO$_2$NR$^{18}$R$^{19}$ where $R^{12}$, $R^{13}$, $R^{14}$, $R^{15}$, $R^{16}$, $R^{17}$, $R^{18}$ and $R^{19}$ are independently of each other hydrogen, alkyl or heteroalkyl. In a further embodiment, the compounds are those wherein Y is a single bond and $R^9$ is —SO$_2$R$^{14}$ or —SO$_2$NR$^{15}$R$^{16}$.

In an additional embodiment, the compounds are those wherein $R^3$ is 5-methylsulfonylethyl or sulfamoylethyl.

Also provided herein is a compound selected from the group consisting of 5-amino-1-(4-fluorophenyl)-4-[3-(2-morpholin-4-ylethoxy)benzoyl]pyrazole, 5-amino-1-(2,4-difluorophenyl)-4-[3-(3-morpholin-4-ylpropyl)benzoyl]pyrazole, 5-amino-4-(3-aminobenzoyl)-1-(4-fluorophenyl)pyrazole, 5-amino-1-(4-fluorophenyl)-4-[3-(3-morpholin-4-ylpropyl)benzoyl]pyrazole, 5-amino-4-[3-(2-aminosulfonylethenyl)benzoyl]-1-(4-fluorophenyl)pyrazole, 5-amino-4-(3-acetylaminobenzoyl)-1-phenylpyrazole, 5-amino-4-[3-(2-aminoethyl)benzoyl]-1-(4-fluorophenyl)pyrazole, 5-amino-1-(4-fluorophenyl)-4-[3-(3-morpholin-4-ylpropylamino)benzoyl]pyrazole, 5-amino-4-[3-(2-aminosulfonylethyl)benzoyl]-1-(4-fluorophenyl)pyrazole and 5-amino-1-(4-fluorophenyl)-4-(3-pyridin-3-ylbenzoyl)pyrazole.

Also provided herein is a compound selected from the group consisting of 5-amino-1-(2-methylphenyl)-4-[3-pyridin-3-yl)benzoyl]pyrazole, 5-amino-1-(2-methylphenyl)-4-[3-(N-oxidopyridin-3-yl)benzoyl]pyrazole, 5-amino-4-[3-(2,3-dihydroxypropoxy)benzoyl]-1-(4-fluorophenyl)pyrazole, 5-amino-4-[3-(1,2-dihydroxyethyl)benzoyl]-1-(4-fluorophenyl)pyrazole, 5-amino-1-(4-fluorophenyl)-4-[3-(sulfamoylbenzoyl]pyrazole, 5-amino-1-(4-fluorophenyl)-4-[3-(3-hydroxy-3-methylbutyl)benzoyl]pyrazole, 5-amino-1-(4-fluorophenyl)-4-[3-(2-(1-hydroxycyclopentyl)ethyl)benzoyl]pyrazole, 5-amino-4-[3-(2-methylsulfonylethyl)benzoyl]-1-(4-fluorophenyl)pyrazole, and 5-amino-1-(2,4-difluorophenyl)-4-[3-(2-hydroxyethylsulfonyl)benzoyl]pyrazole.

Further provided herein is a compound selected from 3-[5-amino-4-(3-iodo-benzoyl)-pyrazol-1-yl]-N-methoxy-4-methyl-benzamide; 3-(5-amino-4-benzoyl-pyrazol-1-yl)-N-methoxy-4-methyl-benzamide; 3-(5-amino-4-benzoyl-pyrazol-1-yl)-4-methyl-benzoic acid; 3-(5-amino-4-benzoyl-pyrazol-1-yl)-N-cyclopropyl-4-methyl-benzamide; 3-[5-amino-4-(3-iodo-benzoyl)-pyrazol-1-yl]-4-methyl-benzoic acid; 3-[5-amino-4-(3-iodo-benzoyl)-pyrazol-1-yl]-N-cyclopropyl-4-methyl-benzamide; {5-amino-1-[2-methyl-5-(4H-[1,2,4]triazol-3-yl)-phenyl]-1H-pyrazol-4-yl}-phenyl-methanone; 3-[5-amino-4-(3-[1,3]dioxolan-2-yl-benzoyl)-pyrazol-1-yl]-N-cyclopropyl-4-methyl-benzamide; 3-[5-amino-4-(3-formyl-benzoyl)-pyrazol-1-yl]-N-cyclopropyl-4-methyl-benzamide; 3-[5-amino-4-(3-hydroxymethyl-benzoyl)-pyrazol-1-yl]-N-cyclopropyl-4-methyl-benzamide; 3-{5-amino-4-[3-(4-methyl-piperazin-1-ylmethyl)-benzoyl]-pyrazol-1-yl}-N-cyclopropyl-4-methyl-benzamide; 3-[5-amino-4-(3-morpholin-4-ylmethyl-benzoyl)-pyrazol-1-yl]-N-cyclopropyl-4-methyl-benzamide; 3-[5-amino-4-(3-morpholin-4-ylmethyl-benzoyl)-pyrazol-1-yl]-N-cyclopropyl-4-methyl-benzamide; 3-[5-amino-4-(3-benzyloxy-benzoyl)-pyrazol-1-yl]-N-cyclopropyl-4-methyl-benzamide; 3-[5-amino-4-(3-hydroxy-benzoyl)-pyrazol-1-yl]-N-cyclopropyl-4-methyl-benzamide; 3-[5-amino-4-(4-methyl-benzoyl)-pyrazol-1-yl]-N-cyclopropyl-4-methyl-benzamide; and 3-(5-amino-4-benzoyl-imidazol-1-yl)-N-cyclopropyl-4-methyl-benzamide.

Also provided herein is a compound selected from 3-[5-amino-4-(3-iodo-benzoyl)-pyrazol-1-yl]-N-methoxy-4-methyl-benzamide; 3-(5-amino-4-benzoyl-pyrazol-1-yl)-N-methoxy-4-methyl-benzamide; 3-(5-amino-4-benzoyl-pyrazol-1-yl)-N-cyclopropyl-4-methyl-benzamide; 3-[5-amino-4-(3-iodo-benzoyl)-pyrazol-1-yl]-N-cyclopropyl-4-methyl-benzamide; {5-amino-1-[2-methyl-5-(4H-[1,2,4]triazol-3-yl)-phenyl]-1H-pyrazol-4-yl}-phenyl-methanone; 3-[5-amino-4-(3-[1,3]dioxolan-2-yl-benzoyl)-pyrazol-1-yl]-N-cyclopropyl-4-methyl-benzamide; 3-[5-amino-4-(3-formyl-benzoyl)-pyrazol-1-yl]-N-cyclopropyl-4-methyl-benzamide; 3-[5-amino-4-(3-hydroxymethyl-benzoyl)-pyrazol-1-yl]-N-cyclopropyl-4-methyl-benzamide; 3-{5-amino-4-[3-(4-methyl-piperazin-1-ylmethyl)-benzoyl]-pyrazol-1-yl}-N-cyclopropyl-4-methyl-benzamide; 3-[5-amino-4-(3-morpholin-4-ylmethyl-benzoyl)-pyrazol-1-yl]-N-cyclopropyl-4-methyl-benzamide; 3-[5-amino-4-(3-morpholin-4-ylmethyl-benzoyl)-pyrazol-1-yl]-N-cyclopropyl-4-methyl-benzamide; 3-[5-amino-4-(3-benzyloxy-benzoyl)-pyrazol-1-yl]-N-cyclopropyl-4-methyl-benzamide; 3-[5-amino-4-(3-hydroxy-benzoyl)-pyrazol-1-yl]-N-cyclopropyl-4-methyl-benzamide; 3-[5-amino-4-(4-methyl-benzoyl)-pyrazol-1-yl]-N-cyclopropyl-4-methyl-benzamide; or 3-(5-amino-4-benzoyl-imidazol-1-yl)-N-cyclopropyl-4-methyl-benzamide.

Also provided is a compound selected from:
3-{5-Amino-4-[3-(2-dimethylamino-ethylcarbamoyl)-benzoyl]-imidazol-1-yl}-N-cyclopropyl-4-methyl-benzamide;
3-[5-Amino-4-(5-chloro-thiophene-2-carbonyl)-imidazol-1-yl]-N-cyclopropyl-4-methyl-benzamide;
3-[5-Amino-4-(3-hydrazinocarbonyl-benzoyl)-imidazol-1-yl]-N-cyclopropyl-4-methyl-benzamide;
3-(5-Amino-4-cyclohexanecarbonyl-imidazol-1-yl)-N-cyclopropyl-4-methyl-benzamide;
3-(5-Amino-4-cyclopentanecarbonyl-imidazol-1-yl)-N-cyclopropyl-4-methyl-benzamide;
3-(5-Amino-4-phenylacetyl-imidazol-1-yl)-N-cyclopropyl-4-methyl-benzamide;
3-[5-Amino-4-(tetrahydro-pyran-4-carbonyl)-imidazol-1-yl]-N-cyclopropyl-4-methyl-benzamide;
3-[5-Amino-4-(3-ethylcarbamoyl-benzoyl)-imidazol-1-yl]-N-cyclopropyl-4-methyl-benzamide; and
3-[5-Amino-4-(3-isopropylcarbamoyl-benzoyl)-imidazol-1-yl]-N-cyclopropyl-4-methyl-benzamide.

Also provided is a compound selected from:
5-Amino-1-(5-cyclopropylcarbamoyl-2-methyl-phenyl)-3-methyl-1H-pyrazole-4-carboxylic acid ethyl ester;
5-Amino-1-(5-cyclopropylcarbamoyl-2-methyl-phenyl)-1H-pyrazole-4-carboxylic acid ethyl ester;
3-(5-Amino-4-cyclopentanecarbonyl-pyrazol-1-yl)-N-cyclopropyl-4-methyl-benzamide;
3-[5-Amino-4-(3-hydrazinocarbonyl-benzoyl)-pyrazol-1-yl]-N-cyclopropyl-4-methyl-benzamide;
5-Amino-1-(5-cyclopropylcarbamoyl-2-methyl-phenyl)-1H-pyrazole-4-carboxylic acid benzylamide;
3-(5-Amino-4-cyclohexanecarbonyl-pyrazol-1-yl)-N-cyclopropyl-4-methyl-benzamide; and
5-Amino-1-(5-cyclopropylcarbamoyl-2-methyl-phenyl)-1H-pyrazole-4-carboxylic acid cyclohexylamide.

Also provided is a compound selected from:
5-Amino-1-(5-cyclopropylcarbamoyl-2-methyl-phenyl)-3-methylsulfanyl-1H-pyrazole-4-carboxylic acid amide;
5-Amino-1-(5-cyclopropylcarbamoyl-2-methyl-phenyl)-3-methanesulfonyl-1H-pyrazole-4-carboxylic acid amide;
5-Amino-1-(5-cyclopropylcarbamoyl-2-methyl-phenyl)-3-methylsulfanyl-1H-pyrazole-4-carboxylic acid ethyl ester;
5-Amino-3-[(3-chloro-benzylcarbamoyl)-methoxy]-1-(5-cyclopropylcarbamoyl-2-methyl-phenyl)-1H-pyrazole-4-carboxylic acid ethyl ester;
3-[5-Amino-4-benzoyl-3-(piperidin-4-yloxy)-pyrazol-1-yl]-N-cyclopropyl-4-methyl-benzamide;
3-(5-Amino-4-benzoyl-3-methanesulfonyl-pyrazol-1-yl)-N-cyclopropyl-4-methyl-benzamide;
3-(5-Amino-4-benzoyl-3-methoxy-pyrazol-1-yl)-N-cyclopropyl-4-methyl-benzamide;
5-Amino-1-(5-cyclopropylcarbamoyl-2-methyl-phenyl)-3-(2-hydroxy-ethoxy)-1H-pyrazole-4-carboxylic acid ethyl ester;
4-[5-Amino-4-benzoyl-1-(5-cyclopropylcarbamoyl-2-methyl-phenyl)-1H-pyrazol-3-yloxy]-piperidine-1-carboxylic acid tert-butyl ester;
3-[5-Amino-4-benzoyl-3-methylsulfanyl-pyrazol-1-yl]-N-cyclopropyl-4-methyl-benzamide; and
3-[5-Amino-4-benzoyl-3-(2-methoxy-ethoxy)-pyrazol-1-yl]-N-cyclopropyl-4-methyl-benzamide.
Also provided is a compound selected from:
3-[5-Amino-4-(3-iodo-benzoyl)-pyrazol-1-yl]-N-methoxy-4-methyl-benzamide;
3-(5-Amino-4-benzoyl-pyrazol-1-yl)-N-methoxy-4-methyl-benzamide;
3-(5-amino-4-benzoyl-pyrazol-1-yl)-4-methyl-benzoic acid;
3-(5-Amino-4-benzoyl-pyrazol-1-yl)-N-cyclopropyl-4-methyl-benzamide;
3-[5-amino-4-(3-iodo-benzoyl)-pyrazol-1-yl]-4-methyl-benzoic acid;
3-[5-amino-4-(3-iodo-benzoyl)-pyrazol-1-yl]-N-cyclopropyl-4-methyl-benzamide;
{5-amino-1-[2-methyl-5-(4H-[1,2,4]triazol-3-yl)-phenyl]-1H-pyrazol-4-yl}-phenyl-methanone;
3-[5-amino-4-(3-[1,3]dioxolan-2-yl-benzoyl)-pyrazol-1-yl]-N-cyclopropyl-4-methyl-benzamide;
3-[5-amino-4-(3-formyl-benzoyl)-pyrazol-1-yl]-N-cyclopropyl-4-methyl-benzamide;
3-[5-amino-4-(3-hydroxymethyl-benzoyl)-pyrazol-1-yl]-N-cyclopropyl-4-methyl-benzamide;
3-{5-amino-4-[3-(4-methyl-piperazin-1-ylmethyl)-benzoyl]-pyrazol-1-yl}-N-cyclopropyl-4-methyl-benzamide;
3-[5-amino-4-(3-morpholin-4-ylmethyl-benzoyl)-pyrazol-1-yl]-N-cyclopropyl-4-methyl-benzamide;
3-{5-Amino-4-[3-(2-morpholin-4-yl-ethoxy)-benzoyl]-pyrazol-1-yl}-N-cyclopropyl-4-methyl-benzamide;
3-[5-amino-4-(3-benzyloxy-benzoyl)-pyrazol-1-yl]-N-cyclopropyl-4-methyl-benzamide;
3-[5-amino-4-(3-hydroxy-benzoyl)-pyrazol-1-yl]-N-cyclopropyl-4-methyl-benzamide;
3-[5-amino-4-(4-methyl-benzoyl)-pyrazol-1-yl]-N-cyclopropyl-4-methyl-benzamide;
3-(5-amino-4-benzoyl-imidazol-1-yl)-N-cyclopropyl-4-methyl-benzamide;
3-[5-Amino-4-cyclohexanecarbonyl-imidazol-1-yl]-N-cyclopropyl-4-methyl-benzamide;
3-(5-Amino-4-cyclopentanecarbonyl-imidazol-1-yl)-N-cyclopropyl-4-methyl-benzamide;
3-(5-Amino-4-phenylacetyl-imidazol-1-yl)-N-cyclopropyl-4-methyl-benzamide;
3-[5-Amino-4-(3-isopropylcarbamoyl-benzoyl)-imidazol-1-yl]-N-cyclopropyl-4-methyl-benzamide;
3-{5-Amino-4-[3-(2-dimethylamino-ethylcarbamoyl)-benzoyl]-imidazol-1-yl}-N-cyclopropyl-4-methyl-benzamide;
3-[5-Amino-4-(3-ethylcarbamoyl-benzoyl)-imidazol-1-yl]-N-cyclopropyl-4-methyl-benzamide;
3-[5-Amino-4-(3-methylcarbamoyl-benzoyl)-imidazol-1-yl]-N-cyclopropyl-4-methyl-benzamide;
3-[5-Amino-4-(3-cyclopropylcarbamoyl-benzoyl)-imidazol-1-yl]-N-cyclopropyl-4-methyl-benzamide;
3-[5-Amino-4-(3-cyclopentylcarbamoyl-benzoyl)-imidazol-1-yl]-N-cyclopropyl-4-methyl-benzamide;
3-{5-Amino-4-[3-(morpholine-4-carbonyl)-benzoyl]-imidazol-1-yl}-N-cyclopropyl-4-methyl-benzamide;
3-{5-Amino-4-[3-(cyclopropylmethyl-carbamoyl)-benzoyl]-imidazol-1-yl}-N-cyclopropyl-4-methyl-benzamide;
3-[5-Amino-4-(tetrahydro-pyran-4-carbonyl)-imidazol-1-yl]-N-cyclopropyl-4-methyl-benzamide;
3-(5-amino-4-benzoyl-3-methoxy-pyrazol-1-yl)-N-cyclopropyl-4-methyl-benzamide;
3-(5-amino-4-benzoyl-3-ethoxy-pyrazol-1-yl)-N-cyclopropyl-4-methyl-benzamide;
3-[5-amino-4-benzoyl-3-(2-methoxy-ethoxy)-pyrazol-1-yl]-N-cyclopropyl-4-methyl-benzamide;
3-[5-amino-4-benzoyl-3-(2-benzyloxy-ethoxy)-pyrazol-1-yl]-N-cyclopropyl-4-methyl-benzamide;
4-[5-amino-4-benzoyl-1-(5-cyclopropylcarbamoyl-2-methyl-phenyl)-1H-pyrazol-3-yloxy]-piperidine-1-carboxylic acid tert-butyl ester;
3-[5-amino-4-benzoyl-3-(piperidin-4-yloxy)-pyrazol-1-yl]-N-cyclopropyl-4-methyl-benzamide, trifluoroacetate salt;
3-(5-amino-4-benzoyl-3-methylsulfanyl-pyrazol-1-yl)-N-cyclopropyl-4-methyl-benzamide;
3-(5-amino-4-benzoyl-3-methanesulfonyl-pyrazol-1-yl)-N-cyclopropyl-4-methyl-benzamide;
5-amino-1-(5-cyclopropylcarbamoyl-2-methyl-phenyl)-3-methylsulfanyl-1H-pyrazole-4-carboxylic acid amide;
5-amino-1-(5-cyclopropylcarbamoyl-2-methyl-phenyl)-3-methanesulfonyl-1H-pyrazole-4-carboxylic acid amide; and
5-amino-1-(5-cyclopropylcarbamoyl-2-methyl-phenyl)-3-methylsulfanyl-1H-pyrazole-4-carboxylic acid ethyl ester.

C. Preparation of the Compounds

Also provided herein is a process for preparing a compound of formula (I), which process involves the steps of:
(i) reacting a 2-keto-3-phenylaminoacrylonitrile of formula 1:

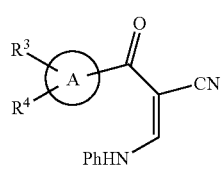

with a hydrazine of formula 2:

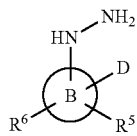

2 where $R^3$, $R^4$, $R^5$ and $R^6$ are as defined herein to provide a compound of formula (I) where $R^1$ is hydrogen; or (ii) reacting a 2-keto-3-phenylaminoacrylonitrile of formula 3:

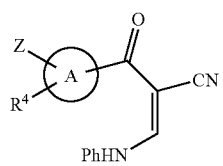

3 where Z is either hydroxy, nitro or halo group and $R^4$ is as defined herein with a hydrazine of formula 2 to provide a compound of formula 4:

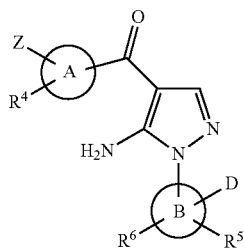

4 followed by conversion of the Z group to the desired $R^3$ group to provide a compound of formula (I) where $R^1$ is hydrogen;

(iii) optionally modifying any of the $R^1$, $R^3$, R', $R^5$ or $R^6$ groups;

(iv) optionally converting the compound of formula (I) prepared in steps (i), (ii) or (iii) above to the corresponding acid addition salt by treatment with an acid;

(v) optionally converting the compound of formula (I) prepared in steps (i), (ii) or (iii) above, to the corresponding free base by treatment with a base; and (vi) optionally separating a mixture of stereoisomers of a compound of formula (I) prepared in steps (i)-(v) above, to give a single stereoisomer.

Also provided herein is a process for preparing a compound of formula (I), which process involves reacting a compound of formula 5:

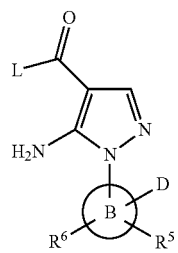

5 where $R^5$ and $R^6$ are as as defined herein and L is a leaving group under organometallic displacement reaction conditions, including, but not limited to, halo, pseudohalo, aryloxy, perfluoroaryloxy, N-alkoxyamino, including N-methoxyamino, with an organometallic reagent of formula:

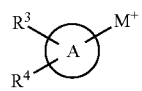

where $R^3$ and $R^4$ are as defined herein and M is a metallic moiety, including, but not limited to, an alkali metal, an alkaline earth metal, and a transitional metal, such as Li, K and Mg, to provide a compound of formula (I) where $R^1$ is hydrogen;

(ii) optionally modifying any of the $R^1$, $R^3$, $R^4$, $R^5$ or $R^6$ groups;

(iii) optionally converting the compound of formula (I) prepared in steps (i) or (ii) above, to the corresponding acid addition salt by treatment with an acid;

(iv) optionally converting the compound of formula (I) prepared in steps (i) or (ii) above, to the corresponding free base by treatment with a base; and optionally separating a mixture of stereoisomers of a compound of formula (I) prepared in steps (i) or (iv) above, to give a single stereoisomer.

The compounds disclosed herein are merely exemplary, and one skilled in the art can be readily prepare compounds in the same manner as that disclosed herein using well known methods of chemical synthesis, including methods similar to those exemplified herein.

Compounds provided herein may generally be prepared according to the following schemes and the knowledge of one skilled in the art. Additional synthetic methods are described, for example, in U.S. Pat. Nos. 6,376,527; 6,316,466 and 6,444,696, and International Patent Application Publication No. WO 99/57101, each of which is incorporated herein by reference.

In addition to the documents incorporated by reference we disclose the following non-limiting examples of methods useful for the production of compounds provided herein (see, Schemes 1-8, infra).

Amines attached to aryl or heteroaryl ring systems are useful as intermediates in the preparation of the compounds provided herein. There are many methods of preparing such intermediates known to one skilled in the art of organic chemistry. Several methods of preparing amines useful in the preparation of the compounds provided herein are illustrated in schemes 1-7.

Substituted aniline of type (II) useful herein can be prepared from commercially available 3-amino-4-methylbenzoic acid as depicted in Scheme 1, using methods similar to those disclosed in International Patent Application Publication No. WO 02/40486. Aniline is protected by a Boc group. This is followed by condensation with methylamine using the coupling agent EDC and HOBt. The Boc group is then removed by HCl in dioxane to give the desired substituted aniline of type (II) as a hydrochloride salt.

Scheme 1

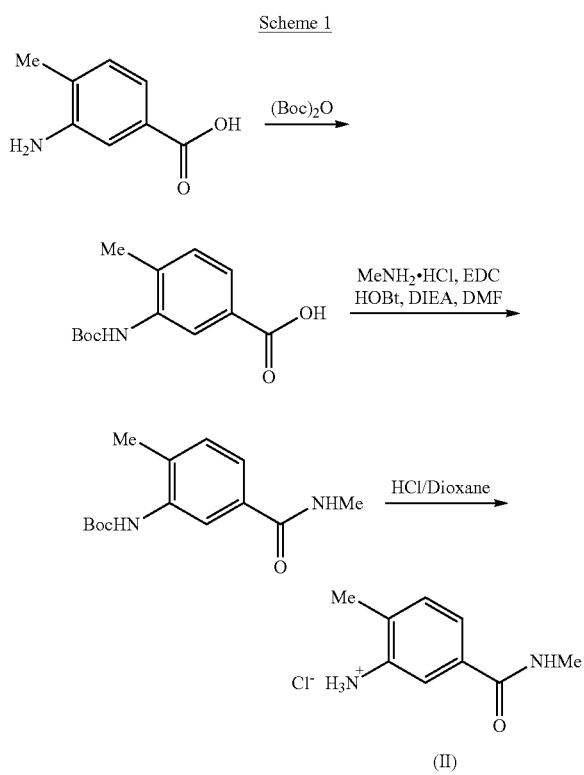

(II)

Substituted anilines of type (III) useful herein can be prepared from commercially available 3-amino-4-methylbenzoic acid as depicted in Scheme 2. Condensation with cyclopropylamine using the coupling agent EDC affords an aniline of type (III).

Scheme 2

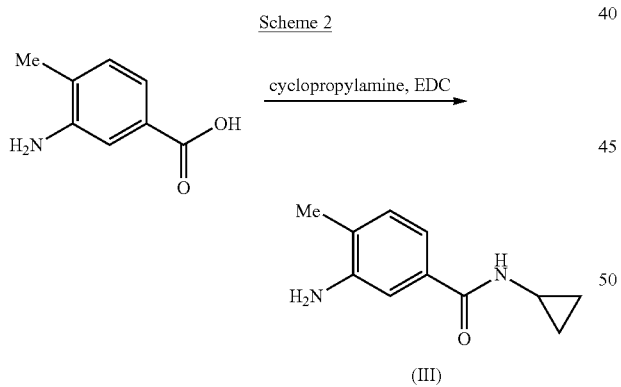

(III)

Substituted anilines of type (IV) useful herein can be prepared from commercially available 4-methyl-3-nitrobenzoic acid as depicted in Scheme 3, using methods similar to those disclosed in International Patent Application Publication No. WO 03/033482. Condensation of the acid with t-butoxycarbonylhydrazide using the coupling agent HBTU and HOBt affords the protected acyl hydrazide. Deprotection with TFA, followed by condensation with triethyl orthoformate yields the oxadiazolyl-substituted nitrotoluene. Hydrogenation of the nitro group gives the desired aniline of type (IV).

Scheme 3

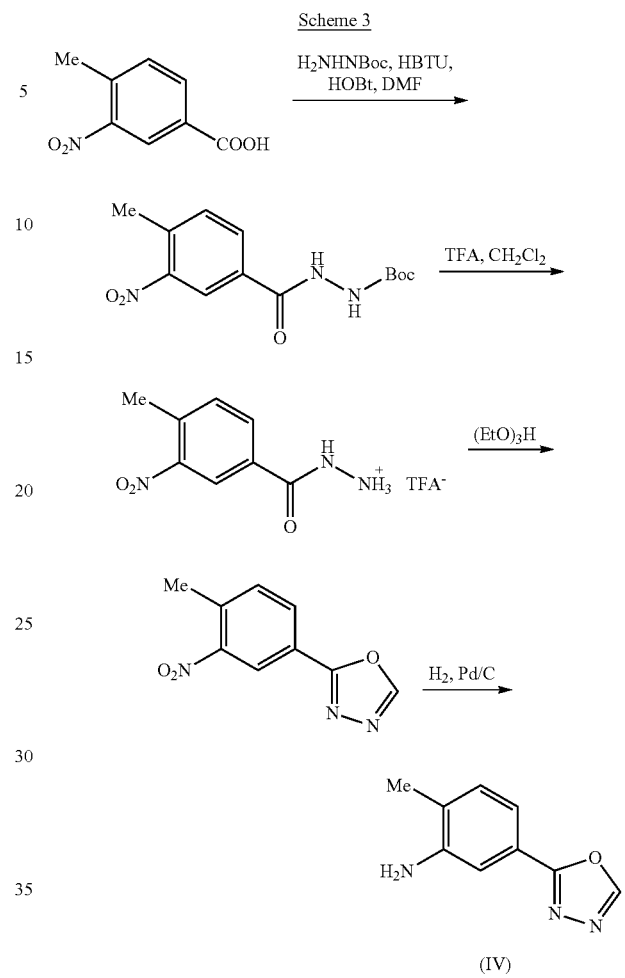

(IV)

Substituted anilines of type (V) useful herein can be prepared from commercially available 4-methyl-3-nitrobenzamide as depicted in Scheme 4, using methods described by Han et al. [*J. Med. Chem.*, 41, 2019-2028 (1998)]. The indicated aryl carboxamide was condensed with N,N-dimethylformamide diethyl acetal. This was followed by reaction with hydrazine in acetic acid to form a triazolyl-substituted nitrotoluene. Hydrogenation of the nitro group gives the desired aniline of type (V).

Scheme 4

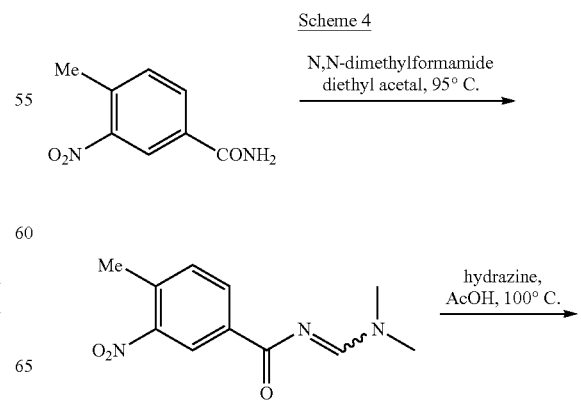

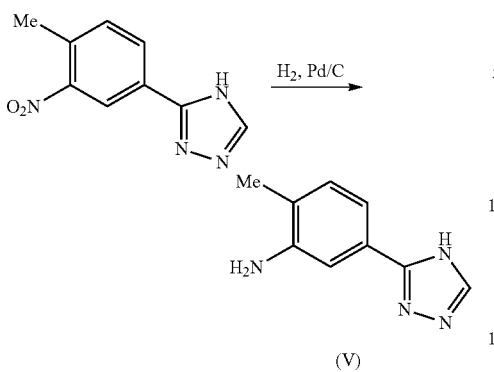

Substituted anilines of type (VI) useful herein can be prepared from commercially available methyl 4-iodobenzoate as depicted in Scheme 5. Nitration of an aromatic precursor followed by reduction of the nitro group yields the aniline. Palladium-catalyzed coupling with ethynyltrimethylsilane, followed by desilylation and saponification gives the desired ethynyl-substituted aminobenzoic acid. Coupling with methoxyamine using the coupling agent EDC affords the desired aniline (VI). See, e.g., *Eur. J. Org. Chem.*, 4607 (2001).

Alternatively, a substituted aniline of type (VI) useful herein can be prepared from 4-amino-3-nitrobenzoic acid as depicted in Scheme 6. Iodide substitution of the aryldiazonium salt, followed by esterification with methanol gives methyl 4-iodo-3-nitrobenzoate. The nitro group can be reduced by SnCl$_2$ to give the desired aniline. Palladium catalyzed coupling with ethynyltrimethyl-silane, followed by desilylation and saponification yields the ethynyl-substituted aminobenzoic acid. Coupling with methoxyamine using the coupling agent EDC affords the aniline (VI). See, e.g., *Eur. J. Org. Chem.*, 4607 (2001).

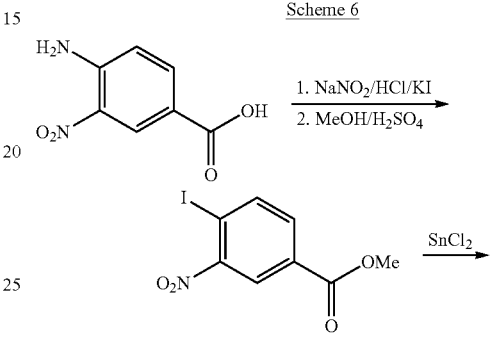

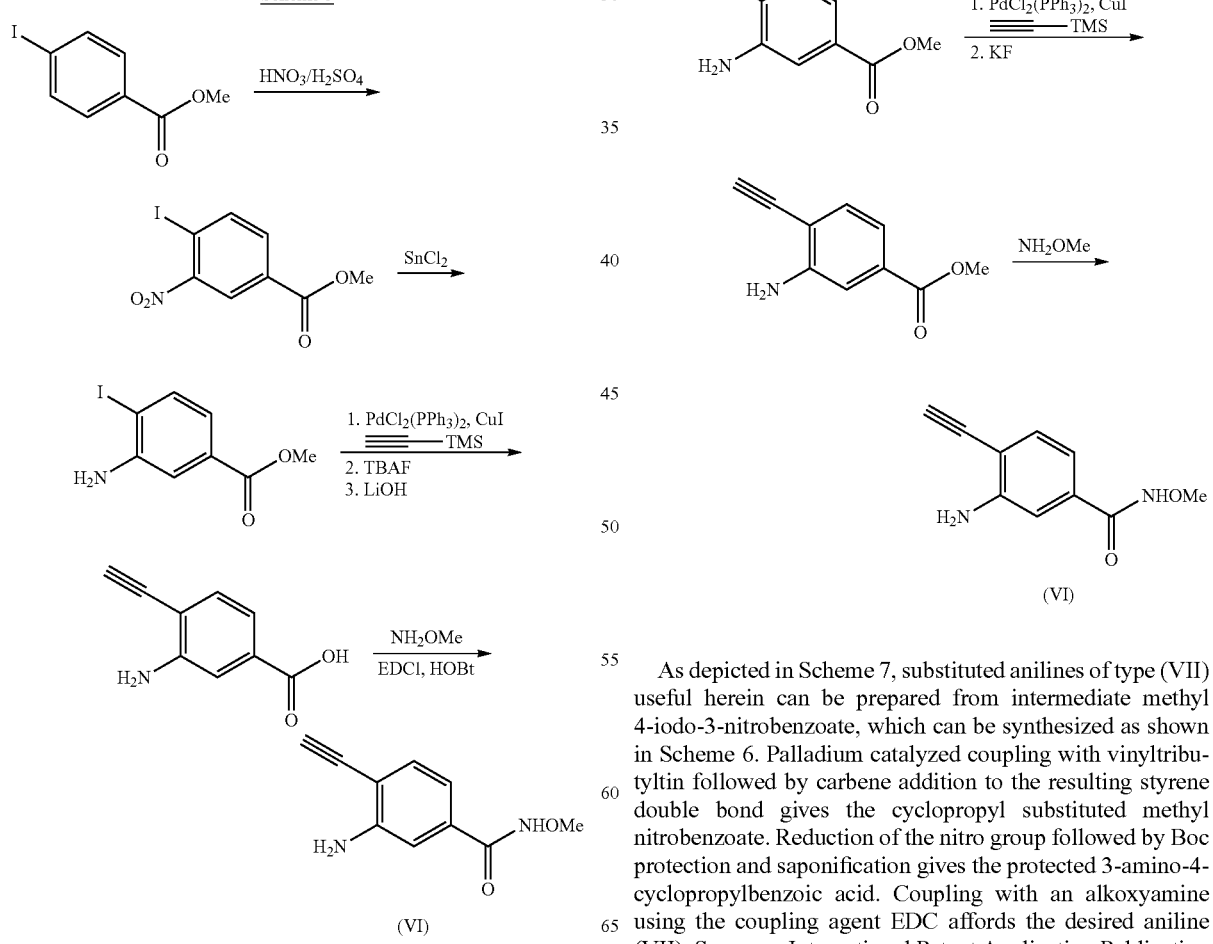

As depicted in Scheme 7, substituted anilines of type (VII) useful herein can be prepared from intermediate methyl 4-iodo-3-nitrobenzoate, which can be synthesized as shown in Scheme 6. Palladium catalyzed coupling with vinyltributyltin followed by carbene addition to the resulting styrene double bond gives the cyclopropyl substituted methyl nitrobenzoate. Reduction of the nitro group followed by Boc protection and saponification gives the protected 3-amino-4-cyclopropylbenzoic acid. Coupling with an alkoxyamine using the coupling agent EDC affords the desired aniline (VII). See, e.g., International Patent Application Publication Nos. WO 02/092087 and WO 02/40486.

Scheme 7

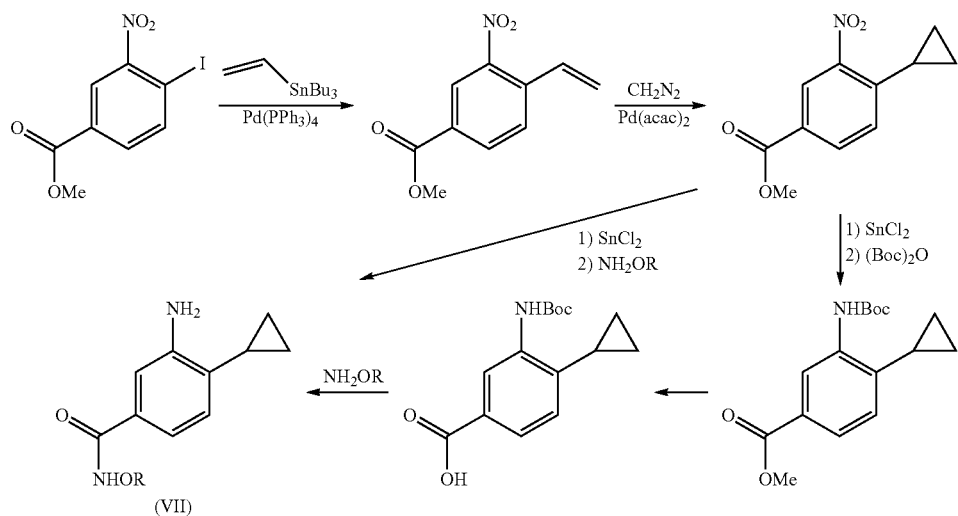

Hydrazines attached to aryl or heteroaryl ring systems are useful as intermediates herein. There are many methods of preparing such intermediates known to one skilled in the art of organic chemistry. One method of preparing some of the hydrazines useful herein is illustrated in Scheme 8.

Aryl hydrazines of type (VIII) useful herein can be prepared from 3-amino-N-methoxy-4-methylbenzamide hydrochloride, which itself can be prepared according to the methods disclosed in International Patent Application Publication No. WO 02/40486. Through the formation of the aryldiazonium salt and its subsequent reduction by $SnCl_2$, the desired hydrazine of type (VIII) is obtained.

Also as depicted in Scheme 8, aryl hydrazines of type (IX) useful herein can be prepared from 3-amino-N-cyclopropyl-4-methylbenzamide, which itself can be prepared according to the methods depicted in Scheme 2. Through the formation of the aryldiazonium salt and its subsequent reduction by $SnCl_2$, the desired hydrazine of type (IX) is obtained.

Similarly, other hydrazines can also be prepared from amines such as those described above in Schemes 1-7.

Scheme 8

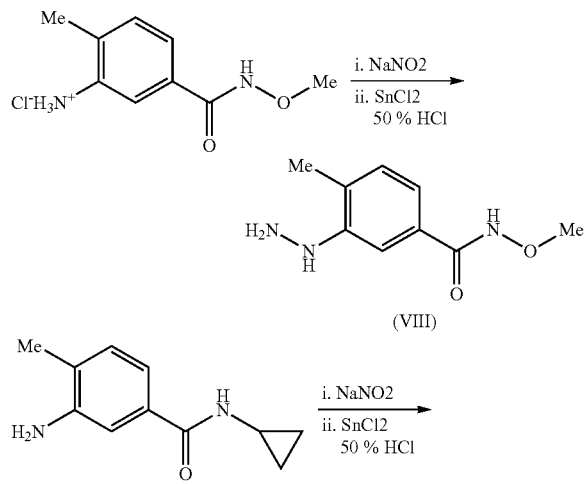

-continued

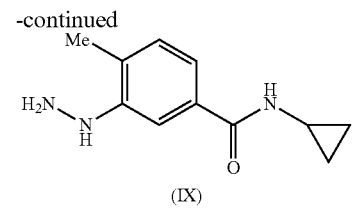

Also, as depicted in Scheme 9, acrylonitriles of type (X) useful herein can be prepared from an aryl ester and acetonitrile. Acetonitrile can be treated with lithium diisopropylamide in THF at −78° C., followed by the addition of the aryl ester to give the corresponding aryloylacetonitrile. This intermediate is then reacted with N,N'-diphenylformamidine in a solvent such as toluene at reflux to give the desired corresponding acrylonitrile of type (X).

Scheme 9

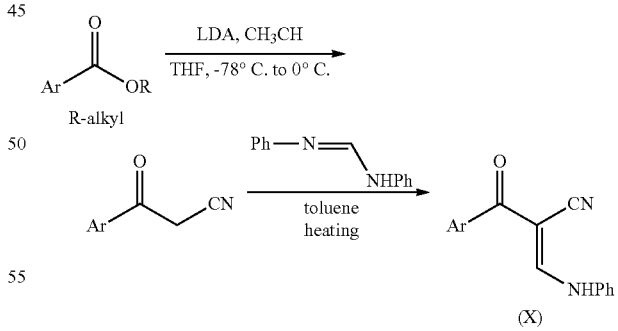

Also, as depicted in Scheme 10, aminopyrazoles of type (XI) useful herein can be prepared from an acrylonitrile of type (X), which itself can be prepared according to the methods depicted in Scheme 9, and hydrazines such as those of type (VIII) and (IX), which themselves can be prepared according to the methods depicted in Scheme 8. The acrylonitrile and the hydrazine are heated to 60 to 100° C. in a solvent such as DMF or ethanol to give the desired aminopyrazole of type (XI).

Scheme 10

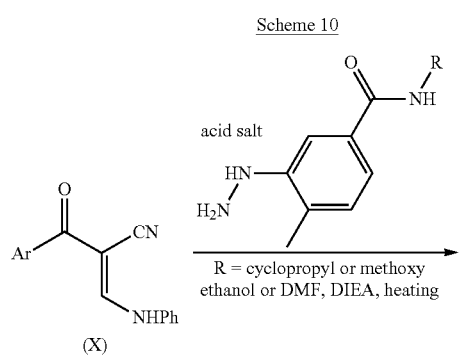

Also, as depicted in Scheme 11, aminopyrazoles of type (XIII) useful herein can be prepared from an acrylonitrile of type (XII), which itself can be prepared by treatment of an acrylonitrile of type (X), prepared according to the methods depicted in Scheme 9, with sodium hydride and carbon disulfide followed by treatment with iodomethane, and hydrazines such as those of type (VIII) and (IX), which themselves can be prepared according to the methods depicted in Scheme 8. The acrylonitrile and the hydrazine are heated to 60 to 100° C. in a solvent such as DMF or ethanol to give the desired aminopyrazole of type (XIII).

Scheme 11

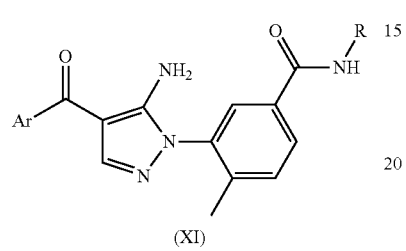

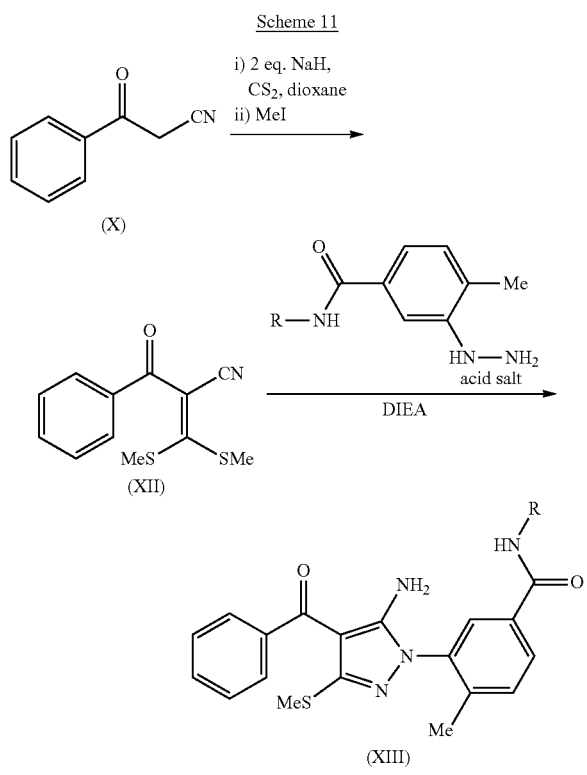

Also, as depicted in Scheme 12, aminopyrazoles of type (XIV) useful herein can be prepared from an acrylonitrile of type (XII), which itself can be prepared according to the methods depicted in Scheme 11, and hydrazines such as those of type (VIII) and (IX), which themselves can be prepared according to the methods depicted in Scheme 8. Treatement of this intermediate (XII) with an alcohol alkoxide prior to with heating at 60 to 100° C. with the hydrazine in a solvent such as DMF or ethanol gives the desired aminopyrazole of type (XIII).

Scheme 12

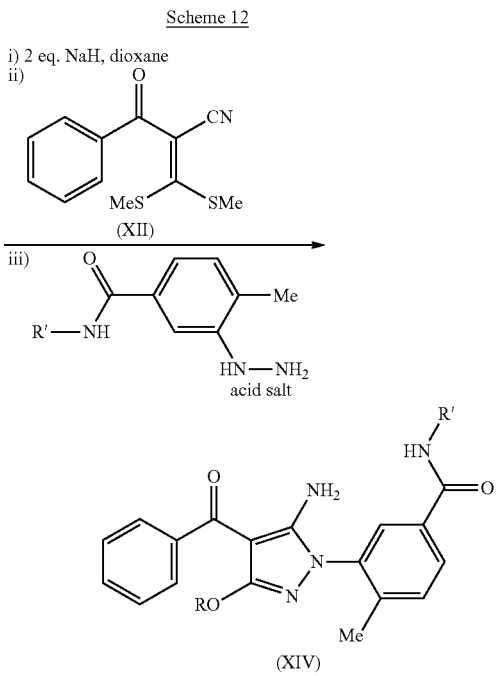

Also, as depicted in Scheme 13, aminoimidazoles of type (XV) useful herein can be prepared from substituted anilines of type (III), which themselves can be prepared according to the methods depicted in Scheme 2. The aniline is heated in triethyl orthoformate. After removal of the solvent in vacuo, the product was reacted with aminomalononitrile p-toluenesulfonate and sodium acetate in acetic acid to give the aminocyanoimidazole intermediate. Reaction of this intermediate with a Grignard reagent gives the desired aminoimidazole of type (XV).

Scheme 13

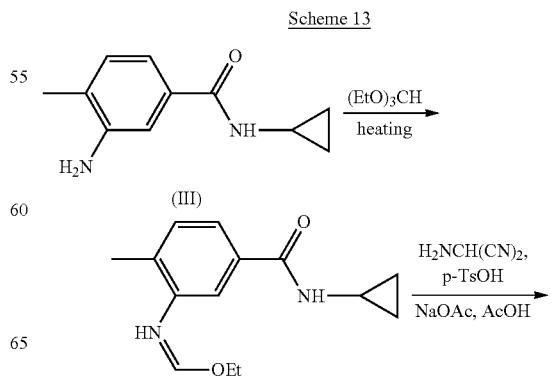

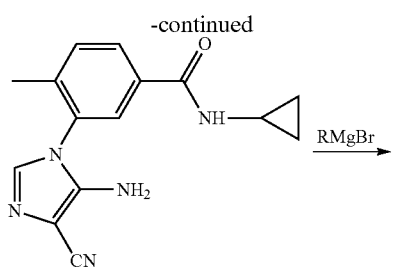

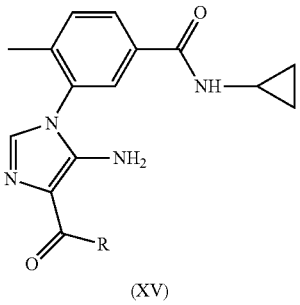

(XV)

Compounds provided herein can be prepared from hydrazines attached to aryl or heteroaryl ring systems using methods disclosed in U.S. Pat. Nos. 6,316,466, 6,376,527 and 6,444,696.

Additional synthetic methods useful in the synthesis of the compounds provided herein are disclosed in the following, the disclosures of which are incorporated herein by reference in their entirety:

1) J. Heterocyclic Chem. 17, 631 (1980)
2) Tetrahedron 55(48), 13703 (1999)
3) European Patent No. EP 0 713 876
4) Chemische Berichte 126(10), 2317 (1993)
5) Journal of Organic Chem. 58(24), 6620 (1993)
6) Tetrahedron Letters 35, 3239 (1973)
7) Journal of Chemical Research, Synopses 1, 2 (1997)
8) Boletin de la Sociedad Quimica del Peru 53(3), 150 (1987)
9) Journal of the Chemical Society, Chemical Communications 2, 35 (1973)
10) Comptes Rendus des Seances de l'Academie des Sciences, Series C: Sciences Chimiques 274(20), 1703 (1972)

Also provided herein are compounds prepared according to a process disclosed herein.

D. Formulation of Pharmaceutical Compositions

Also provided herein is a pharmaceutical composition comprising a compound provided herein. The composition can be used, for example, as a medicament. The composition can contain, for example, a pharmaceutically acceptable excipient or carrier. A composition or medicament provided herein can be used for the treatment, prevention or amelioration of one or more symptoms of p38 kinase mediated diseases or disorders, including inflammatory diseases.

Thus, provided herein are pharmaceutical compositions capable of treating p38-kinase-associated conditions, including TNF-α, IL-1, and/or IL-8 mediated conditions, as described above. The compositions may contain other therapeutic agents, as described herein, and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds provided herein may be administered by any means suitable for the condition to be treated, which may depend on the need for site-specific treatment or quantity of drug to be delivered. Topical administration is generally useful for skin-related diseases, and systemic treatment is generally used for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps. Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable nonirritating excipients, such as cocoa butter, synthetic glyceride esters or polyethylene glycols, which are solid at ordinary temperatures but liquefy and/or dissolve in the rectal cavity to release the drug.

The effective amount of a compound provided herein may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Subjects for treatment include animals, generally mammalian species such as humans, and domestic animals such as dogs, cats, horses, and the like. Thus, when the term "patient" is used herein, this term is intended to include all subjects, in particular mammalian species, including humans, that are affected by mediation of p38 enzyme levels.

Also provided in one embodiment is a process for the manufacture of medicaments which process involves bringing a compound provided herein together with a pharmaceutically acceptable excipient and bringing the mixture into a galenical administration form.

E. Methods of Use of the Compounds and Compositions

In a further embodiment, the compounds provided herein can be used in the treatment, prevention, or amelioration of one or more symptoms of inflammatory diseases. A compound provided herein can be used, in another embodiment, for the manufacture of a medicament for the treatment orprophylaxis of inflammatory diseases.

The compounds provided herein are selective inhibitors of p38 kinase activity, and in particular, isoforms p38α and p38β. Accordingly, compounds provided herein are useful for treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. Provided herein are methods of treating a disease by administering a compound provided herein that inhibits p38 kinase activity. Also provided herein are methods for inhibiting or delaying the onset of a disease or disorder by administering a compound provided herein. Methods provided herein can be used to achieve a full or partial reduction of the symptoms of a disease or disease state, and/or to alleviate, ameliorate, or lessen, the disease or disorder and/or its symptoms. When reference is made herein to inhibition of "p-38α/βkinase," this means that either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

In view of their activity as inhibitors of p38α/β kinase, compounds provided herein are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, SARS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin induced platelet aggregation, endotoxemia and/or toxic shock syndrome, and conditions associated with prostaglandin endoperoxidase synthase-2.

In addition, p38 inhibitors provided herein inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus. When the terms "p38-associated condition" or "p38-associated disease or disorder" are used herein, each is intended to encompass all of the conditions identified above as if repeated at length, as well as any other condition that is affected by p38 kinase activity.

Thus, provided herein are methods for treating such conditions, involving administering to a subject in need thereof an effective amount of at least one compound provided herein or a pharmaceutically acceptable derivative thereof. The methods of treating p38 kinase-associated conditions may involve administering compounds provided herein alone or in combination with each other and/or other suitable therapeutic agents useful in treating such conditions. Exemplary of such other therapeutic agents include corticosteroids, rolipram, calphostin, CSAIDs, 4-substituted imidazo[1,2-A]quinoxalines as disclosed in U.S. Pat. No. 4,200,750 and in S. Ceccarelli et al. (1998) *European Journal of Medicinal Chemistry* 33:943-955; interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathioprine and cyclophosphamide; TNF-α inhibitors such as tenidap, anti- TNF antibodies or soluble TNF receptor, and rapamycin (sirolimus or Rapamune) or derivatives thereof.

The above other therapeutic agents, when employed in combination with the compounds provided herein, may be used, for example, in those amounts indicated in the Physicians' Desk Reference (PDR) or as otherwise determined by one of ordinary skill in the art. In the methods provided herein, such other therapeutic agent(s) may be administered prior to, simultaneously with, or following the administration of the inventive compounds.

The following Examples illustrate embodiments herein, and are not intended to limit the scope of the claims. Abbreviations employed in the Examples are defined below. Compounds of the Examples are identified by the example and step in which they are prepared (for example, "1A" denotes the title compound of step A of Example 1), or by the example only where the compound is the title compound of the example (for example, "2" denotes the title compound of Example 2).

ABBREVIATIONS

Ph=phenyl
Bz=benzyl
t-Bu=tertiary butyl
Me=methyl
Et=ethyl
Pr=propyl
Iso-P or i-Pr=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DCM or $CH_2Cl_2$=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-1-yl-N,N,N',N'-tetramethyluronim hexafluorophosphate
KOH=potassium hydroxide
$K_2CO_3$=potassium carbonate
$POCl_3$=phosphorous oxychloride
KOtBu=potassium t-butoxide
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
$Na_2S_2O_3$=sodium thiosulfate
$Na_2SO_4$=sodium sulfate
Pd=palladium
Pd/C=palladium on carbon
min=minute(s)
L=liter
mL=milliliter
µL=microliter
g=gram(s)
mg=milligram(s)
mol=moles
mmol=millimole(s)
meq=milliequivalent RT or rt=room temperature
ret. t. or $t_R$=HPLC retention time (minutes)
sat or sat'd=saturated General Methods. Mass spectral data were obtained on a Thermo Finnigan LCQ Duo Ion Trap mass spectrometer. In the Examples: "HPLC (6 minute gradient)" refers to Keystone C18 Beta Basic column, 0.4 mL/min flow rate, 6 minute linear gradient elution (start solvent % B=0; final solvent % B=100), solvent A: acetonitrile+0.025% TFA; solvent B=$H_2O$+0.025% TFA. "HPLC (4 minute gradient)" refers to Keystone C18 Beta Basic column, 0.5 mL/min flow rate, 4 minute linear gradient elution (start solvent % B=0; final solvent % B=100), solvent A: acetonitrile+0.025% TFA; solvent B=$H_2O$+0.025% TFA.

EXAMPLE 1

Preparation of 3-[5-Amino-4-(3-iodo-benzoyl)-pyrazol-1-yl]-N-methoxy-4-methyl-benzamide

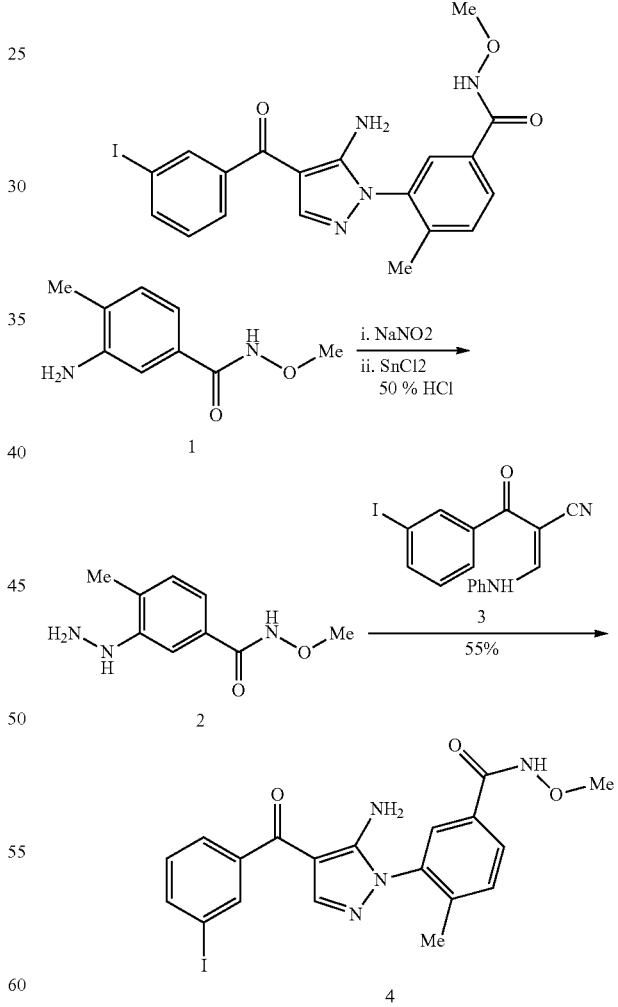

A. 3-Hydrazino-N-methoxy-4-methyl-benzamide

To a stirred solution of 3-amino-N-methoxy-4-methylbenzamide 1 (102 mg, 0.56 mmol, preparation: International Patent Application Publication No. WO 02/40486 A2, pg. 66) in water (5 ml) at 0° C. was added conc. HCl (5 mL) followed by the addition of sodium nitrite (43 mg, 0.62 mmol). The reaction mixture was stirred at 0° C. for 40 min then a solution of tin(II)chloride (241 mg, 1.27 mmol) in conc. HCl (1 mL) was added and the mixture was stirred for 1 hr then allowed to stand at −20° C. for 20 hr before it was warmed to RT and concentrated to a white solid. The solid was triturated with ethanol, the solids were filtered, and the filtrate concentrated to provide 3-hydrazino-N-methoxy-4-methyl-benzamide 2 as white solid (486 mg) as a mixture with tin salts and ethanol which was used without further purification. HPLC (6 minute gradient) $t_R$ 0.78 min; MS m/z 195.9 [M+H]$^+$.

B. 3-[5-Amino-4-(3-iodo-benzoyl)-pyrazol-1-yl]-N-methoxy-4-methyl-benzamide

To a stirred solution 3-hydrazino-N-methoxy-4-methyl-benzamide 2 (116 mg, estimated 0.14 mmol) in EtOH (10 ml) was added 2-(3-iodo-benzoyl)-3-phenylamino-acrylonitrile 3 (59 mg, 0.14 mmol, preparation: International Patent Application Publication No. WO 02/57101 A1, pg. 84) and mixture was heated (bath T=65-70° C.) for 4 hr, when additional 3-hydrazino-N-methoxy-4-methyl-benzamide 2 (80 mg, 0.11 mmol) was added and the mixture was heated at the same temperature for 27 hr. It was cooled to room temperature, concentrated and redissolved in EtOAc before it was washed with water and brine, dried over Na$_2$SO$_4$, concentrated to give a crude semisolid. The mixture was then purified by flash chromatography, eluting with 1:1 EtOAc/hexanes to remove impurities then 100% EtOAc give 3-[5-amino-4-(3-iodo-benzoyl)-pyrazol-1-yl]-N-methoxy-4-methyl-benzamide 4 as an off-white solid (38 mg, 0.08 mmol, 55%). HPLC (6 minute gradient) $t_R$ 3.49 min; MS m/z 476.96 [M+H]$^+$; $^1$H NMR (CD$_3$OD, 300 MHz) δ 8.10 (s, 1 H), 7.95 (d, J=8.0, 1 H), 7.88 (d, J=8.0, 1 H), 7.82 (m, 2 H), 7.78 (s, 1 H), 7.58 (d, J=8.0, 1 H), 7.33 (t, J=7.8, 1 H), 5.02 (s. 3 H), 2.33 (s, 3 H) ppm; $^{13}$C NMR (DMSO-d$_6$, 125 MHz.) δ 189.3, 154.3, 143.5, 143.3, 142.0, 138.3, 137.4, 133.5, 132.9, 132.0, 130.4, 128.8, 128.4, 104.8, 95.4, 64.8, 18.2 ppm.

EXAMPLE 2

Preparation of 3-(5-Amino-4-benzoyl-pyrazol-1-yl)-N-methoxy-4-methyl-benzamide

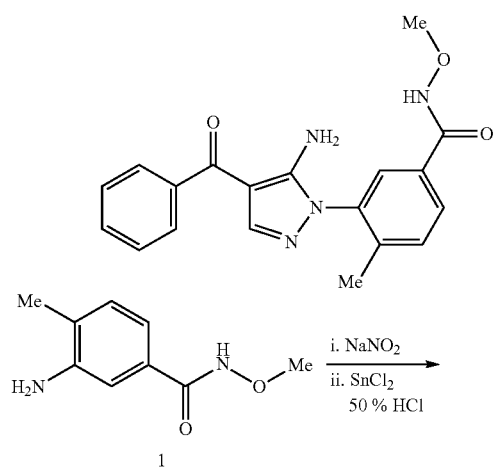

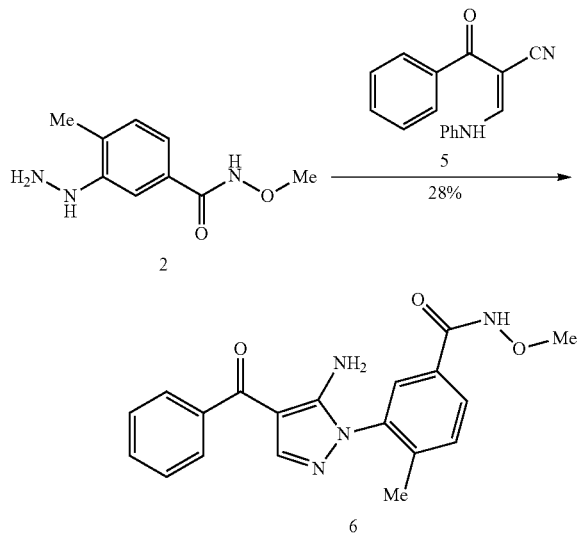

To a stirred solution of 3-amino-N-methoxy-4-methyl-benzamide 1 (104 mg, 0.58 mmol) in water (2 ml) at 0° C. was added conc. HCl (2 mL) followed by the addition of sodium nitrite (44 mg, 0.63 mmol). The reaction mixture was stirred at 0° C. for 40 minutes then a solution of tin(II)chloride (245 mg, 1.30 mmol) in conc. HCl (1 mL) was added and the mixture was stirred for 40 minutes then allowed to stand at −20° C. for 20 hours before it was warmed to RT and concentrated to a white solid. The solid was triturated with ethanol, the solids were removed, and 2-benzoyl-3-phenylamino-acrylonitrile 5 (144 mg, 0.58 mmol, preparation: Grothaus, J. Am. Chem. Soc. 58, 1334 (1936)) was added and the mixture heated (bath T=65-70° C.) for 16 hr. The mixture was cooled to RT, concentrated and purified by flash chromatography, eluting with 1:1 EtOAc/hexanes to remove impurities then 100% EtOAc to give 3-(5-amino-4-benzoyl-pyrazol-1-yl)-N-methoxy-4-methyl-benzamide 6 as an off-white solid (41 mg, 0.12 mmol, 28%). HPLC (4 minute gradient) $t_R$ 1.93 min; MS m/z 351.1 [M+H]$^+$; $^1$H NMR (DMSO-d$_6$, 300 MHz) δ 11.88 (s 1 H, NH), 7.803 (m, 4 H), 7.56 (m, 4 H), 7.01 (s, 2 H, NH$_2$), 3.32 (s, $\overline{3}$ H), 2.162 (s, 3 H) ppm; $^{13}$C NMR (DMSO-d$_6$, $\overline{125}$ MHz) δ 187.6, 151.9, 141.2, 139.7, 139.6, 135.7, 131.4, 131.2, 130.9, 128.5, 128.1, 127.8, 126.4, 102.6, 63.2, 17.2 ppm.

EXAMPLE 3

Preparation of 3-(5-amino-4-benzoyl-pyrazol-1-yl)-4-methyl-benzoic acid

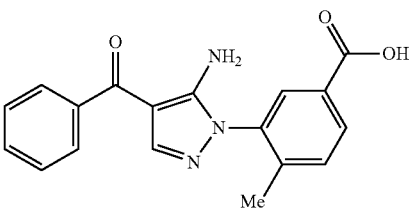

δ 187.6, 166.3, 152.0, 141.3, 141.2, 139.6, 135.9, 131.6, 131.2, 130.1, 129.8, 128.6, 127.8, 102.6, 17.4 ppm.

EXAMPLE 4

Preparation of 3-(5-amino-4-benzoyl-pyrazol-1-yl)-N-cyclopropyl-4-methyl-benzamide

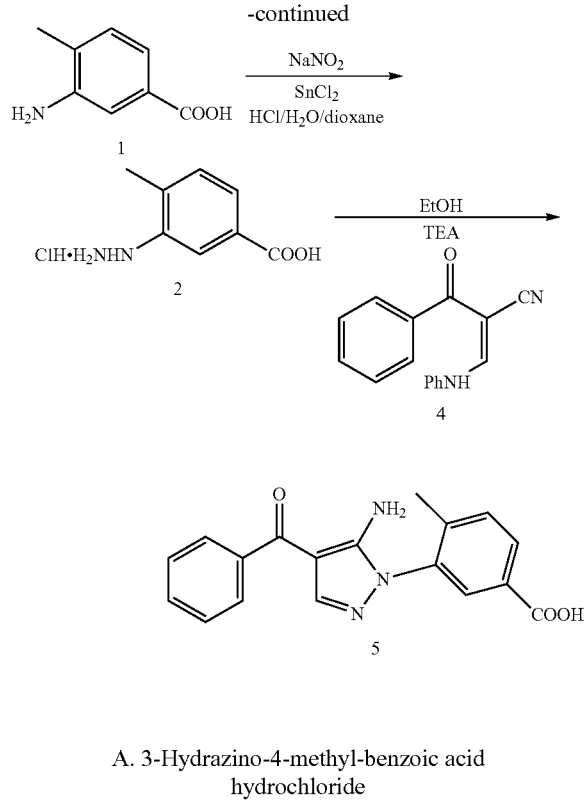

A. 3-Hydrazino-4-methyl-benzoic acid hydrochloride

To a stirred solution of 3-amino-4-methylbenzoic acid 1 (5.64 g, 31.2 mmol, 1.0 eq) in 100 mL of dioxane and 100 mL of water at 0° C. was added 100 mL of conc. HCl followed by the portionwise addition of sodium nitrite (2.82 g, 40.9 mmol, 1.1 eq) as a solid at a rate to control gas evolution and foaming over 45 minutes. A clear brown solution resulted. Anhydrous tin(II)chloride (15.62 g, 83.7 mmol, 2.25 eq) was dissolved in conc. HCl (25 mL) and added dropwise over 25 mL at 0° C. After 1 hour, the precipitate was filtered and washed with dioxanes then dried under vacuum to provide 3-hydrazino-4-methyl-benzoic acid hydrochloride 2 as a tan solid (4.98 g, 66%): HPLC (4 minute gradient) $t_R$ 0.97 min; MS m/z 167 [M+H]$^+$; $^1$H (300 MHz, DMSO-$d_6$) δ 10.03 (s, 1 H, COOH), 7.89 (s, 1 H), 7.51 (s, 1 H), 7.27 (d, J=8.0, 1 H), 3.38 (s, 3 H, NHNH$_2$), 2.23 (s, 3 H) ppm.

B. 3-(5-Amino-4-benzoyl-pyrazol-1-yl)-4-methyl-benzoic acid

To a stirred solution of 3-hydrazino-4-methyl-benzoic acid hydrochloride 2 (242 mg, 1.19 mmol, 1.0 eq) in 25 mL of ethanol was added 2-benzoyl-3-phenylamino-acrylonitrile 4 (296 mg, 1.19 mmol, 1.0 eq, preparation: Grothasu, Davis, *J. Am. Chem. Soc.*, 58, 1334 (1936)) and triethylamine (161 μL, 1.19 mmol, 1.0 eq) and the mixture was heated to 65° C. All solids dissolved when temperature reached 65° C. After three hours, LC-MS indicates consumption of the hydrazine. The solids were filtered to provide 3-(5-amino-4-benzoyl-pyrazol-1-yl)-4-methyl-benzoic acid 5 (95 mg, 25%) as a beige solid: HPLC (4 minute gradient) $t_R$ 2.10 min; MS m/z 322 [M+H]$^+$; $^1$H NMR (DMSO-$d_6$, 300 MHz) δ 7.99 (d, J=7.6, 1 H), 7.81 (s, 2 H), 7.78 (s, 1 H), 7.57 (m, 4 H), 7.02 (s, 2 H, NH$_2$), 2.18 (s, 3 H) ppm; $^{13}$C NMR (DMSO-$d_6$, 75 MHz)

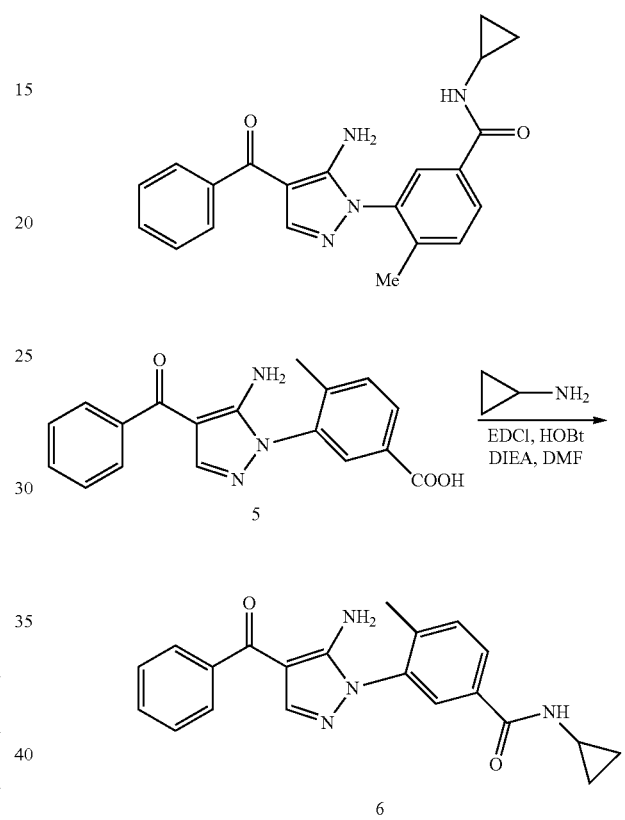

To a stirred solution of 3-(5-amino-4-benzoyl-pyrazol-1-yl)-4-methyl-benzoic acid 5 (Example 3, 700 mg, 2.18 mmol, 1.0 eq) in 30 mL of DMF was added EDCI (855 mg 4.35 mmol, 2.0 eq), HOBt (589 mg, 4.35 mmol, 2.0 eq), and diisopropylethylamine (1.59 mL, 8.71 mmol, 4.0 eq) and the solution was stirred for 15 minutes at room temperature when cyclopropylamine (302 μL, 4.35 mmol, 2.0 eq) was added and the reaction stirred for 1 hour. The mixture was diluted with EtOAc (300 mL) and washed with water (2×25 mL) and brine (25 mL), dried (Na$_2$SO$_4$) and concentrated. The product was purified by flash chromatography on silica gel eluted with 8/2 EtOAc/MeOH to provide the product as a brown oil. The product was further purified by trituration with 1/1/1 EtOAc/hexanes/CH$_2$Cl$_2$ and dried under vacuum to provide 3-(5-amino-4-benzoyl-pyrazol-1-yl)-N-cyclopropyl-4-methyl-benzamide 6 (387 mg, 50%) as a white powder: HPLC (4 minute gradient) $t_R$ 2.11 min; MS m/z 361 [M+H]$^+$; $^1$H NMR (CD$_3$OD, 300 MHz) δ 7.92 (d, J=7.6, 1 H), 7.81 (m, 4 H), 7.54 (m, 4 H), 2.85 (m, 1 H), 2.22 (s, 3 H), 0.80 (d, J=5.7, 2 H), 0.63 (s, 2 H) ppm; $^{13}$C NMR (CD$_3$OD, 75 MHz) δ 191.2, 170.1, 153.8, 143.3, 142.0, 141.1, 136.9, 134.8, 132.9, 132.7, 130.1, 129.7, 129.2, 128.1, 104.8, 24.1, 17.7, 6.6 ppm.

EXAMPLE 5

Preparation of 3-[5-amino-4-(3-iodo-benzoyl)-pyrazol-1-yl]-4-methyl-benzoic acid

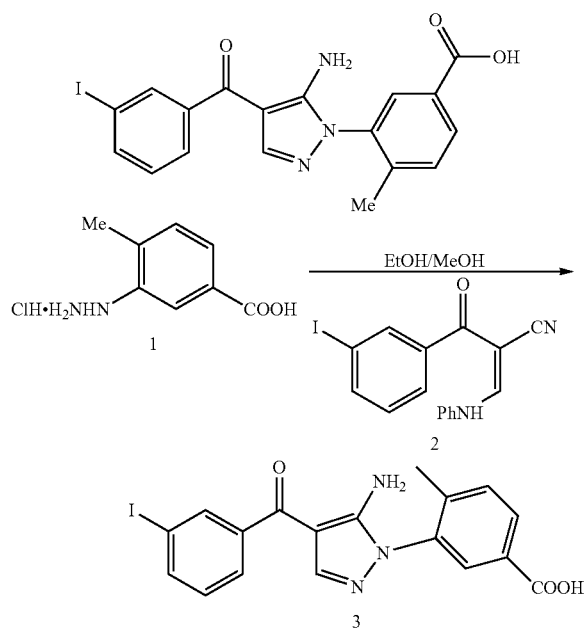

To a stirred solution of 3-hydrazino-4-methyl-benzoic acid hydrochloride 1 (Example 3A, 314 mg, 1.54 mmol, 1.0 eq) in 50 mL of ethanol and 5 mL of methanol was added 2-(3-iodo-benzoyl)-3-phenylamino-acrylonitrile 2 (579 mg, 1.54 mmol, preparation: International Patent Application Publication No. WO 02/57101 A1, pg. 84). The mixture was heated to 75° C. for 18 h. The precipitated solids were collected on a flitted filter and were washed with ethanol to provide 3-[5-Amino-4-(3-iodo-benzoyl)-pyrazol-1-yl]-4-methyl-benzoic acid 3 (153 mg, 22%) as a white solid. MS m/z 448 [M+H]$^+$; $^1$H NMR (300 MHz, DMSO-d$_6$) δ 2.18 (s, 3H), 7.05 (bs, 2H), 7.34 (dd, J$_1$=J$_2$=7.7 Hz), 7.58 (d, J=8.1 Hz, 1H), 7.78 (s, 1H), 7.81 (m, 2H), 7.94 (m, 1H), 7.98 (m, 1H), 8.03 (m, 1H) ppm.

EXAMPLE 6

Preparation of 3-[5-amino-4-(3-iodo-benzoyl)-pyrazol-1-yl]-N-cyclopropyl-4-methyl-benzamide

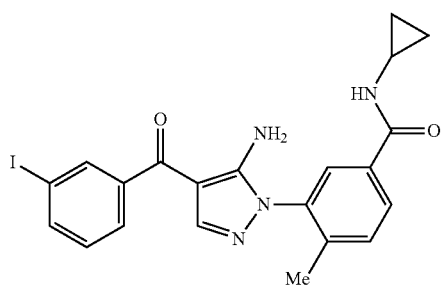

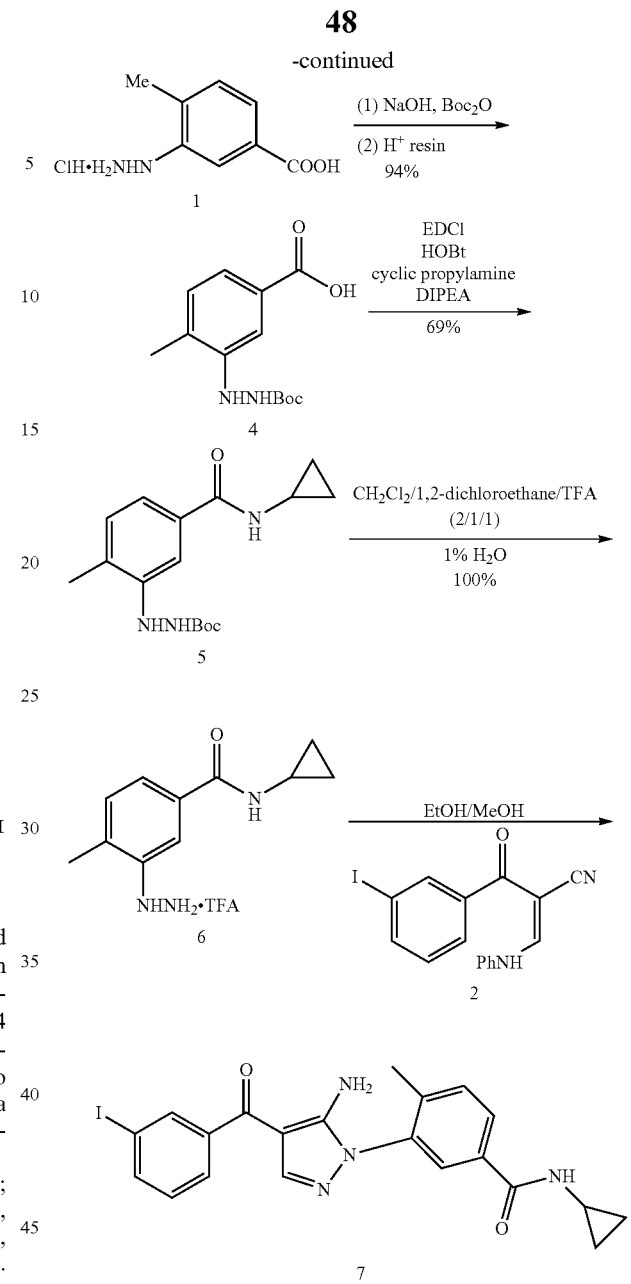

A. 3-(N'-tert-Butoxycarbonyl-hydrazino)-4-methyl-benzoic acid

3-Hydrazino-4-methyl-benzoic acid hydrochloride 1 (Example 3A, 13 g, 64.5 mmol) was dissolved into dioxane (200 mL) and H$_2$O (100 mL). Aqueous NaOH (5.16 g NaOH in 100 mL H$_2$O, 2×64.5 mmol) was added followed by the addition of (Boc)$_2$O (15.5 g, 1.1×64.5 mmol) immediately. The reaction mixture was stirred at room temperature for 2 hrs. Concentrated on rotavapor. Then H$_2$O and CH$_2$Cl$_2$ (some MeOH) were added. With stirring strong H$^+$ resin was added to neutralize the mixture to pH<2. Filtered and the resin was washed with CH$_2$Cl$_2$ and MeOH. The aqueous layer was washed with CH$_2$Cl$_2$ (added some MeOH) for two times. The combined organic layer was dried over Na$_2$SO$_4$ (some EtOAc was added). Filtration and concentration gave 3-(N'-tert-butoxycarbonyl-hydrazino)-4-methyl-benzoic acid 4 (16 g, 94%) as a white solid. $^1$H NMR (300 MHz, CDCl$_3$) δ 1.48 (s, 9H), 2.27 (s, 3H), 5.76 (s, 1H), 7.14 (d, J=7.7 Hz, 1H), 7.56 (d, J=7.7 Hz, 1H), 7.61 (s, 1H) ppm.

B. N'-(5-Cyclopropylcarbamoyl-2-methyl-phenyl)-hydrazinecarboxylic acid tert-butyl ester 3-(N'-tert-Butoxycarbonyl-hydrazino)-4-methyl-benzoic acid 4 (14 g, 52.6 mmol) was dissolved in DMF (250 mL). EDCI (20 g, 105.2 mmol) and HOBt (16 g, 105.2 mmol) were added. The mixture was stirred at room temperature for 30 min. Cyclopropylamine (7.4 mL, 105.2 mmol) was added, followed by DIPEA (37 mL, 4×52.6 mmol). The reaction mixture was stirred at room temperature for 18 h. After concentration of the reaction mixture in vacuo, H$_2$O was added. The mixture was then extracted with CH$_2$Cl$_2$ three times. The organic layer was washed with aqueous NaCl solution. Dried over Na$_2$SO$_4$, filtration and concentration gave a white solid. The crude product was dissolved in CH$_2$Cl$_2$/MeOH, and then purified by silica gel column chromatography (CH$_2$Cl$_2$/EtOAc, gradient 2/1 to 1/1) to give the desire product. The product was further purified by recrystallization from EtOAc/CH$_2$Cl$_2$; washing of the collected solids with EtOAc gave N'-(5-cyclopropylcarbamoyl-2-methyl-phenyl)-hydrazinecarboxylic acid tert-butyl ester 5 (11 g, 69%). $^1$H NMR (300 MHz, CDCl$_3$) δ 0.58 (m, 2H), 0.84 (m, 2H), 1.48 (s, 9H), 2.23 (s, 3H), 2.87 (m, 1H), 5.69 (bs, 1H), 6.17 (bs, 1H), 6.39 (brs, 1H), 7.70 (m, 2H), 7.32 (s, 1H) ppm.

C. N-Cyclopropyl-3-hydrazino-4-methyl-benzamide, trifluoroacetic acid salt

N'-(5-Cyclopropylcarbamoyl-2-methyl-phenyl)-hydrazinecarboxylic acid tert-butyl ester 5 was dissolved in CH$_2$Cl$_2$/TFA (2/1) with 2% H$_2$O and the mixture was stirred at room temperature for 3 hrs. Concentration in vacuo gave a syrup. CH$_2$Cl$_2$ and toluene was added, and concentration in vacuo again gave N-cyclopropyl-3-hydrazino-4-methyl-benzamide, trifluoroacetic acid salt 6 as an off-white solid. (Yield: 100%). MS m/z 206 [M+H]$^+$; $^1$H NMR (300 MHz, D$_2$O) δ 0.68 (m, 2H), 0.88 (m, 2H), 2.31 (s, 3H), 2.79 (m, 1H), 7.31 (s, 1H), 7.36 (bs, 2H) ppm.

D. 3-[5-Amino-4-(3-iodo-benzoyl)-pyrazol-1-yl]-N-cyclopropyl-4-methyl-benzamide To a stirred solution of N-cyclopropyl-3-hydrazino-4-methyl-benzamide, trifluoroacetic acid salt 6 (648 mg, 1.74 mmol, 1.0 eq) in 2 mL of ethanol was added 2-(3-iodo-benzoyl)-3-phenylamino-acrylonitrile 2 (550 mg, 1.74 mmol, preparation: International Patent Application Publication No. WO 02/57101 A1, pg. 84) and DIEA (0.50 mL, 2.9 mmol). The mixture was heated to 160° C. for 40 min using microwave. The mixture was concentrated in vacuo. The crude product was purified by silica gel column chromatography (EtOAc/hex, gradient 1/1 to 2/1) to give 3-[5-Amino-4-(3-iodo-benzoyl)-pyrazol-1-yl]-N-cyclopropyl-4-methyl-benzamide 7 (589 mg, 70%) as a white solid. MS m/z 497 [M+H]$^+$; $^1$H NMR (300 MHz, CDCl$_3$) δ0.60 (m, 2H), 0.86 (m, 2H), 2.24 (s, 3H), 2.87 (m, 1H), 5.81 (bs, 2H), 6.35 (bs, 1H), 7.25 (dd, J$_1$=J$_2$=7.8 Hz, 1H), 7.45 (d, J=8.1 Hz, 1H), 7.69 (d, J=1.7 Hz, 1H), 7.80 (m, 3H), 7.89 (m, 1H), 8.00 (s, 1H) ppm.

EXAMPLE 7

Preparation of {5-amino-1-[2-methyl-5-(4H-[1,2,4]triazol-3-yl)-phenyl]-1H-pyrazol-4-yl}-phenyl-methanone

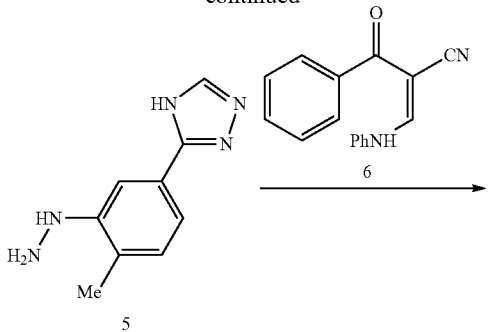

A. N-Dimethylaminomethylene-4-methyl-3-nitro-benzamide

4-Methyl-3-nitro-benzamide 1 (10 g, 56 mmol) was suspended in 80 mL of N,N-dimethylformamide dimethylacetal and was then heated to 95° C. for 2 h. The red solution was allowed to cool to room temperature with stirring. After another 2 h, the resulting red precipitate was collected on a fritted filter, and was washed three times with Et$_2$O to give N-dimethylaminomethylene-4-methyl-3-nitro-benzamide 2 as a red solid (8.7 g, 66%). HPLC (4 minute gradient) t$_R$ 1.76 min; MS m/z 236.0 [M+H]$^+$.

B. 3-(4-Methyl-3-nitro-phenyl)-4H-[1,2,4]triazole

To a solution of N-dimethylaminomethylene-4-methyl-3-nitro-benzamide 2 (8.6 g, 37 mmol) in 250 mL of acetic acid was added dropwise anhydrous hydrazine (4.7 mL, 180 mL). The now light orange solution was heated to 95° C. for 1.5 h before allowing to cool and to stir at room temperature for 18 h. Acetic acid was removed in vacuo, and the residue was partitioned between H$_2$O and EtOAc. The organic layer was washed twice with saturated NaHCO$_3$ solution, then dried over MgSO$_4$. After filtration and concentration in vacuo, the residue was triturated with warm EtOAc, and the resulting off-white solid was collected on a fitted filter to give 3-(4-methyl-3-nitro-phenyl)-4H-[1,2,4]triazole 3 (5.8 g, 77%). HPLC (4 minute gradient) t$_R$ 1.82 min; MS m/z 205.1 [M+H]$^+$; $^1$H NMR (300 MHz, DMSO-d$_6$) δ8.57 (bs, 1 H), 8.46 (s, 1 H), 8.12 (d, J=7.9, 1 H), 7.56 (d, J=7.9, 1 H), 2.5 (s, 3 H) ppm; $^{13}$C NMR (DMSO-d$_6$, 125 MHz) δ 149.1, 133.5, 130.1, 121.3, 19.5 ppm.

C. 2-Methyl-5-(4H-[1,2,4]triazol-3-yl)-phenylamine 3-(4-Methyl-3-nitro-phenyl)-4H[1,2,4]triazole 3 (5.75 g, 28.2 mmol) was suspended in 220 mL of ethanol with 2.35 mL (ca. 28.2 mmol) of concentrated aqueous HCl. Under nitrogen, 900 mg of 10% palladium on activated carbon (dry) was added carefully. Hydrogen gas was bubbled through the reaction mixture via a balloon attached to a syringe needle for 5 minutes. The reaction mixture was then stirred under an atmosphere of hydrogen gas maintained by a balloon at room temperature for 5 h. The catalyst was removed by filtration through a short pad a Celite. The filtrate was concentrated in vacuo, and the residue was neutralized with saturated NaHCO$_3$ solution. The mixture was extracted with EtOAc six times and the combined organic layers were dried over MgSO$_4$. After filtration and concentration in vacuo, the residue was recrystallized in EtOAc to give 2-methyl-5-(4H-[1,2,4]triazol-3-yl)-phenylamine 4 (4.5 g, 92%) as an off-white solid. HPLC (4 minute gradient) t$_R$ 0.79 min; MS m/z 175.2 [M+H]$^+$; $^1$H NMR (300 MHz, MeOH-d$_3$) δ8.10 (bs, 1 H), 7.54 (s, 1 H), 7.29 (m, 2 H), 7.15 (d, J=7.6, 2 H), 2.23 (s, 3 H) ppm.

D. [2-Methyl-5-(4H-[1,2,4]triazol-3-yl)-phenyl]-hydrazine

2-Methyl-5-(4H-[1,2,4]triazol-3-yl)-phenylamine 4 (200 mg, 1.15 mmol, preparation) in dioxane (5 ml) and water (5 ml) at 0° C. was added conc. HCl (10 mL) followed by the addition of sodium nitrite (87 mg, 1.26 mmol). The reaction mixture was stirred at 0° C. for 40 min then a solution of tin(II)chloride (481 mg, 2.59 mmol) in conc. HCl (1 mL) was added dropwise. The mixture was stirred for 2 hr at 0° C. which resulted in a white solid precipitate. The solid was collected by filtration and identified as [2-methyl-5-(4H-[1,2,4]triazol-3-yl)-phenyl]-hydrazine 5 (261 mg) which was used without further purification. HPLC (4 minute gradient) t$_R$ 0.71 min; MS m/z 190.1 [M+H]$^+$.

E. {5-Amino-1-[2-methyl-5-(4H-[1,2,4]triazol-3-yl)-phenyl]-1H-pyrazol-4-yl-phenyl-methanone To a stirred solution of [2-methyl-5-(4H-[1,2,4]triazol-3-yl)-phenyl]-hydrazine 5 (261 mg, estimated 1.15 mmol) in EtOH (25 ml) was added 2-benzoyl-3-phenylamino-acrylonitrile 6 (285 mg, 1.15 mmol, preparation: Grothaus, J. Am. Chem. Soc. 58, 1334 (1936)) and the mixture was heated to 65-70° C. for 12-16 hours. It was cooled to room temperature, concentrated to give crude product. The mixture was then purified by flash chromatography, eluting with 1:1 EtOAc/Hexanes to give {5-amino-1-[2-methyl-5-(4H-[1,2,4]triazol-3-yl)-phenyl]-1H-pyrazol-4-yl}-phenyl-methanone 7 as a white solid (21 mg, 0.09 mmol, 8%). HPLC (4 minute gradient) t$_R$ 1.89 min; MS m/z 345.2 [M+H]$^+$; $^1$H NMR (DMSO-d$_6$, 500 MHz) δ 8.40 (d, 1 H), 8.24 (bs, 1 H), 8.14 (s, 1 H), 8.12 (d, 2 H), 7.34 (bs, 2 H), 7.92-7.85 (m, 4 H), 2.49 (s, 3 H) ppm; $^{13}$C NMR (DMSO-d$_6$, 500 MHz) δ152.9, 142.2, 140.5, 137.1, 132.7 132.2, 129.4, 128.8, 127.6, 126.0, 103.6, 18.1 ppm.

EXAMPLE 8

Preparation of 3-[5-amino-4-(3-[1,3]dioxolan-2-yl-benzoyl)-pyrazol-1-yl]-N-cyclopropyl-4-methyl-benzamide

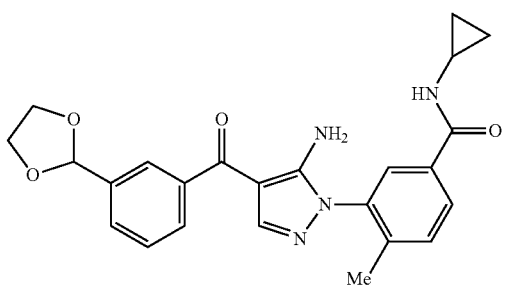

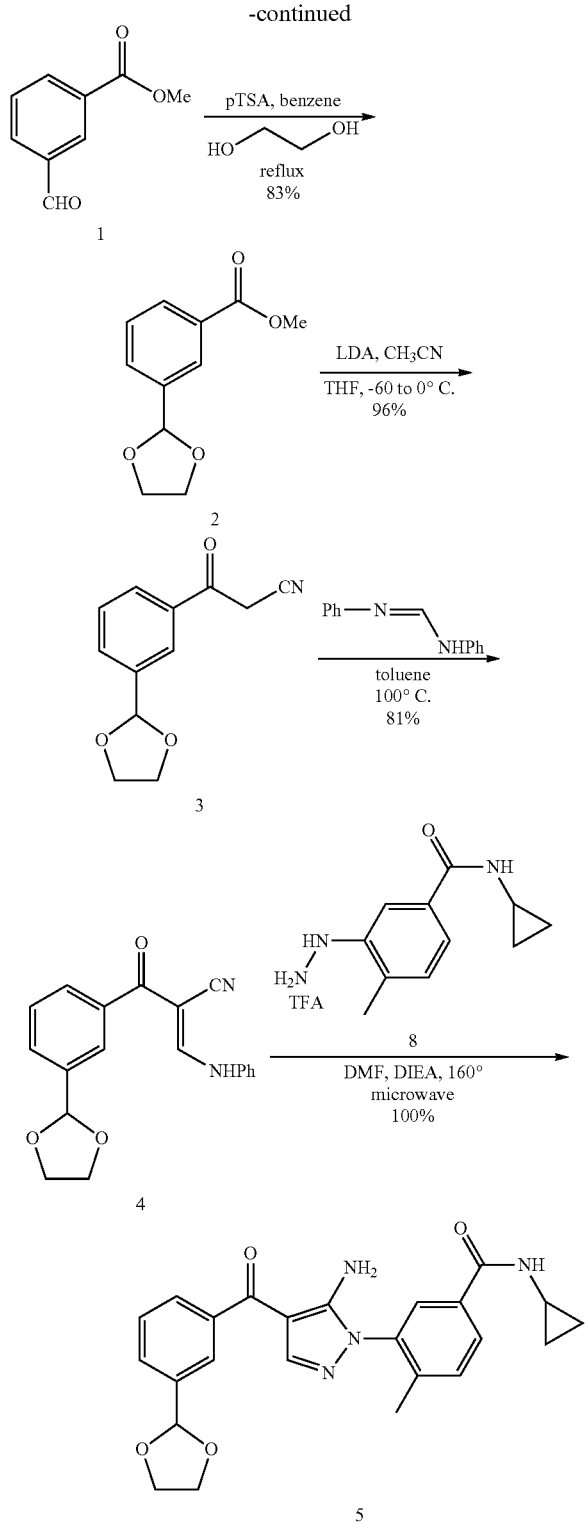

A. 3-[1,3]Dioxolan-2-yl-benzoic acid methyl ester

A mixture of 3-formyl-benzoic acid methyl ester 1 (6.09 g, 37.2 mmol), ethylene glycol (2.28 mL, 40.9 mmol) and p-toluenesulfonic acid monohydrate (0.78 g, 4.09 mmol) was refluxed overnight with Dean-Stark apparatus. TLC plate showed that all the starting material has disappeared. Poured the reaction mixture into a mixture of cooled aqueous NaHCO$_3$ and EtOAc. The organic layer was separated and dried over Na$_2$SO$_4$. Filtered and concentrated to give the crude product that was purified by silica gel chromatography (eluent: 8/1 hexane/ethyl acetate). The desired 3-[1,3]dioxolan-2-yl-benzoic acid methyl ester 2 was obtained as a colorless oil (6.41 g, 83%). $^1$H NMR (300 MHz, CDCl$_3$). $\delta$3.92 (s, 3H), 4.01 (m, 2 H), 4.13 (m, 2 H), 5.85 (s, 1 H), 7.46 (dd, J$_1$=J$_2$=7.7 Hz, 1H), 7.68 (dt, J$_1$=7.7 Hz, J$_2$=1.2 Hz, 1 H), 8.05 (dt, J$_1$=7.7 Hz, J$_2$=1.5 Hz, 1 H), 8.16 (dd, J$_1$=J$_2$=1.5 Hz, 1H) ppm.

B. 3-(3-[1,3]-Dioxolan-2-yl-phenyl)-3-oxo-propionitrile

To a mixture of acetonitrile (1.90 mL, 36.4 mmol) in THF (60 mL) was added LDA (1.8 M in THF, 33.9 mL) at −78° C. After stirring the mixture for 20 min at −78° C., 3-[1,3]dioxolan-2-yl-benzoic acid methyl ester 2 (6.06 g, 29.1 mmol) in THF (20 ml) was added all at once. The mixture was stirred at −78° C. for 1.5 h and then warmed to 0° C. and stirred for 1 h at this temperature. Saturated NH$_4$Cl was added to quench the reaction. The mixture was extracted with EtOAc three times. Organic layers were combined and dried over Na$_2$SO$_4$. Filtration and concentration in vacuo gave a residue that was purified by silica gel chromatography (CH$_2$Cl$_2$, then 20/1 CH$_2$Cl$_2$/ethyl acetate). The desired 3-(3-[1,3]dioxolan-2-yl-phenyl)-3-oxo-propionitrile 3 was obtained as a white solid (5.71 g, 96%). $^1$H NMR (300 MHz, CDCl$_3$) δ 4.12 (m, 6H), 5.86 (s, 1H), 7.55 (dd, J$_1$=J$_2$=7.7 Hz, 1H), 7.77 (d, J=7.7 Hz, 1 H), 7.92 (d, J=7.7 Hz, 1 H), 8.01 (s, 1H) ppm.

C. 2-(3-[1,3]-Dioxolan-2-yl-benzoyl)-3-phenylamino-acrylonitrile

The mixture of 3-(3-[1,3]dioxolan-2-yl-phenyl)-3-oxo-propionitrile 3 (3.07 g, 15.0 mmol) and N,N'-diphenylformamidine (4.10 g, 21 mmol) in toluene was heated to reflux for 18 h. Concentration in vacuo gave a residue that was purified by silica gel chromatography (hexanes/EtOAc, gradient from 3/1 to 2/1 then 1/1). The desired 2-(3-[1,3]dioxolan-2-yl-benzoyl)-3-phenylamino-acrylonitrile 4 was obtained as a yellow solid (3.88 g, 81%). $^1$H NMR (300 MHz, CDCl$_3$) δ 4.12 (m, 4H), 5.92 (s, 1H), 7.26 (m, 4H), 7.47 (m, 3H), 7.65 (d, J=7.7 Hz, 1H), 7.94 (dt, J$_1$=7.7 Hz, J$_2$=1.3 Hz, 1H), 8.05 (m, 2H) ppm.

D. 3-[5-Amino-4-(3-[1,3]dioxolan-2-yl-benzoyl)-pyrazol-1-yl]-N-cyclopropyl-4-methyl-benzamide A mixture of 2-(3-[1,3]dioxolan-2-yl-benzoyl)-3-phenylamino-acrylonitrile 4 (0.20 g, 0.62 mmol), N-cyclopropyl-3-hydrazino-4-methyl-benzamide, trifluoroacetic acid salt 8 (Example 6C, 0.20 g, 0.62 mmol) and DIEA (0.5 mL) in DMF (3 mL) was heated to 160° C. for 40 min using microwave. The mixture was then cooled down to room temperature and concentrated. The obtained residue was purified by silica gel chromatography (gradient from 1/4 Hexanes/EtOAc to 100% EtOAc). The desired 3-[5-amino-4-(3-[1,3]dioxolan-2-yl-benzoyl)-pyrazol-1-yl]-N-cyclopropyl-4-methyl-benzamide 5 was obtained as an orange solid (0.26 g, 100%). MS m/z 433.2 [M+H]$^+$; $^1$H NMR (300 MHz, CDCl$_3$) δ0.60 (m, 2H), 0.86 (m, 2H), 2.24 (s, 3H), 2.87 (m, 1H), 4.11 (m, 4H), 5.85

(m, 3H), 6.51 (bs, 1H), 7.43 (d, J=8.0 Hz, 1H), 7.45 (dd, J$_1$=J$_2$=7.6 Hz, 1H), 7.70 (m, 2H), 7.82 (m, 3H), 7.95 (s, 1H), 8.00 (s, 1H) ppm.

EXAMPLE 9

Preparation of 3-[5-amino-4-(3-formyl-benzoyl)-pyrazol-1-yl]-N-cyclopropyl-4-methyl-benzamide

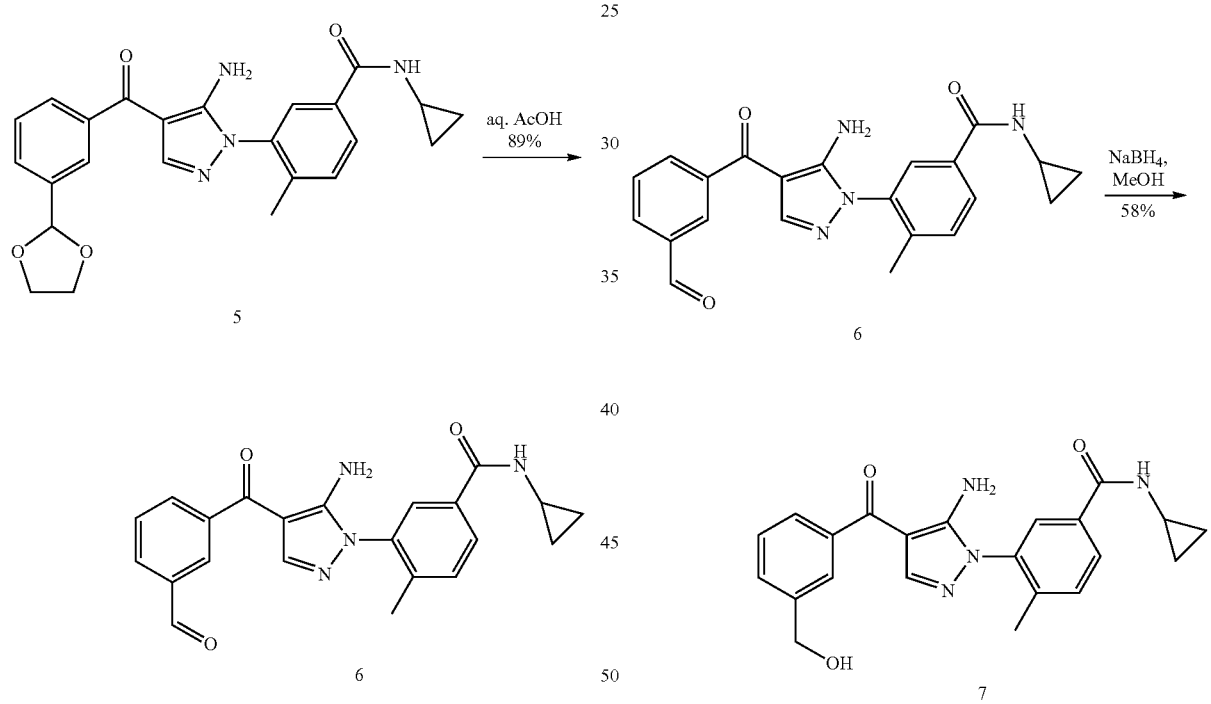

A mixture of 3-[5-amino-4-[1,3]dioxolan-2-yl-benzoyl)-pyrazol-1-yl]-N-cyclopropyl-4-methyl-benzamide 5 (Example 8, 1.14 g, 2.6 mmol) was suspended in aqueous AcOH (10 mL, 1.5 M in H$_2$O). Glacial AcOH was added dropwise until a clear solution was obtained. The reaction mixture was stirred at room temperature overnight. Evaporation of the solvent under reduced pressure to give a residue.

Toluene and EtOAc were added and the mixture was concentrated again to give the crude product that could be purified by silica gel chromatography (hexanes/EtOAc: 1/4). The desired 3-[5-amino-4-(3-formyl-benzoyl)-pyrazol-1-yl]-N-cyclopropyl-4-methyl-benzamide 6 was obtained as a yellow foamy solid (0.91 g, 89%). MS m/z 389.1 [M+H]$^+$; $^1$H NMR (300 MHz, CDCl$_3$) δ 0.61 (m, 2 H), 0.85 (dd, J$_1$=6.9 Hz, J$_2$=12.4 Hz, 2 H), 2.25 (s, 3 H), 2.87 (m, 1 H), 5.95 (brs, 2 H), 6.57 (brs, 1 H), 7.44 (d, J=8.0 Hz, 1 H), 7.67-7.78 (m, 4 H), 8.07 (s, 1 H), 8.09 (d, J=1.3 Hz, 1 H), 8.31 (s, 1 H), 10.12 (s, 1 H) ppm.

EXAMPLE 10

Preparation of 3-[5-amino-4-(3-hydroxymethyl-benzoyl)-pyrazol-1-yl]-N-cyclopropyl-4-methyl-benzamide

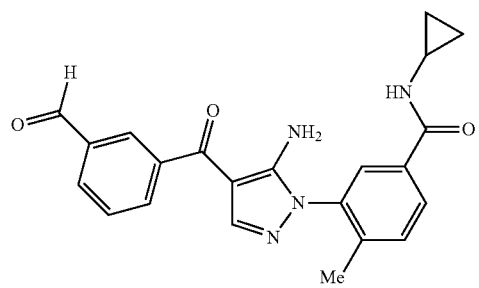

To a mixture of 3-[5-amino-4-(3-formyl-benzoyl)-pyrazol-1-yl]-N-cyclopropyl-4-methyl-benzamide 6 (38 mg, 0.098 mmol) in methanol (3 mL) was added NaBH$_4$ (11 mg, 0.29 mmol). The reaction mixture was stirred at room temperature for 1 h. Aqueous NaOH was added to quench the reaction and the mixture was extracted with ethyl acetate. The organic layer was separated and washed with water and saturated NaCl solution. The organic was then dried over Na$_2$SO$_4$, filtered and concentrated to give a residue that could be purified by silica gel chromatography (eluent: 1/4 hexanes/EtOAc). The desired 3-[5-amino-4-(3-hydroxymethyl-benzoyl)-pyrazol-1-yl]-N-cyclopropyl-4-methyl-benzamide 7 was obtained as a white solid (22 mg, 58%). MS m/z 391.2 [M+H]$^+$; $^1$H NMR (300 MHz, CDCl$_3$) δ 0.56 (m, 2H), 0.82

(m, 2H), 2.22 (s, 3H), 2.82 (m, 1H), 4.75 (s, 2H), 5.91 (brs, 2H), 6.75 (brs, 1H), 7.49 (m, 3H), 7.76 (m, 4H), 7.99 (s, 1H) ppm.

EXAMPLE 11

Preparation of 3-{5-amino-4-[3-(4-methyl-piperazin-1-ylmethyl)-benzoyl]-pyrazol-1-yl}-N-cyclopropyl-4-methyl-benzamide

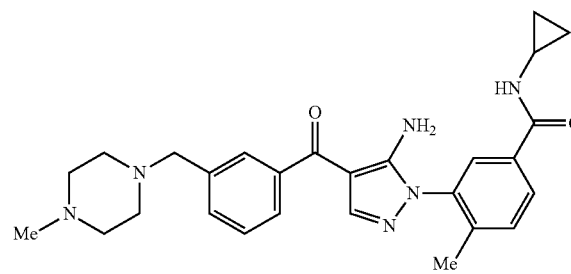

To a mixture of 3-[5-amino-4-(3-formyl-benzoyl)-pyrazol-1-yl]-N-cyclopropyl-4-methyl-benzamide 6 (Example 9, 1.0 eq) and 1-methyl-piperazine (1.09 eq) in equal volume of 1,2-dichloroethane and dichloromethane was added AcOH (0.96 eq) Sodium triacetoxyborohydride (1.5 eq) was then added. The reaction mixture was stirred at room temperature for 2 h. Aqueous NaOH was added to quench the reaction and the mixture was extracted with ethyl acetate. The organic layer was separated and washed with water and saturated NaCl solution. The organic layer was then dried over $Na_2SO_4$, filtered and concentrated to give a residue that could be purified by silica gel chromatography (eluent: 9/1 $CH_2Cl_2$/methanol then 9/1/0.05 $CH_2Cl_2$/MeOH/$NH_3H_2O$). Yield 67%. MS m/z 473.3 [M+H]$^+$; $^1$H NMR (300 MHz, CDCl$_3$) δ0.61 (m, 2H), 0.86 (m, 2H), 2.26 (s, 3H), 2.30 (s, 3H), 2.52 (brs, 8 H), 2.90 (m, 1H), 3.60 (s, 2H), 5.87 (brs, 1H), 6.30 (brs, 2H), 7.45 (m, 3H), 7.70 (m, 2H), 7.83 (m, 3H) ppm.

EXAMPLE 12

Preparation of 3-[5-amino-4-(3-morpholin-4-ylmethyl-benzoyl)-pyrazol-1-yl]-N-cyclopropyl-4-methyl-benzamide

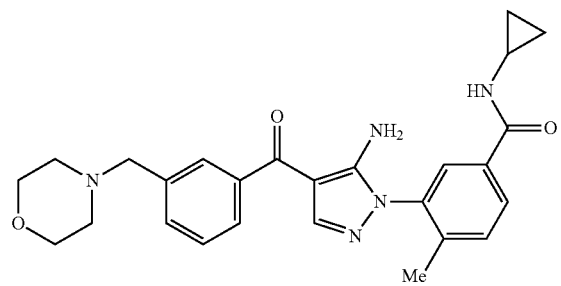

Similar procedure as in Example 11 except morpholine was used in place of 1-methyl-piperidine. Yield 45%. MS m/z 460.2 [M+H]$^+$; $^1$H NMR (300 MHz, CDCl$_3$) δ0.61 (m, 2H), 0.87 (m, 2H), 2.26 (s, 3H), 2.25 (s, 3H), 2.49 (m, 4H), 2.90 (m, 1H), 3.59 (s, 2H), 3.72 (t, J=4.4 Hz, 2H), 5.85 (brs, 2H), 6.35 (brs, 1H), 7.45 (m, 3H), 7.71 (m, 2H), 7.83 (m, 3H) ppm.

EXAMPLE 13

Preparation of 3-{5-Amino-4-[3-(2-morpholin-4-yl-ethoxy)-benzoyl]-pyrazol-1-yl}-N-cyclopropyl-4-methyl-benzamide

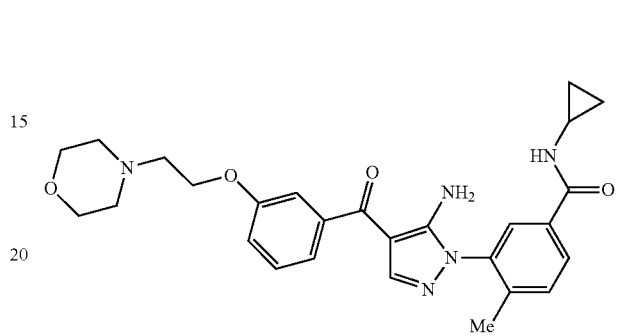

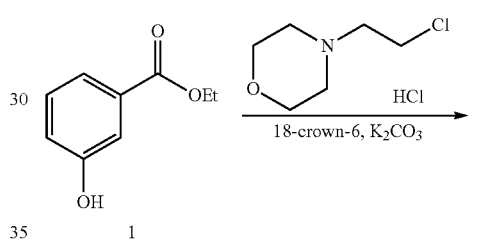

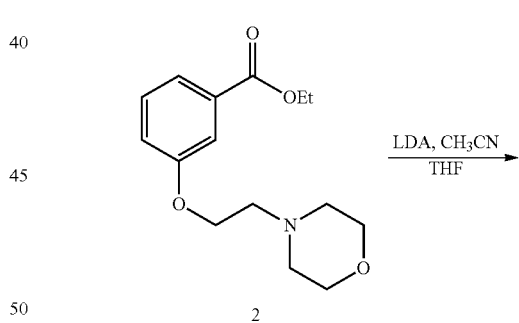

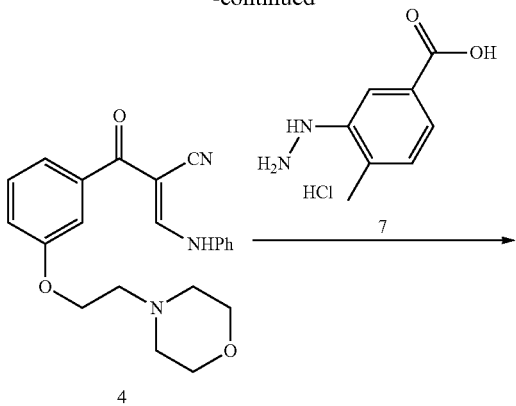

A. 3-(2-Morpholin-4-yl-ethoxy)-benzoic acid ethyl ester

Potassium carbonate (6.2 g, 45 mmol) was added to a DMF solution (100 mL) of ethyl 3-hydroxybenzoate 1 (3.32 g, 20 mmol), 4-(2-chloroethyl)-morpholine hydrochloride (5.58 g, 30 mmol) and 18-crown-6 (20 mg). The mixture was stirred at 100° C. for 20 hr. Solvent was removed in vacuo and the residue was suspended in ethyl acetate. The organic layer was washed by saturated NaHCO$_3$ solution and then brine, and was dried over sodium sulfate. Solvent was evaporated to yield the product 3-(2-morpholin-4-yl-ethoxy)-benzoic acid ethyl ester 2 as a light yellow oil (5.3 g, 95%). HPLC (4 minute gradient) $t_R$ 1.47 min; MS m/z 280.2 [M+H]$^+$.

B. 3-[3-(2-Morpholin-4-yl-ethoxy)-phenyl]-3-oxo-propionitrile

Lithium diisopropylamide (16.4 mL, 29.6 mmol, 1.8M solution in heptane/tetrahydrofuran/ethylbenzene) was added dropwise to the solution of acetonitrile (1.2 g, 29.6 mmol) in dry tetrahydrofuran (20 mL) at −78° C. in nitrogen atmosphere. After stirring the reaction mixture for 30 min, a solution of 3-(2-morpholin-4-yl-ethoxy)-benzoic acid ethyl ester 2 (5.5 g, 19.7 mmol) in dry tetrahydrofuran (20 mL) was added dropwise and stirred at −78° C. for 1 hr. Water was added and the aqueous layer was separated and acidified with dilute hydrochloric acid to pH 7. The product was extracted into ethyl acetate. The organic layer was washed with brine and then dried over sodium sulfate. The solvent was removed in vacuo to give 3-[3-(2-morpholin-4-yl-ethoxy)-phenyl]-3-oxo-propionitrile 3 as a light yellow oil (4.8 g). HPLC (4 minute gradient) $t_R$ 1.11 min; MS m/z 275.2 [M+H]$^+$.

C. 2-[3-(2-Morpholin-4-yl-ethoxy)-benzoyl]-3-phenylamino-acrylonitrile

A mixture of 3-[3-(2-morpholin-4-yl-ethoxy)-phenyl]-3-oxo-propionitrile 3 (4.8 g, 17.5 mmol) and N,N-diphenylformamidine (1.2 g, 24.5 mmol) in dry toluene (100 mL) was heated at 110° C. for 3 hr under a nitrogen atmosphere. Solvent was removed and the oily residue was subjected to silica gel column chromatography (gradient 100% EtOAc to 100/10/1 EtOAc/MeOH/Et$_3$N) to yield 2-[3-(2-morpholin-4-yl-ethoxy)-benzoyl]-3-phenylamino-acrylonitrile 4 light yellow solid (3.1 g, 47%). HPLC (4 minute gradient) $t_R$ 2.04 min; MS m/z 378.2 [M+H]$^+$.

D. 3-{5-Amino-4-[3-(2-morpholin-4-yl-ethoxy)-benzoyl]-pyrazol-1-yl}-4-methyl-benzoic acid 2-[3-(2-Morpholin-4-yl-ethoxy)-benzoyl]-3-phenylamino-acrylonitrile 4 (189 mg, 0.5 mmol) and 3-hydrazino-4-methyl-benzoic acid hydrochloride 7 (Example 3A 152 mg, 0.75 mmol) were suspended in N,N-dimethylformamide (5 mL) and heated at 160° C. using microwave for 30 min. Solvent was evaporated and the residue was subjected to column chromatography (EtOAc~MeOH). Product 3-{5-amino-4-[3-(2-morpholin-4-yl-ethoxy)-benzoyl]-pyrazol-1-yl}-4-methyl-benzoic acid 5 was obtained as a light yellow solid (200 mg). HPLC (4 minute gradient) $t_R$ 1.60 min; MS m/z 451.2 [M+H]$^+$.

E. 3-{5-Amino-4-[3-(2-morpholin-4-yl-ethoxy)-benzoyl]-pyrazol-1-yl}-N-cyclopropyl-4-methyl-benzamide A mixture of 3-{5-amino-4-[3-(2-morpholin-4-yl-ethoxy)-benzoyl]-pyrazol-1-yl}-4-methyl-benzoic acid 5 (400 mg, 0.89 mmol), cyclopropylamine (0.89 mmol), EDCI (340 mg, 1.78 mmol), HOBt (272 mg, 1.78 mmol) and diisopropylethylamine (459 mg, 3.56 mmol) in dry N,N-dimethylformamide (10 mL) was stirred at room temperature for 18 h. Solvent was evaporated and the residue was suspended in EtOAc and washed by water, saturated NaHCO$_3$ solution and brine. The organic layer was dried over sodium sulfate. Product 3-{5-amino-4-[3-(2-morpholin-4-yl-ethoxy)-benzoyl]-pyrazol-1-yl}-N-cyclopropyl-4-methyl-benzamide 6 was obtained as a light yellow solid (45 mg, 10%) after purification by column chromatography (100/10/1 EtOAc/MeOH/Et₃N). HPLC (4 minute gradient) $t_R$ 1.69 min; MS m/z 490.24 [M+H]⁺.

EXAMPLE 14

Preparation of 3-[5-amino-4-(3-benzyloxy-benzoyl)-pyrazol-1-yl]-N-cyclopropyl-4-methyl-benzamide

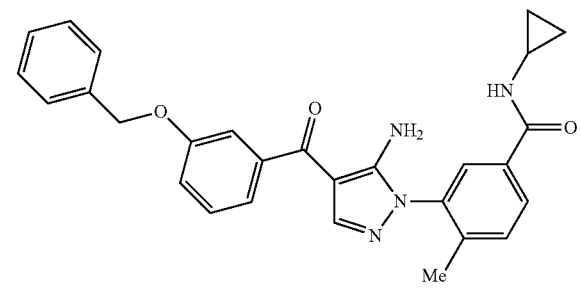

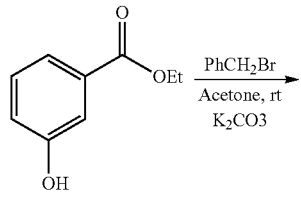

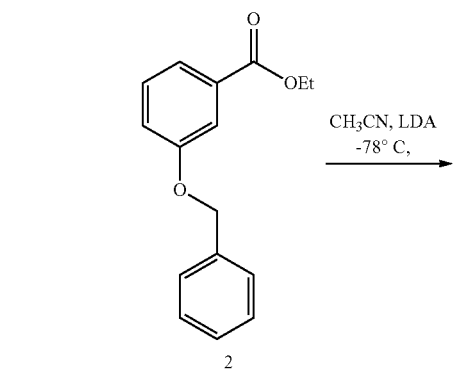

A. 3-Benzyloxy-benzoic acid ethyl ester

K₂CO₃ (6.9 g, 50 mmol) and 18-crown-6 were added to a solution of 3-hydroxy-benzoic acid ethyl ester 1 (8.3 g, 50 mmol) in acetone (100 mL) and the mixture was stirred at room temperature for 18 h. Solid was removed by filtration. Filtrate was concentrated in vacuo to give 3-benzyloxy-benzoic acid ethyl ester 2 as a colorless liquid.

B. 3-(3-Benzyloxy-phenyl)-3-oxo-propionitrile

LDA (1.8 M, 100 mmol, 56 mL) was added to a solution of acetonitrile (4.1 g, 100 mmol) in THF (100 mL, dry) at −78° C. under nitrogen. The mixture was stirred at −78° C. for 30 min. A solution of 3-benzyloxy-benzoic acid ethyl ester 2 in 50 mL anhydrous THF was then added dropwise to the reaction mixture. The mixture was stirred at −78° C. for 1 h before water was added. The organic phase was separated. The aqueous phase was acidified by hydrochloride acid until pH~2, and was extracted by EtOAc. THF and EtOAc layers were combined and washed by water, brine, dried over Na₂SO₄. Solvent was removed in vacuo and the solid residue was triturate with Et₂O and dried in vacuo. The desired product 3-(3-benzyloxy-phenyl)-3-oxo-propionitrile 3 was obtained as a light brown solid (11.0 g, 87%).

C. 2-(3-Benzyloxy-benzoyl)-3-dimethylamino-acrylonitrile

N,N-Dimethylformamide dimethyl acetal (10 mL) was added to the solution of 3-(3-benzyloxy-phenyl)-3-oxo-propionitrile 3 (2.5 g, 10 mmol.) in DMF (20 mL, dry) and the mixture was stirred at 100° C. for 3 hr. Solvent was removed and the residue was purified by silica gel column chromatography (EtOAc as eluent). Product 2-(3-benzyloxy-benzoyl)-3-dimethylamino-acrylonitrile 4 was obtained as a light yellow solid (2.6 g, 90%).

D. 3-[5-Amino-4-(3-benzyloxy-benzoyl)-pyrazol-1-yl]-N-cyclopropyl-4-methyl-benzamide 2-(3-Benzyloxy-benzoyl)-3-dimethylamino-acrylonitrile 4 (147 mg, 0.5 mmol) and N-cyclopropyl-3-hydrazino-4-methyl-benzamide, trifluoroacetic acid salt 8 (Example 6C, 240 mg, 0.75 mmol) were dissolved in DMF (5 mL) and was heated at 160° C. in microwave oven for 30 min. Solvent was removed and the residue was purified by column (3:1 EtOAc/hexanes). Product 3-[5-amino-4-(3-benzyloxy-benzoyl)-pyrazol-1-yl]-N-cyclopropyl-4-methyl-benzamide 6 was obtained as a light yellow solid (120 mg, 52%).

EXAMPLE 15

Preparation of 3-[5-amino-4-(3-hydroxy-benzoyl)-pyrazol-1-yl]-N-cyclopropyl-4-methyl-benzamide

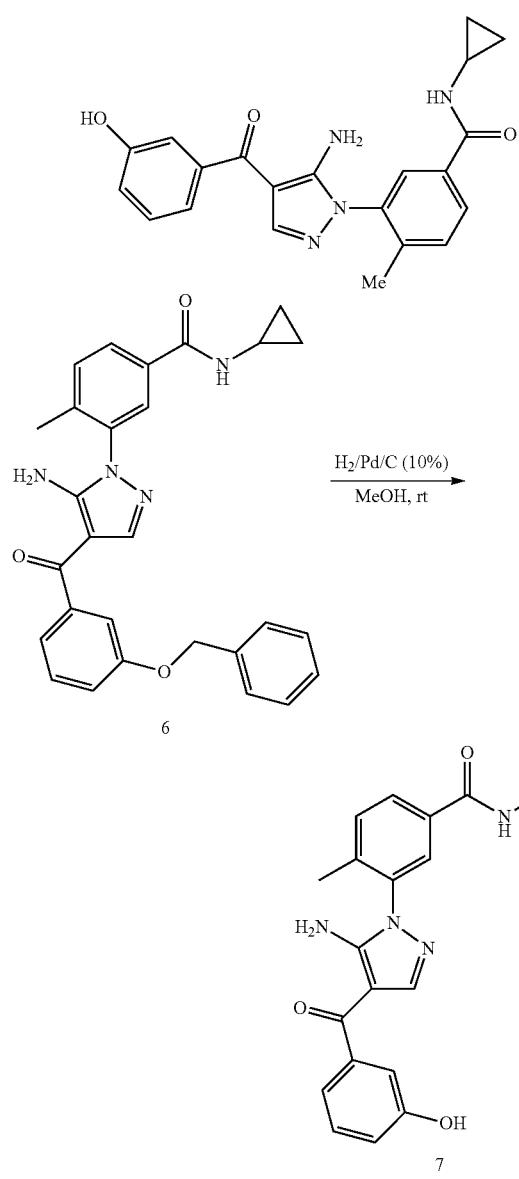

3-[5-Amino-4-(3-benzyloxy-benzoyl)-pyrazol-1-yl]-N-cyclopropyl-4-methyl-benzamide 6 (200 mg, 0.43 mmol) was dissolved in MeOH (10 mL). Catalyst 10% palladium on activated carbon (dry) was added and was stirred in an atmosphere of hydrogen for 2 h. The catalyst was removed by filtration and solvent was removed in vacuo. Product 3-[5-amino-4-(3-hydroxy-benzoyl)-pyrazol-1-yl]-N-cyclopropyl-4-methyl-benzamide 7 was obtained as a light yellow solid (140 mg, 87%).

EXAMPLE 16

Preparation of 3-[5-amino-4-(4-methyl-benzoyl)-pyrazol-1-yl]-N-cyclopropyl-4-methyl-benzamide

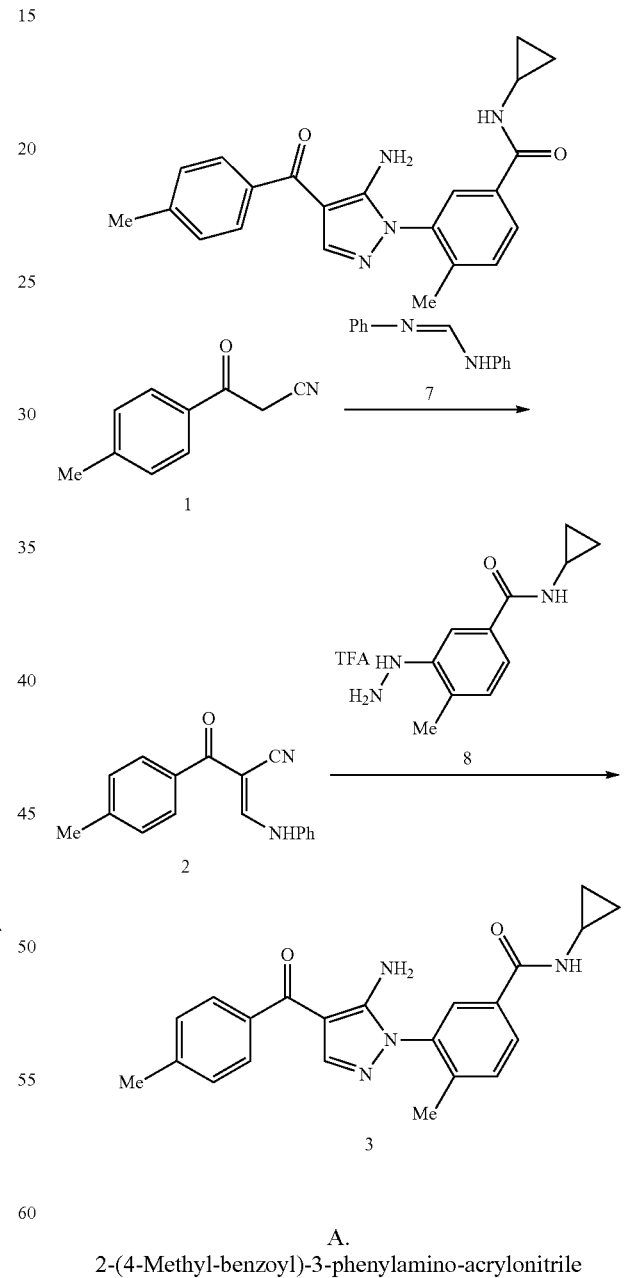

A. 2-(4-Methyl-benzoyl)-3-phenylamino-acrylonitrile

A mixture of 4-toluoylacetonitrile 1 (4.0 g, 25 mmol) and N,N-diphenylformamidine (4.9 g, 25 mmol) in dry toluene (50 mL) was heated at 85° C. for 16 h under nitrogen. The mixture was cooled to room temperature and 170 mL of hexanes was added. A yellow precipitate was formed after the mixture was stirred at room temperature for 5 minutes. The solid was collected of a fritted flask, and was washed with hexanes to give pure 2-(4-methyl-benzoyl)-3-phenylamino-acrylonitrile 2 (4.5 g, 68%). $^1$H NMR (300 MHz, CDCl$_3$) δ 8.04 (d, J=13.0, 1 H), 7.86 (d, J=7.9, 2 H), 7.42 (t, J=7.4, 1 H), 7.28-7.25 (m, 3 H), 7.19 (d, J=7.6, 1 H), 2.41 (s, 3 H) ppm.

B. 3-[5-amino-4-(4-methyl-benzoyl)-pyrazol-1-yl]-N-cyclopropyl-4-methyl-benzamide A mixture of 2-(4-methyl-benzoyl)-3-phenylamino-acrylonitrile 2 (205 mg, 0.78 mmol), N-cyclopropyl-3-hydrazino-4-methyl-benzamide trifluoroacetic acid salt 7 (Example 6C, 250 mg, 0.78 mmol) and diisopropylethylamine (0.14 mL, 0.78 mmol) in 8 mL of ethanol was heated at 65° C. in for 18 h. Solvent was removed and the residue was purified by silica gel column chromatography (EtOAc/hexanes, gradient from 1/3 to 3/1). The product can be further purified by trituration with Et$_2$O to give 3-[5-amino-4-(4-methyl-benzoyl)-pyrazol-1-yl]-N-cyclopropyl-4-methyl-benzamide 3 as a white solid (64 mg, 22%). HPLC (4 minute gradient) t$_R$ 2.26 min; MS m/z 375.2 [M+H]$^+$; $^1$H NMR (300 MHz, DMSO-d$_6$) δ 8.51 (d, J=4.0, 1 H), 7.93 (d, J=8.0, 1 H), 8.51 (d, J=4.0, 1 H), 7.83 (bs, 1 H), 7.82 (s, 1 H), 7.70 (d, J=7.9, 2H), 7.53 (d, J=8.0, 1 H), 7.35 (d, J=7.9, 2 H), 6.95 (bs, 2 H), 2.86 (m, 1 H), 2.40 (s, 3 H), 2.14 (s, 3 H), 0.68 (m, 2 H), 0.56 (m, 2 H); $^{13}$C NMR (300 MHz, DMSO-d$_6$) δ 187.4, 166.0, 151.9, 141.3, 141.1, 139.2, 136.9, 135.6, 133.0, 131.2, 129.1, 128.3, 128.0, 126.5, 102.6, 23.1, 21.0, 17.2, 5.6 ppm.

EXAMPLE 17

Preparation of 3-(5-amino-4-benzoyl-imidazol-1-yl)-N-cyclopropyl-4-methyl-benzamide

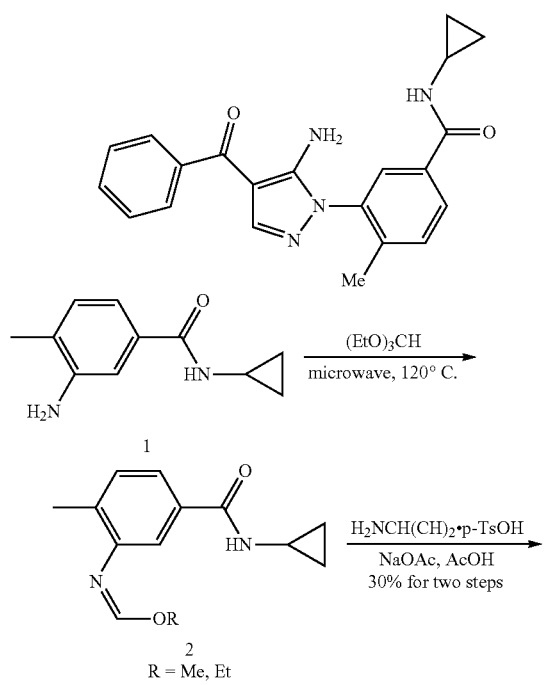

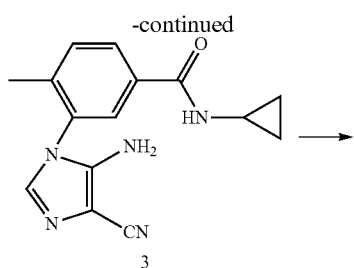

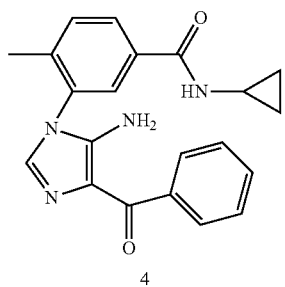

A. 3-(5-Amino-4-cyano-imidazol-1-yl)-N-cyclopropyl-4-methyl-benzamide

A mixture of 3-amino-N-cyclopropyl-4-methyl-benzamide 1 (380 mg, 2.0 mmol) in 2.0 mL of triethyl orthoformate was stirred at 120° C. in microwave for 20 minutes. The solvent was removed under reduced pressure. The residue was dissolved in 5 mL of acetic acid and then was added aminomalononitrile p-toluenesulfonate (506 mg, 2.0 mmol) and sodium acetate (164 mg, 2.0 mmol). The reaction mixture was stirred at room temperature overnight. The mixture was diluted with 20 mL of water and then its pH was adjusted to 8.0 by aqueous NaOH. The resulting mixture was extracted with EtOAc (3×50 mL). The combined organic layers were washed with water (10 mL) and brine (10 mL), dried over MgSO$_4$, filtered and concentrated in vacuo evaporated. The residue was purified by silica gel column chromatography (10/1, methylene chloride:methanol) to give 3-(5-amino-4-cyano-imidazol-1-yl)-N-cyclopropyl-4-methyl-benzamide 3 as a colorless solid (170 mg, 30%). HPLC (4 minute gradient) t$_R$=1.39 min; MS m/z 282 [M+H].

B. 3-(5-Amino-4-benzoyl-imidazol-1-yl)-N-cyclopropyl-4-methyl-benzamide

To a solution of 3-(5-amino-4-cyano-imidazol-1-yl)-N-cyclopropyl-4-methyl-benzamide 3 (56.4 mg, 0.2 mmol) in dry THF (10 ml) under nitrogen was added phenylmagnesium bromide (1M, 1 mL) at room temperature. After 1 h, HCl solution (3N, 10 ml) was added and the mixture was stirred overnight. The solution was neutralized with dilute aqueous NaOH. The mixture was extracted with ethyl acetate (100 mL x2), washed with water and dried over Na$_2$SO$_4$. Evaporation of the solvent gave a residue which was purifiedd by HPLC to give 3-(5-Amino-4-benzoyl-imidazol-1-yl)-N-cyclopropyl- 4-methyl-benzamide as a while solid (56 mg, 78%). LCMS (4 minute gradient) $t_R$=2.07 min; MS m/z 361.17 [M+H]$^+$

EXAMPLE 18

Preparation of 3-(5-Amino-4-cyclohexanecarbonyl-imidazol-1-yl)-N-cyclopropyl-4-methyl-benzamide

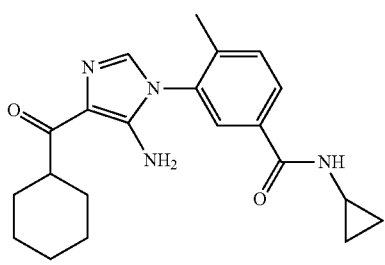

Similar procedure as in Example 17 except cyclohexylmagnesium bromide was used in place of phenyl magnesium bromide. HPLC (4 minute 10-90 gradient) $t_R$ 2.01 min; MS m/z 367.29 [M+H]$^+$.

EXAMPLE 19

Preparation of 3-(5-Amino-4-cyclopentanecarbonyl-imidazol-1-yl)-N-cyclopropyl-4-methyl-benzamide

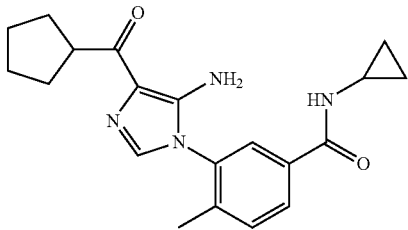

Similar procedure as in Example 17 except cyclopentylmagnesium bromide was used in place of phenyl magnesium bromide. HPLC (4 minute 10-90 gradient) $t_R$ 1.92 min; MS m/z 353.22 [M+H]$^+$.

EXAMPLE 20

Preparation of 3-(5-Amino-4-phenylacetyl-imidazol-1-yl)-N-cyclopropyl-4-methyl-benzamide

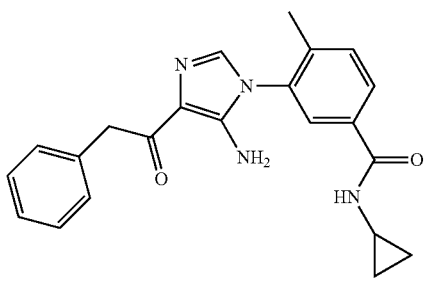

Similar procedure as in Example 17 except benzylmagnesium bromide was used in place of phenyl magnesium bromide. HPLC (4 minute 10-90 gradient) $t_R$ 2.14 min; MS m/z 375.20 [M+H]$^+$.

EXAMPLE 21

Preparation of 3-[5-Amino-4-(3-isopropylcarbamoyl-benzoyl)-imidazol-1-yl]-N-cyclopropyl-4-methyl-benzamide

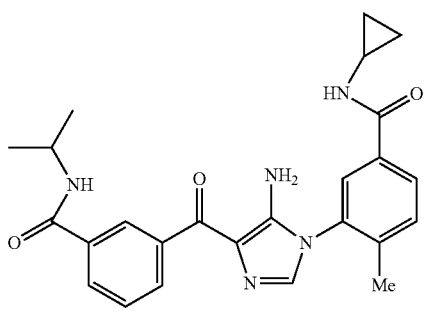

-continued

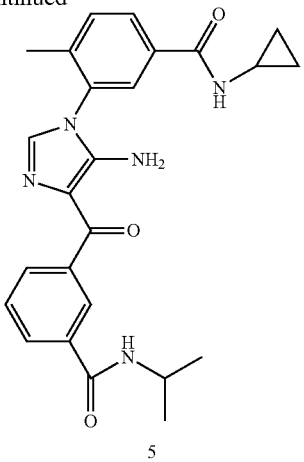

5

A. 3-[5-Amino-1-(5-cyclopropylcarbamoyl-2-methyl-phenyl)-1H-imidazole-4-carbonyl]-benzoic acid To a solution of 3-iodobenzoic acid tert-butyl ester (4.6 g) in THF (20 mL) at −40° C. under $N_2$ was added cyclohexylmagnesium chloride (2M in THF, 8.5 mL). The solution was kept at −40° C. to 0° C. for 20 min., when 3-(5-amino-4-cyano-imidazol-1-yl)-N-cyclopropyl-4-methyl-benzamide was added and the reaction was kept at rt for 1 h. Then HCl (4 M, 10 mL) was added and the mixture was heated at 40 to 45° C. overnight. The mixture was neutralized with $K_2CO_3$ solution and extracted with EtOAc (2×100 mL) and the combined organics dried over $Na_2SO_4$, and concentrated. Purification of the crude product by column chromatography (EtOAc: MeOH=6:1) gave the desired product (0.46 g).

B 3-[5-Amino-4-(3-isopropylcarbamoyl-benzoyl)-imidazol-1-yl]-N-cyclopropyl-4-methyl-benzamide A solution of acid 4 (160 mg), EDCI (90 mg), and N-hydroxysucinimide (53 mg) in DMF (2 mL) was reacted at rt overnight. Water (12 ml) was added and the solution was extracted with EtOAc (15 mL×2), dried over $Na_2SO_4$. Evaporation of solvent gave a residue, into which EtOAc (4 mL) and 2-propylamine (1.2 eq) was added. The reaction was kept at rt for 1 h., then concentrated and the crude product purified by column chromatography to give the desired product (yield: 80%). HPLC (4 minute gradient) $t_R$=2.00 min; MS m/z 446.19 $[M+H]^+$.

EXAMPLE 22

Preparation of 3-{5-Amino-4-[3-(2-dimethylaminoethylcarbamoyl)-benzoyl]-imidazol-1-yl}-N-cyclopropyl-4-methyl-benzamide

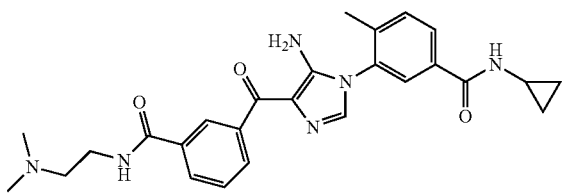

Similar procedure as in Example 21 except 2-dimethylaminoethylamine was used in place of isopropylamine. HPLC (4 minute 10-90 gradient) $t_R$ 2.18 min; MS m/z 475.15 $[M+H]^+$.

EXAMPLE 23

Preparation of 3-[5-Amino-4-(3-ethylcarbamoyl-benzoyl)-imidazol-1-yl]-N-cyclopropyl-4-methyl-benzamide

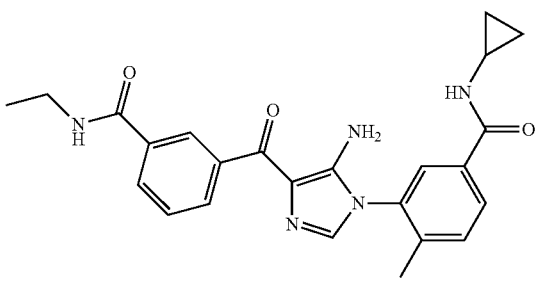

Similar procedure as in Example 21 except ethylamine was used in place of isopropylamine. HPLC (4 minute 10-90 gradient) $t_R$ 1.70 min; MS m/z 432.18 $[M+H]^+$.

EXAMPLE 24

Preparation of 3-[5-Amino-4-(3-methylcarbamoyl-benzoyl)-imidazol-1-yl]-N-cyclopropyl-4-methyl-benzamide

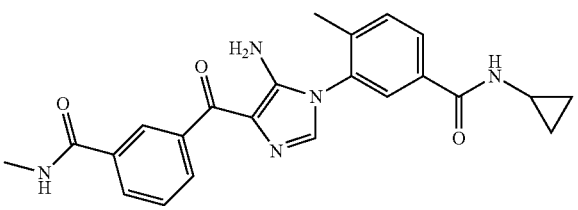

Similar procedure as in Example 21 except methylamine was used in place of isopropylamine. HPLC (4 minute 10-90 gradient) $t_R$ 1.61 min; MS m/z 418.15 $[M+H]^+$.

EXAMPLE 25

Preparation of 3-[5-Amino-4-(3-cyclopropylcarbamoyl-benzoyl)-imidazol-1-yl]-N-cyclopropyl-4-methyl-benzamide

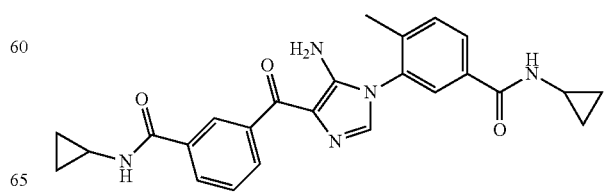

Similar procedure as in Example 21 except cyclopropylamine was used in place of isopropylamine. HPLC (4 minute 10-90 gradient) $t_R$ 1.74 min; MS m/z 444.14 [M+H]$^+$.

EXAMPLE 26

Preparation of 3-[5-Amino-4-(3-cyclopentylcarbamoyl-benzoyl)-imidazol-1-yl]-N-cyclopropyl-4-methyl-benzamide

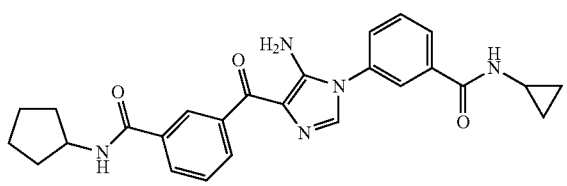

Similar procedure as in Example 21 except cyclopentylamine was used in place of isopropylamine. HPLC (4 minute 10-90 gradient) $t_R$ 1.95 min; MS m/z 472.24 [M+H]$^+$.

EXAMPLE 27

Preparation of 3-[5-Amino-4-[3-(morpholine-4-carbonyl)-benzoyl]-imidazol-1-yl]-N-cyclopropyl-4-methyl-benzamide

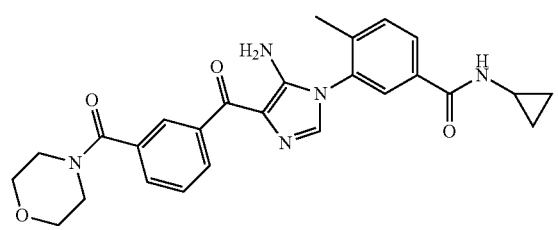

Similar procedure as in Example 21 except morpholine was used in place of isopropylamine. HPLC (4 minute 10-90 gradient) $t_R$ 1.67 min; MS m/z 474.17 [M+H]$^+$.

EXAMPLE 28

Preparation of 3-{5-Amino-4-[3-(cyclopropylmethyl-carbamoyl)-benzoyl]-imidazol-1-yl}-N-cyclopropyl-4-methyl-benzamide

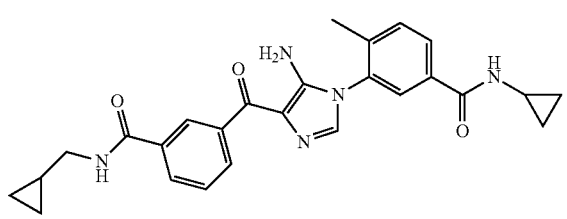

Similar procedure as in Example 21 except cyclopropylmethylamine was used in place of isopropylamine. HPLC (4 minute 10-90 gradient) $t_R$ 1.86 min; MS m/z 458.23 [M+H]$^+$.

EXAMPLE 29

Preparation of 3-[5-Amino-4-(tetrahydro-pyran-4-carbonyl)-imidazol-1-yl]-N-cyclopropyl-4-methyl-benzamide

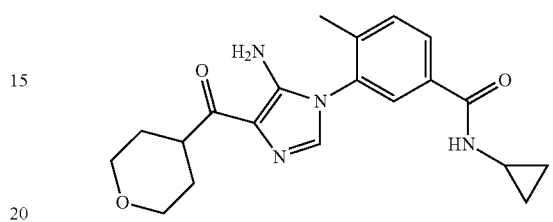

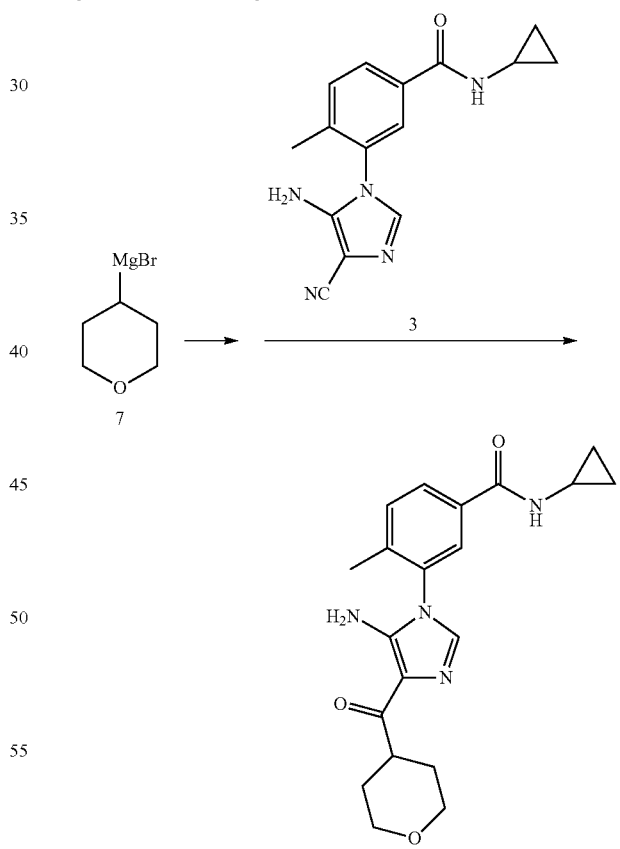

A. 4-bromo-tetrahydro-pyran

Tetrahydro-4H-pyran-4-ol (1.0 g, 10 mmol), carbon tetrabromide (3.6 g, 1 mmol) and triphenylphosphine (3.1 g, 12 mmol) were dissolved in CH$_2$Cl$_2$ (25 mL) and stirred at room

73 temperature overnight. The crude reaction mixture was concentrated then purified by flash chromatography on silica gel (EtOAc:Hexanes=1:20), and the product was obtained as a colorless oil (1.4 g, 87%).

B. 3-[5-Amino-4-(tetrahydro-pyran-4-carbonyl)-imidazol-1-yl]-N-cyclopropyl-4-methyl-benzamide A solution of 4-bromo-tetrahydro-pyran (0.82 g, 5 mmol) in dry THF (10 mL) was added dropwise to the suspension of magnesium (132 mg, 5.5 mmol) and iodine (25 mg) in dry THF (20 mL) at 50° C. under $N_2$. The mixture was stirred for 30 min after addition at 50° C., then cooled to room temperature. Then a THF (10 mL) solution of 3-(5-amino-4-cyano-imidazol-1-yl)-N-cyclopropyl-4-methyl-benzamide (90 mg, 0.32 mmol) was added to the reaction mixture and it was stirred at room temperature for 3 h then quenched with HCl (2N) and stirred at room temperature overnight. The pH of the solution was adjusted pH ~8 with saturated aqueous $K_2CO_3$ was and it was extracted with EtOAc. The organic layer was washed by water and brine, dried over $Na_2SO_4$, and concentrated. The crude product was purified by column chromatography on silical gel (EtOAc~EtOAc:MeOH:$Et_3N$=100:10:1), and the product was obtained as a beige solid (35 mg, 30%). HPLC (4 minute gradient) $t_R$=3.05 min; MS m/z 369.18 $[M+H]^+$.

EXAMPLE 30

Preparation of 3-(5-amino-4-benzoyl-3-methoxy-pyrazol-1-yl)-N-cyclopropyl-4-methyl-benzamide

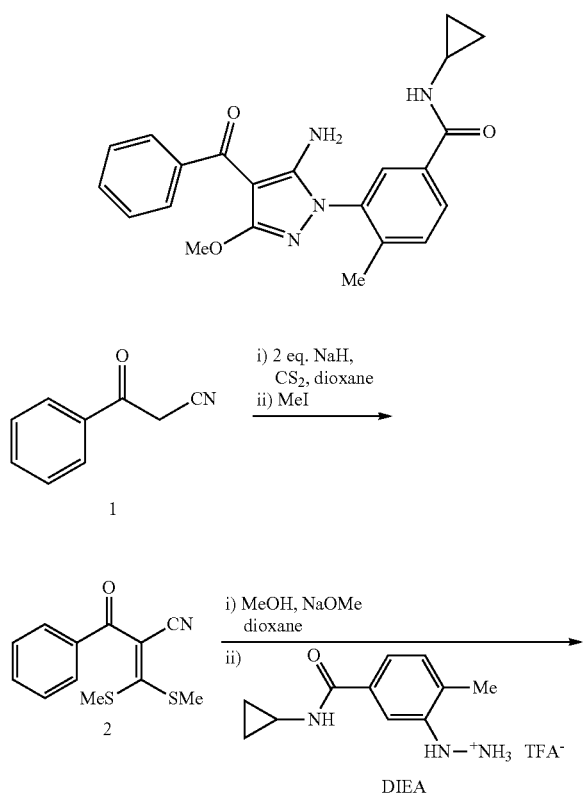

74

-continued

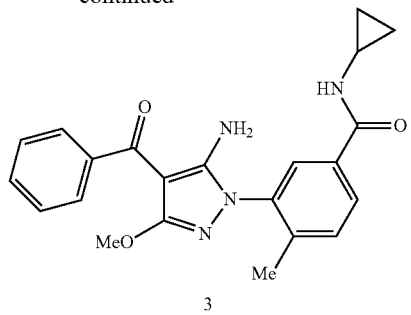

3

A. 2-Benzoyl-3,3-bis-methylsulfanyl-acrylonitrile

To a stirred solution of benzoylacetonitrile 1 (7.50 g, 51.7 mmol) in THF (100 ml) at 0° C. was added dry sodium hydride (2.61 g, 103 mmol). The resulting suspension was stirred at 0° C. for 45 min before carbon disulfide (2.39 ml, 54.8 mmol) was added. The reaction was then stirred at room temperature for 2 h. The resulting red solution was cooled to 0° C., and iodomethane (6.75 ml, 109 mmol) was added. The mixture was stirred at room temperature for 18 h. Solvent was removed in vacuo. The residue was diluted in ether and was washed with brine. The aqueous layer was extracted twice with ether. The combined organic layers were washed twice with 5% sodium thiosulfate, and then brine. The organic layer was dried over $MgSO_4$, filtered and concentrated to give 2-benzoyl-3,3-bis-methylsulfanyl-acrylonitrile 2 as a yellow powder (9.5 g, 74%). The product was used in the next step without further purification.

B. 3-(5-Amino-4-benzoyl-3-methoxy-pyrazol-1-yl)-N-cyclopropyl-4-methyl-benzamide Sodium (317 mg, 13.8 mmol) was added to methanol (10 ml) at 0° C. After all of the sodium was consumed, this solution of sodium methoxide was added to a stirred solution of 2-benzoyl-3,3-bis-methylsulfanyl-acrylonitrile 2 (3.12 g, 12.5 mmol) in dioxane (30 ml) at 0° C. The reaction was warmed to room temperature and then heated to 80° C. for 3 h. The dark red solution was cooled to room temperature and was added to a solution of N-cyclopropyl-3-hydrazino-4-methyl-benzamide trifluoroacetic acid salt (4.00 g, 12.5 mmol) and diisopropylethylamine (2.18 ml, 12.5 mmol) in dioxane (15 ml). The mixture was heated to 85° C. for another 6 h. The solvent was removed in vacuo. The residue was diluted in saturated $NaHCO_3$ solution and was extracted three times with EtOAc. Combined organic layers were dried over $MgSO_4$, filtered and concentrated. The crude product was purified by flash chromatography ($SiO_2$, gradient of 75 to 90% EtOAc/hexanes) and recrystallization from EtOAc to give the desired 3-(5-amino-4-benzoyl-3-methoxy-pyrazol-1-yl)-N-cyclopropyl-4-methyl-benzamide 3 as a white solid (950 mg, 19%). HPLC (4 minute 10-90 gradient) $t_R$ 2.33 min; MS m/z 391.2 $[M+H]^+$; $^1$H NMR (DMSO-$d_6$, 300 MHz) δ 8.50 (d, J=3.4, 1 H), 7.91 (d, J=7.9, 1 H), 7.85 (s, 1 H), 7.61 (d, J=6.9, 2 H), 7.41-7.62 (m, 4 H), 7.00 (bs, 2 H), 3.66 (s, 3 H), 2.87 (m. 1 H), 2.20 (s, 3 H), 0.70 (m, 2 H), 0.85 (m, 2 H) ppm; $^{13}$C NMR (DMSO-$d_6$, 125 MHz) δ 188.1, 166.0, 159.5, 152.8, 140.1, 139.5, 135.5, 132.9, 131.1, 130.6, 128.1, 128.0, 127.4, 126.8, 91.0, 55.2, 23.0, 15.1, 5.6 ppm.

EXAMPLE 31

Preparation of 3-(5-amino-4-benzoyl-3-ethoxy-pyrazol-1-yl)-N-cyclopropyl-4-methyl-benzamide

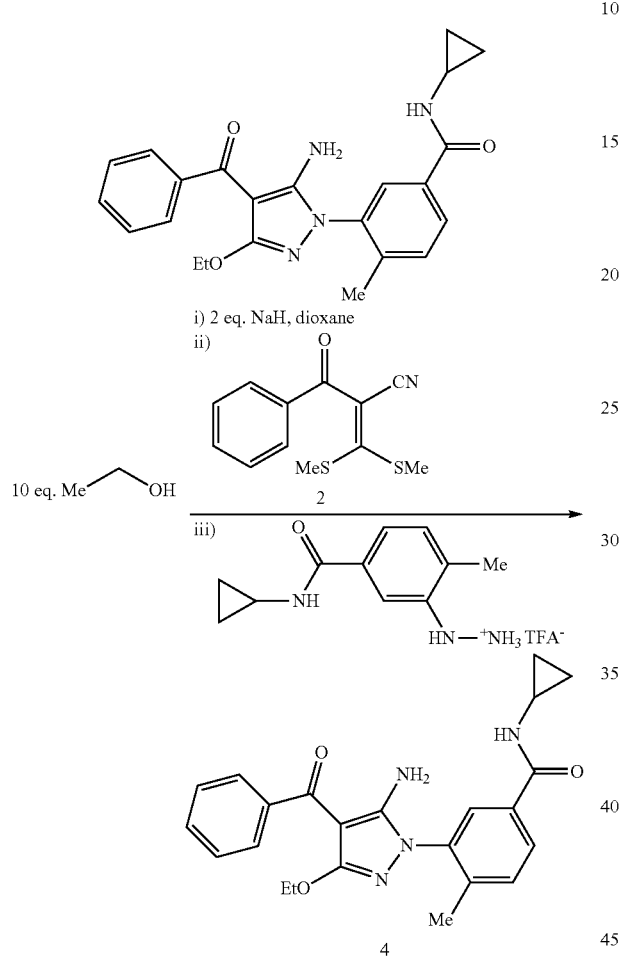

Ethanol (0.47 ml, 8.0 mmol) was added to a suspension of dry sodium hydride (41 mg, 1.6 mmol) in dioxane (2 ml). The mixture was stirred at room temperature for 10 min. 2-Benzoyl-3,3-bis-methylsulfanyl-acrylonitrile 2 (0.20 g, 0.80 mmol) was added, and the mixture was stirred at 85° C. for 2.5 h. The mixture was cooled to room temperature. N-Cyclopropyl-3-hydrazino-4-methyl-benzamide trifluoroacetic acid salt (0.26 g, 0.80 mmol) was added and the reaction was heated to 85° C. for another 3 h. Solvents were removed in vacuo. The residue was diluted in saturated NaHCO$_3$ solution and was extracted three times with EtOAc. Combined organic layers were dried over MgSO$_4$, filtered and concentrated. The crude product was purified by flash chromatography (SiO$_2$, gradient of 75 to 85% EtOAc/hexanes). The product was further purified by washing with a warm mixture of EtOAc and hexanes to give the desired 3-(5-amino-4-benzoyl-3-ethoxy-pyrazol-1-yl)-N-cyclopropyl-4-methyl-benzamide 4 as a white solid (27 mg, 8.3%). HPLC (4 minute 10-90 gradient) $t_R$ 2.37 min; MS m/z 405.2 [M+H]$^+$; $^1$H NMR (DMSO-d$_6$, 300 MHz) δ 8.49 (d, J=4.0, 1 H), 7.90 (d, J=8.0, 1 H), 7.85 (s, 1 H), 7.62 (d, J=7.1, 2 H), 7.50 (d, J=7.5, 2 H), 7.41-7.45 (m, 2 H), 6.99 (bs, 2 H), 4.05 (q, J=7.0, 2 H), 2.87 (m, 1 H), 2.19 (s, 3 H), 1.09 (t, J=7.0, 3 H), 0.69 (m, 2 H), 0.58 (m, 2 H) ppm; $^{13}$C NMR (DMSO-d$_6$, 125 MHz) δ 188.2, 166.0, 158.9, 152.6, 140.0, 139.5, 135.5, 132.9, 131.1, 130.6, 128.1, 127.2, 126.7, 91.2, 63.4, 23.0, 17.3, 14.2, 5.6 ppm.

EXAMPLE 32

Preparation of 3-[5-amino-4-benzoyl-3-(2-methoxy-ethoxy)-pyrazol-1-yl]-N-cyclopropyl-4-methyl-benzamide

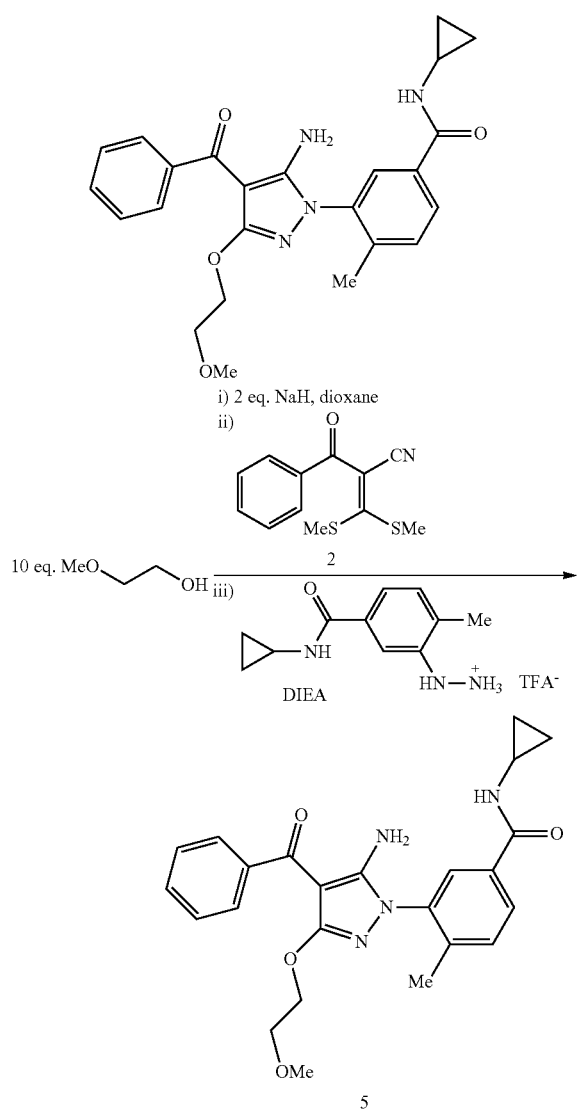

Dry sodium hydride (21 mg, 0.84 mmol) was added to a solution of 2-methoxyethanol (0.63 ml, 8.0 mmol) in dioxane (2 ml) at 0° C. The mixture was stirred at room temperature for 30 min. 2-Benzoyl-3,3-bis-methylsulfanyl-acrylonitrile 2 (0.20 g, 0.80 mmol) was added, and the mixture was stirred at 85° C. for 4 h. The mixture was cooled to room temperature. N-Cyclopropyl-3-hydrazino-4-methyl-benzamide trifluoroacetic acid salt (0.26 g, 0.80 mmol), followed by diisopropylethylamine (0.14 ml, 0.80 mmol), was added and the reaction was heated to 85° C. for another 11 h. Solvents were removed in vacuo. The residue was diluted in saturated NaHCO₃ solution and was extracted three times with EtOAc. Combined organic layers were dried over MgSO₄, filtered and concentrated. The crude product was purified by flash chromatography (SiO₂, gradient of 70 to 90% EtOAc/hexanes). The product was further purified by washing with a warm mixture of EtOAc and hexanes to give the desired 3-[5-amino-4-benzoyl-3-(2-methoxy-ethoxy)-pyrazol-1-yl]-N-cyclopropyl-4-methyl-benzamide 5 as a white solid (60 mg, 17%). HPLC (4 minute 10-90 gradient) $t_R$ 2.17 min; MS m/z 435.2 [M+H]⁺; ¹H NMR (DMSO-d₆, 500 MHz) δ 8.47 (s, 1 H), 7.89 (d, J=7.9, 1 H), 7.83 (s, 1 H), 7.64 (d, J=7.4, 2 H), 7.49 (d, J=7.7, 2 H), 7.40-7.43 (m, 2 H), 6.99 (bs, 2 H), 4.12 (m, 2 H), 3.42 (m, 2 H), 3.12 (s, 3 H), 2.86 (m, 1 H), 2.07 (s, 3 H), 0.69 (m, 2 H), 0.56 (m, 2 H) ppm.

EXAMPLE 33

Preparation of 3-[5-amino-4-benzoyl-3-(2-benzyloxy-ethoxy)-pyrazol-1-yl]-N-cyclopropyl-4-methyl-benzamide (2 ml) at 0° C. The mixture was stirred at room temperature for 35 min. 2-Benzoyl-3,3-bis-methylsulfanyl-acrylonitrile 2 (0.20 g, 0.80 mmol) was added, and the mixture was stirred at 80° C. for 2.5 h. The mixture was cooled to room temperature. N-Cyclopropyl-3-hydrazino-4-methyl-benzamide trifluoroacetic acid salt (0.26 g, 0.80 mmol) was added and the reaction was heated to 80° C. for another 8.5 h. After the reaction mixture was cooled to room temperature, solvents were removed in vacuo. The residue was diluted in saturated NaHCO₃ solution and was extracted three times with EtOAc. Combined organic layers were dried over MgSO₄, filtered and concentrated. The crude product was purified by flash chromatography (SiO₂, gradient of 60 to 85% EtOAc/hexanes). The product was further purified by washing with warm EtOAc to give the desired 3-[5-amino-4-benzoyl-3-(2-benzyloxy-ethoxy)-pyrazol-1-yl]-N-cyclopropyl-4-methyl-benzamide 6 as an off-white solid (74 mg, 18%). HPLC (4 minute 10-90 gradient) $t_R$ 2.57 min; MS m/z 511.2 [M+H]⁺; ¹H NMR (DMSO-d₆, 300 MHz) δ 8.49 (d, J=4.0, 1 H), 7.90 (d, J=8.0, 1 H), 7.85 (s, 1 H), 7.66 (d, J=7.1, 2 H), 7.49 (m, 2 H), 7.27-7.40 (m, 5 H), 7.22 (d, J=6.7, 2 H), 7.02 (bs, 2 H), 4.34 (s, 2 H), 4.19 (m, 2 H), 3.57 (m, 2 H), 2.87 (m, 1 H), 2.17 (s, 3 H), 0.69 (m, 2 H), 0.59 (m, 2 H) ppm.

EXAMPLE 34

Preparation of 4-[5-amino-4-benzoyl-1-(5-cyclopropylcarbamoyl-2-methyl-phenyl)-1H-pyrazol-3-yloxy]-piperidine-1-carboxylic acid tert-butyl ester

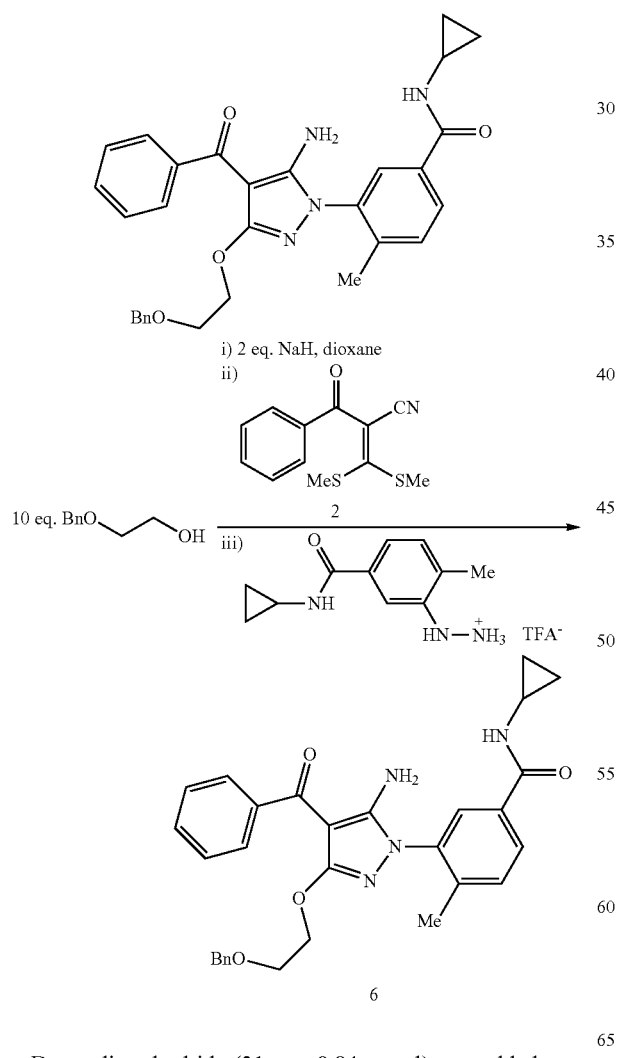

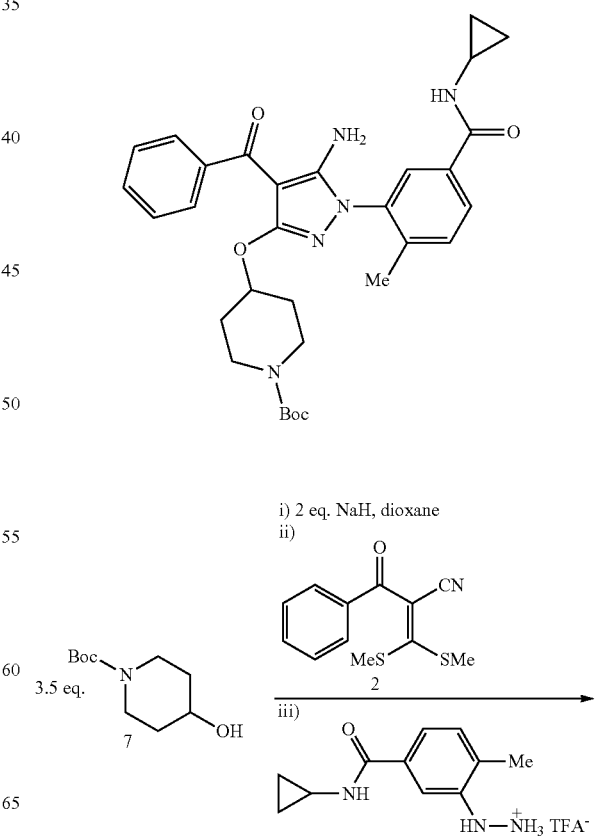

Dry sodium hydride (21 mg, 0.84 mmol) was added to a solution of 2-benzyloxyethanol (1.1 ml, 8.0 mmol) in dioxane -continued

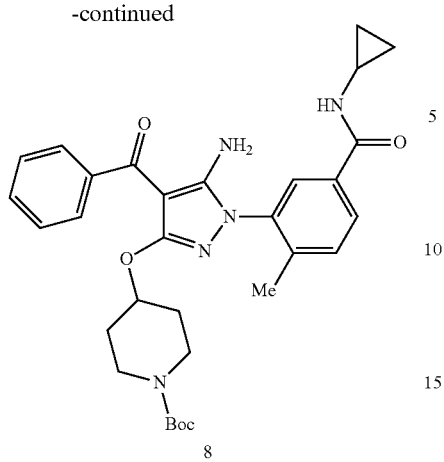

8

Dry sodium hydride (41.0 mg, 1.60 mmol) was added to a solution of 4-hydroxy-piperidine-1-carboxylic acid tert-butyl ester 7 (0.565 g, 2.81 mmol) in dioxane (2 ml) at 0° C. The mixture was stirred at room temperature for 45 min. 2-Benzoyl-3,3-bis-methylsulfanyl-acrylonitrile 2 (0.20 g, 0.80 mmol) was added, and the mixture was stirred at 65° C. for 4 h. The mixture was cooled to room temperature. N-Cyclopropyl-3-hydrazino-4-methyl-benzamide trifluoroacetic acid salt (0.26 g, 0.80 mmol) was added and the reaction was heated to 80° C. for another 3 h. After the reaction mixture was cooled to room temperature, solvents were removed in vacuo. The residue was diluted in saturated NaHCO$_3$ solution and was extracted three times with EtOAc. Combined organic layers were dried over MgSO$_4$, filtered and concentrated. The crude product was purified by flash chromatography (SiO$_2$, gradient of 65 to 85% EtOAc/hexanes). The product was further purified by washing the with warm EtOAc to give the desired 4-[5-amino-4-benzoyl-1-(5-cyclopropylcarbamoyl-2-methyl-phenyl)-1H-pyrazol-3-yloxy]-piperidine-1-carboxylic acid tert-butyl ester 8 as an off-white solid (70 mg, 16%). HPLC (4 minute 10-90 gradient) $t_R$ 2.63 min; MS m/z 559.9 [M+H]$^+$; $^1$H NMR (DMSO-d$_6$, 300 MHz) δ 8.49 (d, J=3.6, 1 H), 7.90 (d, J=8.1, 1 H), 7.84 (s, 1 H), 7.59 (d, J=7.7, 2 H), 7.40-7.51 (m, 4 H), 6.99 (bs, 2 H), 4.75 (m, 1 H), 3.18 (m, 2 H), 2.99 (m, 2 H), 2.87 (m, 1 H), 2.19 (s, 3 H), 1.68 (m, 2 H), 1.43 (m, 2 H), 1.37 (s, 9 H), 0.71 (m, 2 H), 0.58 (m, 2 H) ppm.

EXAMPLE 35

Preparation of 3-[5-amino-4-benzoyl-3-(piperidin-4-yloxy)-pyrazol-1-yl]-N-cyclopropyl-4-methyl-benzamide, trifluoroacetate salt

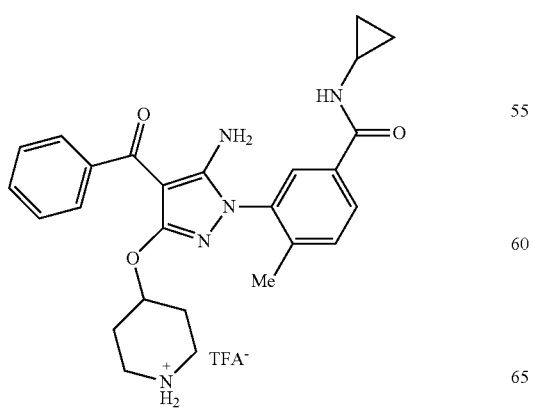

-continued

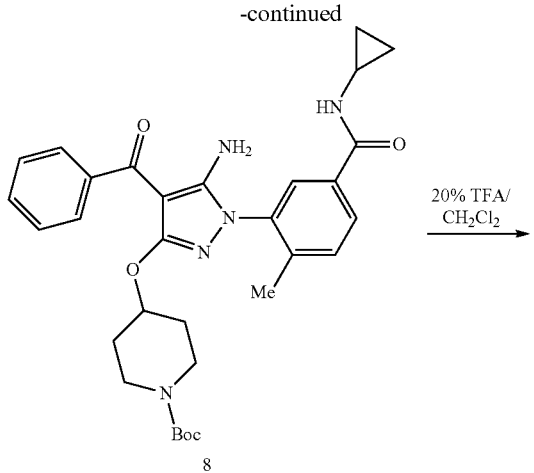

8

To a solution of 4-[5-amino-4-benzoyl-1-(5-cyclopropylcarbamoyl-2-methyl-phenyl)-1H-pyrazol-3-yloxy]-piperidine-1-carboxylic acid tert-butyl ester 8 (5.0 mg, 0.0089 mmol) in dichloromethane (2.0 ml) was added trifluoroacetic acid (0.5 ml). The mixture was stirred at room temperature for 3 h. Volatiles were removed in vacuo and the residue was washed with ether and a small amount of EtOAc to give the desired 3-[5-amino-4-benzoyl-3-(piperidin-4-yloxy)-pyrazol-1-yl]-N-cyclopropyl-4-methyl-benzamide, trifluoroacetate salt 9 as a white solid (3.0 mg, 59%). HPLC (4 minute 10-90 gradient) $t_R$ 1.75 min; MS m/z 460.1 [M+H]$^+$; $^1$H NMR (DMSO-d$_6$, 300 MHz) δ 8.50 (d, J=4.0, 1 H), 8.33 (bs, 2 H), 7.90 (d, J=8.0, 1 H), 7.83 (s, 1 H), 7.62 (d, J=7.0, 2 H), 7.44-7.52 (m, 4 H), 7.03 (bs, 2 H), 4.82 (m, 1 H), 2.97 (m, 2 H), 2.85 (m, 1 H), 2.73 (m, 2 H), 2.27 (s, 3 H), 1.91 (m, 2 H), 1.73 (m, 2 H), 0.71 (m, 2 H), 0.57 (m, 2 H) ppm.

EXAMPLE 36

Preparation of 3-(5-amino-4-benzoyl-3-methylsulfanyl-pyrazol-1-yl)-N-cyclopropyl-4-methyl-benzamide

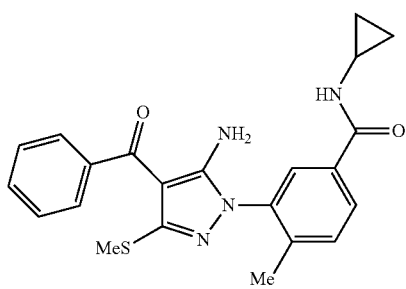

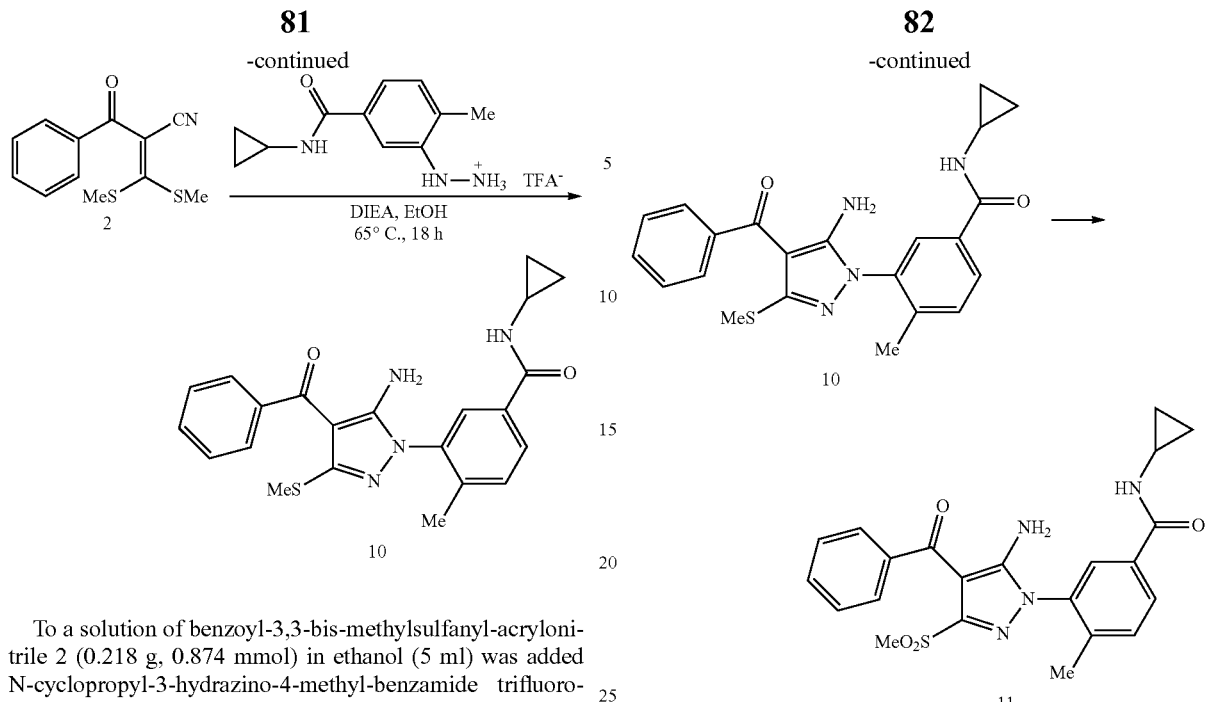

To a solution of benzoyl-3,3-bis-methylsulfanyl-acrylonitrile 2 (0.218 g, 0.874 mmol) in ethanol (5 ml) was added N-cyclopropyl-3-hydrazino-4-methyl-benzamide trifluoroacetic acid salt (0.243 g, 0.874 mmol) and diisopropylethylamine (0.152 ml, 0.874 mmol). The mixture was heated to 65° C. for 18 h. The mixture was cooled to room temperature. Solvents were removed in vacuo. The residue was diluted in saturated NaHCO$_3$ solution and was extracted three times with EtOAc. Combined organic layers were dried over MgSO$_4$, filtered and concentrated. The crude product was purified by flash chromatography (SiO$_2$, gradient of 65 to 100% EtOAc/hexanes). The product was further purified by washing with a warm mixture of EtOAc and hexanes to give the desired 3-(5-amino-4-benzoyl-3-methylsulfanyl-pyrazol-1-yl)-N-cyclopropyl-4-methyl-benzamide 10 as an off-white solid (57 mg, 16%). HPLC (4 minute 10-90 gradient) $t_R$ 2.34 min; MS m/z 407.1 [M+H]$^+$; $^1$H NMR (DMSO-d$_6$, 300 MHz) δ 8.50 (d, J=4.0, 1 H), 7.93 (dd, J=1.2, 7.9, 1 H), 7.86 (s, 1 H), 7.45-7.57 (m, 6 H), 6.85 (bs, 2 H), 2.88 (m, 1 H), 2.23 (s, 3 H), 2.18 (s, 3 H), 0.69 (m, 2 H), 0.58 (m, 2 H) ppm; $^{13}$C NMR (DMSO-d$_6$, 125 MHz) δ 189.3, 165.9, 152.8, 148.0, 140.4, 139.3, 135.4, 132.9, 131.2, 130.6, 128.4, 128.1, 127.2, 126.6, 102.0, 23.0, 17.3, 13.4, 5.6 μm.

EXAMPLE 37

Preparation of 3-(5-amino-4-benzoyl-3-methanesulfonyl-pyrazol-1-yl)-N-cyclopropyl-4-methyl-benzamide To a suspension of 3-(5-amino-4-benzoyl-3-methylsulfanyl-pyrazol-1-yl)-N-cyclopropyl-4-methyl-benzamide 10 (40 mg, 0.098 mmol) in dichloromethane (1 ml) was added 3-chloroperoxybenzoic acid (70-75%, 53 mg, 0.22 mmol). The resulting solution was stirred at room temperature for 2 h, and then stored at 4° C. overnight. Upon warming to room temperature, the product began to precipitate. The white solid was collected on a fitted funnel and was washed with dichloromethane and ether to give the desired 3-(5-amino-4-benzoyl-3-methanesulfonyl-pyrazol-1-yl)-N-cyclopropyl-4-methyl-benzamide 11 (27 mg, 63%). HPLC (4 minute 10-90 gradient) $t_R$ 1.98 min; MS m/z 439.08 [M+H]$^+$; $^1$H NMR (DMSO-d$_6$, 300 MHz) δ 8.53 (d, J=3.7, 1 H), 7.97 (d, J=8.1, 1 H), 7.92 (s, 1 H), 7.76 (d, J=7.2, 1 H), 7.48-7.64 (m, 5 H), 6.30 (bs, 2 H), 3.29 (s, 3 H), 2.88 (m, 1 H), 2.17 (s, 3 H), 0.69 (m, 2 H), 0.58 (m, 2 H) ppm.

EXAMPLE 38

Preparation of 5-amino-1-(5-cyclopropylcarbamoyl-2-methyl-phenyl)-3-methylsulfanyl-1H-pyrazole-4-carboxylic acid amide

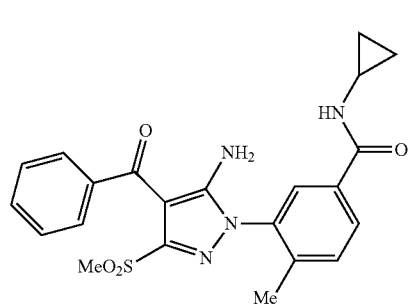

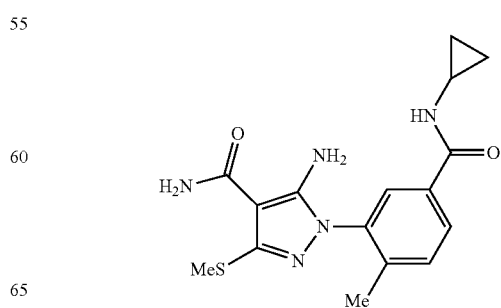

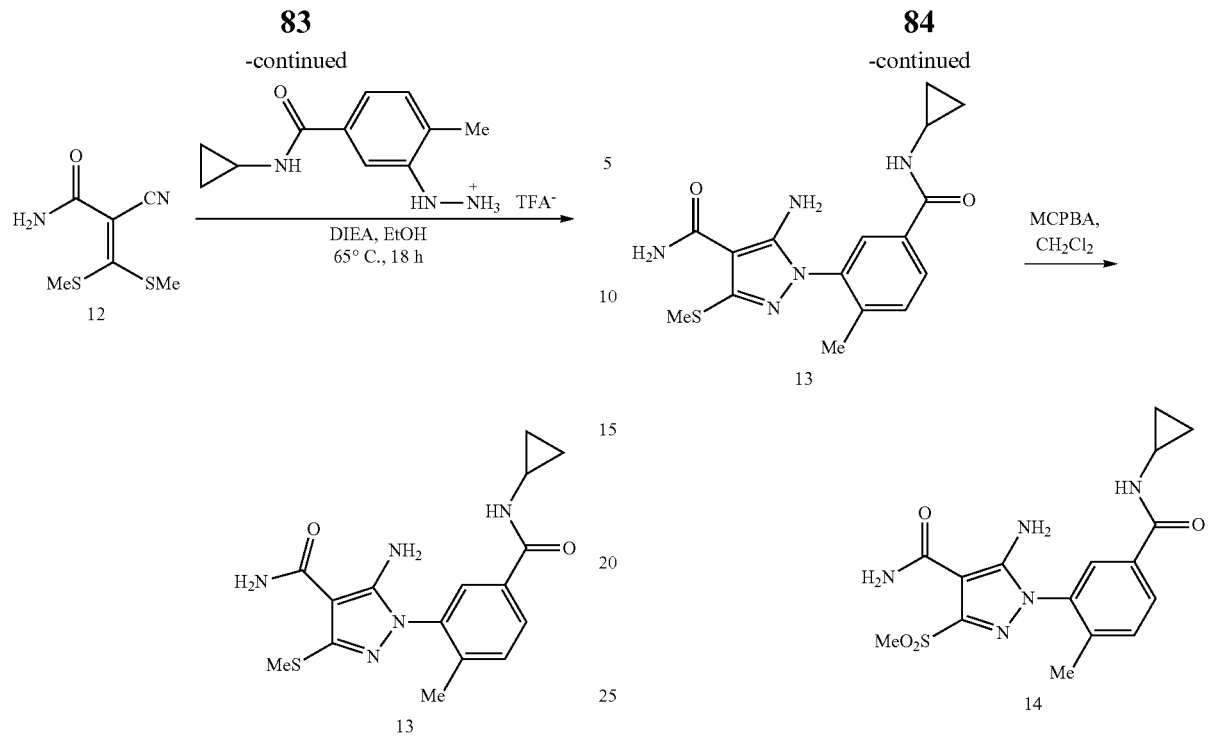

To a solution of 2-cyano-3,3-bis-methylsulfanyl-acrylamide 12 (100 mg, 0.574 mmol) in ethanol (5 ml) was added N-cyclopropyl-3-hydrazino-4-methyl-benzamide trifluoroacetic acid salt (0.183 g, 0.574 mmol) and diisopropylethylamine (0.100 ml, 0.574 mmol). The mixture was heated to 65° C. for 18 h. The mixture was cooled to room temperature. Solvents were removed in vacuo. EtOAc was added to the residue and a solid precipitated. The solid was collected on a fitted funnel and was washed with EtOAc and ether to give the desired 5-amino-1-(5-cyclopropylcarbamoyl-2-methyl-phenyl)-3-methylsulfanyl-1H-pyrazole-4-carboxylic acid amide 13. HPLC (4 minute 10-90 gradient) $t_R$ 1.98 min; MS m/z 439.08 [M+H]$^+$; $^1$H NMR (DMSO-d$_6$, 500 MHz) δ 8.47 (d, J=3.7, 1 H), 7.90 (d, J=7.9, 1 H), 7.78 (s, 1 H), 7.49 (d, J=8.0, 1 H), 6.81 (bs, 2 H), 6.30 (s, 2 H), 2.86 (m, 1 H), 2.45 (s, 3 H), 2.11 (s, 3 H), 0.68 (m, 2 H), 0.57 (m, 2 H) ppm.

To a suspension of 5-amino-1-(5-cyclopropylcarbamoyl-2-methyl-phenyl)-3-methylsulfanyl-1H-pyrazole-4-carboxylic acid amide 13 (100 mg, 0.289 mmol) in dichloromethane (3 ml) was added 3-chloroperoxybenzoic acid (70-75%, 157 mg, 0.637 mmol). The resulting clear solution was stirred at room temperature for 16 h. Saturated NaHCO$_3$ solution was added and the mixture was vigorously stirred for f min. The resulting suspension was filtered on a fritted funnel, and the collected solid was washed three times with H$_2$O, and three times with ether to give the desired 5-amino-1-(5-cyclopropylcarbamoyl-2-methyl-phenyl)-3-methanesulfonyl-1H-pyrazole-4-carboxylic acid amide 14 as a white solid (87 mg, 80%). HPLC (4 minute 10-90 gradient) $t_R$ 1.66 min; MS m/z 378.1 [M+H]$^+$; $^1$H NMR (DMSO-d$_6$, 500 MHz) δ 8.49 (s, 1 H), 7.95 (d, J=7.6, 1 H), 7.83 (s, 1 H), 7.53 (d, J=7.8, 1 H), 7.46 (bs, 2 H), 6.74 (bs, 2 H), 3.40 (s, 3 H), 2.84 (m, 1 H), 2.09 (s, 3 H), 0.68 (m, 2 H), 0.55 (m, 2 H) ppm.

EXAMPLE 39

Preparation of 5-amino-1-(5-cyclopropylcarbamoyl-2-methyl-phenyl)-3-methanesulfonyl-1H-pyrazole-4-carboxylic acid amide

EXAMPLE 40

Preparation of 5-amino-1-(5-cyclopropylcarbamoyl-2-methyl-phenyl)-3-methylsulfanyl-1H-pyrazole-4-carboxylic acid ethyl ester

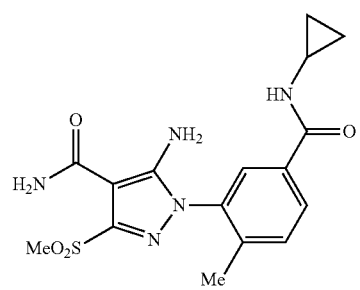

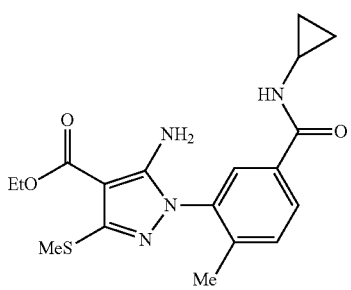

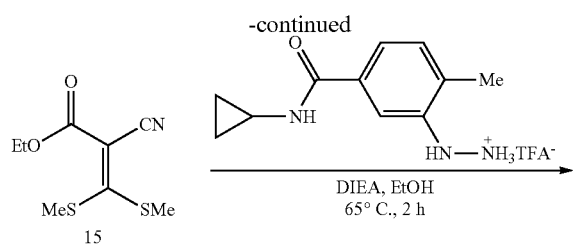

To a solution of 2-cyano-3,3-bis-methylsulfanyl-acrylic acid ethyl ester 15 (78.0 mg, 0.359 mmol) in ethanol (3 ml) was added N-cyclopropyl-3-hydrazino-4-methyl-benzamide trifluoroacetic acid salt (0.100 g, 0.313 mmol) and diisopropylethylamine (0.0626 ml, 0.359 mmol). The mixture was heated to 65° C. for 2 h. The mixture was cooled to room temperature. Solvents were removed in vacuo. EtOAc and ether was added to the residue and a solid precipitated. The solid was collected on a flitted funnel and was washed with EtOAc and ether to give the desired 5-amino-1-(5-cyclopropylcarbamoyl-2-methyl-phenyl)-3-methylsulfanyl-1H-pyrazole-4-carboxylic acid ethyl ester 16 as a white solid (80 mg, 59%). HPLC (4 minute 10-90 gradient) $t_R$ 2.18 min; MS m/z 375.1 [M+H]$^+$; $^1$H NMR (DMSO-d$_6$, 300 MHz) δ 8.47 (d, J=3.7, 1 H), 7.90 (d, J=7.9, 1 H), 7.78 (s, 1 H), 7.49 (d, J=8.0, 1 H), 6.81 (bs, 2 H), 6.30 (s, 2 H), 2.86 (m, 1 H), 2.45 (s, 3 H), 2.11 (s, 3 H), 0.68 (m, 2 H), 0.57 (m, 2 H) ppm. HPLC (4 minute 10-90 gradient) $t_R$ 1.66 min; MS m/z 378.1 [M+H]$^+$; $^1$H NMR (DMSO-d$_6$, 300 MHz) δ 8.50 (d, J=2.6, 1 H), 7.92 (d, J=7.9, 1 H), 7.81 (s, 1 H), 7.51 (d, J=7.9, 1 H), 6.24 (bs, 2 H), 4.22 (q, J=6.6, 2 H), 2.88 (m, 1 H), 2.35 (s, 3 H), 2.14 (s, 3 H), 1.29 (t, J=6.7, 3 H), 0.72 (m, 2 H), 0.58 (m, 2 H) ppm; $^{13}$C NMR (DMSO-d$_6$, 125 MHz) δ 166.0, 163.1, 151.8, 148.5, 139.4, 135.8, 132.9, 131.1, 128.2, 126.7, 91.3, 58.9, 23.0, 17.2, 14.4, 12.3, 5.6 ppm.

EXAMPLE 41

Preparation of 3-[5-Amino-4-(3-chlorobenzoyl)-pyrazol-1-yl]-N-cyclopropyl-4-methyl-benzamide

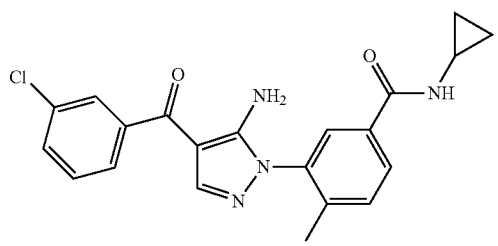

A. 2-(3-Chlorobenzoyl)-3-phenylaminoacrylonitrile

A solution of 3-chlorobenzoylacetonitrile (476 mg, 2.66 mmol, 1.0 eq) and diphenylformamidine (522 mg, 2.66 mmol, 1.0 eq) in 25 mL of toluene was stirred at room temperature for 2 h then heated to 100° C. overnight. The solution was cooled and diluted with hexanes. The resulting solid was filtered and dried to provide the desired product (566 mg, 75%). HPLC (4 minute 10-95 gradient) $t_R$ 2.97 min; MS m/z 283.2 [M+H]$^+$; $^1$H NMR (CDCl$_3$), δ 8.06 (d, J=13.2 Hz, 1 H), 7.85 (m, 2 H), 7.46 (m, 4 H), 7.27 (m, 4 H) ppm.

B. 3-[5-Amino-4-(3-chlorobenzoyl)-pyrazol-1-yl]-N-cyclopropyl-4-methyl-benzamide A solution of 2-(3-chlorobenzoyl)-3-phenylaminoacrylonitrile (63 mg, 0.22 mmol, 1.0 eq), N-cyclopropyl-3-hydrazino-4-methylbenzamide trifluoroacetate (72 mg, 0.22 mmol, 1 eq), and triethylamine (31 μL, 0.22 mmol, 1.0 eq) in 10 mL of ethanol was heated to 65° C. for 20 h. After cooling, the mixture was concentrated and the residue purified by flash chromatography on silica gel packed and eluted with 7/3 hexanes/ethyl acetate to remove byproducts followed by 3/2 ethyl acetate/hexanes to elute the title compound (33 mg, 38%) as a brown solid. HPLC (4 minute 10-95 gradient) $t_R$ 2.35 min; MS m/z 395.1 [M+H]$^+$; $^1$H NMR (CD$_3$OD), δ 7.92 (d, J=7.2 Hz, 1 H), 7.77 (m, 4 H), 7.55 (m, 3 H), 2.85 (m, 1 H), 2.23 (s, 3 H), 0.80 (d, J=5.5 Hz, 2 H), 0.63 (d, J=2.0 Hz, 2 H) ppm; $^{13}$C NMR (CD$_3$OD), δ 187.1, 168.1, 151.9, 141.0, 140.9, 140.0, 134.9, 133.8, 132.8, 130.9, 130.5, 129.4128.1, 127.0, 126.1, 125.6, 102.6, 22.1, 15.7, 4.6 ppm.

EXAMPLE 42

Preparation of 3-[5-Amino-4-(3-methyl-benzoyl)-pyrazol-1-yl]-N-cyclopropyl-4-methylbenzamide

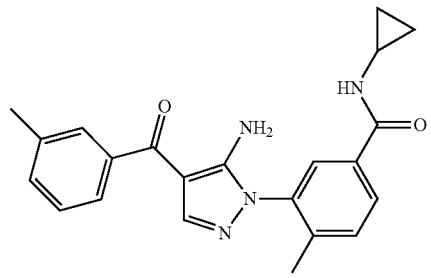

Similar procedure as Example 41 except that 3-methylbenzoylacetonitrile was used in place of 3-chlorobenzoylacetonitrile. HPLC (4 minute 10-95 gradient) $t_R$ 2.27 min; MS m/z 375.16 [M+H]$^+$; $^1$H NMR (CD$_3$OD), δ 7.92 (d, J=7.0 Hz, 1 H), 7.83 (s, 1 H), 7.80 (s, 1 H), 7.57 (m, 3 H), 7.42 (m, 2 H), 2.85 (heptet, J=3.6 Hz, 1 H), 2.45 (s, 3 H), 2.23 (s, 3 H), 0.80 (d, J=5.4 Hz, 2 H), 0.64 (s, 2 H) ppm.

EXAMPLE 43

Preparation of 3-[5-Amino-4-(2-methylbenzoyl)-pyrazol-1-yl]-N-cyclopropyl-4-methyl-benzamide

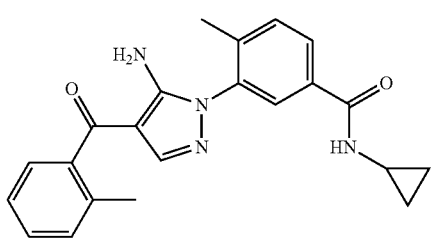

Similar procedure as Example 41 except that 2-methylbenzoylacetonitrile was used in place of 3-chlorobenzoylacetonitrile. HPLC (4 minute 10-90 gradient) $t_R$ 2.21 min; MS m/z 375.15 [M+H]⁺.

EXAMPLE 44

Preparation of 3-[5-Amino-4-(2-methoxy-benzoyl)-pyrazol-1-yl]-N-cyclopropyl-4-methyl-benzamide

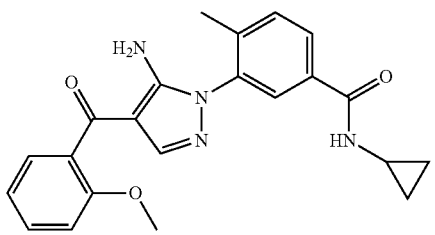

Similar procedure as Example 41 except that 2-methoxybenzoylacetonitrile was used in place of 3-chlorobenzoylacetonitrile. HPLC (4 minute 10-90 gradient) $t_R$ 2.03 min; MS m/z 391.16 [M+H]⁺.

EXAMPLE 45

Preparation of 3-[5-Amino-4-(4-chlorobenzoyl)-pyrazol-1-yl]-N-cyclopropyl-4-methyl-benzamide

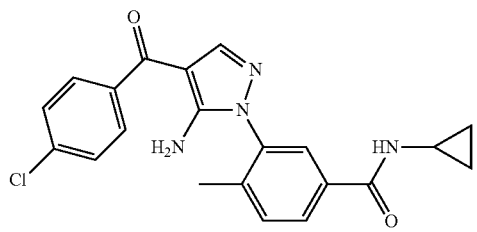

Similar procedure as Example 41 except that 3-methylbenzoylacetonitrile was used in place of 3-chlorobenzoylacetonitrile. HPLC (4 minute 10-90 gradient) $t_R$ 1.65 min; MS m/z 394.2 [M+H]⁺.

EXAMPLE 46

Preparation of 3-[5-Amino-4-(2-chlorobenzoyl)-pyrazol-1-yl]-N-cyclopropyl-4-methyl-benzamide

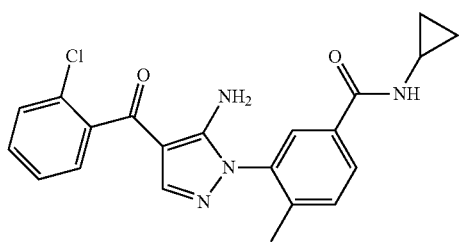

A. 2-(2-Chlorobenzoyl)-3-phenylaminoacrylonitrile

A solution of 2-chlorobenzoylacetonitrile (1.0 g, 5.6 mmol, 1.0 eq) and diphenylformamidine (1.10 g, 5.6 mmol, 1.0 eq) in 50 mL of toluene was heated to 85° C. overnight. The heat source was removed and desired product slowly began to precipitate from solution. The resulting solid was filtered and dried to provide the desired product (826 mg, 52%). HPLC (4 minute 10-90 gradient) $t_R$ 3.13 min; MS m/z 283.2 [M+H]⁺.

B. 3-[5-Amino-4-(2-chlorobenzoyl)-pyrazol-1-yl]-N-cyclopropyl-4-methyl-benzamide A solution of 2-(2-chlorobenzoyl)-3-phenylaminoacrylonitrile (93 mg, 0.33 mmol, 1.0 eq), N-cyclopropyl-3-hydrazino-4-methylbenzamide trifluoroacetate (104 mg, 0.33 mmol, 1 eq), and triethylamine (31 µL, 0.22 mmol, 1.0 eq) in 20 mL of ethanol was heated to 60° C. for 48 h. After cooling, the mixture was concentrated and the residue was dissolved in minimal ethyl acetate. 100 ml diethyl ether was added and the precipitate was filtered and dried to provide desired product (50 mg, 39%). HPLC (4 minute 10-90 gradient) $t_R$ 2.51 min; MS m/z 395.1 [M+H]⁺; ¹H NMR (DMSO), δ 8.50 (d, J=3.8 Hz, 1 H), 7.93 (d, J=8.0 Hz, 1 H), 7.84 (s, 1 H), 7.57 (m, 5 H) 7.32 (s, 1 H), 7.01 (s, 2 H) 3.37 (m, 2 H), 2.86 (m, 1 H), 2.14 (s, 3 H), 1.09 (t, 2H), 0.68 (m, 2 H), 0.58 (m, 2 H) ppm

EXAMPLE 47

Preparation of 3-[5-Amino-4-(3-methoxy-benzoyl)-pyrazol-1-yl]-4,N-dimethyl-benzamide

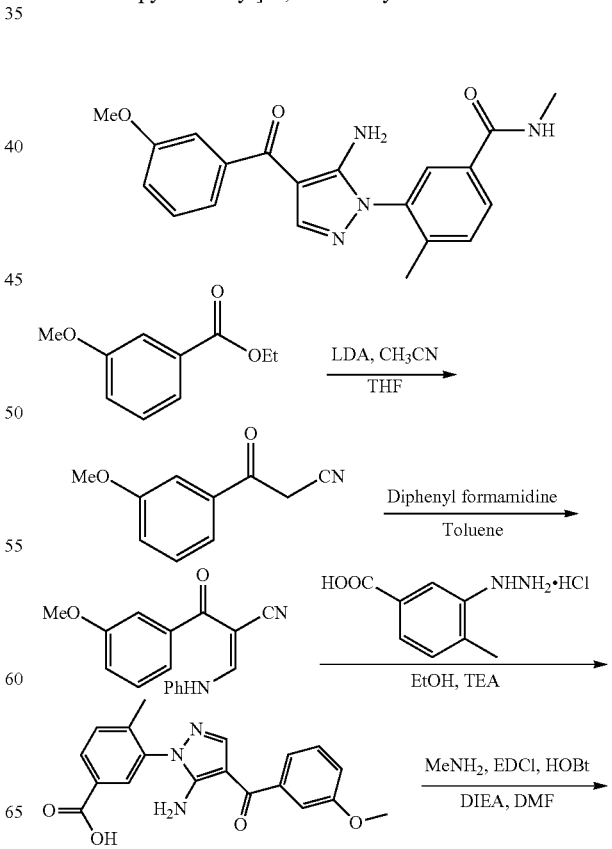

-continued

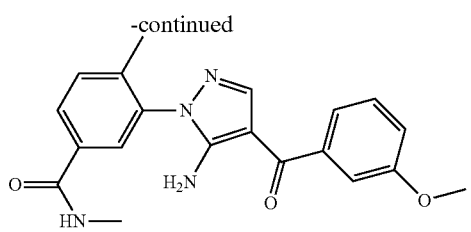

A. 3-methxoybenzoylacetonitrile

To a stirred solution of ethyl 3-methoxybenozoate (3.05 mL, 18.6 mmol, 1. eq) and acetonitrile (1.19 mL, 22.9 mmol, 1.23 eq) in 5 mL of THF at −50° C. under $N_2$ was added via cannula a freshly prepared solution of LDA (diisopropylamine, 5.3 mL, 38.0 mmol, 2.04 eq and 2.5 M n-butyllithium in hexanes, 15.25 mL, 38.0 mmol, 2.04 eq). The reaction was stirred at this temperature for 3 h then warmed to 0° C. for 1 h. The reaction was quenched with 10 mL of sat. $NH_4Cl$ and allowed to warm to room temperature. The mixture was extracted with EtOAc and the organic layer washed with water and brine, dried ($Na_2SO_4$), and concentrated. The residue was purified by flash chromatography on silica gel to provide the product as an off-white solid.

B. 2-(3-Methoxybenzoyl)-3-phenylamino-acrylonitrile

A solution of 3-methoxybenzoylacetonitrile (1.20 g, 68.5 mmol, 1.0 eq) and diphenylformamidine (1.34 g, 68.5 mmol, 1.0 eq) in 25 mL of toluene was stirred at room temperature for 2 h then heated to 100° C. overnight. The solution was cooled and diluted with hexanes. The resulting solid was filtered and dried to provide the desired product. HPLC (4 minute 10-90 gradient) $t_R$ 3.05 min; MS m/z 279.2 $[M+H]^+$.

C. 3-[5-Amino-4-(3-methoxybenzoyl)-pyrazol-1-yl]-4-methyl-benzoic acid

A solution of 2-(3-chlorobenzoyl)-3-phenylaminoacrylonitrile (63 mg, 0.22 mmol, 1.0 eq), 3-hydrazino-4-methylbenzoic acid hydrochloride (72 mg, 0.22 mmol, 1 eq), and triethylamine (31 µL, 0.22 mmol, 1.0 eq) in 10 mL of ethanol was heated to 65° C. for 20 h. After cooling, the mixture was concentrated and the residue purified by flash chromatography on silica gel packed and eluted with 7/3 hexanes/ethyl acetate to remove byproducts followed by 3/2 ethyl acetate/hexanes to elute the title compound (15 mg, 32%) as a brown solid. HPLC (4 minute 10-90 gradient) $t_R$ 2.13.min; MS m/z 352.2 $[M+H]^+$.

D. 3-[5-Amino-4-(3-methoxybenzoyl)-pyrazol-1-yl]-4,N-dimethyl-benzamide

To a stirred solution of 3-[5-Amino-4-(3-methoxybenzoyl)-pyrazol-1-yl]-4-methylbenzoic acid C (50 mg, 0.14 mmol, 1.0 eq) in 10 mL of DMF was added EDCI (41 mg 0.21 mmol, 1.5 eq), HOBt (29 mg, 1.5 mmol, 2.0 eq), and diisopropylethylamine (55 mg, 0.43 mmol, 3.0 eq) and the solution was stirred for 15 minutes at room temperature when methylamine hydrochloride (13 mg, 0.19 mmol, 1.5 eq) was added and the reaction stirred for 1 hour. The mixture was diluted with EtOAc (300 mL) and washed with water (2×25 mL) and brine (25 mL), dried ($Na_2SO_4$) and concentrated. The product was purified by flash chromatography on silica gel to provide the product to provide the product (15 mg, 32%) as a brown solid: HPLC (4 minute 10-90 gradient) $t_R$ 1.97 min; MS m/z 365.2 $[M+H]^+$.

EXAMPLE 48

Preparation of 5-Amino-1-(5-cyclopropylcarbamoyl-2-methyl-phenyl)-1H-pyrazole-4-carboxylic acid ethyl ester

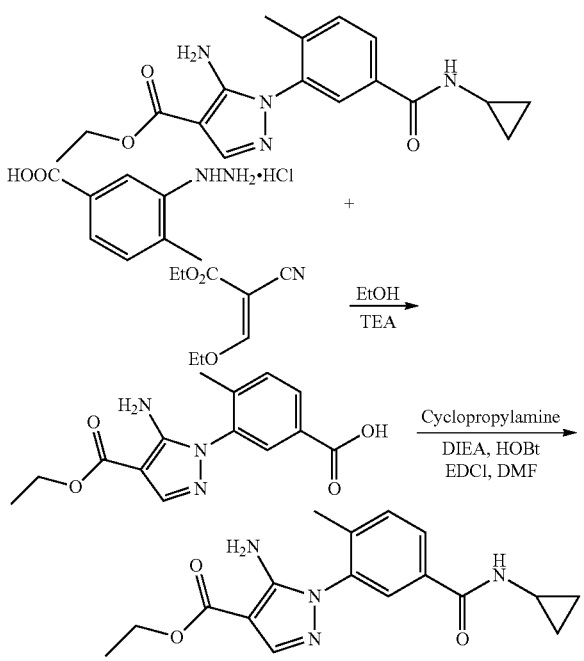

A. 5-Amino-1-(5-carboxy-2-methyl-phenyl)-1H-pyrazole-4-carboxylic acid ethyl ester To a stirred solution of 3-hydrazino-4-methylbenzoic acid hydrochloride (Example 3A, 478 mg, 2.36 mmol, 1.0 eq) in 20 mL of ethanol were added ethyl(ethoxymethylene)cyanoacrylate (399 mg, 2.36 mmol, 1.0 eq) and triethylamine (329 µL, 2.36 mmol, 1.0 eq) and the mixture was heated at 65° C. for 5 hrs. After standing at room temperature overnight, additional 3-hydrazino-4-methylbenzoic acid hydrochloride (159 mg, 0.78 mmol, 0.3 eq) and triethylamine (110 µL, 0.78 mmol, 0.3 eq) and heated for 2.5. The mixture was cooled to room temperature and concentrated. The crude residue was purified by flash chromatography on silica gel (gradient elution from 7/3 hexanes/EtOAc to 1/1 to elute byproducts followed by EtOAc and 9/1 EtOAc/MeOH to elute product) to provide the product as a brown solid (464 mg, 68%). HPLC (4 minute 10-95 gradient) $t_R$ 1.87 min; MS m/z 290.1$[M+H]^+$; $^1$H NMR ($CD_3OD$), δ 8.08 (d, J=7.0 Hz, 1 H), 7.93 (s, 1 H), 7.76 (s, 1 H), 7.54 (d, J=8.0 Hz, 1 H), 4.29 (q, J=7.1 Hz, 2 H), 2.19 (s, 3 H), 1.35 (d, J=7.1 Hz, 3 H), ppm; $^{13}$C NMR ($CD_3OD$), δ 166.5, 163.8, 150.4, 141.7, 139.9, 135.3, 130.8, 129.5, 128.6, 93.8, 58.8, 15.8, 12.9 ppm.

B. 5-Amino-1-(5-cyclopropylcarbamoyl-2-methyl-phenyl)-1H-pyrazole-4-carboxylic acid ethyl ester To a solution of 5-amino-1-(5-carboxy-2-methyl-phenyl)-1H-pyrazole-4-carboxylic acid ethyl ester (47 mg, 0.16 mind, 1.0 eq), EDCI (62 mg, 0.32 mmol, 2.0 eq), HOBt (44 mg, 0.32 mmol, 2.0 eq), and diisopropylethyl amine (119 µL, 0.32 mmol, 2.0 eq) in DMF (5 mL) which had been stirred at RT for 15 min was added cyclopropylamine (23 µL, 0.32 mmol, 2.0 eq). After stirring overnight, the solution was diluted with EtOAc and water and the organic layer was washed with water and brine, dried ($Na_2SO_4$) and concentrated. The crude residue was purified by flash chromatography on silica gel eluted with 8/2 EtOAc/hexanes to provide the product as a colorless oil (42 mg, 79%). HPLC (4 minute 10-95 gradient) $t_R$ 1.84 min; MS m/z 329.09 [M+H]$^+$; $^1$H NMR (CD$_3$OD), δ 7.96 (s, 1 H, NH), 7.88 (d, J=7.9 Hz, 1 H), 7.78 (s, 1 H), 7.75 (s, 1 H), 7.50 (d, J=8.0 Hz, 1 H), 4.28 (q, J=7.1 Hz, 2 H), 2.83 (m, 1 H), 2.16 (s, 3 H), 1.35 (d, J=7.0 Hz, 3 H), 0.78 (dd, J=12.3, 7.0 Hz, 2 H), 0.63 (dd, J=7.0, 4.5 Hz, 2 H) ppm; $^{13}$C NMR (CD$_3$OD), δ 170.1, 165.8, 152.3, 142.1, 141.8, 137.2, 134.6, 132.8, 130.0, 128.2, 128.1, 95.8, 60.8, 24.1, 17.6, 14.9, 6.6 ppm.

EXAMPLE 49

Preparation of 5-Amino-1-(5-cyclopropylcarbamoyl-2-methyl-phenyl)-3-methyl-1H-pyrazole-4-carboxylic acid ethyl ester

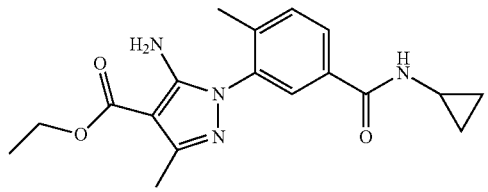

A. 5-Amino-1-(5-carboxy-2-methyl-phenyl)-3-methyl-1H-pyrazole-4-carboxylic acid ethyl ester To a stirred solution of 3-hydrazino-4-methylbenzoic acid hydrochloride (Example 3A, 353 mg, 1.74 mmol, 1.0 eq) in 15 mL of ethanol were added 2-cyano-3-ethoxy-but-2-enoic acid ethyl ester (prepared as described by Xia et al., *J. Med. Chem.*, 1997, 40, 4372) (319 mg, 1.746 mmol, 1.0 eq) and triethylamine (242 µL, 1.74 mmol, 1.0 eq) and the mixture was heated at 65° C. overnight. The mixture was cooled to room temperature and concentrated. The crude residue was purified by flash chromatography on silica gel (loaded with CH$_2$Cl$_2$, and packed and eluted with gradient from 6/4 hexanes/EtOAc to elute byproducts followed by 8/2 EtOAc/hexanes and 8/2 EtOAc/MeOH to elute product) to provide the product as a brown solid (464 mg, 68%). HPLC (4 minute 10-95 gradient) $t_R$ 1.97 min; MS m/z 304.1 [M+H]$^+$ B. 5-Amino-1-(5-cyclopropylcarbamoyl-2-methyl-phenyl)-3-methyl-1H-pyrazole-4-carboxylic acid ethyl ester To a solution of 5-amino-1-(5-carboxy-2-methyl-phenyl)-3-methyl-1H-pyrazole-4-carboxylic acid ethyl ester (150 mg, 0.49 mmol, 1.0 eq), EDCI (190 mg, 0.98 mmol, 2.0 eq), HOBt (134 mg, 0.98 mmol, 2.0 eq), and diisopropylethyl amine (362 µL, 0.98 mmol, 2.0 eq) in DMF (5 mL) which had been stirred at RT for 15 min was added cyclopropylamine (68 µL, 0.98 mmol, 2.0 eq). After stirring overnight, the solution was diluted with EtOAc and water and the organic layer was washed with water (2×) and brine, dried (Na$_2$SO$_4$) and concentrated. The crude residue was purified by flash chromatography on silica gel (gradient elution, 3/2 EtOAc/hexanes then 100% EtOAc) to provide the product as a white solid (29 mg, 17%). HPLC (4 minute 10-95 gradient) $t_R$ 1.97 min; MS m/z 343 [M+H]$^+$; $^1$H NMR (CD$_3$OD), δ 7.87 (d, J=7.1 Hz, 1 H), 7.76 (s, 1 H), 7.50 (d, J=8.0 Hz, 1 H), 4.29 (q, J=7.0 Hz, 2 H), 2.84 (m, 1 H), 2.34 (s, 3 H), 2.18 (s, 3 H), 1.36 (t, J=7.0 Hz, 3 H), 0.79 (d, J=5.5 Hz, 2 H), 0.62 (s, 2 H) ppm; $^{13}$C NMR (CD$_3$OD), δ 168.1, 164.4, 151.3, 149.8, 140.1, 135.2, 132.6, 130.7, 127.9, 126.3, 92.0, 58.6, 22.1, 15.7, 12.9, 12.6, 4.6 ppm.

EXAMPLE 50

Preparation of 5-Amino-3-[(3-chloro-benzylcarbamoyl)-methoxy]-1-(5-cyclopropylcarbamoyl-2-methyl-phenyl)-1H-pyrazole-4-carboxylic acid ethyl ester

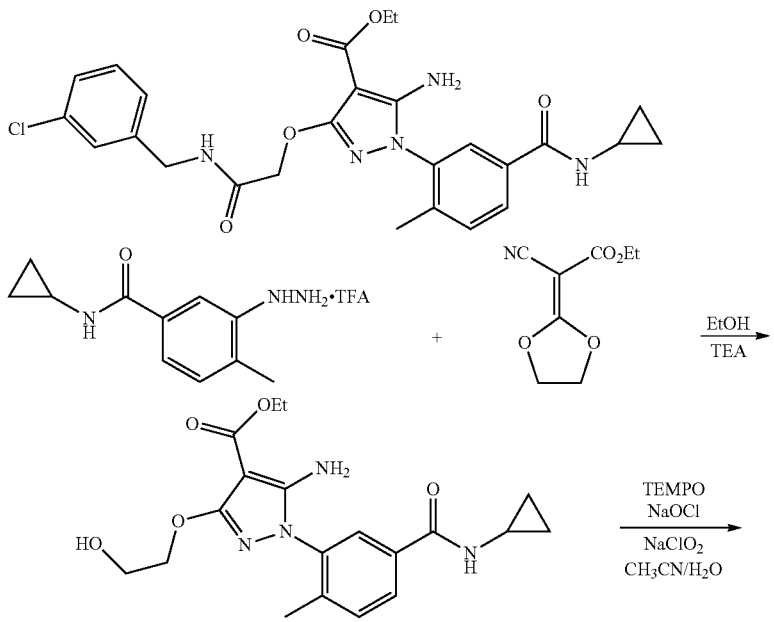

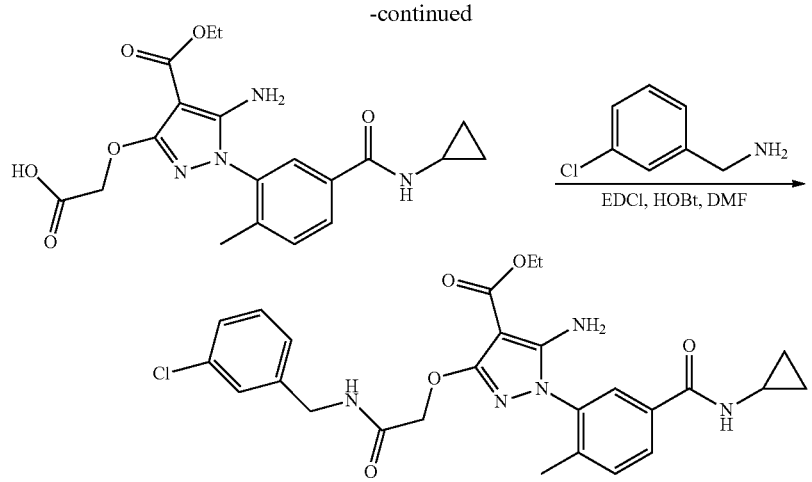

A. 5-Amino-1-(5-cyclopropylcarbamoyl-2-methyl-phenyl)-3-(2-hydroxy-ethoxy)-1H-pyrazole-4-carboxylic acid ethyl ester A stirred solution of cyano-[1,3]dioxolan-2-ylidene-acetic acid ethyl ester (prepared as described by Neidlein and Kikelj, *Synthesis*, 1988, 981, 266 mg, 1.45 mmol, 1.0 eq), N-cyclopropyl-3-hydrazino-4-methyl-benzamide trifluoroacetate (Example 6 C, 463 mg, 1.45 mmol, 1.0 eq), and triethylamine (405 μL, 2.9 mmol, 2.0 eq) in 20 mL of ethanol was heated to 65° C. overnight. After cooling to room temperature, the mixture was concentrated and the residue purified by flash chromatography on silica gel (eluted with 1/1 hexanes/EtOAc followed by 100% EtOAc) to provide the desired compound as a tan solid (350 mg, 62%). HPLC (4 minute 10-95 gradient) $t_R$ 1.59 min; MS ink 389.06 [M+H]$^+$; $^1$H NMR (CD$_3$OD), δ 7.87 (d, J=7.9 Hz, 1 H), 7.78 (s, 1 H), 7.49 (d, J=7.8 Hz, 1 H), 4.29 (dd, J=14.9, 6.9 Hz, 2 H), 4.19 (d, J=4.3 Hz, 2 H), 3.84 (d, J=4.4 Hz, 2 H), 2.84 (m, 1 H), 2.22 (s, 3 H), 1.35 (t, J=7.3 Hz, 3 H), 0.81 (d, J=5.3 Hz, 2 H), 0.63 (s, 2 H) ppm.

B. 5-Amino-3-carboxymethoxy-1-(5-cyclopropylcarbamoyl-2-methyl-phenyl)-1H-pyrazole-4-carboxylic acid ethyl ester To a stirred solution of alcohol 50A (48 mg, 0.12 mmol, 1.0 eq) in 5 mL of acetonitrile was added 2,2',6,6'-tetramethylpiperidinyloxyl (TEMPO) (catalytic) and the solution heated to 35° C. Then a solution of sodium chlorite (17 mg, 0.24 mmol, 2.0 eq) in 2 mL of water (2 mL) and an aqueous solution of sodium hypochlorite diluted to 2% (1 mL) were added simultaneously dropwise and the heating was continued for 24 hours. A bright orange color developed. The reaction was cooled to RT and diluted with water then quenched with 1M Na$_2$SO$_3$ and stirred for 30 minutes. The mixture was washed with EtOAc, then the pH of the aqueous layer was adjusted from pH=8 to pH=2 with 3 M HCl, and extracted with CH$_2$Cl$_2$. The CH$_2$Cl$_2$ extracts were dried and concentrated to provide the product as a yellow solid. HPLC (4 minute 10-95 gradient) $t_R$ 1.70 min; MS m/z 403.02 [M+H]$^+$; $^1$H NMR (CD$_3$OD), δ 7.83 (d, J=7.9 Hz, 1 H), 7.52 (s, 1 H), 7.46 (d, J=7.9 Hz, 1 H), 4.73, (s, 2 H), 4.19 (q, J=7.1 Hz, 2 H), 2.84 (m, 1 H), 2.18 (s, 3 H), 1.31 (t, J=7.0 Hz, 3 H), 0.78 (d, J=6.1 Hz, 2 H), 0.62 (s, 2 H) ppm; $^{13}$C NMR (CD$_3$OD), δ 171.1, 170.2, 168.4, 163.6, 159.7, 151.3, 140.5, 135.2, 132.5, 130.7, 127.6, 126.2, 80.9, 59.6, 58.7, 22.1, 15.8, 12.5, 4.6 ppm.

C. 5-Amino-3-[(3-chloro-benzylcarbamoyl)-methoxy]-1-(5-cyclopropylcarbamoyl-2-methyl-phenyl)-1H-pyrazole-4-carboxylic acid ethyl ester To a stirred solution of acid 50B (28 mg, 0.7 mmol, 1.0 eq), EDCI (32 mg, 0.17 mmol, 2.4 eq), HOBt (22 mg, 0.16 mmol, 2.4 mmol) in 3.0 mL of DMF at room temperature was added 3-chlorobenzylamine (18 μL, 0.07 mmol, 1.0 eq) and the mixture was stirred overnight. The mixture was diluted with EtOAc, washed with water (x2) and brine, dried (Na$_2$SO$_4$), and concentrated. The residue was purified by flash chromatography on silica gel eluted with 9/1 EtOAc/hexanes to provide the product as a clear oil (16 mg, 44%). HPLC (4 minute 10-95 gradient) $t_R$ 2.34 min; MS m/z 525.99 [M+H]$^+$; $^1$H NMR (CD$_3$OD), δ 7.85 (d, J=7.9 Hz, 1 H), 7.56 (s, 1H), 7.47 (d, J=8.0 Hz, 1 H), 7.25 (m, 3 H), 4.73, (s, 2 H), 4.45 (s, 2 H), 4.25 (q, J=7.0 Hz, 2 H), 2.84 (m, 1 H), 2.17 (s, 3 H), 1.27 (t, J=7.0 Hz, 3 H), 0.80 (dd, J=12.3, 6.7 Hz, 2 H), 0.62 (d, J=2.2 Hz, 2 H) ppm; $^{13}$C NMR (CD$_3$OD), δ 168.9, 168.3, 163.4, 159.6, 151.1, 140.3, 140.1, 135.2, 133.6, 132.6, 130.8, 129.1, 127.7, 126.6, 126.4, 125.0, 66.3, 58.8, 41.1, 22.1, 15.9, 12.9, 4.6 ppm.

EXAMPLE 51

Preparation of 3-(5-amino-4-benzoyl-pyrazol-1-yl)-N-cyclopropyl-4-methyl-benzamide

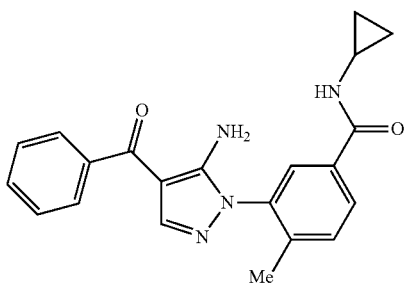

-continued

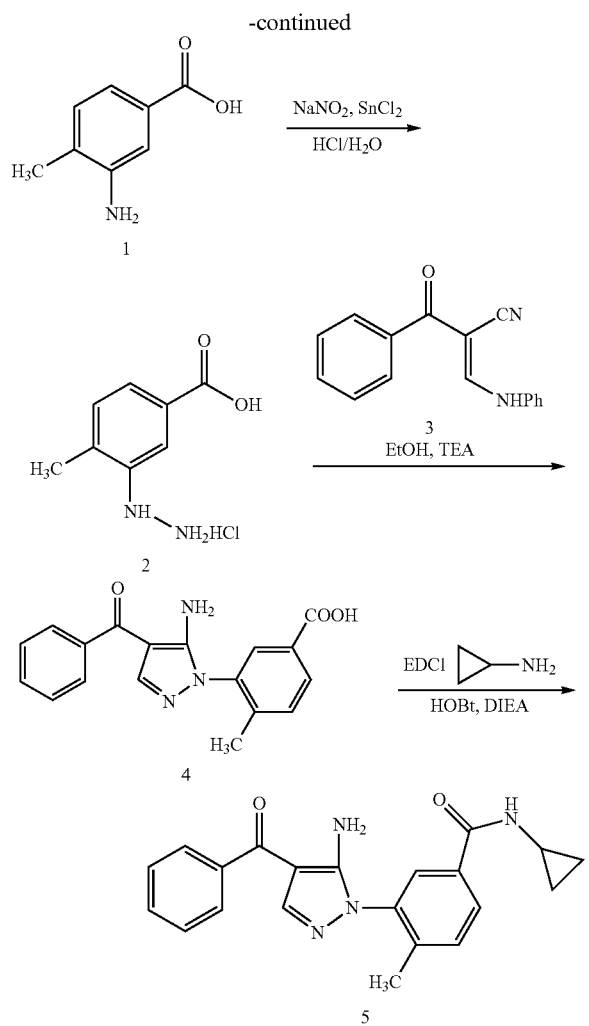

A. 3-Hydrazino-4-methylbenzoic acid hydrochloride

A solution of 3-amino-4-methyl benzoic acid 1 (100 g, 0.66 mol, 1.0 equiv) in water (1.78 L) was cooled to 0-5° C. using ice-water. Conc. HCl (1.78 L) and sodium nitrite (68.5 g, 0.99 mol, 1.5 equiv) were added in sequence at 0-5° C. The reaction mixture was stirred at the 0-5° C. for 1 hour. Stannous chloride dihydrate (336 g, 1.488 mol, 2.25 equiv) in conc. HCl (540 ml) was added at 0-5° C. The mixture was stirred at the same temperature for 2 hours. Solid formed during the course of the reaction was filtered and washed with water (3×500 ml). Dried under vacuum at 25-30° C. for 15 hours to provide then the crude material was (110 g) dissolved in ethanol (1 L) and stirred at 70° C. for 1 hour. The material is filtered at hot and washed with ethanol (50 ml) and air dried to get the pure hydrazine 2 (60 g, 45%) as an off white solid.

B. 3-(5-Amino-4-benzoyl-pyrazol-1-yl)-4-methyl-benzoic acid

To a stirred solution of hydrazine 2 (59 g, 0.29 mol, 1.0 equiv) in ethanol (4.5 L) was added 3 (65 g, 0.262 mol, 0.9 equiv, preparation: Grothasu, Davis, *J. Am. Chem. Soc.*, 58, 1334 (1936)) and triethylamine (29 g, 0.29 mol, 1.0 equiv). The mixture was heated to 65° C. At 65° C. the reaction mixture became homogenous and was stirred at 65° C. for 4 hours. Product was precipitated out during the reaction. The solids were filtered in hot condition and dried to provide acid 4 (45 g, 53%) as an off-white crystalline solid. HPLC (Waters X-Terra 5 micron C18 column 4.6 mm×250 mm, 1.0 mL/min, mobile phase: 0.1% TEA in H₂O/acetonitrile 40/60, 30 min elution) $t_R$ 2.12 min, 96.6% purity; $^1$H NMR (DMSO-$d_6$, 400 MHz) is consistent with Example 3.

C. 3-(5-amino-4-benzoyl-pyrazol-1-yl)-N-cyclopropyl-4-methylbenzamide

To a stirred solution of acid 4 (46 g, 0.143 mol, 1.0 equiv) in DMF (1.9 L) was added EDCl (57.5 g, 0.299 mol, 2.09 equiv), HOBt (41.4 g, 0.306, 2.14 equiv) and diisopropylethylamine (76.6 g, 0.59 mol, 4.15 equiv) and the solution was stirred for 20 minutes at room temperature. Then it was cooled to 15-20° C. and cyclopropylamine (20.6 g, 0.36 mol, 2.51 equiv) was added and stirred at room temperature. The reaction was monitored by TLC. After 14 hours, since the reaction was not complete and additional cyclopropylamine (9.36 g, 0.16 mol, 1.14 equiv) was added and stirring was continued for two hours. DMF was removed under reduced pressure at 50-55° C. To the residue EtOAc (1 L) and water (500 ml) were added and the mixture was stirred for 10 minutes. The mixture was extracted and the organic layer was collected. The aqueous layer was extracted with EtOAc (2×250 ml). The combined organic layer was washed with sodium bicarbonate (2×500 ml) and brine (2×500 ml), dried over anhydrous sodium sulfate and concentrated. To the residue EtOAc/dichloromethane/hexane (50 ml/50 ml/50 ml) was added, the mixture was stirred for 10 minutes, and filtered to provide the product (34.1 g, 65.7%) as an off white crystalline solid. HPLC (Waters X-Terra 5 micron C18 column 4.6 mm×250 mm, 1.0 mL/min, mobile phase: 0.1% TEA in H₂O/acetonitrile 50/50, 30 min elution) $t_R$ 5.53 min, 99.3% purity; MS m/z 360 [M]⁺; $^1$H NMR (DMSO-$d_6$, 400 MHz) is consistent with Example 4.

EXAMPLE 52

Preparation of 3-[5-Amino-4-(3-cyanobenzoyl)-pyrazol-1-yl]-N-cyclopropyl-4-methylbenzamide

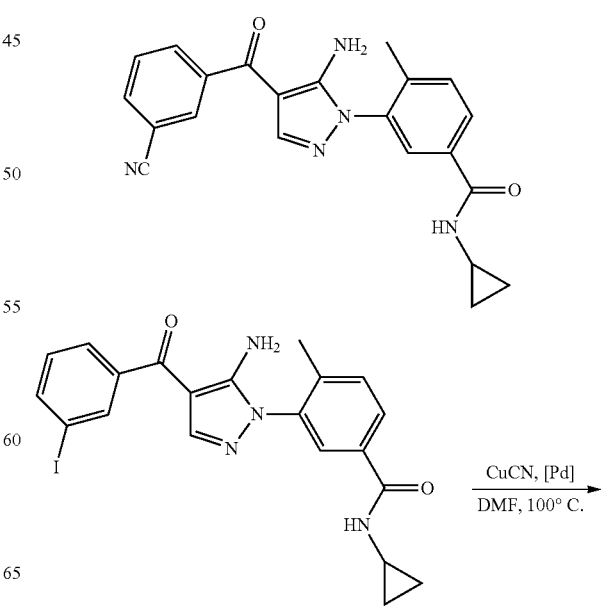

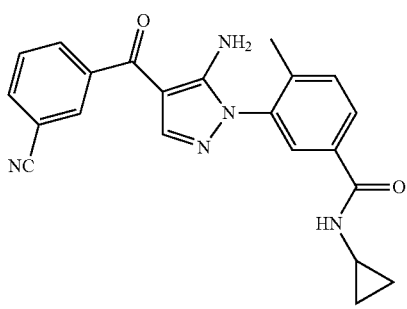

To a solution of 3-[5-amino-4-(3-iodobenzoyl)-pyrazol-1-yl]-N-cyclopropyl-4-methylbenzamide (110 mg, 0.23 mmol) in DMF (5 mL) was added CuCN (40 mg, 0.45 mmol) and tetrakis(triphenylphosphine)palladium (catalytic) and the mixture was heated at 100° C. over night under $N_2$. The solvent was removed and the residue was suspended in EtOAc, and solids were filtered off. The filtrate was washed by water, brine, dried over $Na_2SO_4$ and concentrated. The crude product was purified by column chromatography on silica gel (EtOAc). Product was obtained as a beige solid (30 mg, 34%). HPLC (4 minute 10-90 gradient) $t_R$ 2.02 min; MS m/z 386.13 [M+H]$^+$.

EXAMPLE 53

Preparation of 3-[5-Amino-4-(3-[1,3,4]oxadiazol-2-yl-benzoyl)-pyrazol-1-yl]-N-cyclopropyl-4-methylbenzamide

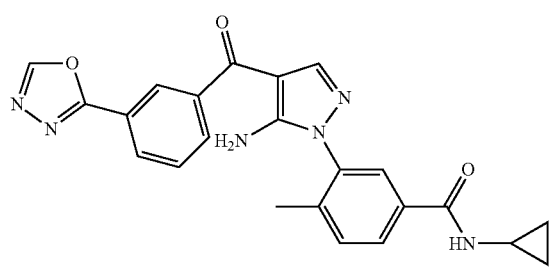

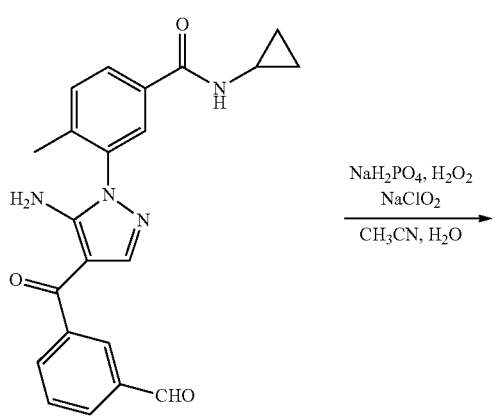

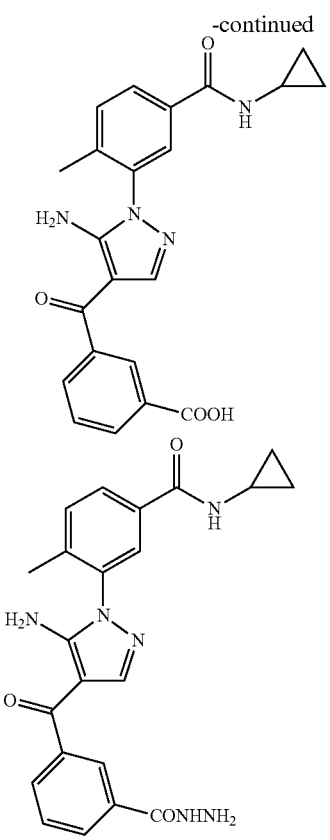

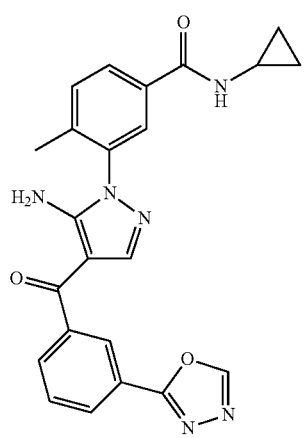

A. 3-[5-Amino-1-(5-cyclopropylcarbamoyl-2-methyl-phenyl)-1H-pyrazole-4-carbonyl]-benzoic acid To a stirred solution of 3-[5-amino-4-(3-formylbenzoyl)-pyrazol-1-yl]-N-cyclopropyl-4-methylbenzamide (900 mg) in $CH_3CN$ (25 mL) were added $NaH_2PO_4$ (55 mg in 2 mL water) and $H_2O_2$ (1.3 g, 30% solution in water) followed by the dropwise addition of an aqueous solution of $NaClO_2$ (365 mg) at 10° C. The mixture was stirred at this temperature for 4 h before $Na_2SO_3$ was added. Solvent was removed and residue was dissolved in EtOAc, the organic layer was washed with water and brine and concentrated. The crude product was purified by column chromatography on silica gel eluted with EtOAc followed by EtOAC:AcOH=100:1), to provide the desired intermediate as a beige foam (345 mg, 37%).

B. 3-[5-Amino-4-(3-hydrazinocarbonylbenzoyl)-pyrazol-1-yl]-N-cyclopropyl-4-methylbenzamide Compound 53A (50 mg, 0.12 mmol), t-butyl carbazate (33 mg, 0.24 mmol), EDCI (46 mg, 0.24 mmol) and HOBt (37 mg, 0.24 mmol) were dissolved in DMF (5 mL, dry) and stirred at room temperature over night. Solvent was removed, the residue was dissolved in EtOAc and the organics were washed by water, $K_2CO_3$ aqueous solution, brine, and dried over $Na_2SO_4$. Then TFA/DCE (5 mL, 1:1) was added and stirred at room temperature for 30 min. Solvent was removed, the residue was dissolved in EtOAc, washed with $K_2CO_3$ aqueous solution and dried over $Na_2SO_4$. Solvent was removed to provide compound B as a beige solid (45 mg, 88%).

C. 3-[5-Amino-4-(3-[1,3,4]oxadiazol-2-yl-benzoyl)-pyrazol-1-yl]-N-cyclopropyl-4-methylbenzamide Trimethyl orthoformate (2 mL) was added to the solution of compound 53B in MeOH (2 mL) and stirred at room temperature over night. Solvent was removed, solid residue was dissolved in 1,4-dioxane, and five drops of a 4M solution of HCl in dioxane was added and the mixture was heated in the microwave at 120° C. for 30 min. The solvent was removed, the residue was dissolved in EtOAc, and the organics were washed with water, brine and the crude product was purified by preparative TLC
(EtOAc MeOH=95:5) to provide product as a beige solid (25 mg, 63%). HPLC (4 minute 10-90 gradient) $t_R$ 1.81 min; MS m/z 429.13 $[M+H]^+$.

EXAMPLE 54

Preparation of 3-{5-Amino-4-[3-(5-methyl-[1,3,4]oxadiazol-2-yl)-benzoyl]-pyrazol-1-yl}-N-cyclopropyl-4-methyl-benzamide

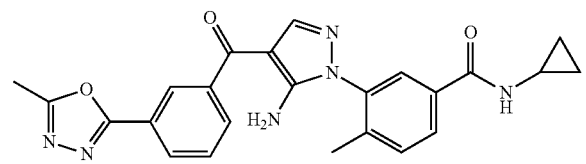

Similar procedure as in Example 53 except trimethylorthoacetate was used in place of trimethyl orthoformate. HPLC (4 minute 10-90 gradient) $t_R$ 1.84 min; MS m/z 443.15 $[M+H]^+$.

EXAMPLE 55

Preparation of 3-{5-Amino-4-[3-(pyrrolidine-1-carbonyl)-benzoyl]-imidazol-1-yl}-N-cyclopropyl-4-methyl-benzamide

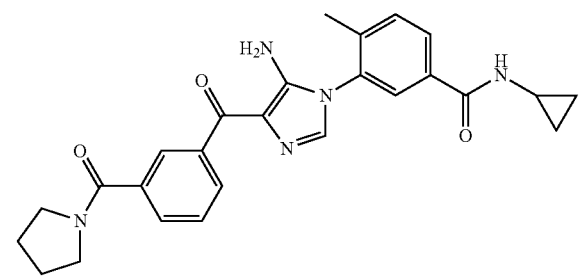

Similar procedure as in Example 21 except pyrrolidine was used in place of isopropylamine. HPLC (4 minute 10-90 gradient) $t_R$ 1.93 min; MS m/z 458.2 $[M+H]^+$.

EXAMPLE 56

Preparation of 3-[5-Amino-4-(3-cyclopropylcarbamoyl-benzoyl)-imidazol-1-yl]-N-cyclopropyl-4-methyl-benzamide

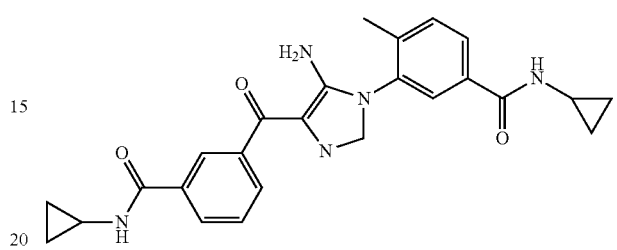

Similar procedure as in Example 21 except cyclopropylamine was used in place of isopropylamine. HPLC (4 minute 10-90 gradient) $t_R$ 1.74 min; MS m/z 444.14 $[M+H]^+$.

EXAMPLE 57

Preparation of 3-[5-Amino-4-(3-carbamoyl-benzoyl)-imidazol-1-yl]-N-cyclopropyl-4-methyl-benzamide

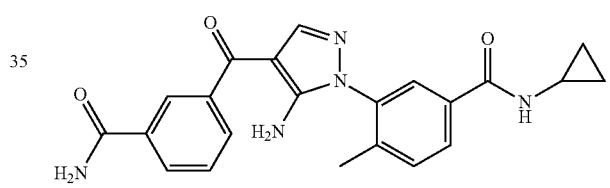

Similar procedure as in Example 21 except ammonia was used in place of isopropylamine. HPLC (4 minute 10-90 gradient) $t_R$ 1.51 min; MS m/z 404.2 $[M+H]^+$.

EXAMPLE 58

Preparation of 3-[5-Amino-4-(3-isopropylcarbamoylbenzoyl)-pyrazol-1-yl]-N-cyclopropyl-4-methyl-benzamide

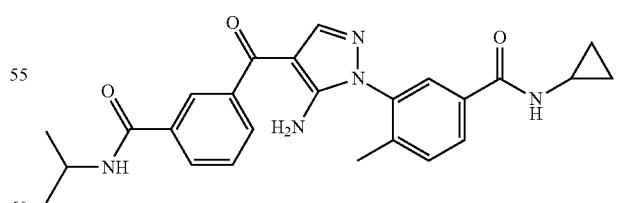

Similar procedure as in Example 21B except 3-[5-amino-1-(5-cyclopropylcarbamoyl-2-methylphenyl)-1H-pyrazole-4-carbonyl]-benzoic acid was used in place of 3-[5-amino-1-(5-cyclopropylcarbamoyl-2-methyl-phenyl)-1H-imidazole-4-carbonyl]-benzoic acid. HPLC (4 minute 10-90 gradient) $t_R$ 1.89 min; MS m/z 446.2 $[M+H]^+$.

EXAMPLES 59-69

The following examples were prepared with a procedure similar to Example 58 except the appropriate amine was used in place of isopropylamine.

TABLE 1

| Ex | Structure | Name | HPLC $t_R$ (min) | MS m/z $[M + H]^+$ |
|----|-----------|------|------------------|---------------------|
| 59 | 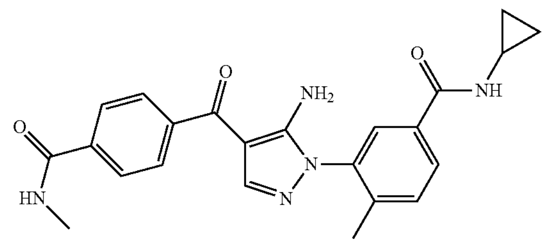 | 3-[5-Amino-4-(4-methylcarbamoyl-benzoyl)-pyrazol-1-yl]-N-cyclopropyl-4-methyl-benzamide | 1.03 | 418.2 |
| 60 | 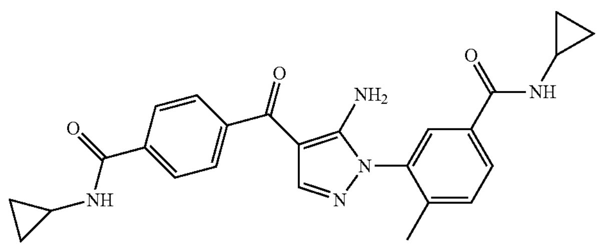 | 3-[5-Amino-4-(4-cyclopropylcarbamoyl-benzoyl)-pyrazol-1-yl]-N-cyclopropyl-4-methyl-benzamide | 1.77 | 444.26 |
| 61 | 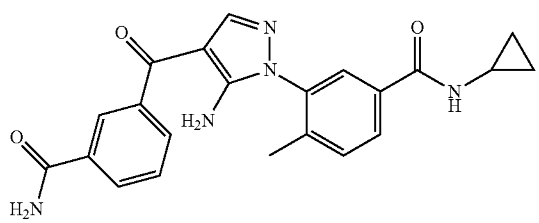 | 3-[5-Amino-4-(3-carbamoyl-benzoyl)-pyrazol-1-yl]-N-cyclopropyl-4-methyl-benzamide | 1.64 | 404.16 |
| 62 | 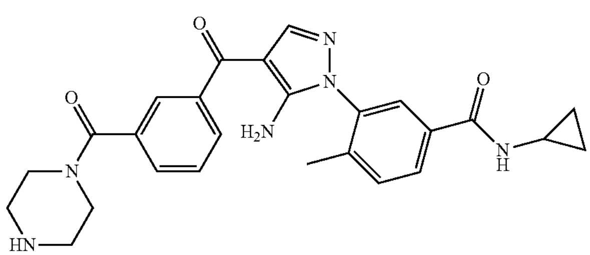 | 3-{5-Amino-4-[3-(piperazine-1-carbonyl)-benzoyl]-pyrazol-1-yl}-N-cyclopropyl-4-methyl-benzamide | 2.27 | 473.21 |
| 63 | 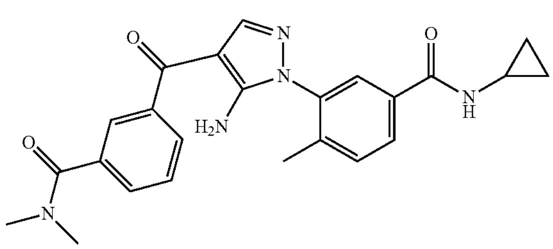 | 3-[5-Amino-4-(3-dimethylcarbamoyl-benzoyl)-pyrazol-1-yl]-N-cyclopropyl-4-methyl-benzamide | 1.71 | 432.21 |

TABLE 1-continued

| Ex | Name | HPLC $t_R$ (min) | MS m/z $[M + H]^+$ |
|---|---|---|---|
| 64 | 3-{5-Amino-4-[3-(cyclopropylmethyl-carbamoyl)-benzoyl]-pyrazol-1-yl}-N-cyclopropyl-4-methyl-benzamide | 1.9 | 458.25 |
| 65 | 3-[5-Amino-4-(3-ethylcarbamoyl-benzoyl)-pyrazol-1-yl]-N-cyclopropyl-4-methyl-benzamide | 1.77 | 432.18 |
| 66 | 3-[5-Amino-4-(3-methylcarbamoyl-benzoyl)-pyrazol-1-yl]-N-cyclopropyl-4-methyl-benzamide | 1.69 | 418.17 |
| 67 | 3-[5-Amino-4-(3-cyclopentylcarbamoyl-benzoyl)-pyrazol-1-yl]-N-cyclopropyl-4-methyl-benzamide | 2.0 | 472.23 |
| 68 | 3-[5-Amino-4-(3-isopropylcarbamoyl-benzoyl)-pyrazol-1-yl]-N-cyclopropyl-4-methyl-benzamide | 1.89 | 446.2 |
| 69 | 3-[5-Amino-4-(3-cyclopropylcarbamoyl-benzoyl)-pyrazol-1-yl]-N-cyclopropyl-4-methyl-benzamide | 1.82 | 444.15 |

EXAMPLES 70-75

The following examples were prepared with a procedure similar to Example 11 except the appropriate amine was used in place of 1-methylpiperazine.

TABLE 2

| Ex | Structure | Name | HPLC $t_R$ (min) | MS m/z $[M + H]^+$ |
|---|---|---|---|---|
| 70 | 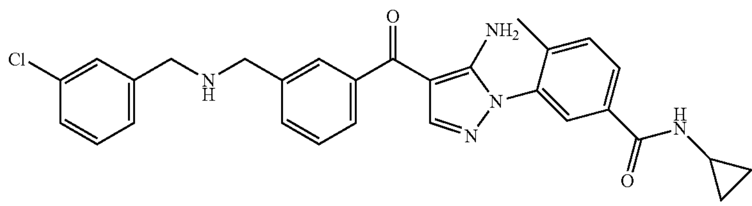 | 3-(5-Amino-4-{3-[(3-chloro-benzylamino)-methyl]-benzoyl}-pyrazol-1-yl)-N-cyclopropyl-4-methyl-benzamide | 1.74 | 514.17 |
| 71 | 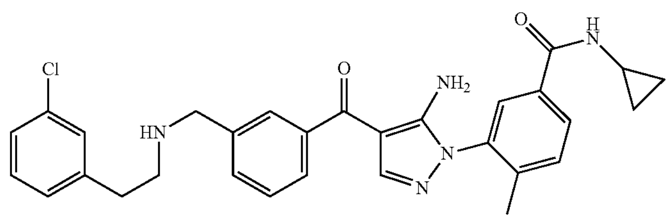 | 3-[5-Amino-4-(3-{[2-(3-chloro-phenyl)-ethylamino]-methyl}-benzoyl)-pyrazol-1-yl]-N-cyclopropyl-4-methyl-benzamide | 1.74 | 528.2 |
| 72 | 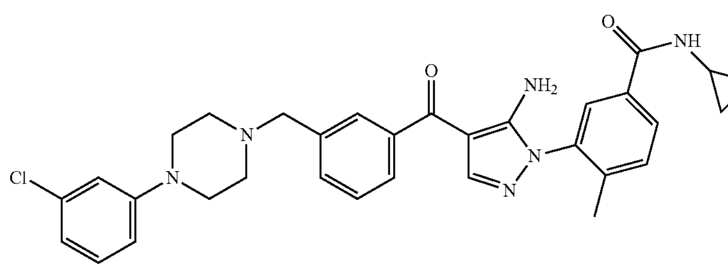 | 3-(5-Amino-4-{3-[4-(3-chloro-phenyl)-piperazin-1-ylmethyl]-benzoyl}-pyrazol-1-yl)-N-cyclopropyl-4-methyl-benzamide | 1.82 | 569.23 |
| 73 | 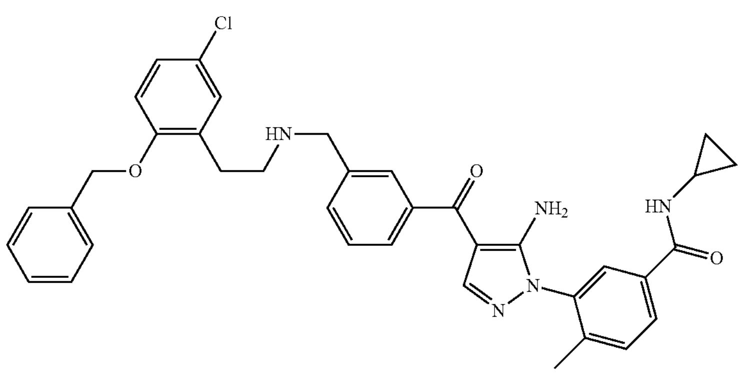 | 3-[5-Amino-4-(3-{[2-(2-benzyloxy-5-chloro-phenyl)-ethylamino]-methyl}-benzoyl)-pyrazol-1-yl]-N-cyclopropyl-4-methyl-benzamide | 2.11 | 634.2 |
| 74 | 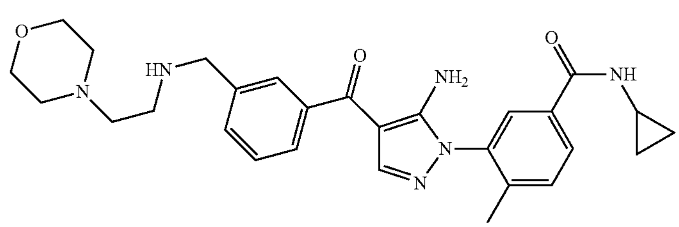 | 3-(5-Amino-4-{3-[(2-morpholin-4-yl-ethylamino)-methyl]-benzoyl}-pyrazol-1-yl)-N-cyclopropyl-4-methyl-benzamide | 1.03 | 503.22 |

TABLE 2-continued

| Ex | Structure | Name | HPLC $t_R$ (min) | MS m/z $[M + H]^+$ |
|---|---|---|---|---|
| 75 | 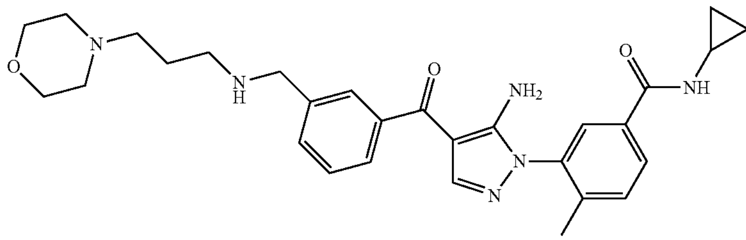 | 3-(5-Amino-4-{3-[(3-morpholin-4-yl-propylamino)-methyl]-benzoyl}-pyrazol-1-yl)-N-cyclopropyl-4-methyl-benzamide | 1.02 | 517.25 |

EXAMPLES 76-93

The following examples were prepared with a procedure similar to Example 17 except the appropriate grignard reagent was used in place of phenylmagnesium bromide.

TABLE 3

| Ex | Structure | Name | HPLC $t_R$ (min) | MS m/z $[M + H]^+$ |
|---|---|---|---|---|
| 76 | 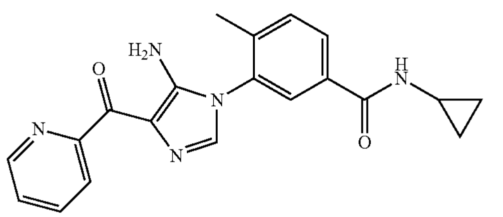 | 3-[5-Amino-4-(pyridine-2-carbonyl)-imidazol-1-yl]-N-cyclopropyl-4-methyl-benzamide | 1.56 | 362.23 |
| 77 | 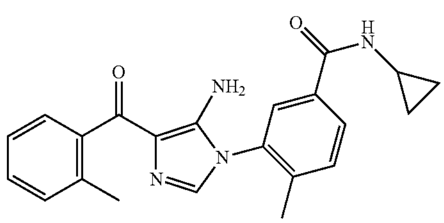 | 3-[5-Amino-4-(2-methyl-benzoyl)-imidazol-1-yl]-N-cyclopropyl-4-methyl-benzamide | 1.95 | 375.1 |
| 78 | 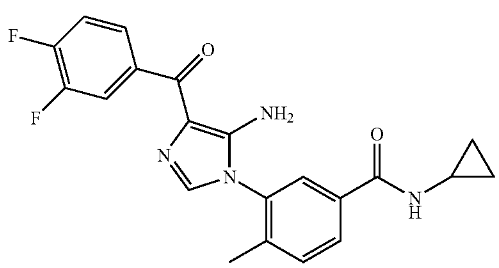 | 3-[5-Amino-4-(3,4-difluoro-benzoyl)-imidazol-1-yl]-N-cyclopropyl-4-methyl-benzamide | 2.53 | 397.17 |
| 79 | 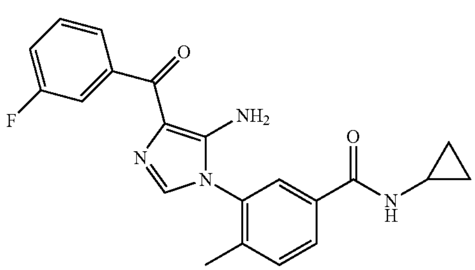 | 3-[5-Amino-4-(3-fluoro-benzoyl)-imidazol-1-yl]-N-cyclopropyl-4-methyl-benzamide | 2.23 | 379.2 |

TABLE 3-continued

| Ex | Structure | Name | HPLC $t_R$ (min) | MS m/z $[M + H]^+$ |
|---|---|---|---|---|
| 80 | 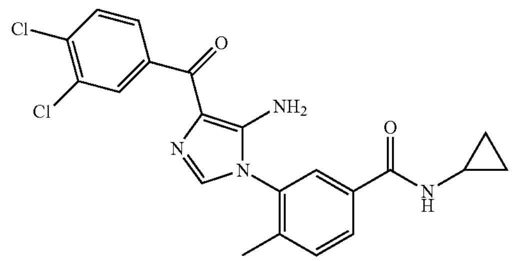 | 3-[5-Amino-4-(3,4-dichloro-benzoyl)-imidazol-1-yl]-N-cyclopropyl-4-methyl-benzamide | 2.95 | 429.11 |
| 81 | 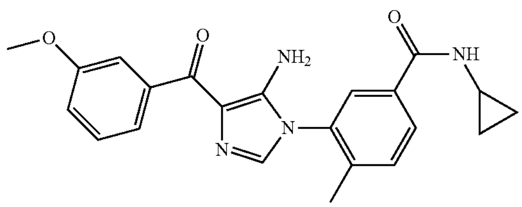 | 3-[5-Amino-4-(3-methoxy-benzoyl)-imidazol-1-yl]-N-cyclopropyl-4-methyl-benzamide | 2.22 | 391.19 |
| 82 | 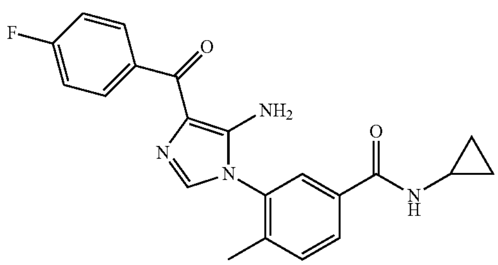 | 3-[5-Amino-4-(4-fluoro-benzoyl)-imidazol-1-yl]-N-cyclopropyl-4-methyl-benzamide | 2.29 | 379.1 |
| 83 | 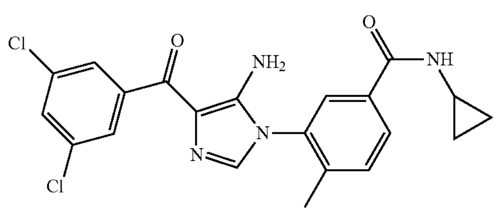 | 3-[5-Amino-4-(3,5-dichloro-benzoyl)-imidazol-1-yl]-N-cyclopropyl-4-methyl-benzamide | 3.07 | 429.13 |
| 84 | 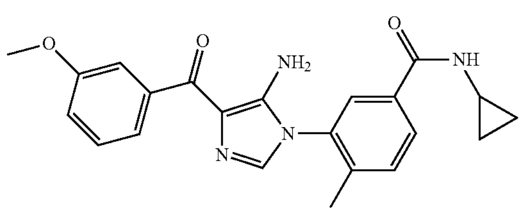 | 3-[5-Amino-4-(4-methoxy-benzoyl)-imidazol-1-yl]-N-cyclopropyl-4-methyl-benzamide | 2.12 | 391.11 |
| 85 | 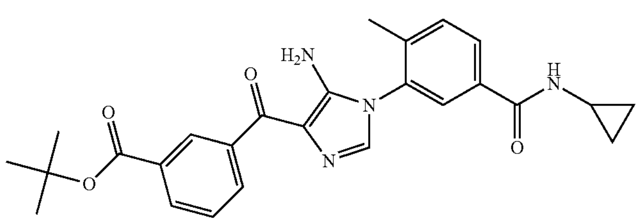 | 3-[5-Amino-1-(5-cyclopropylcarbamoyl-2-methyl-phenyl)-1H-imidazole-4-carbonyl]-benzoic acid tert-butyl ester | 2.53 | 461.05 |

TABLE 3-continued

| Ex | Structure | Name | HPLC $t_R$ (min) | MS m/z $[M + H]^+$ |
|---|---|---|---|---|
| 86 | 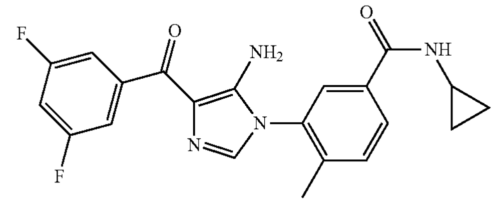 | 3-[5-Amino-4-(3,5-dichloro-benzoyl)-imidazol-1-yl]-N-cyclopropyl-4-methyl-benzamide | 2.58 | 397.18 |
| 87 | 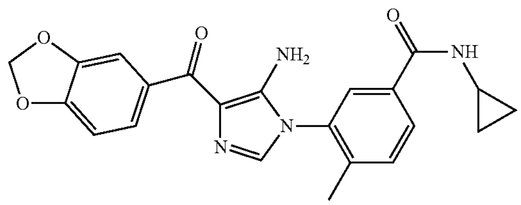 | 3-[5-Amino-4-(benzo[1,3]dioxole-5-carbonyl)-imidazol-1-yl]-N-cyclopropyl-4-methyl-benzamide | 2.12 | 405.11 |
| 88 | 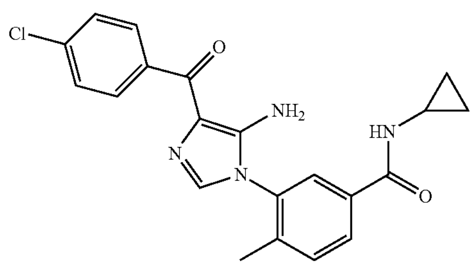 | 3-[5-Amino-4-(4-chloro-benzoyl)-imidazol-1-yl]-N-cyclopropyl-4-methyl-benzamide | 2.54 | 395.15 |
| 89 | 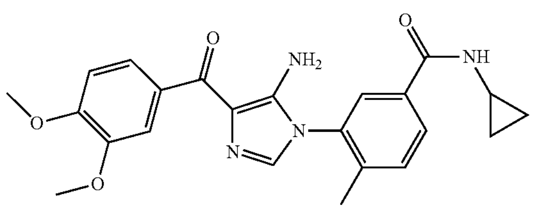 | 3-[5-Amino-4-(3,4-dimethoxy-benzoyl)-imidazol-1-yl]-N-cyclopropyl-4-methyl-benzamide | 1.95 | 420.1 |
| 90 | 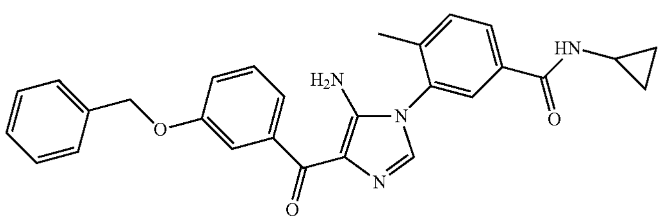 | 3-[5-Amino-4-(3-benzyloxy-benzoyl)-imidazol-1-yl]-N-cyclopropyl-4-methyl-benzamide | 2.51 | 467 |
| 91 | 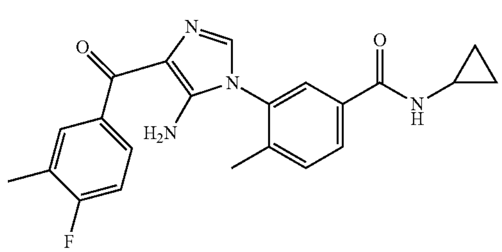 | 3-[5-Amino-4-(4-fluoro-3-methyl-benzoyl)-imidazol-1-yl]-N-cyclopropyl-4-methylbenzamide | 2.25 | 393 |

TABLE 3-continued

| Ex | Structure | Name | HPLC $t_R$ (min) | MS m/z $[M + H]^+$ |
|---|---|---|---|---|
| 92 | 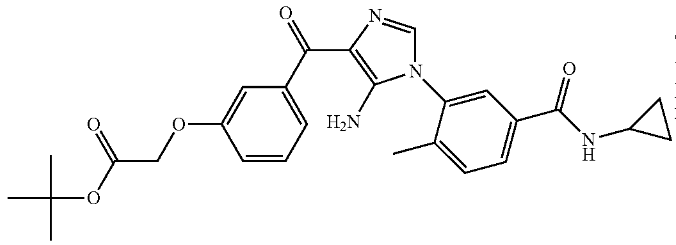 | {3-[5-Amino-1-(5-cyclopropylcarbamoyl-2-methyl-phenyl)-1H-imidazole-4-carbonyl]-phenoxy}-acetic acid tert-butyl ester | 2.23 | 491 |
| 93 | 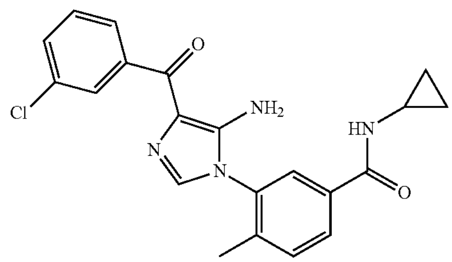 | 3-[5-Amino-4-(3-chloro-benzoyl)-imidazol-1-yl]-N-cyclopropyl-4-methyl-benzamide | 2.54 | 395.17 |

EXAMPLE 94

Preparation of 3-(5-Amino-4-benzoyl-2-methyl-imidazol-1-yl)-N-cyclopropyl-4-methyl-benzamide

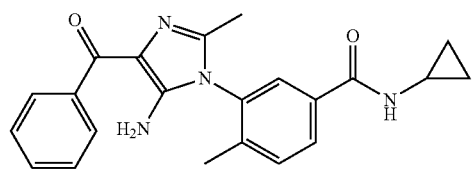

Similar procedure as in except 17 except triethylorthoacetate was used in place of triethylorthoformate. HPLC (4 minute 10-90 gradient) $t_R$ 1.56 min; MS m/z 375 [M+H]$^+$.

EXAMPLE 95

Preparation of 3-(5-Amino-4-benzoyl-2-propyl-imidazol-1-yl)-N-cyclopropyl-4-methyl-benzamide

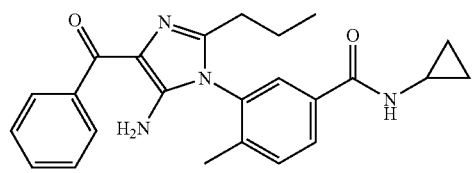

Similar procedure as in except 17 except triethylorthbutyrate was used in place of triethylorthoformate. HPLC (4 minute 10-90 gradient) $t_R$ 2.14 min; MS m/z 403[M+H]$^+$.

EXAMPLE 96

Preparation of 3-[5-Amino-4-(3-carbamoylmethoxybenzoyl)-pyrazol-1-yl]-N-cyclopropyl-4-methylbenzamide

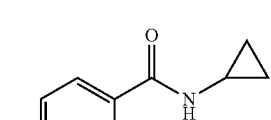

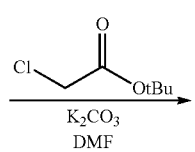

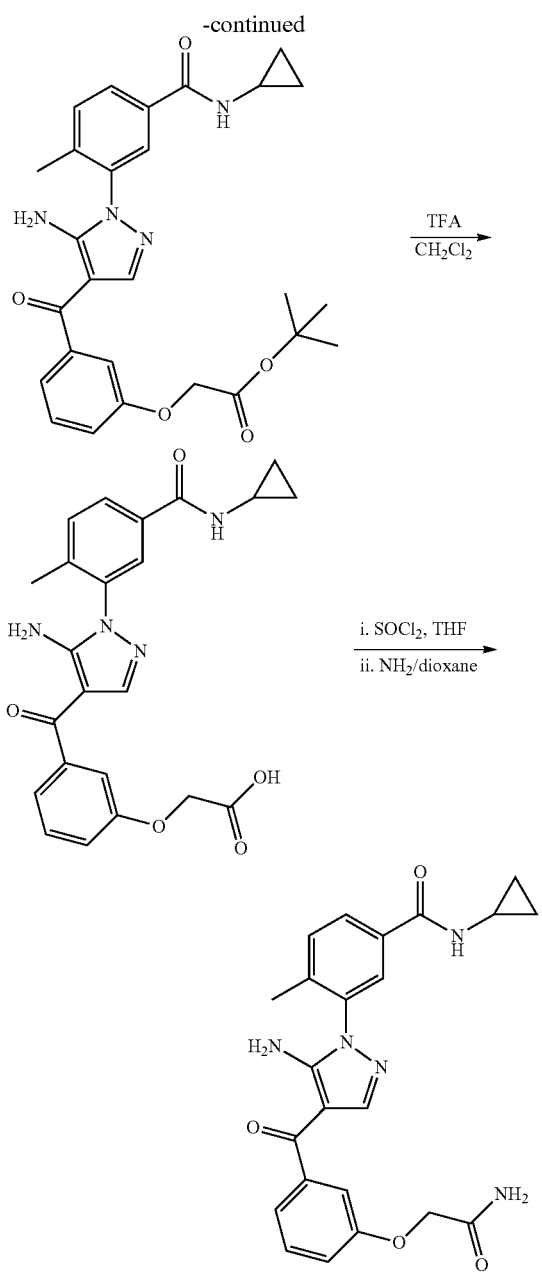

A. {3-[5-Amino-1-(5-cyclopropylcarbamoyl-2-methyl-phenyl)-1H-pyrazole-4-carbonyl]-phenoxy}-acetic acid To a stirred solution of 3-[5-amino-4-(3-hydroxy-benzoyl)-pyrazol-1-yl]-N-cyclopropyl-4-methylbenzamide (400 mg, 1.06 mmol) and t-butyl chloroacetate (319 mg, 2.12 mmol) in DMF (20 mL) was added $K_2CO_3$ (292 mg, 2.12 mmol) and the mixture was heated at 100° C. overnight. The solvent was removed, and the residue was suspended in EtOAc, washed by water, brine, dried over $Na_2SO_4$, and concentrated. The crude product was purified by column chromatography on silica gel (EtOAc:Hexane=3:1) to provide the product as a light yellow oil (140 mg, 27%).

B. {3-[5-Amino-1-(5-cyclopropylcarbamoyl-2-methyl-phenyl)-1H-pyrazole-4-carbonyl]-phenoxy}-acetic acid The oil (180 mg, 0.37 mmol) from last step was dissolved in DCM (5 mL), TFA (5 mL) was added and stirred at room temperature over night. Volatile organics were removed, toluene was added then removed in vacuo to provide the product as a white solid (140 mg, 88%).

C. 3-[5-Amino-4-(3-carbamoylmethoxy-benzoyl)-pyrazol-1-yl]-N-cyclopropyl-4-methylbenzamide To a solution of the intermediate obtained in the previous step in THF (5 mL) was added $SOCl_2$ (1 mL) and the mixture was stirred at room temperature for 2 h. The volatiles were removed, then $NH_3$ (0.5 M dioxane solution) was added and the mixture was stirred at room temperature for 30 min. The solvent was removed, and the residue was purified by preparative TLC (EtOAc:MeOH:$Et_3$N=100:10:1) and then by preparatory HPLC to provide the product as a beige solid (4.2 mg, 10%). HPLC (4 minute 10-90 gradient) $t_R$ 1.78 min; MS m/z 434.14 $[M+H]^+$.

EXAMPLES 97-105

The following examples were prepared with a procedure similar to Example 96 except the appropriate amine was used in place of ammonia.

TABLE 4

| Ex | Structure | Name | HPLC $t_R$ (min) | MS m/z $[M + H]^+$ |
|---|---|---|---|---|
| 97 | 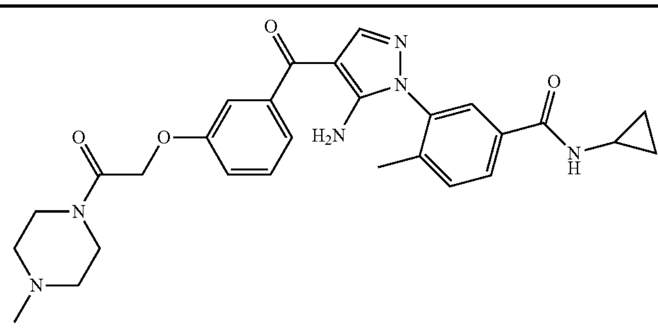 | 3-(5-Amino-4-{3-[2-(4-methyl-piperazin-1-yl)-2-oxo-ethoxy]-benzoyl}-pyrazol-1-yl)-N-cyclopropyl-4-methyl-benzamide | 1.56 | 517.22 |

TABLE 4-continued

| Ex | Structure | Name | HPLC $t_R$ (min) | MS m/z $[M + H]^+$ |
|---|---|---|---|---|
| 98 | 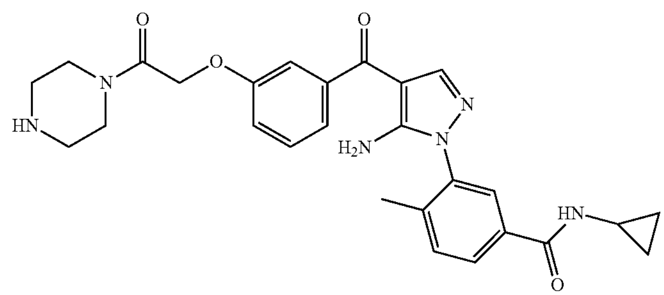 | 3-{5-Amino-4-[3-(2-oxo-2-piperazin-1-yl-ethoxy)-benzoyl]-pyrazol-1-yl}-N-cyclopropyl-4-methyl-benzamide | 1.48 | 503.21 |
| 99 | 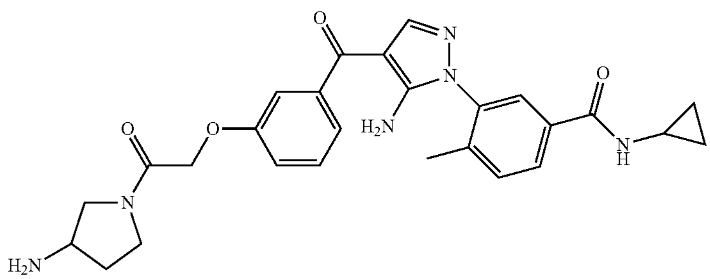 | 3-(5-Amino-4-{3-[2-(3-amino-pyrrolidin-1-yl)-2-oxo-ethoxy]-benzoyl}-pyrazol-1-yl)-N-cyclopropyl-4-methyl-benzamide | 1.63 | 503.2 |
| 100 | 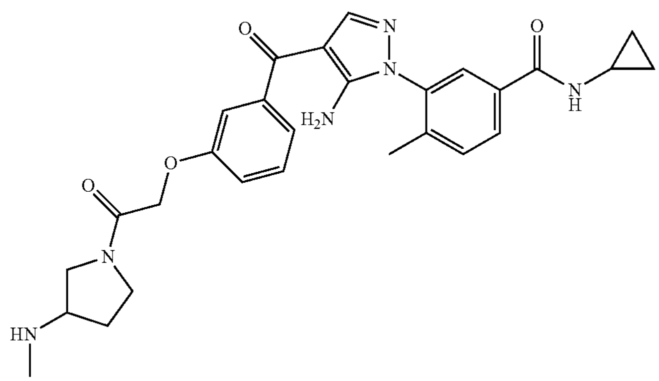 | 3-(5-Amino-4-{3-[2-(3-methylamino-pyrrolidin-1-yl)-2-oxo-ethoxy]-benzoyl}-pyrazol-1-yl)-N-cyclopropyl-4-methyl-benzamide | 1.51 | 517.22 |
| 101 | 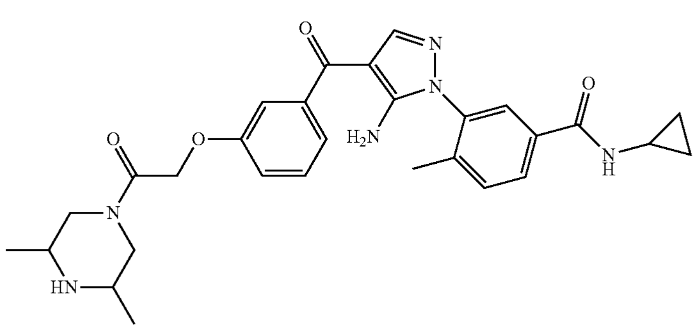 | 3-(5-Amino-4-{3-[2-(3,5-dimethyl-piperazin-1-yl)-2-oxo-ethoxy]-benzoyl}-pyrazol-1-yl)-N-cyclopropyl-4-methyl-benzamide | 1.62 | 531.26 |

TABLE 4-continued

| Ex | Structure | Name | HPLC t_R (min) | MS m/z [M + H]+ |
|---|---|---|---|---|
| 102 | 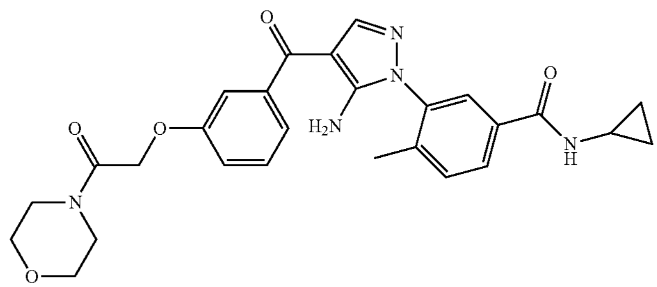 | 3-{5-Amino-4-[3-(2-morpholin-4-yl-2-oxo-ethoxy)-benzoyl]-1-yl}-N-cyclopropyl-4-methyl-benzamide | 1.92 | 504.2 |
| 103 | 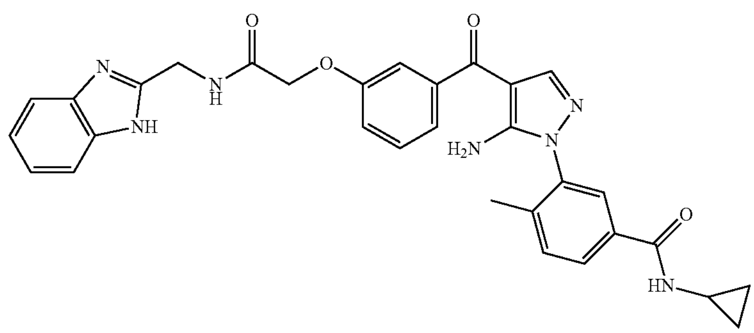 | 3-[5-Amino-4-(3-{[(1H-benzoimidazol-2-ylmethyl)-carbamoyl]-methoxy}-benzoyl)-pyrazol-1-yl]-N-cyclopropyl-4-methyl-benzamide | 1.54 | 564.21 |
| 104 | 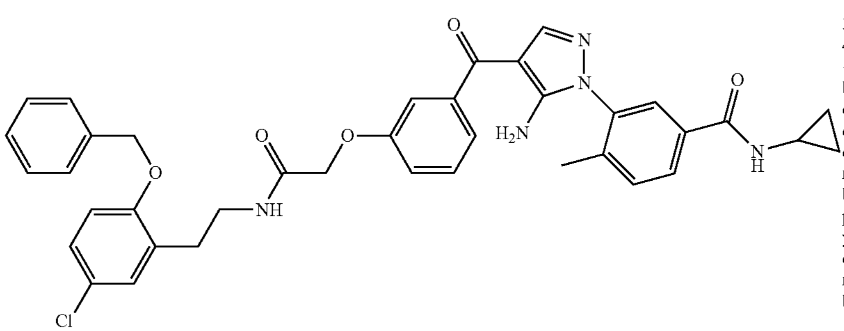 | 3-[5-Amino-4-(3-{[2-(2-benzyloxy-5-chloro-phenyl)-ethyl-carbamoyl]-methoxy}-benzoyl)-pyrazol-1-yl]-N-cyclopropyl-4-methyl-benzamide | 3.2 | 678.26 |
| 105 | 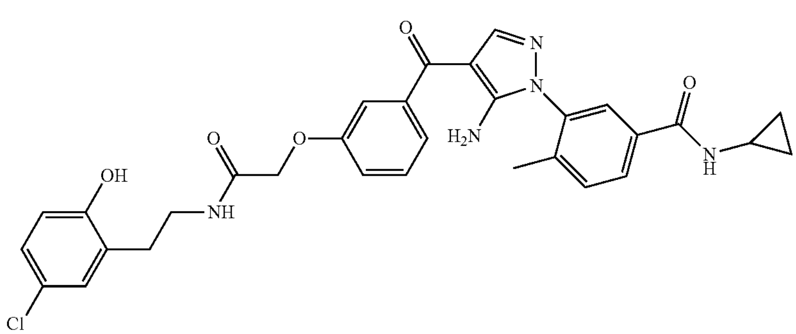 | 3-[5-Amino-4-(3-{[2-(5-chloro-2-hydroxy-phenyl)-ethylcarbamoyl]-methoxy}-benzoyl)-pyrazol-1-yl]-N-cyclopropyl-4-methyl-benzamide | 2.49 | 588.19 |

EXAMPLE 106

Preparation of 3-[5-Amino-4-(3-pyrazin-2-yl-benzoyl)-pyrazol-1-yl]-N-cyclopropyl-4-methylbenzamide

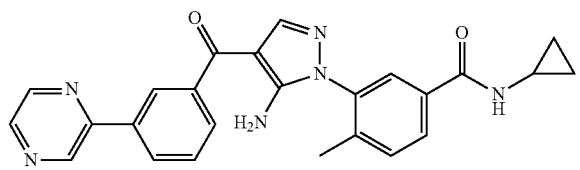

To a stirred solution of 3-[5-amino-4-(3-iodo-benzoyl)-pyrazol-1-yl]-N-cyclopropyl-4-methylbenzamide (130 mg, 0.27 mmol) and 2-tributylstannylpyrazine (119 mg, 0.32 mmol) in DMF (2 mL) was added tetrakis(triphenylphosphine) palladium (catalytic) and the mixture was heated in microwave at 160° C. for 15 min. The solvent was removed and the residue was dissolved in EtOAc. The organics were washed by water, brine and concentrated. The crude material was purified by preparatory HPLC to provide the desired product as beige solid (6.2 mg, 5%). HPLC (4 minute 10-90 gradient) $t_R$ 2.12 min; MS m/z 439.19 [M+H]$^+$.

EXAMPLE 107

Preparation of 3-[5-Amino-4-(3-pyridin-2-yl-benzoyl)-pyrazol-1-yl]-N-cyclopropyl-4-methylbenzamide

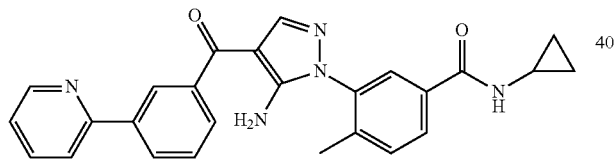

Similar procedure as in Example 106 except 2-tributylstannylpyridine was used in place of 2-tributylstannylpyrazine. HPLC (4 minute 10-90 gradient) $t_R$ 1.94 min; MS m/z 438.26 [M+H]$^+$.

EXAMPLE 108

Preparation of 3-[5-Amino-4-(pyridine-2-carbonyl)-pyrazol-1-yl]-N-cyclopropyl-4-methyl-benzamide

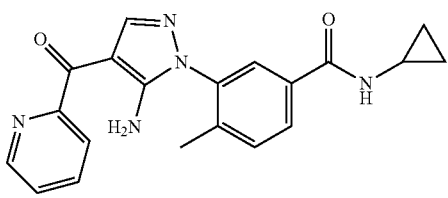

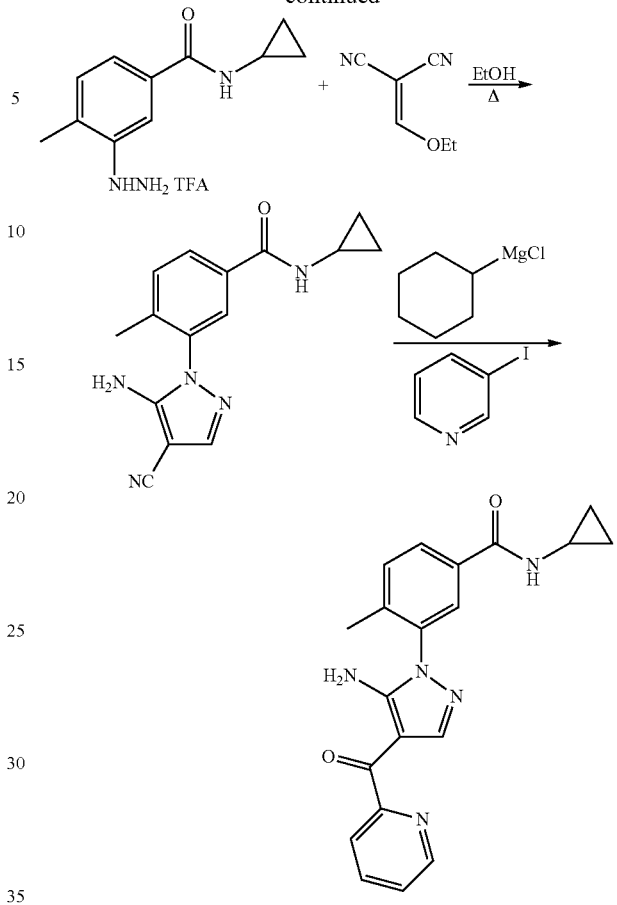

A. 3-(5-Amino-4-cyano-pyrazol-1-yl)-N-cyclopropyl-4-methylbenzamide

DIPEA (3.4 g, 26.5 mmol) was added to the solution of N-cyclopropyl-3-hydrazino-4-methyl-benzamide trifluoroacetate (8.45 g, 26.5 mmol) and 2-ethoxymethylene malononitrile (3.2 g, 26.5 mmol) in EtOH (100 mL) and stirred at 65° C. for 3 h. The solvent was removed the residue was suspended in EtOAc (~100 mL), and water was added to this suspension. The solid product was filtered. The filtrate was washed by water, brine, dried over Na$_2$SO$_4$, concentrated, and purified by column chromatography on silica gel eluted with EtOAc. The product, combined from filtration and chromatography, was obtained as a beige solid (7.1 g, 96%).

B. 3-[5-Amino-4-(pyridine-2-carbonyl)-pyrazol-1-yl]-N-cyclopropyl-4-methyl-benzamide Cyclohexylmagnesium chloride (5 mL, 2.0 M in Et$_2$O) was added dropwise to the solution of 2-iodopyridine (1.03 g, 5 mmol) in THF (15 mL) at −20° C. The mixture was stirred at this temperature for 20 min before 3-(5-Amino-4-cyano-pyrazol-1-yl)-N-cyclopropyl-4-methyl-benzamide (140 mg, 0.5 mmol) was added, then stirred at room temperature overnight. The reaction was quenched by the addition of K$_2$CO$_3$ aqueous solution, then the mixture was extracted with EtOAc and the organic layers washed with water and brine. Purification by column chromatography on silica gel eluted with EtOAc provided the product as a white solid (60 mg, 33%). HPLC (4 minute 10-90 gradient) $t_R$ 2.09 min; MS m/z 362.20 [M+H]$^+$.

EXAMPLE 109

Preparation of 3-(5-Amino-4-cyclopentanecarbonyl-pyrazol-1-yl)-N-cyclopropyl-4-methylbenzamide

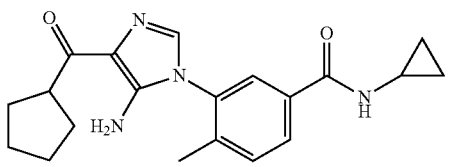

Similar procedure as in Example 17B except 3-[5-amino-4-(3-cyano-benzoyl)-pyrazol-1-yl]-N-cyclopropyl-4-methyl-benzamide was used in place of 3-(5-amino-4-cyano-imidazol-1-yl)-N-cyclopropyl-4-methyl-benzamide and cyclopentylmagnesium bromide was used in place of phenyl magnesium bromide. HPLC (4 minute 10-90 gradient) $t_R$ 2.54 min; MS m/z 353.19 [M+H]$^+$.

EXAMPLES 110-126

The following examples were prepared with a procedure similar to Example 109 except the appropriate grignard reagent was used in place of cyclopentylmagnesium bromide.

TABLE 5

| Ex | Structure | Name | HPLC $t_R$ (min) | MS m/z [M + H]$^+$ |
|---|---|---|---|---|
| 110 | 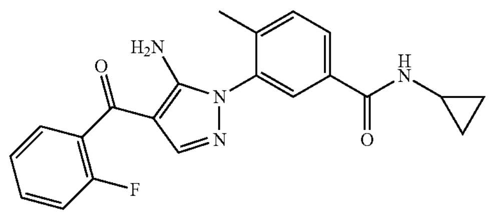 | 3-[5-Amino-4-(benzo[1,3]dioxole-5-carbonyl)-pyrazol-1-yl]-N-cyclopropyl-4-methylbenzamide | 2.67 | 405.16 |
| 111 | 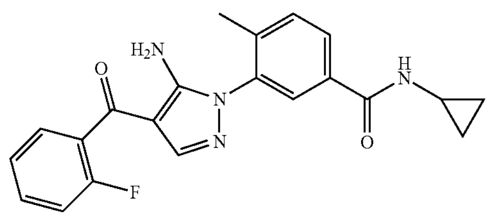 | 3-[5-Amino-4-(2-fluoro-benzoyl)-pyrazol-1-yl]-N-cyclopropyl-4-methyl-benzamide | 2.05 | 379.13 |
| 112 | 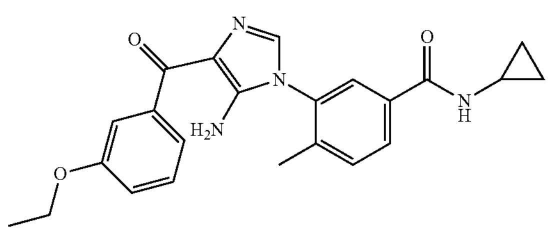 | 3-[5-Amino-4-(3-ethoxy-benzoyl)-pyrazol-1-yl]-N-cyclopropyl-4-methyl-benzamide | 2.58 | 405.17 |
| 113 | 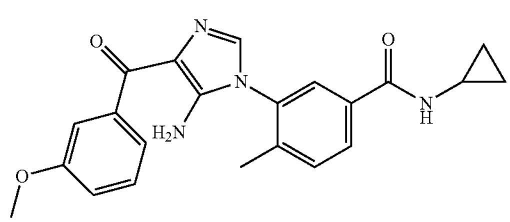 | 3-[5-Amino-4-(3-methoxy-benzoyl)-pyrazol-1-yl]-N-cyclopropyl-4-methyl-benzamide | 2.37 | 391.17 |
| 114 | 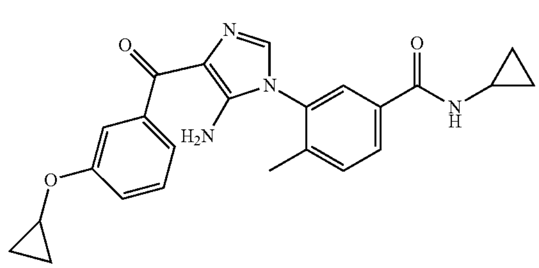 | 3-[5-Amino-4-(3-cyclopropoxy-benzoyl)-pyrazol-1-yl]-N-cyclopropyl-4-methyl-benzamide | 2.68 | 417.2 |

TABLE 5-continued

| Ex | Structure | Name | HPLC t$_R$ (min) | MS m/z [M + H]$^+$ |
|---|---|---|---|---|
| 115 | 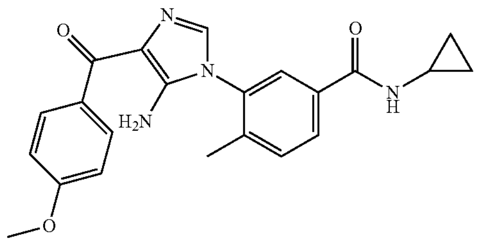 | 3-[5-Amino-4-(4-methoxy-benzoyl)-pyrazol-1-yl]-N-cyclopropyl-4-methyl-benzamide | 2.24 | 391.19 |
| 116 | 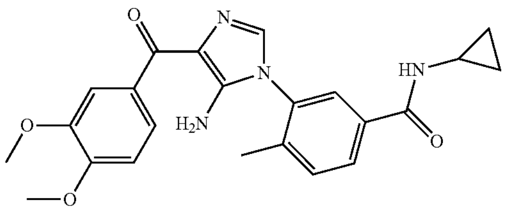 | 3-[5-Amino-4-(3,4-dimethoxy-benzoyl)-pyrazol-1-yl]-N-cyclopropyl-4-methyl-benzamide | 2.11 | 421.17 |
| 117 | 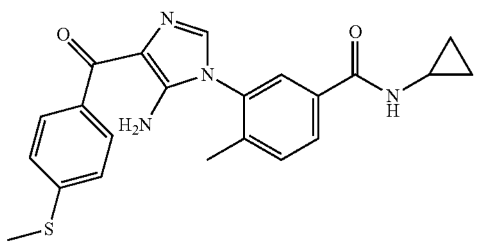 | 3-[5-Amino-4-(4-methylsulfanyl-benzoyl)-pyrazol-1-yl]-N-cyclopropyl-4-methyl-benzamide | 2.59 | 407.14 |
| 118 | 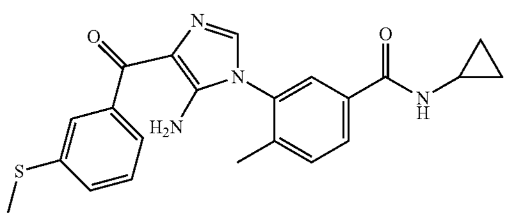 | 3-[5-Amino-4-(3-methylsulfanyl-benzoyl)-pyrazol-1-yl]-N-cyclopropyl-4-methyl-benzamide | 2.61 | 407.15 |
| 119 | 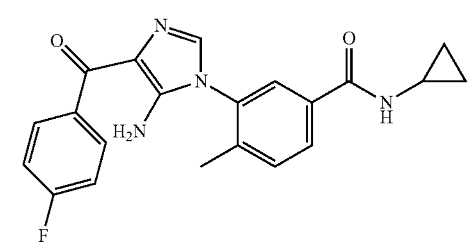 | 3-[5-Amino-4-(4-fluoro-benzoyl)-pyrazol-1-yl]-N-cyclopropyl-4-methyl-benzamide | 2.18 | 379.23 |
| 120 | 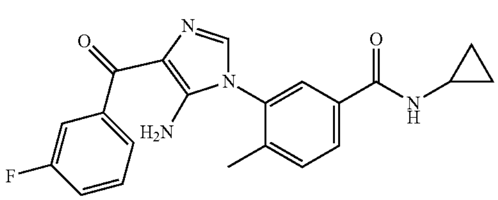 | 3-[5-Amino-4-(3-fluoro-benzoyl)-pyrazol-1-yl]-N-cyclopropyl-4-methyl-benzamide | 2.18 | 379.15 |

TABLE 5-continued

| Ex | Structure | Name | HPLC $t_R$ (min) | MS m/z $[M + H]^+$ |
|---|---|---|---|---|
| 121 | 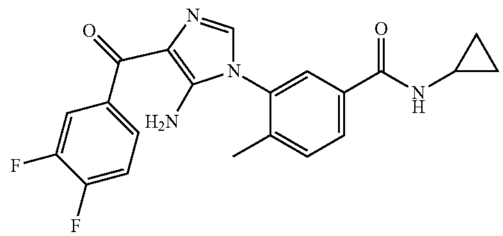 | 3-[5-Amino-4-(3,4-difluoro-benzoyl)-pyrazol-1-yl]-N-cyclopropyl-4-methyl-benzamide | 2.25 | 3.97.16 |
| 122 | 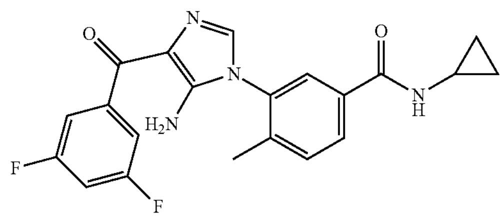 | 3-[5-Amino-4-(3,5-difluoro-benzoyl)-pyrazol-1-yl]-N-cyclopropyl-4-methyl-benzamide | 2.28 | 397.17 |
| 123 | 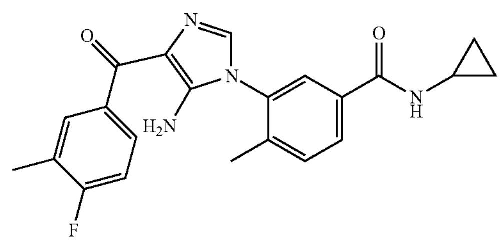 | 3-[5-Amino-4-(4-fluoro-3-methyl-benzoyl)-pyrazol-1-yl]-N-cyclopropyl-4-methyl-benzamide | 2.32 | 393.23 |
| 124 | 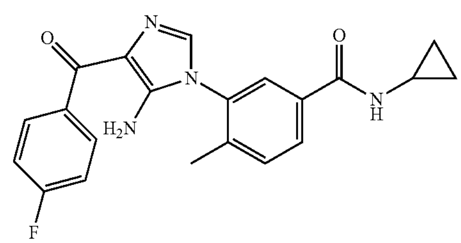 | 3-[5-Amino-4-(4-fluoro-benzoyl)-pyrazol-1-yl]-N-cyclopropyl-4-methyl-benzamide | 2.15 | 379.17 |
| 125 | 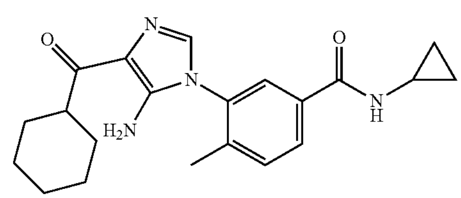 | 3-(5-Amino-4-cyclohexanecarbonyl-pyrazol-1-yl)-N-cyclopropyl-4-methyl-benzamide | 2.75 | 367.22 |
| 126 | 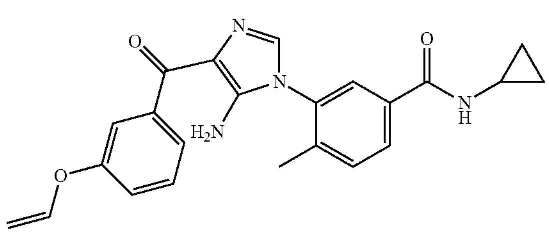 | 3-[5-Amino-4-(3-vinyloxy-benzoyl)-pyrazol-1-yl]-N-cyclopropyl-4-methyl-benzamide | 2.64 | 403.15 |

EXAMPLE 127

Preparation of 3-{5-Amino-4-[3-([1,3,4]oxadiazol-2-ylmethoxy)-benzoyl]-pyrazol-1-yl}-N-cyclopropyl-4-methylbenzamide

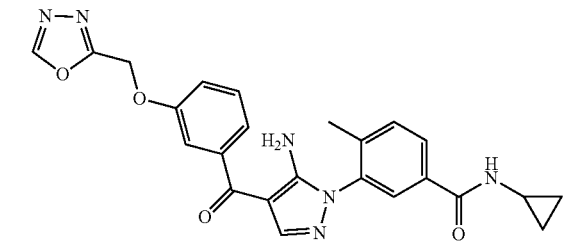

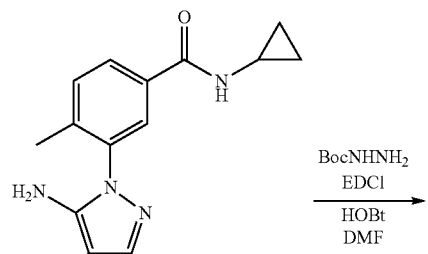

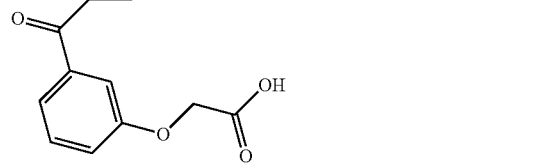

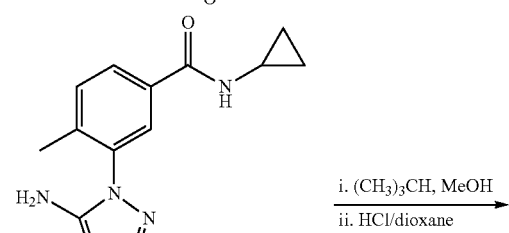

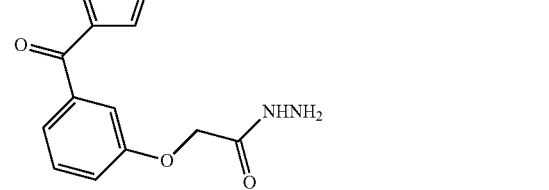

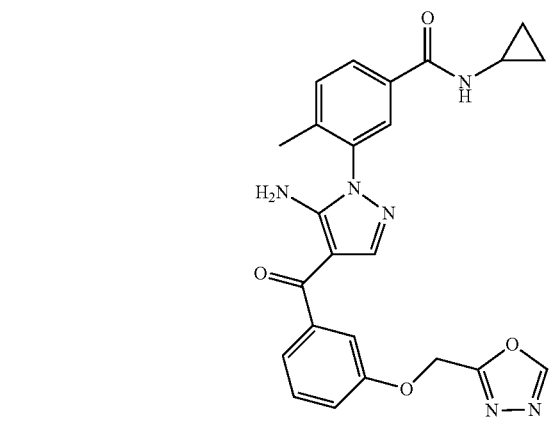

A. 3-[5-Amino-4-(3-hydrazinocarbonylmethoxy-benzoyl)-pyrazol-1-yl]-N-cyclopropyl-4-methylbenzamide Compound 97A (300 mg, 0.69 mmol), t-butyl carbazate (182 mg, 1.38 mmol), EDCI (263 mg, 1.38 mmol) and HOBt (211 mg, 1.38 mmol) were dissolved in DMF (10 mL, dry) and stirred at room temperature for 2 h. Solvent was removed, residue was dissolved in EtOAc, washed by water, $K_2CO_3$ aqueous solution, brine, and dried over $Na_2SO_4$. Then TFA/DCE (5 mL, 1:1) was added and stirred at room temperature for 30 min. Solvent was removed, residue was dissolved in EtOAc, washed with $K_2CO_3$ aqueous solution and dried over $Na_2SO_4$. The crude resiude was purified by column chromatography on silica gel (EtOAc MeOH=10:1), and the desired compound was obtained as a white solid (88 mg, 28%).

B. 3-{5-Amino-4-[3-([1,3,4]oxadiazol-2-ylmethoxy)-benzoyl]-pyrazol-1-yl}-N-cyclopropyl-4-methylbenzamide Trimethyl orthoformate (3 mL) was added to the solution of compound 52B (48 mg, 0.11 mmol) in MeOH (3 mL) and stirred at room temperature over night. Solvent was removed, solid residue was dissolved in 1,4-dioxane, five drops of HCl in dioxane (4M) was added, and the mixture heated in microwave at 120° C. for 30 min. Solvent was removed, residue was dissolved in EtOAc, washed with water and brine. The crude product was purified by preparatory HPLC, and the product was obtained as a white solid (3.3 mg, 6.7%). HPLC (4 minute 10-90 gradient) $t_R$ 2.07 min; MS m/z 459.13 $[M+H]^+$.

EXAMPLE 128

Preparation of 5-Amino-1-(5-cyclopropylcarbamoyl-2-methyl-phenyl)-1H-pyrazole-4-carboxylic acid (2-methyl-cyclohexyl)-amide

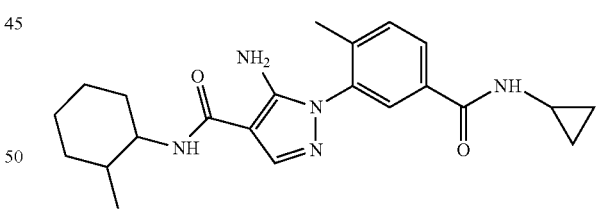

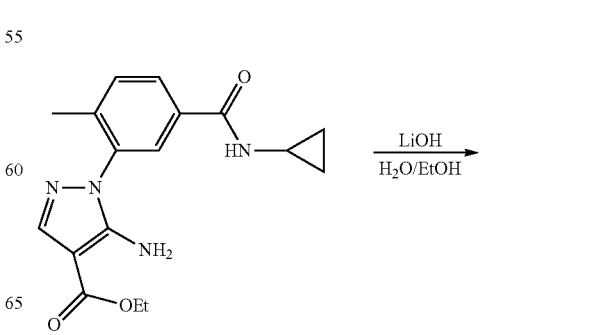

-continued

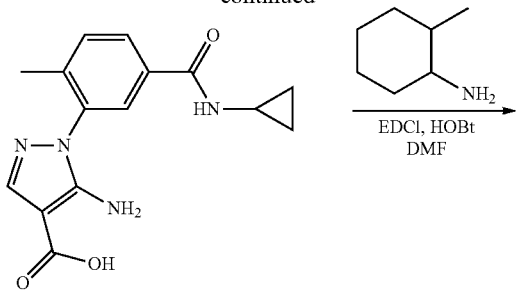

A. 5-Amino-1-(5-cyclopropylcarbamoyl-2-methyl-phenyl)-1H-pyrazole-4-carboxylic acid A solution of 5-amino-1-(5-cyclopropylcarbamoyl-2-methyl-phenyl)-1H-pyrazole-4-carboxylic acid ethyl ester (1.0 g, see Example 44), LiOH (1.2 g) in water/ethanol (15 ml/20 ml) was heated at 50° C. overnight. The solution was neutralized with dilute HCl (2M), and extracted with ethyl acetate (200 ml×2), dried over Na$_2$SO$_4$. The solvent was evaporated under reduced pressure and ethyl acetate and diethyl ether was added. The resulting solid was filtered to give the desired 5-amino-1-(5-cyclopropylcarbamoyl-2-methylphenyl)-1H-pyrazole-4-carboxylic acid. (0.8 g; yield: 88%.).

B. 5-Amino-1-(5-cyclopropylcarbamoyl-2-methyl-phenyl)-1H-pyrazole-4-carboxylic acid (2-methyl-cyclohexyl)-amide A solution of 5-amino-1-(5-cyclopropylcarbamoyl-2-methylphenyl)-1H-pyrazole-4-carboxylic acid (21 mg), 2-methylcyclohexylamine (10 mg), EDCI (28 mg) and HOBt (12 mg) in DMF (0.75 ml) was reacted at room temperature for 24 h. Water (4 ml) was added and the solution was extracted with ethyl acetate (3 mL×2). The organic phase was then washed with water (3 mL), dried over Na$_2$SO$_4$ and evaporated. The residue was purified by preparative TLC plate to give the desired product 5-amino-1-(5-cyclopropylcarbamoyl-2-methylphenyl)-1H-pyrazole-4-carboxylic acid (2-methylcyclohexyl)-amide (19 mg, 70%). HPLC (4 minute gradient) t$_R$ 2.34 min; MS m/z 396.31 [M+H]$^+$.

EXAMPLES 129-156

The following examples were prepared with a procedure similar to Example 128 except the appropriate amine was used in place of 2-methylcyclohexylamine.

TABLE 6

| Ex | Structure | Name | HPLC t$_R$ (min) | MS m/z [M + H]$^+$ |
|---|---|---|---|---|
| 129 | 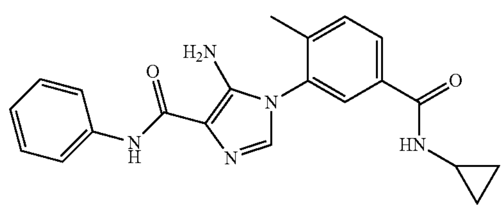 | 5-Amino-1-(5-cyclopropylcarbamoyl-2-methyl-phenyl)-1H-pyrazole-4-carboxylic acid phenylamide | 2.4 | 376.2 |
| 130 | 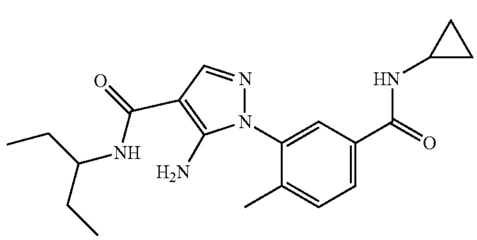 | 5-Amino-1-(5-cyclopropylcarbamoyl-2-methyl-phenyl)-1H-pyrazole-4-carboxylic acid (1-ethyl-propyl)-amide | 2.16 | 370.3 |
| 131 | 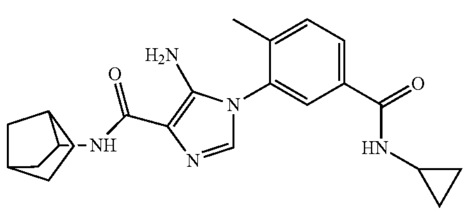 | 5-Amino-1-(5-cyclopropylcarbamoyl-2-methyl-phenyl)-1H-pyrazole-4-carboxylic acid bicyclo[2.2.1]hept-2-ylamide | 2.41 | 394.3 |

TABLE 6-continued

| Ex | Structure | Name | HPLC $t_R$ (min) | MS m/z $[M + H]^+$ |
|---|---|---|---|---|
| 132 | 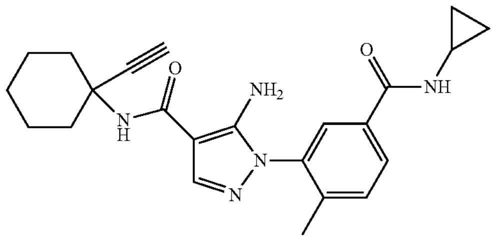 | 5-Amino-1-(5-cyclopropylcarbamoyl-2-methyl-phenyl)-1H-pyrazole-4-carboxylic acid (1-ethy | 2.57 | 406.2 |
| 133 | 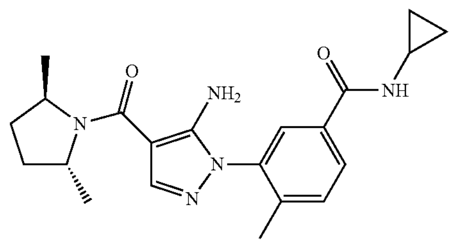 | 3-[5-Amino-4-(2,5-dimethyl-pyrrolidine-1-carbonyl)-pyrazol-1-yl]-N-cyclopropyl-4-methyl-benzamide | 2.17 | 383.29 |
| 134 | 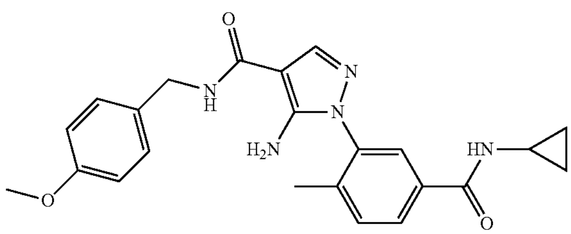 | 5-Amino-1-(5-cyclopropylcarbamoyl-2-methyl-phenyl)-1H-pyrazole-4-carboxylic acid 4-methoxy-benzylamide | 2.15 | 420.3 |
| 135 | 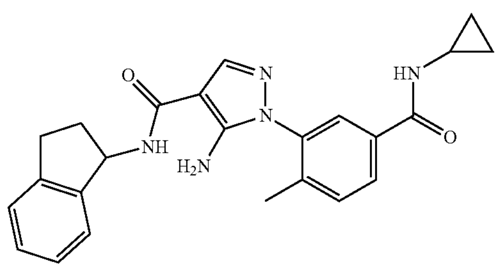 | 5-Amino-1-(5-cyclopropylcarbamoyl-2-methyl-phenyl)-1H-pyrazole-4-carboxylic acid indan-1-ylamide | 2.35 | 416.75 |
| 136 | 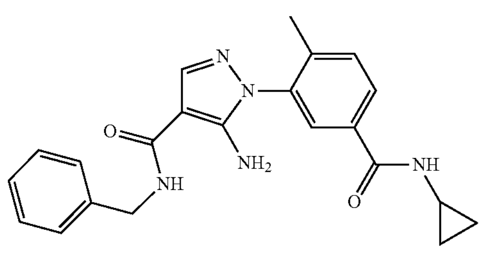 | 5-Amino-1-(5-cyclopropylcarbamoyl-2-methyl-phenyl)-1H-pyrazole-4-carboxylic acid benzylamide | 2.04 | 390.23 |
| 137 | 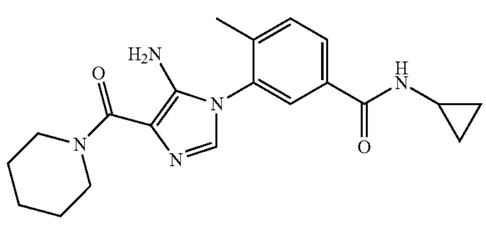 | 3-[5-Amino-4-(piperidine-1-carbonyl)-pyrazol-1-yl]-N-cyclopropyl-4-methyl-benzamide | 2.05 | 368.16 |

TABLE 6-continued

| Ex | Structure | Name | HPLC $t_R$ (min) | MS m/z $[M + H]^+$ |
|---|---|---|---|---|
| 138 | 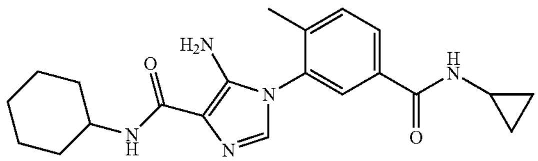 | 5-Amino-1-(5-cyclopropylcarbamoyl-2-methyl-phenyl)-1H-pyrazole-4-carboxylic acid cyclohexylamide | 2.19 | 382.25 |
| 139 | 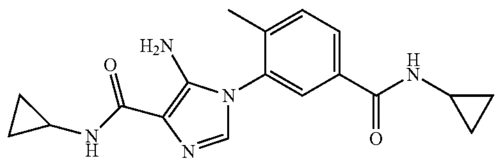 | 5-Amino-1-(5-cyclopropylcarbamoyl-2-methyl-phenyl)-1H-pyrazole-4-carboxylic acid cyclopropylamide | 1.72 | 340.23 |
| 140 | 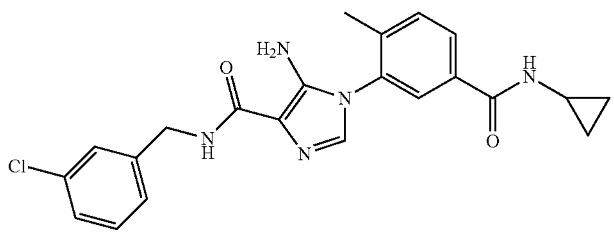 | 5-Amino-1-(5-cyclopropylcarbamoyl-2-methyl-phenyl)-1H-pyrazole-4-carboxylic acid chlorobenzylamide | 2.31 | 424.31 |
| 141 | 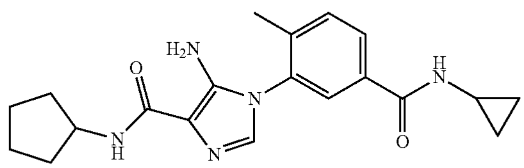 | 5-Amino-1-(5-cyclopropylcarbamoyl-2-methyl-phenyl)-1H-pyrazole-4-carboxylic acid cyclopentylamide | 2.03 | 368.29 |
| 142 | 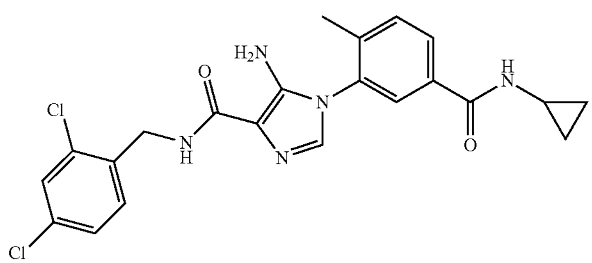 | 5-Amino-1-(5-cyclopropylcarbamoyl-2-methyl-phenyl)-1H-pyrazole-4-carboxylic acid 2,4-dichloro-benzylamide | 2.54 | 458.24 |
| 143 | 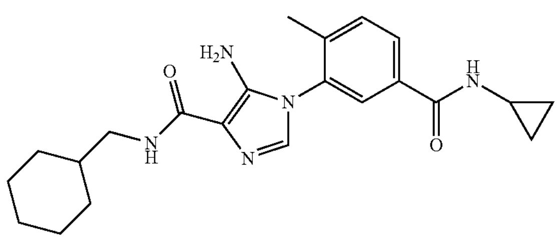 | 5-Amino-1-(5-cyclopropylcarbamoyl-2-methyl-phenyl)-1H-pyrazole-4-carboxylic acid cyclohexylmethyl-amide | 2.38 | 396.4 |
| 144 | 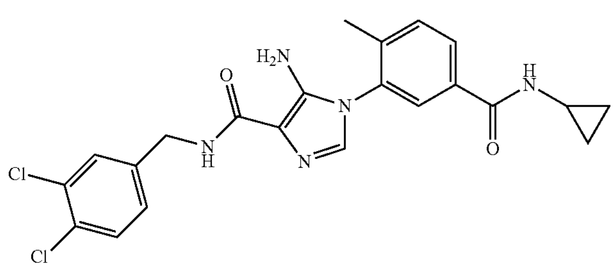 | 5-Amino-1-(5-cyclopropylcarbamoyl-2-methyl-phenyl)-1H-pyrazole-4-carboxylic acid 3,4-dichloro-benzylamide | 2.5 | 458.23 |

TABLE 6-continued

| Ex | Structure | Name | HPLC $t_R$ (min) | MS m/z $[M + H]^+$ |
|---|---|---|---|---|
| 145 | 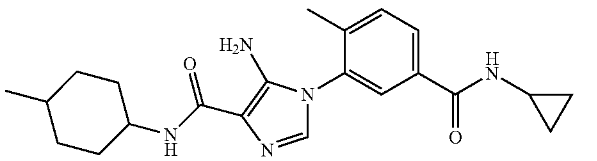 | 5-Amino-1-(5-cyclopropylcarbamoyl-2-methyl-phenyl)-1H-pyrazole-4-carboxylic acid (4-methyl-cyclohexyl)-amide | 2.45 | 396.32 |
| 146 | 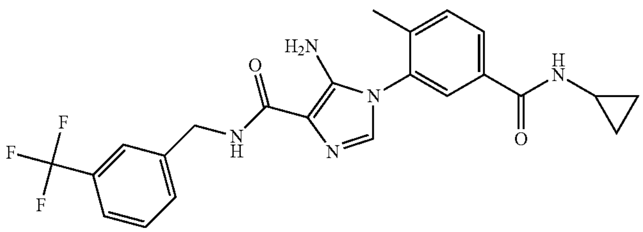 | 5-Amino-1-(5-cyclopropylcarbamoyl-2-methyl-phenyl)-1H-pyrazole-4-carboxylic acid 3-trifluoromethyl benzylamide | 2.44 | 458.25 |
| 147 | 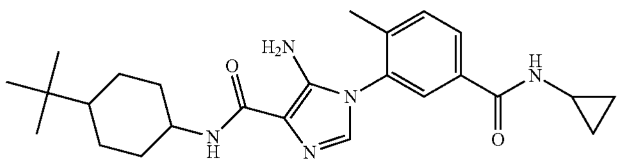 | 5-Amino-1-(5-cyclopropylcarbamoyl-2-methyl-phenyl)-1H-pyrazole-4-carboxylic acid (4-tert-butyl-cyclohexyl)-amide | 2.86 | 438.4 |
| 148 | 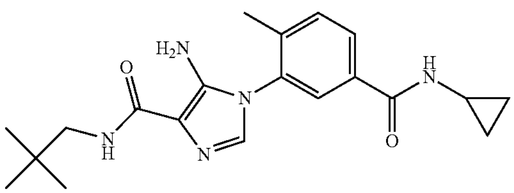 | 5-Amino-1-(5-cyclopropylcarbamoyl-2-methyl-phenyl)-1H-pyrazole-4-carboxylic acid (2,2-dimethyl-propyl)-amide | 2.19 | 370.28 |
| 149 | 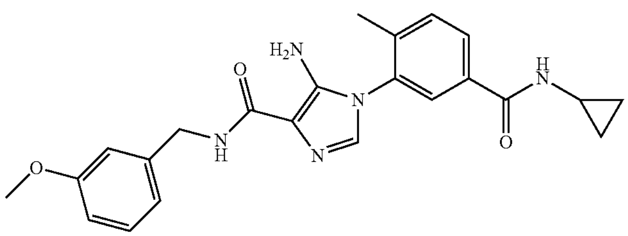 | 5-Amino-1-(5-cyclopropylcarbamoyl-2-methyl-phenyl)-1H-pyrazole-4-carboxylic acid 3-methoxy-benzylamide | 2.13 | 420.29 |
| 150 | 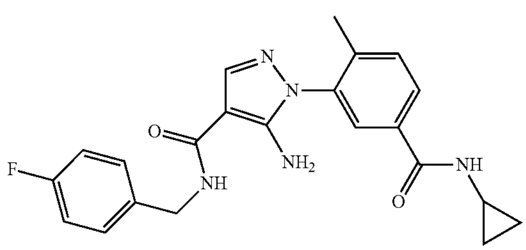 | 5-Amino-1-(5-cyclopropylcarbamoyl-2-methyl-phenyl)-1H-pyrazole-4-carboxylic acid 4-fluoro-benzylamide | 2.19 | 408.26 |
| 151 | 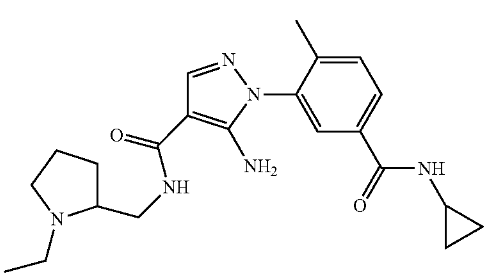 | 5-Amino-1-(5-cyclopropylcarbamoyl-2-methyl-phenyl)-1H-pyrazole-4-carboxylic acid (1-ethyl-pyrrolidin-2-ylmethyl)-amide | 1.41 | 411.28 |

TABLE 6-continued

| Ex | Structure | Name | HPLC $t_R$ (min) | MS m/z $[M + H]^+$ |
|---|---|---|---|---|
| 152 | 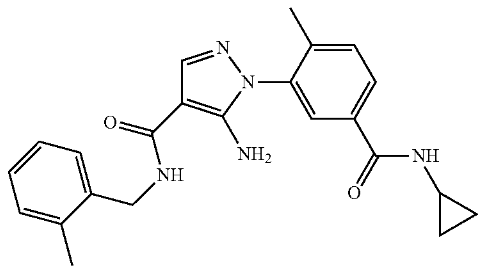 | 5-Amino-1-(5-cyclopropylcarbamoyl-2-methyl-phenyl)-1H-pyrazole-4-carboxylic acid 2-methyl-benzylamide | 2.26 | 404.33 |
| 153 | 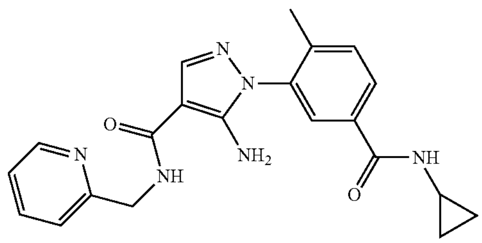 | 5-Amino-1-(5-cyclopropylcarbamoyl-2-methyl-phenyl)-1H-pyrazole-4-carboxylic acid-(pyridin-2-ylmethyl)-amide | 1.39 | 391.14 |
| 154 | 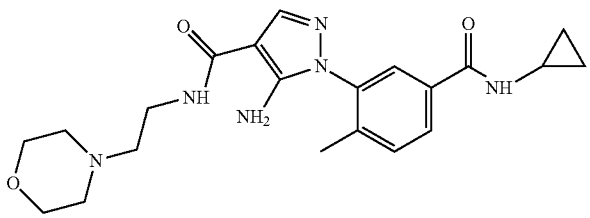 | 5-Amino-1-(5-cyclopropylcarbamoyl-2-methyl-phenyl)-1H-pyrazole-4-carboxylic acid (2-morpholin-4-yl-ethyl)-amide | 1.12 | 413.25 |
| 155 | 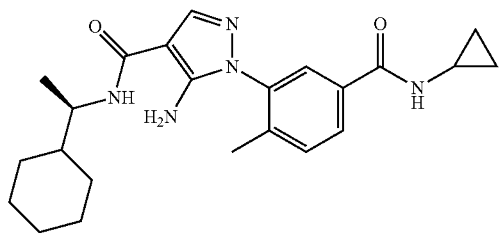 | 5-Amino-1-(5-cyclopropylcarbamoyl-2-methyl-phenyl)-1H-pyrazole-4-carboxylic acid (1-cyclohexyl-ethyl)-amide | 2.53 | 410.45 |
| 156 | 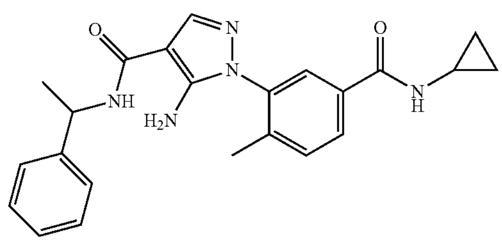 | 5-Amino-1-(5-cyclopropylcarbamoyl-2-methyl-phenyl)-1H-pyrazole-4-carboxylic acid (1-phenyl-ethyl)-amide | 2.22 | 404.28 |

EXAMPLE 157

Preparation of 5-Amino-1-(5-cyclopropylcarbamoyl-2-methyl-phenyl)-1H-pyrazole-4-carboxylic acid (2,2-dimethyl-propyl)-amide

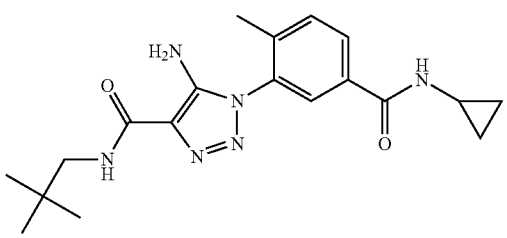

Similar procedure as in Example 128 except neopentylamine was used in place of isopropylamine. HPLC (4 minute 10-90 gradient) $t_R$ 2.19 min; MS m/z 370.32 [M+H]$^+$.

EXAMPLE 158

Preparation of 5-Amino-1-(5-cyclopropylcarbamoyl-2-methyl-phenyl)-1H-pyrazole-4-carboxylic acid (1-ethyl-pyrrolidin-2-ylmethyl)-amide

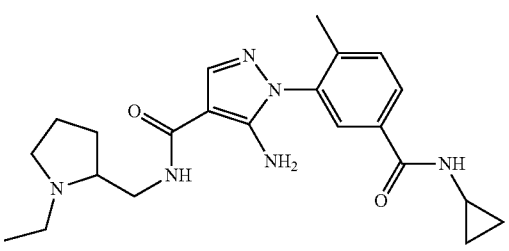

Similar procedure as in Example 128 except 2-(aminomethyl)-1-ethylpyrrolidine was used in place of isopropylamine. HPLC (4 minute 10-90 gradient) $t_R$ 1.41 min; MS m/z 411.25 [M+H]$^+$.

EXAMPLE 159

Preparation of 5-Amino-1-(5-cyclopropylcarbamoyl-2-methyl-phenyl)-1H-pyrazole-4-carboxylic acid (2-pyrrolidin-1-yl-ethyl)-amide

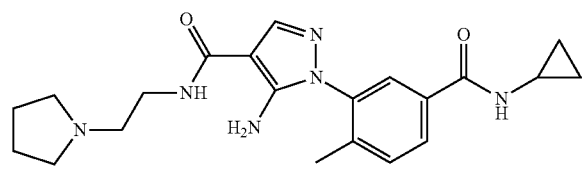

Similar procedure as in Example 128 except 1-(2-aminoethyl)pyrrolidine was used in place of isopropylamine. HPLC (4 minute 10-90 gradient) $t_R$ 1.34 min; MS m/z 397.22 [M+H]$^+$.

EXAMPLE 160

Preparation of 5-Amino-1-(5-cyclopropylcarbamoyl-2-methyl-phenyl)-1H-pyrazole-4-carboxylic acid cyclohexyl-methyl-amide

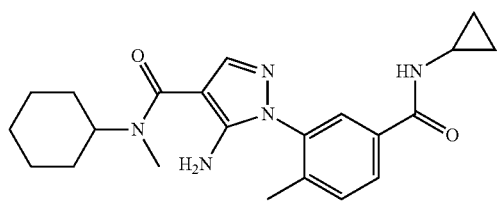

Similar procedure as in Example 57 except N-methylcyclohexylamine was used in place of isopropylamine. HPLC (4 minute 10-90 gradient) $t_R$ 2.37 min; MS m/z 396.3 [M+H]$^+$.

EXAMPLE 161

Preparation of 3-[5-Amino-4-(3-cyanobenzoyl)-pyrazol-1-yl]-N-cyclopropyl-4-methylbenzamide

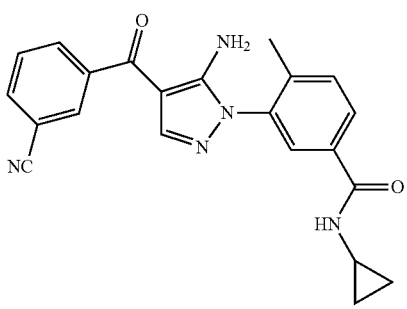

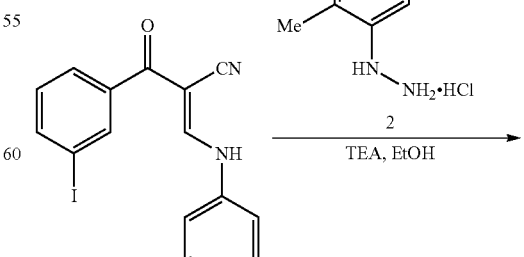

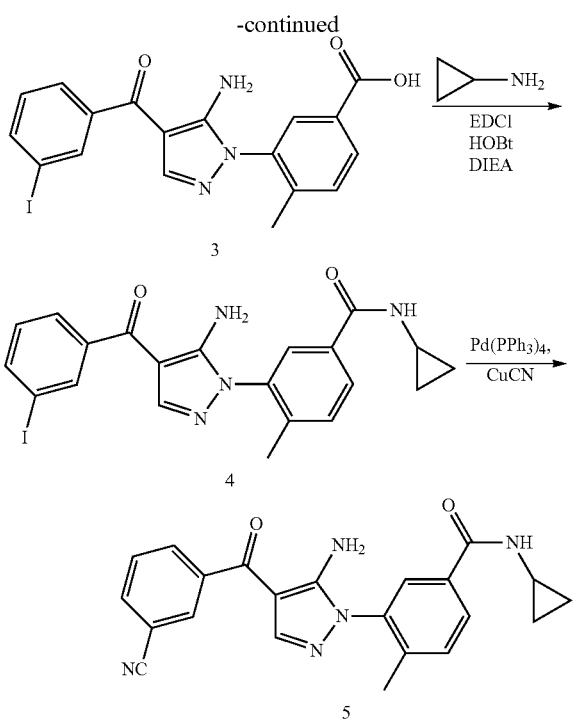

A. 3-[5-amino-4-(3-iodobenzoyl)-pyrazol-1-yl]-4-methylbenzoic acid

To a stirred solution of hydrazine 2 (32.5 g, 0.160 mol, 1.0 equiv) in ethanol (3.6 L) was added 1 (60 g, 0.160 mol, 1.0 equiv, preparation: International Patent Application Publication No. WO 02/57101 A1, pg. 84)) and triethylamine (16.56 g, 0.16 mol, 1.0 equiv) and the mixture was heated to 65° C. All solids dissolved when temperature reached 65° C. After cooling, the solids were filtered to provide acid 3 (22 g, 30%) as a light brown solid. HPLC (Waters X-Terra 5 micron C18 column 4.6 mm×250 mm, 1.0 mL/min, mobile phase: 0.1% TEA in H₂O/acetonitrile 40/60, 30 min elution) $t_R$ 6.74 min, 95.2% purity;

B. 3-[5-amino-4-(3-iodobenzoyl)-pyrazol-1-yl]-N-cyclopropyl-4-methyl-benzamide

To a stirred solution of acid 3 (21 g, 0.0469 mol, 1.0 equiv) in DMF (30 ml) was added EDCI (17 g, 0.0886 mol, 2.0 equiv), HOBt (12.6 g, 0.0939, 2.0 equiv) and diisopropylethylamine (24.2 g, 0.18 mol, 4.0 equiv) and the solution was stirred for 15 minutes at room temperature when cyclopropylamine (10.7 g, 0.0939, 2.0 equiv) was added and the reaction stirred for 1 hour. The mixture was added to water and extracted with EtOAc (1 L) and washed with water (2×200 ml) and brine (200 ml), dried over anhydrous sodium sulfate and concentrated. The product was purified by flash chromatography on silica gel eluted with 8/2 EtOAc/hexanes to provide the product as brown oil. The product was further purified by trituration with Isopropyl ether (1 L) and dried under vacuum to provide the amide 4 (12 g, 50%) as an off white solid.

C. 3-[5-Amino-4-(3-cyanobenzoyl)-pyrazol-1-yl]-N-cyclopropyl-4-methylbenzamide

To a stirred solution of iodide 4 (7.4 g, 0.015 mol, 1.0 equiv) in N,N-dimethyl formamide (25 ml) under N₂ was added copper cyanide. The resultant suspension was refluxed for 1 hour. The reaction was monitored by TLC and checked for the completion. Heating was discontinued and the reaction mixture was cooled down to 80° C. Ice water (15 ml), 25% aqueous ammonia (15 ml), and ethyl acetate (50 ml) were added to quench the reaction. The mixture was filtered to remove the solids. From the filtrate organic layer was separated. The organic layer was washed with water, saturated brine and dried over anhydrous sodium sulfate. Solvent was removed under reduced pressure and the crude material dried at 60° C. under high vacuum then purified by column with ethyl acetate as eluent to provide the product (3 g, 51%) as an off white solid. HPLC (Waters X-Terra 5 micron C18 column 4.6 mm×250 mm, 1.0 mL/min, mobile phase: 0.1% TEA in H₂O/acetonitrile 70/30, 30 min elution) $t_R$ 23.70 min, 99.4% purity; ¹H NMR (400 MHz, CDCl₃) δ 8.10 (t, J=2.9 Hz, 1 H), 8.06 (t, J=2.7 Hz, 1 H), 8.04 (m, 1 H), 7.85 (t, J=2.5 Hz, 1 H), 7.83 (m, 1 H), 7.81 (d, J=1.8 Hz, 1 H), 7.95 (d, J=1.6 Hz, 1 H), 7.37 (s, 1 H), 7.65 (t, J=7.8 Hz, 1 H), 7.45 (d, J=8.0 Hz, 1 H), 6.41 (s, 1 H), 5.94 (s, 2 H), 2.88 (m, 1 H), 2.24 (s, 3 H), 0.86 (dd, J=6.9, 6.1 Hz, 2 H) 0.61 (m, 2 H) ppm; ¹³C NMR (400 MHz, CDCl₃) δ 186.6, 167.2, 151.5, 141.3, 140.7, 140.3, 135.1, 134.5, 134.0, 132.2, 131.8, 129.5, 128.7, 126.2, 118.1, 113.0, 103.7, 30.9, 23.2, 17.7, 6.8 ppm.

EXAMPLE 162

Preparation of 3-[5-Amino-4-(3-pyrazin-2-yl-benzoyl)-imidazol-1-yl]-N-cyclopropyl-4-methylbenzamide

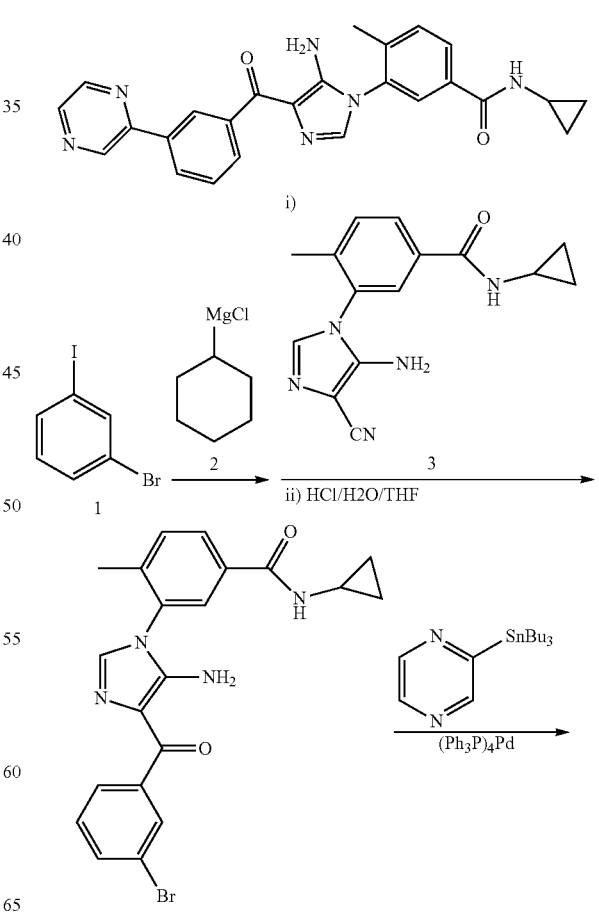

145

-continued

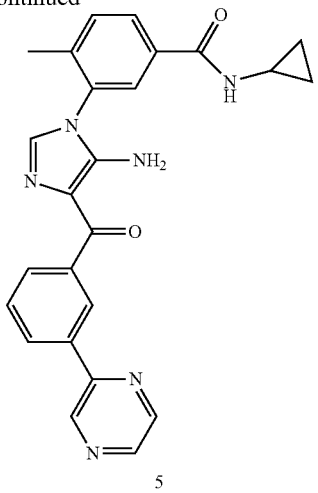

5

A. Preparation of 3-[5-Amino-4-(3-bromobenzoyl)-imidazol-1-yl]-N-cyclopropyl-4-methylbenzamide To a solution of 3-bromo-1-iodobenzene (2.82 g) in THF (20 mL) at −40° C. under N₂ was added cyclohexylmagnesium chloride (2M in THF, 6 mL). The solution was kept at −40° C. to 0° C. for 20 min. then 3-(5-amino-4-cyano-imidazol-1-yl)-N-cyclopropyl-4-methyl-benzamide (0.18 g) was added and the reaction was kept at rt for 1 h. Then HCl (4 M, 20 mL) was added and the mixture was kept at rt for two days. The mixture was neutralized with K₂CO₃ solution and extracted with EtOAc (2×100 mL) and the combined organics dried over Na₂SO₄, and concentrated. Purification of the crude product by column chromatography (EtOAc) gave the desired product (0.15 g, 54%). HPLC (4 minute 10-90 gradient) $t_R$ 1.85 min; MS m/z 438.10, 441.07 [M+H]⁺.

B. Preparation of 3-[5-Amino-4-(3-pyrazin-2-yl-benzoyl)-imidazol-1-yl]-N-cyclopropyl-4-methyl-benzamide A solution of 3-[5-amino-4-(3-bromobenzoyl)-imidazol-1-yl]-N-cyclopropyl-4-methylbenzamide (60 mg), 2-tributyltinpyrazine (120 uL) and tetrakis(triphenylphosphine)palladium(0) (30 mg) in 1,4-dioxane (0.8 mL) was heated under microwave radiation at 160° C. for 25 min. Water (3 ml) was added and the mixture was extracted with ethyl acetate (4 mL×2). Evaporation of the solvent and purification by preparatory TLC (EtOAc MeOH=10:1) gave the desired product (38 mg, 63%). HPLC (4 minute 10-90 gradient) $t_R$ 2.18 min; MS m/z 439.27 [M+H]⁺.

EXAMPLE 163

Preparation of 3-[5-Amino-4-(3-pyrimidin-5-yl-benzoyl)-imidazol-1-yl]-N-cyclopropyl-4-methyl-benzamide

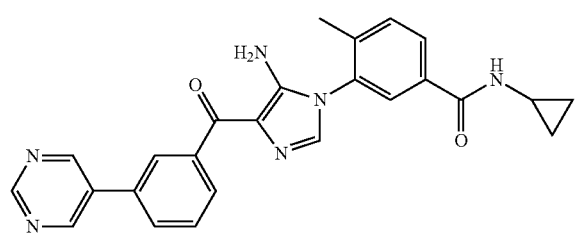

146

Similar procedure as in Example 162 except 4-tributylstannylpyrimidine was used in place of 2-tributylstannylpyrazine. HPLC (4 minute 10-90 gradient) $t_R$ 1.93 min; MS m/z 439.19 [M+H]⁺.

EXAMPLE 164

Preparation of 3-[5-Amino-4-(3-pyrimidin-5-yl-benzoyl)-imidazol-1-yl]-N-cyclopropyl-4-methyl-benzamide

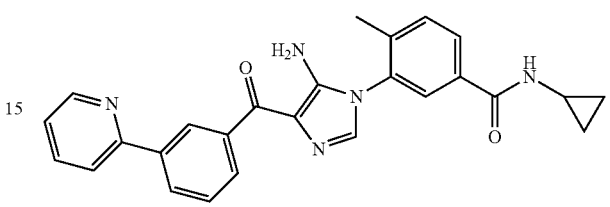

Similar procedure as in Example 162 except 2-tributylstannylpyridine was used in place of 2-tributylstannylpyrazine. HPLC (4 minute 10-90 gradient) $t_R$ 2.04 min; MS m/z 438.25 [M+H]⁺.

EXAMPLE 165

Preparation of 3-[5-Amino-4-(3-pyrimidin-2-yl-benzoyl)-imidazol-1-yl]-N-cyclopropyl-4-methyl-benzamide

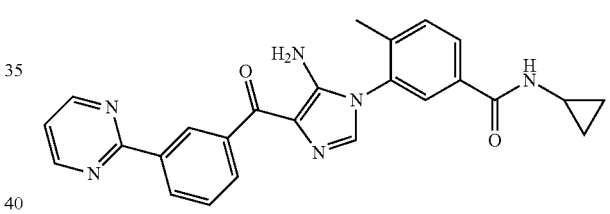

Similar procedure as in Example 162 except 2-tributylstannylpyrimidine was used in place of 2-tributylstannylpyrazine. HPLC (4 minute 10-90 gradient) $t_R$ 2.49 min; MS m/z 439.24 [M+H]⁺.

EXAMPLE 166

Preparation of 5-Amino-1-(5-cyclopropylcarbamoyl-2-methylphenyl)-4-methylsulfonylbenzoyl-1H-imidazole

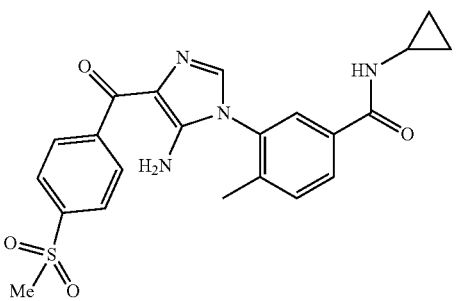

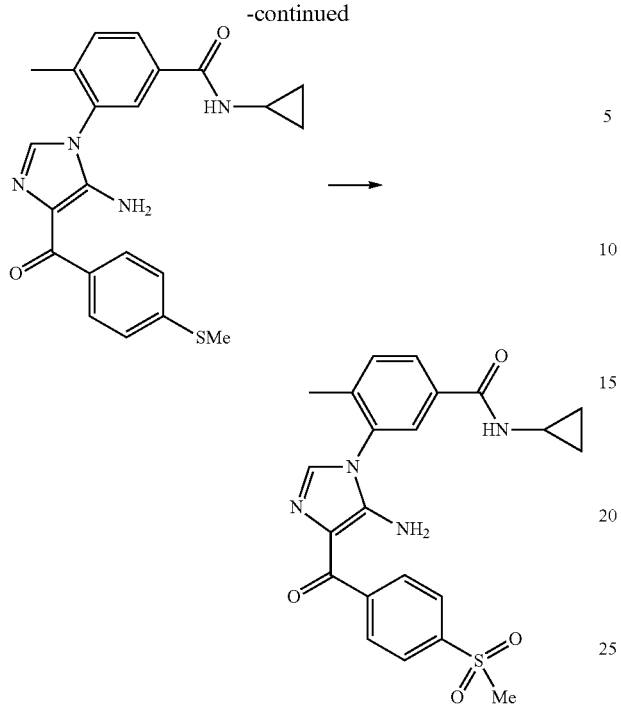

A solution of 5-amino-1-(5-cyclopropylcarbamoyl-2-methylphenyl)-4-methylsulfonylbenzoyl-1H-imidazole (64 mg) and Oxone® (242 mg) in water/methanol (2 ml/2 ml) was reacted at room temperature for 2 hours. The solution was evaporated and THF/MeOH (2 ml/2 ml) was added. The mixture was heated to dissolve the organic materials and filtered. The filtrate was concentrated under reduced pressure and the residue was purified by preparative HPLC to provide the product (1.6 mg). HPLC (4 minute 10-90 gradient) $t_R$ 1.90 min; MS m/z 439.15 [M+H]⁺.

EXAMPLE 167

Preparation of 5-Amino-1-(5-cyclopropylcarbamoyl-2-methylphenyl)-4-[3-(5-methyl)oxadiazol-3-ylbenzoyl]-1H-imidazole

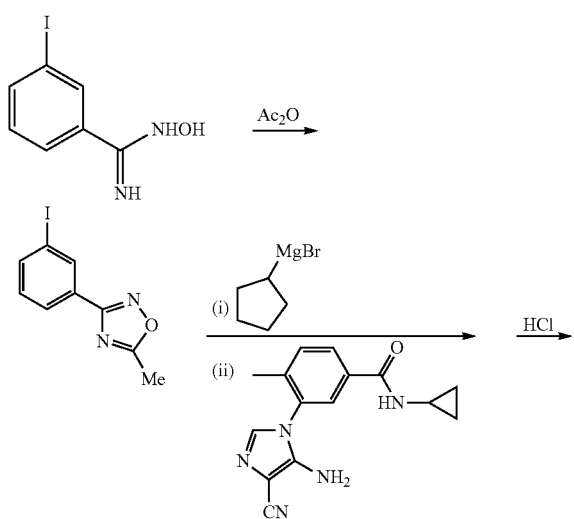

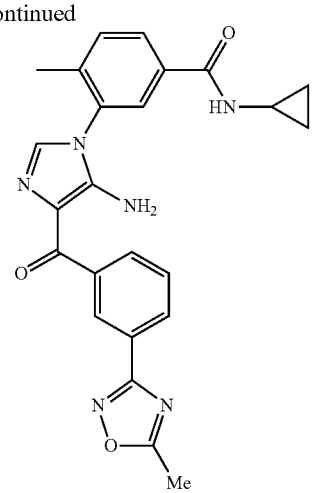

A mixture of N-hydroxy-3-iodobenzimidine (1.31 g), acetic anhydride (1 mL) and catalytic amount of p-toluenesulfonic acid was heated in acetic acid (10 mL) at 90° C. for 6 hour. The solvent was evaporated and water and methanol (1:1; 100 mL)) was added. The resulting precipitate was filtered to give the desired product (1.1 g).

To a solution 3-(3-iodophenyl)-5-methyloxadiazole (0.286 g) in THF (15 ml) under $N_2$ was added cyclopentylmagnesiumbromide (2 M, 1.1 mL) at −20° C. The temperature was gradually raised to 5-10° C. It took about 20 minutes. Then 5-amino-1-(5-cyclopropylcarbamoyl-2-methylphenyl)-4-cyanoimidazole (96 mg) was added and the reaction was kept at room temperature for 0.5 hour. Then diluted HCl (4M, 12 mL) was added and the reaction was heated at 60° C. for 3 hour. After petition in water and ethyl acetate, the final product was purified by column chromatography (Ethyl acetate/Hexane=1:1). HPLC (4 minute 10-90 gradient) $t_R$ 2.03 min; MS m/z 443.20 [M+H]⁺.

EXAMPLE 168

Preparation of 3-(5-Amino-4-{3-[2-(4-methyl-piperazin-1-yl)-ethoxy]-benzoyl}-pyrazol-1-yl)-N-cyclopropyl-4-methyl-benzamide

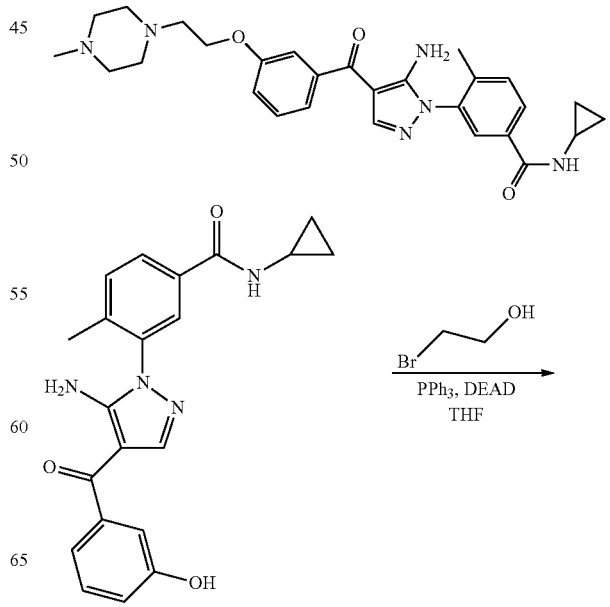

-continued

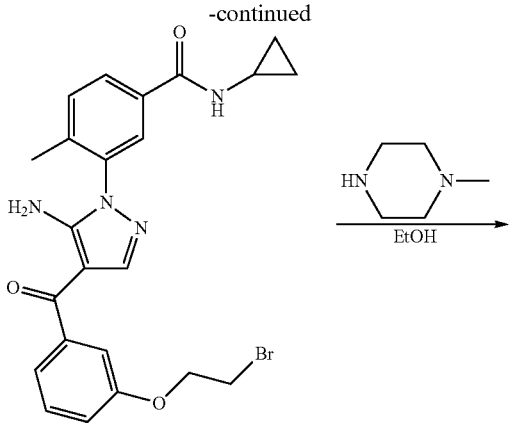

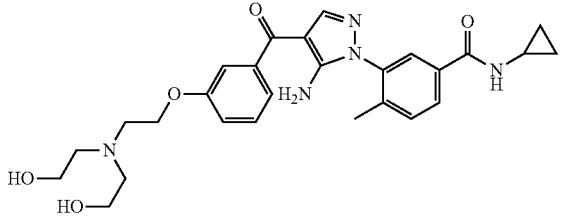

A. 3-{5-Amino-4-[3-(2-bromo-ethoxy)-benzoyl]-pyrazol-1-yl}-N-cyclopropyl-4-methylbenzamide

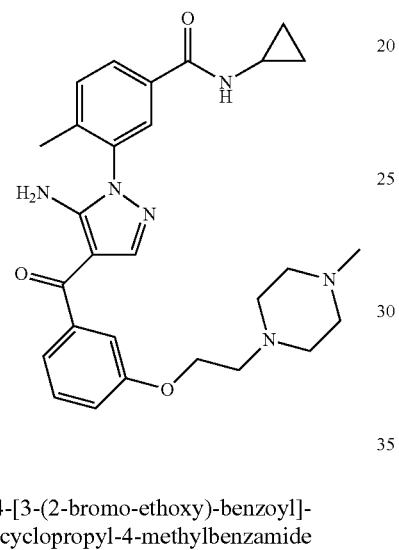

To a solution of 3-[5-amino-4-(3-hydroxy-benzoyl)-pyrazol-1-yl]-N-cyclopropyl-4-methyl-benzamide (472 mg, 1.26 mmol) in THF (dry, 20 mL) at 0° C. was added of 2-bromo-ethanol (785 mg, 6.3 mmol), PPh₃ (1.3 g, 5.04 mmol) and diethyl azodicarboxylate (877 mg, 5.04 mmol) and the mixture was stirred at room temperature for 72 h. An aqueous solution of NH₄Cl was added then the THF layer was isolated. The aqueous layer was extracted by EtOAc. The combined organic phase was washed by brine, purified by preparatory HPLC, to provide the product as a white solid (360 mg, 59%). HPLC (4 minute 10-90 gradient) $t_R$ 2.72 min; MS m/z 483.14/485.09 [M+H]⁺.

B. 3-(5-Amino-4-{3-[2-(4-methyl-piperazin-1-yl)-ethoxy]-benzoyl}-pyrazol-1-yl)-N-cyclopropyl-4-methylbenzamide To the suspension of 3-{5-amino-4-[3-(2-bromoethoxy)-benzoyl]-pyrazol-1-yl}-N-cyclopropyl-4-methyl-benzamide (24 mg, 0.05 mmol) in EtOH (1 ml) was added 1-methylpiperazine (100 mg, 1 mmol) and the mixture was stirred at 80° C. overnight. The solvent was removed, residue was dissolved in EtOAc, washed by water, dried over Na₂SO₄. Solvent was removed, desired product was obtained as a colorless oil (18 mg, 72%). HPLC (4 minute gradient) $t_R$ 1.33 min; MS m/z 503.29 [M+H]⁺.

EXAMPLE 169

Preparation of 3-[5-Amino-4-(3-{2-[bis-(2-hydroxy-ethyl)-amino]-ethoxy}-benzoyl)-pyrazol-1-yl]-N-cyclopropyl-4-methyl-benzamide

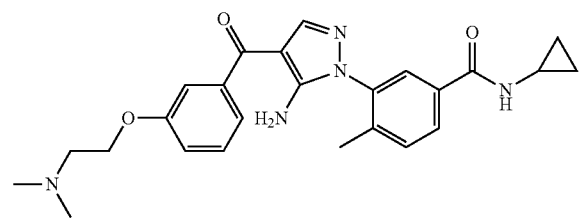

Similar procedure as in Example 168 except 2-[bis-(2-hydroxyethyl)-amino]-ethanol was used in place of 1-methylpiperazine. HPLC (4 minute 10-90 gradient) $t_R$ 1.39 min; MS m/z 508.24 [M+H]⁺.

EXAMPLE 170

Preparation of 3-{5-Amino-4-[3-(2-dimethylamino-ethoxy)-benzoyl]-pyrazol-1-yl}-N-cyclopropyl-4-methyl-benzamide

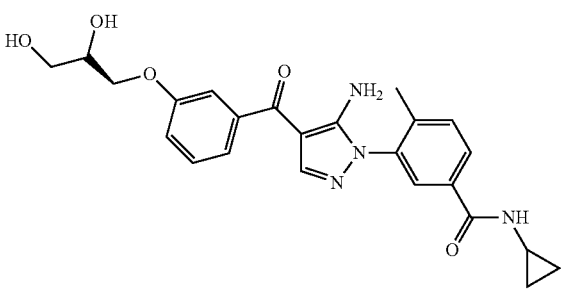

Similar procedure as in Example 168 except 2-dimethylaminoethanol was used in place of 1-methylpiperazine. HPLC (4 minute 10-90 gradient) $t_R$ 1.59 min; MS m/z 448.22 [M+H]⁺.

EXAMPLE 171

Preparation of 3-{5-Amino-4-[3-(2,3-dihydroxy-propoxy)-benzoyl]-pyrazol-1-yl}-N-cyclopropyl-4-methylbenzamide 151
-continued

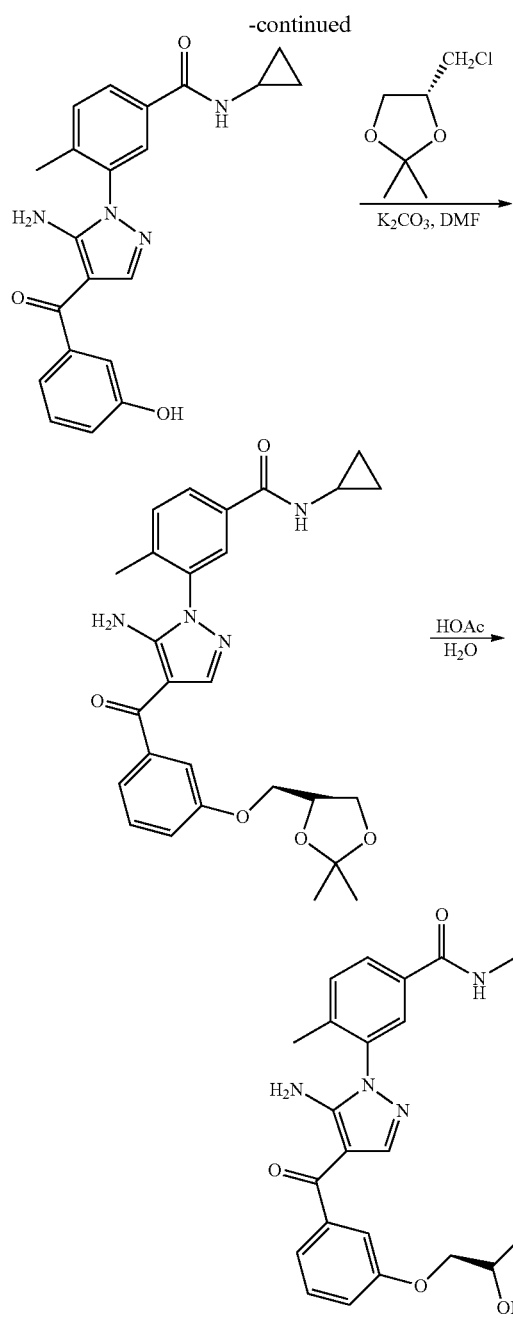

A. 3-{5-Amino-4-[3-(2,2-dimethyl-[1,3]dioxolan-4-ylmethoxy)-benzoyl]-pyrazol-1-yl}-N-cyclopropyl-4-methyl-benzamide To a stirred solution of 3-[5-amino-4-(3-hydroxy-benzoyl)-pyrazol-1-yl]-N-cyclopropyl-4-methylbenzamide (75 mg, 0.2 mmol) and 4-chloromethyl-2,2-dimethyl-[1,3]dioxolane (36 mg, 0.24 mmol) were dissolved in DMF (4 ml) was added $K_2CO_3$ and the mixture stirred at 150° C. for 2 h in microwave oven. The solvent was removed, residue was dissolved in EtOAc, washed by water, brine, dried over $Na_2SO_4$, and concentrated. The residue was purified by column chromatography (EtOAc: Hex=3:1) and the product was obtained as a colorless oil (18 mg, 18%). HPLC (4 minute gradient) $t_R$ 2.57 min; MS m/z 491.11 [M+H]$^+$.

152

B. 3-{5-Amino-4-[3-(2,3-dihydroxy-propoxy)-benzoyl]-pyrazol-1-yl}-N-cyclopropyl-4-methylbenzamide Compound 171A (10 mg) was dissolved in HOAc (1 ml), 0.5 ml water was added, and the mixture was stirred at 50° C. overnight. The solvent was removed and the residue was purified by preparative TLC (EtOAc), to provide the product as a light yellow oil (4.1 mg, 45%). HPLC (4 minute 10-90 gradient) $t_R$ 1.73 min; MS m/z 451.21 [M+H]$^+$.

EXAMPLE 172

Preparation of 3-(5-Amino-4-{3-[2-(4-chloro-phenoxy)-ethoxy]-benzoyl}-pyrazol-1-yl)-N-cyclopropyl-4-methyl-benzamide

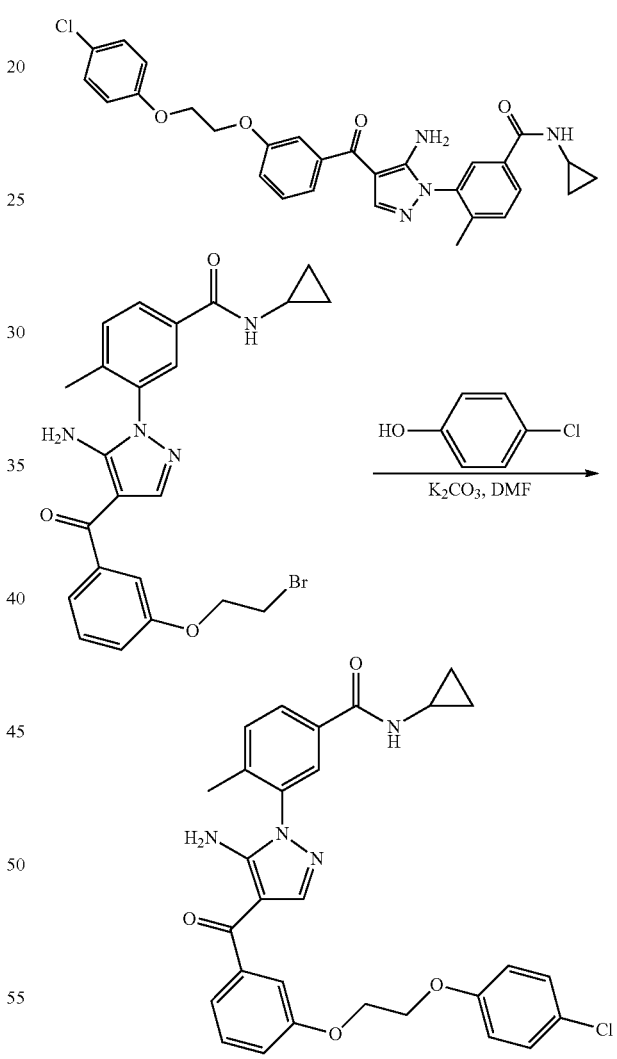

To a stirred solution of 3-{5-amino-4-[3-(2-bromoethoxy)-benzoyl]-pyrazol-1-yl}-N-cyclopropyl-4-methyl-benzamide (24 mg, 0.05 mmol) and 4-chlorophenol (128 mg, 1 mmol) in DMF (1 mL), was added $K_2CO_3$ (138 mg, 1 mmol) and the mixture was stirred at 100° C. for 2 h. The mixture was cooled and the solids were filtered off. The filtrated was concentrated and purified by preparatory HPLC, to provide the product as a beige solid (10 mg, 38%). HPLC (4 minute 10-90 gradient) $t_R$ 2.77 min; MS m/z 531.21 [M+H]$^+$.

EXAMPLE 173

Preparation of 3-{5-Amino-4-[3-(4H-[1,2,4]triazol-3-yl)-benzoyl]-pyrazol-1-yl}-N-cyclopropyl-4-methyl-benzamide

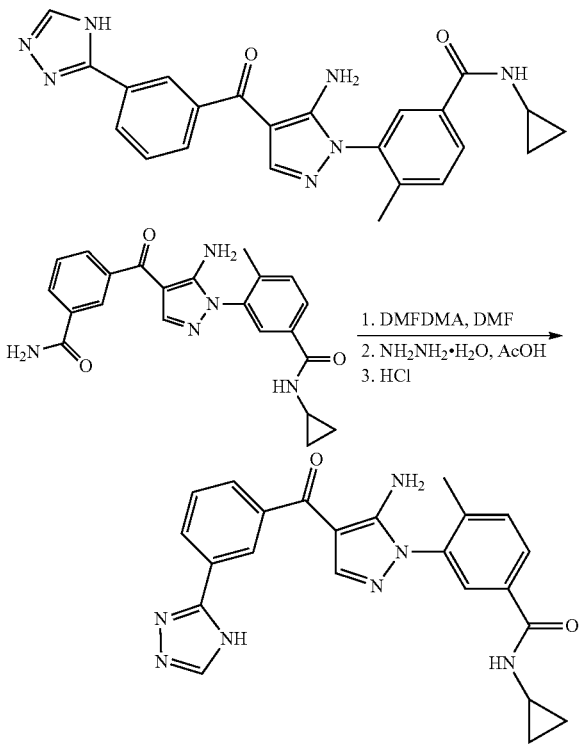

To a stirred solution of 3-[5-amino-4-(3-carbamoyl-benzoyl)-pyrazol-1-yl]-N-cyclopropyl-4-methylbenzamide (120 mg) in DMF (2 mL), was added N,N-dimethylformamide dimethyl acetal (5 ml) and the solution was stirred at 80° C. overnight. The solvent was removed, residue was dissolved in AcOH (5 ml), hydrazine monohydrate (3 ml) was added and the mixture stirred at 90° C. overnight. The solution was acidified with hydrochloric acid to pH~1 and stirred at 80° C. overnight. The solvent was removed and the residue was resuspended in EtOAc, then washed by aqueous K₂CO₃ solution, water, and brine, and concentrated. The crude product was purified by column chromatography on silica gel eluted with EtOAc to provide product as a white solid (65 mg, 51%). HPLC (4 minute 10-90 gradient) $t_R$ 1.58 min; MS m/z 428.18 [M+H]⁺.

EXAMPLE 174

Preparation of 3-{5-Amino-4-[3-(4H-[1,2,4]triazol-3-yl)-benzoyl]-pyrazol-1-yl}-N-cyclopropyl-4-methyl-benzamide

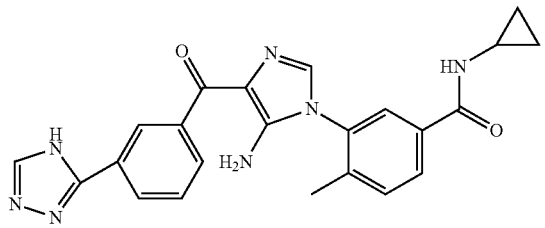

Similar procedure as in Example 173 except 3-[5-amino-4-(3-carbamoyl-benzoyl)-imidazol-1-yl]-N-cyclopropyl-4-methyl-benzamide was used in place of 3-[5-amino-4-(3-carbamoyl-benzoyl)-pyrazol-1-yl]-N-cyclopropyl-4-methylbenzamide. HPLC (4 minute 10-90 gradient) $t_R$ 1.58 min; MS m/z 428.24 [M+H]⁺.

EXAMPLE 175

Preparation of {5-Amino-1-[2-methyl-5-(5-methyl-[1,3,4]oxadiazol-2-yl)-phenyl]-1H-pyrazol-4-yl}-phenyl-methanone

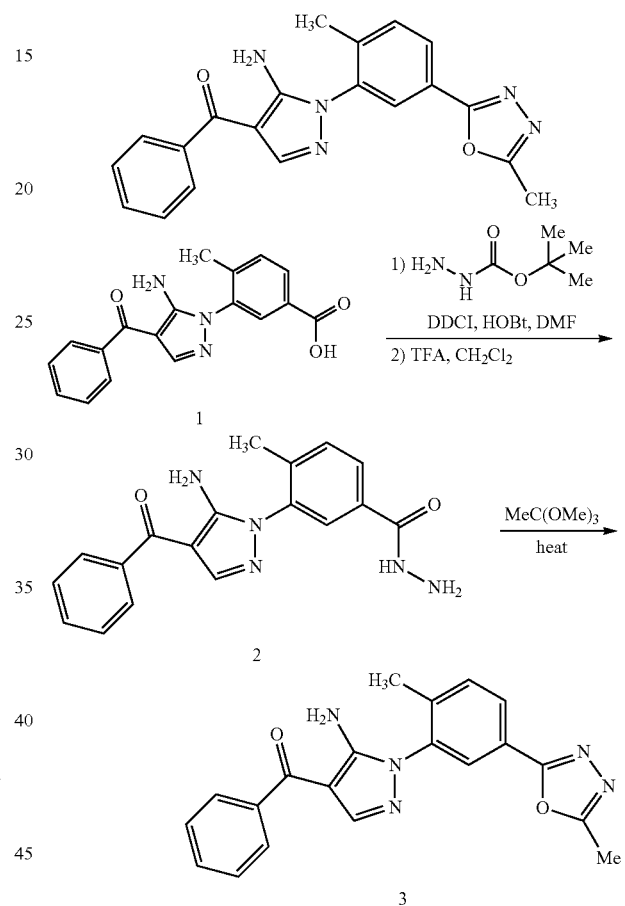

A. N-[3-(5-Amino-4-benzoyl-pyrazol-1-yl)-4-methyl-benzoyl]-hydrazinecarboxylic acid tert-butyl ester To DMF (10 mL) at rt was added 3-(5-amino-4-benzoyl-pyrazol-1-yl)-4-methyl-benzoic acid 1 (0.50 g, 1.56 mmol, 1.0 eq), t-butylcarbazate (0.206 g, 1.56 mmol, 1.0 eq), EDCI (0.313 g, 1.63 mmol, 1.05 eq) and HOBt (0.238 g, 1.56 mmol, 1.0 eq). The reaction was stirred for 19 h, poured into brine (100 mL) and extracted with EtOAc (2×20 mL). The organic extracts were combined were washed with brine (1×20 mL). The brine layer was separated and extracted with EtOAc (1×10 mL). All organic extracts were combined dried over Na₂SO₄, filtered and concentrated in vacuo. This material was dissolved in CH₂Cl₂ (10 mL) and cooled to 0° C. TFA (3 mL) was added and the reaction mixture allowed to warm to rt over 2 h. The solvent was removed in vacuo to give crude solid which was triturated with EtOAc/ether (1/1) giving 2 (180 mg, 26%) as a light tan in color solid.

B. {5-Amino-1-[(2-methyl-5-(5-methyl-[1,3,4]oxa-diazol-2-yl)-phenyl]-1H-pyrazol-4-yl}-phenyl-methanone 2 (50 mg, 0.15 mmol, 1.0 eq) was added to trimethylorthoacetate (3 ml) and heated to 140° C. in a microwaved closed container for 20 minutes. Solvent was removed in vacuo and redissovled in trimethylorthoacetate (4 mL) and again heated to 140° C. for 20 minutes. The solvent was removed in vacuo and the material was dissolved in DMF and heated to 230° C. for 10 minutes. The material was purified by flash chromatography (silica gel, EtOAc/hexanes 80/20) to give 3 (5.8 mg): MS m/z 360 [M+H]$^+$

EXAMPLE 176

The ability of the compounds provided herein to inhibit the synthesis or the activity of cytokines can be demonstrated using the following in vitro assays.

Generation of p38 kinases cDNAs of human p38α and β were cloned by PCR. The α and β cDNAs were subcloned into DEST2 plasmid (Gateway, InVitrogen). His$_6$-p38 fusion protein was expressed in *E. coli* and purified from bacterial lysates by affinity chromatography using Ni$^{+2}$-NTA-agarose. His$_6$-p38 protein was activated by incubating with constitutively active MKK6. Active p38 was separated from MKK6 by affinity chromatography. Constitutively active MKK6 was generated in a manner similar to Raingeaud et al. [*Mol. Cell. Biol.,* 1247-1255 (1996)].

TNF-α Production by LPS-Stimulated PBMCs

Heparinized human whole blood was obtained from healthy volunteers. Peripheral blood mononuclear cells (PBMCs) were purified from human whole blood by Accu-paque density gradient centrifugation and resuspended at a concentration of $5\times10^6$/ml in assay medium (RPMI medium containing 10% fetal bovine serum). 175 µL of cell suspension was incubated with 10 µL of test compound (in 4% DMSO) in 96-well tissue culture plates for 30 minutes at RT. 15 µL of LPS (13.33 ug/ml stock) was then added to the cell suspension and the plate was incubated for 18 hours at 37° C. in a humidified atmosphere containing 5% CO$_2$. Following incubation, the culture medium was collected and stored at –20° C.

THP-1 cells (TIB-202, ATCC) were washed and resuspended at a concentration of $1\times10^5$/ml in assay medium (RPMI medium containing 3% fetal bovine serum). 175 µL of cell suspension was incubated with 10 µL of test compound (in 4% DMSO) in 96-well tissue culture plates for 30 minutes at RT. 15 µL of LPS (13.33 ug/ml stock) was then added to the cell suspension and the plate was incubated for 18 hours at 37° C. in a humidified atmosphere containing 5% CO$_2$. Following incubation, the culture medium was collected and stored at –20° C.

TNF-α concentration in the medium was quantified using a standard ELISA kit (BioSource International, Camarillo, Calif.). Concentrations of TNF-α and IC$_{50}$ values for test compounds (concentration of compound that inhibited LPS-stimulated TNF-α production by 50%) were calculated by four parameter logistic curve (SigmaPlot, SPSS, Inc.).

p38α Assay

The p38α assay employed is based on measurement of ADP released in the reaction of interest through NADH oxidation obtained by coupling with pyruvate kinase and lactate dehydrogenase reactions. The assays were performed in 384-well UV-plates. The final volume was 25 µL prepared from the addition of 2.5 µL compound dissolved in 10% DMSO, 17.5 µL of assay buffer and 5 µL of ATP. Assay buffer contains the following reagents to give final concentration in the assay: 25 mM HEPES, 20 mM 2-glycerophosphate, pH 7.6, 10 mM MgCl$_2$, 0.1 mM sodium orthovanadate, 0.5 mM phosphoenolpyruvate, 0.12 mM NADH, 3.1 mg/ml LDH, 6.67 mg/ml pyruvate kinase, 0.25 mM peptide substrate, 2 mM DTT, 0.005% Tween 80 and 20 nM p38α kinase from Upstate. Test compounds are preincubated zith p38α kinase for 60 min and the reaction started by addition of ATP to 0.15 mM final concentration. Reaction rates were measured at 340 nm using SpectraMax plate-reading spectrophotometer for 10 min at 37° C. Inhibition data were analyzed by non-linear least-squares regression using SigmaPlot.

TNF-α Production by LPS-Stimulated Mice

Mice (Balb/c female, 6-8 weeks of age, Taconic Labs; n=8/treatment group) were injected intraperitoneally with lipopolysaccharide (LPS) (50 ug/kg of *E. coli* strain 0111:B4, Sigma) suspended in sterile saline. Ninety minutes later, mice were sedated by CO$_2$:O$_2$ inhalation and a blood sample was obtained. Serum was separated and analyzed for TNF-α concentrations by commercial ELISA assay per the manufacturer's instructions (BioSource International). Test compounds were administered orally at various times before LPS injection. The compounds were dosed either as suspensions or as solutions in various vehicles or solubilizing agents.

Results

The compounds exemplified herein all showed activity in the above assays as inhibitors of p38 kinase. The p38 inhibitory activity of certain compounds provided herein are shown in the Table below. For p38 kinase IC$_{50}$ values, "+++" represents <1 µM, "++" represents between 1.0 and 10 µM and "+" represents >10 µM.

| Example | p38α IC$_{50}$ |
|---|---|
| 1 | +++ |
| 2 | +++ |
| 3 | ++ |
| 4 | +++ |
| 5 | ++ |
| 6 | +++ |
| 7 | +++ |
| 8 | +++ |
| 9 | +++ |
| 10 | +++ |
| 18 | +++ |
| 29 | +++ |
| 30 | +++ |
| 33 | +++ |
| 34 | +++ |
| 48 | +++ |
| 49 | +++ |
| 50 | +++ |
| 52 | +++ |
| 53 | +++ |
| 76 | +++ |
| 87 | +++ |
| 128 | +++ |
| 129 | +++ |
| 135 | +++ |
| 148 | +++ |
| 171 | +++ |

Since modifications will be apparent to those of skill in the art, the claimed subject matter is intended to be limited only by the scope of the appended claims.

What is claimed is:

1. A method of treating or ameliorating one or more symptoms of p38 kinase-mediated diseases or disorders selected from the group consisting of rheumatoid arthritis, comprising administering to a subject in need thereof a compound of the formula:

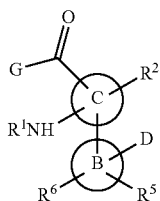

or a pharmaceutically acceptable salt thereof, wherein:
$R^1$ is hydrogen, acyl or —P(O)(OH)$_2$;
$R^2$ is hydrogen, halo, alkyl, or alkylthio;
G is phenyl substituted with $R^3$ and $R^4$;
B is phenyl;
C is a pyrazole or imidazole;
D is C(O)NH(cyclopropyl);
$R^3$ is selected from the group consisting of:
(a) amino, alkylamino or dialkylamino;
(b) acylamino;
(c) optionally substituted phenyl or naphthyl;
(d) heteroalkylcarbonyl;
(e) —Y-(alkylene)-$R^9$ where: Y is a single bond, —O—, —NH— or —S(O)$_n$— (where n is an integer from 0 to 2); and $R^9$ is halo, cyano, optionally substituted phenyl, —COOH, —COR$^{10}$, —COOR$^{11}$, —CONR$^{12}$R$^{13}$, —SO$_2$R$^{14}$, —SO$_2$NR$^{15}$R$^{16}$, —NHSO$_2$R$^{17}$ or —NHSO$_2$NR$^{18}$R$^{19}$, where $R^{10}$ is alkyl, $R^{11}$ is alkyl, and $R^{12}$, $R^{13}$, $R^{14}$, $R^{15}$, $R^{16}$, $R^{17}$$R^{18}$ and $R^{19}$ are, independently of each other, hydrogen or alkyl;
(f) —CONR$^{25}$R$^{26}$ where $R^{25}$ and $R^{26}$ independently represent hydrogen, alkyl, heteroalkyl, or $R^{25}$ and $R^{26}$ together with the nitrogen to which they are attached form an optionally substituted heterocyclyl ring;
(g) —S(O)$_n$R$^{27}$ where n is an integer from 0 to 2, and $R^{27}$ is alkyl, heteroalkyl, or —NR$^{28}$R$^{29}$ where $R^{28}$ and $R^{29}$ are, independently of each other, hydrogen, alkyl or heteroalkyl;
(h) cycloalkylalkyl, cycloalkylalkenyl and cycloalkylalkynyl, all optionally substituted with alkyl, halo, hydroxy or amino;
(i) Z-alkylene-NR$^{30}$R$^{31}$ or Z-alkylene-OR$^{32}$ where Z is —NH—, —N(lower alkyl)- or —O—, and $R^{30}$, $R^{31}$ and $R^{32}$ are independently of each other, hydrogen, alkyl or heteroalkyl;
(j) —OC(O)-alkylene-CO$_2$H or —OC(O)—NR'R" where R' and R" are independently hydrogen or alkyl;
(k) hydrogen;
(l) halo;
(m) cyano;
(n) hydroxy;
(o) optionally substituted alkoxy;
(p) C(L)R$^{40}$, where L is O; $R^{40}$ is hydrogen, optionally substituted alkyl, optionally substituted alkenyl, optionally substituted alkynyl, optionally substituted phenyl, optionally substituted cycloalkyl, C(L)R$^{56}$, halo, OR$^{55}$, SR$^{55}$, NR$^{57}$R$^{58}$ or SiR$^{52}$R$^{53}$R$^{54}$; where $R^{52}$, $R^{53}$ and $R^{54}$ are selected as in (i) or (ii) as follows (i) $R^{52}$, $R^{53}$ and $R^{54}$ are each independently hydrogen, alkyl, alkenyl, alkynyl, phenyl, cycloalkyl, OR$^{55}$ or NR$^{62}$R$^{63}$; or (ii) any two of $R^{52}$, $R^{53}$ and $R^{54}$ together form alkylene, alkenylene, alkynylene, heteroalkylene; and the other is selected as in (i); $R^{55}$ is hydrogen, alkyl, alkenyl, alkynyl, phenyl or cycloalkyl; $R^{56}$ is hydrogen, alkyl, alkenyl, alkynyl, phenyl, cycloalkyl, OR$^{55}$ or NR$^{64}$R$^{65}$; where $R^{64}$ and $R^{65}$ are each independently hydrogen, alkyl, alkenyl, alkynyl, phenyl, cycloalkyl, OR$^{66}$ or NR$^{62}$R$^{63}$, or $R^{64}$ and $R^{65}$ together form alkylene, alkenylene, alkynylene, heteroalkylene, where $R^{66}$ is hydrogen, alkyl, alkenyl, alkynyl, phenyl or cycloalkyl; $R^{57}$ and $R^{58}$ are selected as in (i) or (ii) as follows (i) $R^{57}$ and $R^{58}$ are each independently hydrogen, optionally substituted alkyl, alkenyl, alkynyl, phenyl, cycloalkyl, OR$^{55}$, NR$^{67}$R$^{68}$ or C(L)R$^{69}$, where $R^{67}$ and $R^{68}$ are each independently hydrogen, alkyl, alkenyl, alkynyl, phenyl or cycloalkyl, or together form alkylene, alkenylene, alkynylene, heteroalkylene; and $R^{69}$ is hydrogen, alkyl, alkenyl, alkynyl, phenyl, cycloalkyl, OR$^{70}$ or NR$^{62}$R$^{63}$, where $R^{70}$ is alkyl, alkenyl, alkynyl, phenyl or cycloalkyl; or (ii) $R^{57}$ and $R^{58}$ together form alkylene, alkenylene, alkynylene, heteroalkylene, or alkylenoxyalkylene; $R^{62}$ and $R^{63}$ are each independently hydrogen, alkyl, alkenyl, alkynyl, phenyl, cycloalkyl, or $R^{62}$ and $R^{63}$ together form alkylene, alkenylene, alkynylene, heteroalkylene; and
(q) optionally substituted alkyl;
$R^4$ is selected from the group consisting of:
(a) hydrogen;
(b) halo;
(c) alkyl;
(d) alkoxy; and
(e) hydroxy;
$R^5$ is selected from the group consisting of
(a) hydrogen;
(b) halo; and
(c) alkyl;
$R^6$ is selected from the group consisting of:
(a) hydrogen;
(b) halo;
(c) alkyl; and
(d) alkoxy.

2. The method according to claim 1, where C is an imidazole ring.

3. The method according to claim 1, where C is a pyrazole ring.

4. The method according to claim 1, wherein the compound is a compound of formula II:

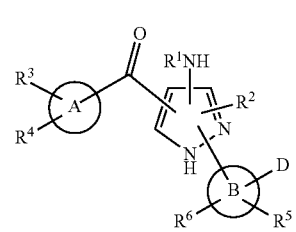

or a pharmaceutically acceptable salt thereof, wherein the A ring is phenyl; and the hydrogen of the ring NH group is replaced by one of the —C(O)-A(R$^3$)(R$^4$), —R$^2$, or- B(D)(R$^6$)(R$^5$) substituents, wherein A refers to the ring A and B refers to ring B in Formula II.

5. The method according to claim 1, wherein the compound is a compound of formula III:

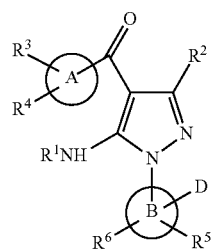

III or a pharmaceutically acceptable salt thereof, wherein the A ring is phenyl.

6. The method according to claim 1, wherein the compound is a compound of formula IV:

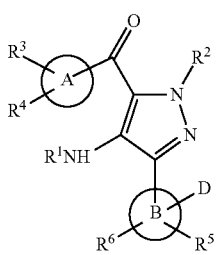

IV or a pharmaceutically acceptable salt thereof, wherein the A ring is phenyl.

7. The method according to claim 1, wherein the compound is a compound of formula V:

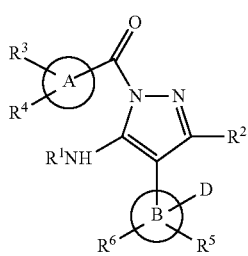

V or a pharmaceutically acceptable salt thereof, wherein the A ring is phenyl.

8. The method according to claim 1, wherein the compound is a compound of formula Va:

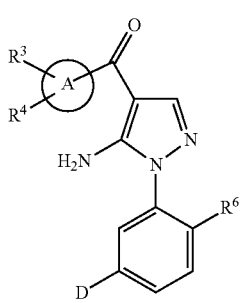

Va or a pharmaceutically acceptable salt thereof, wherein the A ring is phenyl.

9. The method according to claim 1, wherein the compound is a compound of formula VI:

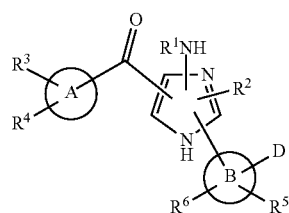

VI or a pharmaceutically acceptable salt thereof, wherein the A ring is phenyl; and the hydrogen of the ring NH group is replaced by one of the —C(O)-A($R^3$)($R^4$), —$R^2$, or —B(D)($R^6$)($R^5$) substituents, wherein A refers to the ring A and B refers to ring B in Formula II.

10. The method according to claim 1, wherein the compound is a compound of formula VII:

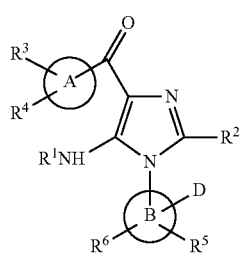

VII or a pharmaceutically acceptable salt thereof, wherein the A ring is phenyl.

11. The method according to claim 1, wherein the compound is a compound of formula VIII:

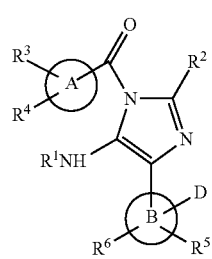

VIII or a pharmaceutically acceptable salt thereof, wherein the A ring is phenyl.

12. The method of claim 1, wherein the compound is selected from the group consisting of: 3-(5-amino-4-benzoyl-pyrazol-1-yl)-N-cyclopropyl-4-methylbenzamide;

3-[5-amino-4-(3-iodo-benzoyl)-pyrazol-1-yl]-N-cyclopropyl-4-methyl-benzamide;

3-[5-amino-4-(3-hydroxymethyl-benzoyl)-pyrazol-1-yl]-N-cyclopropyl-4-methyl-benzamide;

3-[5-amino-4-(3-hydroxy-benzoyl)-pyrazol-1-yl]-N-cyclopropyl-4-methyl-benzamide

3-[5-amino-4-(4-methyl-benzoyl)-pyrazol-1-yl]-N-cyclopropyl-4-methyl-benzamide; and 3-[5-amino-4-(3-cyano-benzoyl)-pyrazol-1-yl]-N-cyclopropyl-4-methyl-benzamide;

or a pharmaceutically acceptable salt thereof.

13. The method of claim 1, wherein the compound is 3-(5-amino-4-benzoyl-pyrazol-1-yl)-N-cyclopropyl-4-methyl-benzamide, or a pharmaceutically acceptable salt thereof.

14. The method of claim 1, wherein the compound is 3-[5-amino-4-(3-cyanobenzoyl)-pyrazol-1-yl]-N-cyclopropyl-4-methyl-benzamide or a pharmaceutically acceptable salt thereof.

* * * * *